United States Patent
Komuro et al.

(10) Patent No.: US 11,548,961 B2
(45) Date of Patent: Jan. 10, 2023

(54) COMPOUND, RESIN, RESIST COMPOSITION AND METHOD FOR PRODUCING RESIST PATTERN

(71) Applicant: SUMITOMO CHEMICAL COMPANY, LIMITED, Tokyo (JP)

(72) Inventors: Katsuhiro Komuro, Osaka (JP); Koji Ichikawa, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 382 days.

(21) Appl. No.: 16/826,835

(22) Filed: Mar. 23, 2020

(65) Prior Publication Data

US 2020/0308095 A1 Oct. 1, 2020

(30) Foreign Application Priority Data

Mar. 25, 2019 (JP) .............................. JP2019-057228

(51) Int. Cl.
| | | |
|---|---|---|
| *C08F 220/30* | (2006.01) | |
| *G03F 7/004* | (2006.01) | |
| *C07C 69/608* | (2006.01) | |
| *C08F 222/14* | (2006.01) | |
| *G03F 7/26* | (2006.01) | |
| *G03F 7/039* | (2006.01) | |
| *G03F 7/16* | (2006.01) | |
| *G03F 7/20* | (2006.01) | |
| *G03F 7/30* | (2006.01) | |

(52) U.S. Cl.
CPC ........ *C08F 220/303* (2020.02); *C07C 69/608* (2013.01); *C08F 222/14* (2013.01); *G03F 7/004* (2013.01); *G03F 7/0045* (2013.01); *G03F 7/0397* (2013.01); *G03F 7/26* (2013.01); *C07C 2601/08* (2017.05); *C07C 2601/14* (2017.05); *G03F 7/162* (2013.01); *G03F 7/20* (2013.01); *G03F 7/30* (2013.01)

(58) Field of Classification Search
CPC .. C08F 222/14; C08F 220/283; G03F 7/0395; G03F 7/0397; G03F 7/004
See application file for complete search history.

(56) References Cited

U.S. PATENT DOCUMENTS

| | | | | |
|---|---|---|---|---|
| 9,086,624 | B2 * | 7/2015 | Sagehashi | G03F 7/0397 |
| 9,951,163 | B2 * | 4/2018 | Tanaka | C07C 69/757 |
| 10,613,437 | B2 * | 4/2020 | Hatakeyama | G03F 7/322 |
| 10,824,073 | B2 * | 11/2020 | Nishikori | G03F 7/0397 |
| 11,061,329 | B2 * | 7/2021 | Ikeda | G03F 7/30 |
| 11,099,479 | B2 * | 8/2021 | Nagamine | C08F 220/281 |
| 2021/0096465 | A1 * | 4/2021 | Fukushima | C09D 133/08 |

FOREIGN PATENT DOCUMENTS

| | | | |
|---|---|---|---|
| JP | 2000-241977 A | 9/2000 | |
| JP | 2008-268743 A | 11/2008 | |
| JP | 2010-254639 A | 11/2010 | |
| JP | 2011-168629 A | 9/2011 | |
| JP | 2015-108809 A | 6/2015 | |
| JP | 2016-099483 A | 5/2016 | |
| JP | 2016-108553 A | 6/2016 | |
| JP | 2016-170360 A | 9/2016 | |
| JP | 2020008624 A * | 1/2020 | ............. G03F 7/004 |
| WO | 2012/133257 A1 | 10/2012 | |
| WO | 2015/045739 A1 | 4/2015 | |

OTHER PUBLICATIONS

Machine translation of JP 2000-241977 (no date).*
Machine translation fo JP 2015-108809 (no date).*
Furukawa et al., "Evaluation of Hydroxyl Derivatives for Chemically Amplified Extreme Ultraviolet Resist," SPIE—International Society for Optical Engineering, Proceedings, Mar. 3, 2010, vol. 7639, pp. 76391L-1-763911-12.
Search Report and Written Opinion dated Sep. 11, 2020, by Belgian Patent Office in corresponding Belgian Patent Application No. 202005183 and an English translation of the Written Opinion. (14 pages).

*Primary Examiner* — Amanda C. Walke
(74) *Attorney, Agent, or Firm* — Buchanan Ingersoll & Rooney PC

(57) ABSTRACT

Disclosed are a compound represented by formula (I), a resin including a structural unit derived from the compound, and a resist composition:

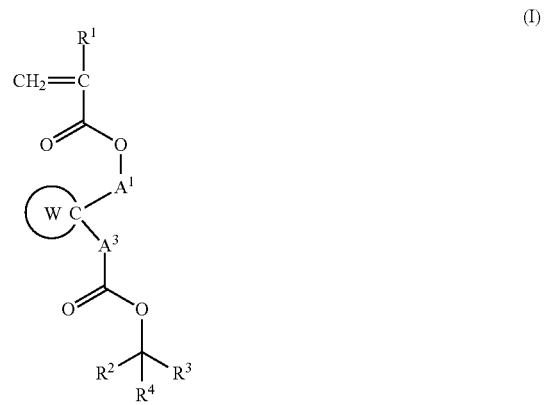

wherein $R^1$ represents an alkyl group which may have a halogen atom, a hydrogen atom or a halogen atom; $A^1$ represents a single bond or *-$A^2$-CO—O—; $A^2$ and $A^3$ represent an alkanediyl group; W represents a divalent monocyclic saturated alicyclic hydrocarbon group; $R^2$ and $R^3$ each represent a hydrogen atom or a hydrocarbon group which may have a fluorine atom, etc., $R^4$ represents a hydrogen atom, —$CH_2$— in the group may be replaced by —O—, —S—, etc., $R^2$ and $R^3$, or $R^2$, $R^3$ and $R^4$ may be bonded each other to form a ring which may have a fluorine atom or an alkyl group.

18 Claims, No Drawings

COMPOUND, RESIN, RESIST COMPOSITION AND METHOD FOR PRODUCING RESIST PATTERN

TECHNICAL FIELD

The present invention relates to a compound, a resin including a structural unit derived from the compound, a resist composition comprising the resin, and a method for producing a resist pattern using the resist composition.

BACKGROUND ART

Patent Document 1 mentions resist compositions comprising a resin composed of each structural unit derived from the following compounds.

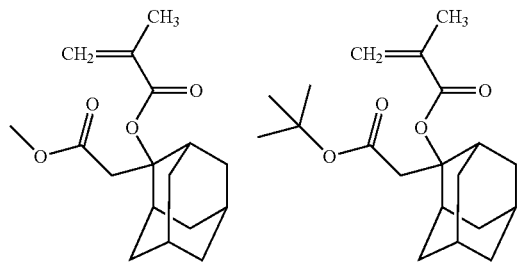

Patent Document 2 also mentions a resist composition comprising a resin composed of a structural unit derived from the following compound.

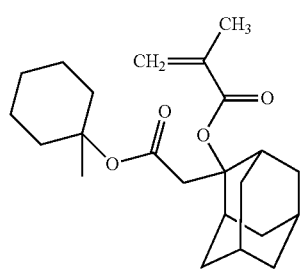

Patent Document 3 also mentions a resist composition comprising a resin composed of a structural unit derived from the following compound.

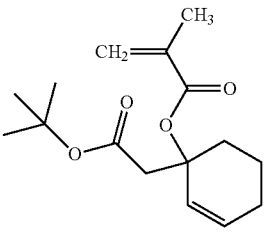

Patent Document 4 also mentions a resist composition comprising a resin composed of a structural unit derived from the following compound.

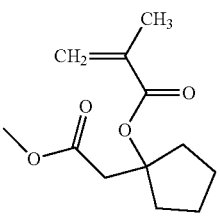

Patent Document 5 also mentions a resist composition comprising a resin composed of a structural unit derived from the following compound.

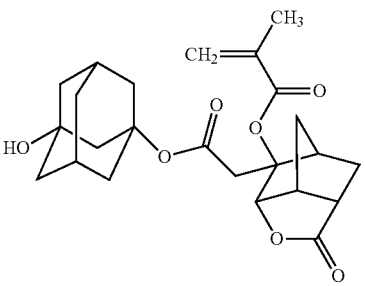

PRIOR ART DOCUMENT

Patent Document

Patent Document 1: JP 2008-268743 A
Patent Document 2: JP 2010-254639 A
Patent Document 3: WO 2015/045739
Patent Document 4: JP 2016-108553 A
Patent Document 5: JP 2015-108809 A

DISCLOSURE OF THE INVENTION

Problems to be Solved by the Invention

The present invention provides a compound that forms a resist pattern with CD uniformity (CDU) which is better than that of a resist pattern formed from a resist composition comprising a resin having a structural unit derived from the above-mentioned compounds.

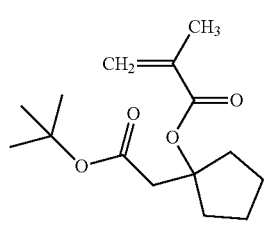

Means for Solving the Problems

The present invention includes the following inventions.

[1] A compound represented by formula (I):

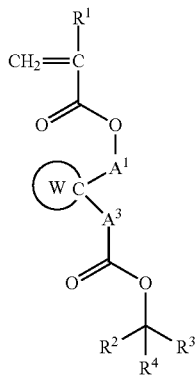

wherein, in formula (I), $R^1$ represents an alkyl group having 1 to 6 carbon atoms which may have a halogen atom, a hydrogen atom or a halogen atom, $A^1$ represents a single bond or *-$A^2$-CO—O—, and * represents a bonding site to an oxygen atom, $A^2$ represents an alkanediyl group having 1 to 6 carbon atoms, W represents a divalent monocyclic saturated alicyclic hydrocarbon group having 3 to 12 carbon atoms, $A^3$ represents an alkanediyl group having 1 to 6 carbon atoms, $R^2$ and $R^3$ each independently represent a hydrogen atom or a hydrocarbon group having 1 to 18 carbon atoms which may have a fluorine atom (—$CH_2$— included in the hydrocarbon group may be replaced by —O—, —S—, —CO— or —$SO_2$—), or $R^2$ and $R^3$ are bonded each other to form a ring having 3 to 36 carbon atoms which may have a fluorine atom or an alkyl group having 1 to 12 carbon atoms (—$CH_2$— included in the alkyl group may be replaced by —O— or —CO—, and —$CH_2$— included in the ring may be replaced by —O—, —S—, —CO— or —$SO_2$—), and $R^4$ represents a hydrogen atom, or $R^2$, $R^3$ and $R^4$ are bonded each other to form a ring having 3 to 36 carbon atoms which may have a fluorine atom or an alkyl group having 1 to 12 carbon atoms (—$CH_2$— included in the alkyl group may be replaced by —O— or —CO—, and —$CH_2$— included in the ring may be replaced by —O—, —S—, —CO— or —$SO_2$—).

[2] The compound according to [1], wherein W is a cyclopentanediyl group or a cyclohexanediyl group.

[3] The compound according to [1] or [2], wherein $A^1$ is a single bond.

[4] The compound according to any one of [1] to [3], wherein $A^3$ is a methylene group.

[5] A resin comprising a structural unit derived from the compound according to any one of [1] to [4].

[6] The resin according to [5], further comprising a structural unit represented by formula (a2-A):

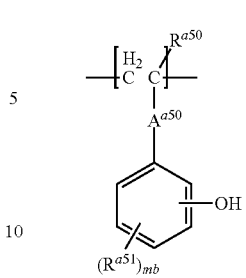

wherein, in formula (a2-A), $R^{a50}$ represents a hydrogen atom, a halogen atom, or an alkyl group having 1 to 6 carbon atoms which may have a halogen atom, $R^{a51}$ represents a halogen atom, a hydroxy group, an alkyl group having 1 to 6 carbon atoms, an alkoxy group having 1 to 6 carbon atoms, an alkylcarbonyl group having 2 to 4 carbon atoms, an alkylcarbonyloxy group having 2 to 4 carbon atoms, an acryloyloxy group or a methacryloyloxy group, $A^{a50}$ represents a single bond or *—$X^{a51}$-($A^{a52}$-$X^{a52}$)$_{nb}$—, and * represents a bonding site to carbon atoms to which —$R^{a50}$ is bonded, $A^{a52}$ represents an alkanediyl group having 1 to 6 carbon atoms, $X^{a51}$ and $X^{a52}$ each independently represent —O—, —CO—O— or —O—CO—, nb represents 0 or 1, and mb represents an integer of 0 to 4, and when mb is an integer of 2 or more, a plurality of $R^{a51}$ may be the same or different from each other.

[7] The resin according to [5] or [6], further comprising a structural unit having an acid-labile group which is different from the structural unit derived from compound represented by formula (I).

[8] The resin according to [7], wherein the resin including a structural unit having an acid-labile group which is different from the structural unit derived from compound represented by formula (I) is a resin including at least one selected from the group consisting of a structural unit represented by formula (a1-1) and a structural unit represented by formula (a1-2):

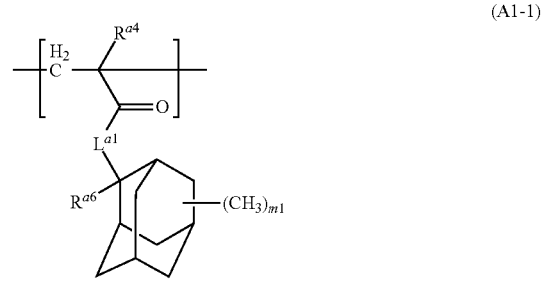

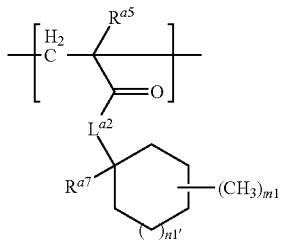

(a1-2)

wherein, in formula (a1-1) and formula (a1-2), $L^{a1}$ and $L^{a2}$ each independently represent —O— or *—O—$(CH_2)_{k1}$—CO—O—, k1 represents an integer of 1 to 7, and * represents a bonding site to —CO—, $R^{a4}$ and $R^{a5}$ each independently represent a hydrogen atom or a methyl group, $R^{a6}$ and $R^{a7}$ each independently represent an alkyl group having 1 to 8 carbon atoms, an alicyclic hydrocarbon group having 3 to 18 carbon atoms, or a group obtained by combining these groups, m1 represents an integer of 0 to 14, n1 represents an integer of 0 to 10, and n1' represents an integer of 0 to 3.

[9] A resist composition comprising the resin according to any one of [5] to [8], and an acid generator.

[10] The resist composition according to [9], further comprising a salt generating an acid having an acidity lower than that of an acid generated from the acid generator.

[11] A method for producing a resist pattern, which comprises:

(1) a step of applying the resist composition according to [9] or [10] on a substrate, (2) a step of drying the applied composition to form a composition layer, (3) a step of exposing the composition layer, (4) a step of heating the exposed composition layer, and (5) a step of developing the heated composition layer.

Effects of the Invention

It is possible to produce a resist pattern with satisfactory CD uniformity (CDU) by using a resist composition comprising a resin including a structural unit derived from a compound of the present invention.

MODE FOR CARRYING OUT THE INVENTION

In the present specification, unless otherwise specified, "(meth)acrylate" means "at least one selected from the group consisting of acrylate and methacrylate". Descriptions such as "(meth)acrylic acid" and "(meth)acryloyl" also have the same meanings. When a structural unit having "$CH_2$=C($CH_3$)—CO—" or "$CH_2$=CH—CO—" is exemplified, a structural unit having both groups shall be similarly exemplified. Also, in the present specification, "derived" or "induced" means that a polymerizable C=C bond included in the molecule becomes a —C—C— group by the polymerization. In groups mentioned in the present specification, regarding groups capable of having both a linear structure and a branched structure, they may have either the linear or branched structure. "Combined group" means a group obtained by bonding two or more exemplified groups, and a valence of the group may appropriately vary depending on the bonding state. When stereoisomers exist, all stereoisomers are included.

In the present specification, "solid component of resist composition" means the total of components excluding the below-mentioned solvent (E) from the total amount of the resist composition.

<Compound (I)>

The compound of the present invention is a compound represented by formula (I) (hereinafter sometimes referred to as "compound (I)"):

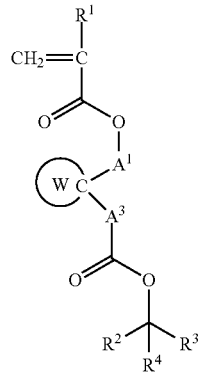

(I)

wherein, in formula (I), $R^1$ represents an alkyl group having 1 to 6 carbon atoms which may have a halogen atom, a hydrogen atom or a halogen atom, $A^1$ represents a single bond or *-$A^2$-CO—O—, and * represents a bonding site to an oxygen atom, $A^2$ represents an alkanediyl group having 1 to 6 carbon atoms, W represents a divalent monocyclic saturated alicyclic hydrocarbon group having 3 to 12 carbon atoms, $A^3$ represents an alkanediyl group having 1 to 6 carbon atoms, $R^2$ and $R^3$ each independently represent a hydrogen atom or a hydrocarbon group having 1 to 18 carbon atoms which may have a fluorine atom (—$CH_2$— included in the hydrocarbon group may be replaced by —O—, —S—, —CO— or —$SO_2$—), or $R^2$ and $R^3$ are bonded each other to form a ring having 3 to 36 carbon atoms which may have a fluorine atom or an alkyl group having 1 to 12 carbon atoms (—$CH_2$— included in the alkyl group may be replaced by —O— or —CO—, and —$CH_2$— included in the ring may be replaced by —O—, —S—, —CO— or —$SO_2$—), and $R^4$ represents a hydrogen atom, or $R^2$, $R^3$ and $R^4$ are bonded each other to form a ring having 3 to 36 carbon atoms which may have a fluorine atom or an alkyl group having 1 to 12 carbon atoms (—$CH_2$— included in the alkyl group may be replaced by —O— or —CO—, and —$CH_2$— included in the ring may be replaced by —O—, —S—, —CO— or —$SO_2$—).

Examples of the alkyl group for $R^1$ include a methyl group, an ethyl group, an n-propyl group, an isopropyl group, an n-butyl group, a sec-butyl group, a tert-butyl group, an n-pentyl group and an n-hexyl group, and an alkyl group having 1 to 4 carbon atoms is preferable, and a methyl group and an ethyl group are more preferable.

Examples of the halogen atom for $R^1$ include a fluorine atom, a chlorine atom, a bromine atom and an iodine atom.

Examples of the alkyl group having a halogen atom for $R^1$ include a trifluoromethyl group, a perfluoroethyl group, a perfluoropropyl group, a perfluoroisopropyl group, a perfluorobutyl group, a perfluorosec-butyl group, a perfluoro-tert-butyl group, a perfluoropentyl group, a perfluorohexyl group, a perchloromethyl group, a perbromomethyl group and a periodomethyl group.

$R^1$ is preferably a hydrogen atom or a methyl group.

Examples of the alkanediyl group having 1 to 6 carbon atoms for $A^1$ and $A^3$ include linear alkanediyl groups such as a methylene group, an ethylene group, a propane-1,3-diyl group, a butane-1,4-diyl group, a pentane-1,5-diyl group and a hexane-1,6-diyl group; branched alkanediyl groups in which liner alkanediyl groups have a side chain of alkyl groups (especially alkyl groups having 1 to 4 carbon atoms, such as a methyl group, an ethyl group, a propyl group, an isopropyl group, a butyl group, a sec-butyl group and a tert-butyl group), for example, an ethane-1,1-diyl group, a propane-1,2-diyl group, a butane-1,3-diyl group, a 2-methylpropane-1,3-diyl group, a 2-methylpropane-1,2-diyl group, a pentane-1,4-diyl group and a 2-methylbutane-1,4-diyl group.

$A^1$ is preferably a single bond, *—CH$_2$—CO—O— or *—C$_2$H$_4$—CO—O—, more preferably a single bond or *—CH$_2$—CO—O—, and still more preferably a single bond.

$A^2$ is preferably an alkanediyl group having 1 to 3 carbon atoms, more preferably a methylene group or an ethylene group, and still more preferably a methylene group.

$A^3$ is preferably an alkanediyl group having 1 to 3 carbon atoms, more preferably a methylene group or an ethylene group, and still more preferably a methylene group.

Examples of the divalent monocyclic saturated alicyclic hydrocarbon group having 3 to 12 carbon atoms for W include a cyclopropanediyl group, a cyclobutanediyl group, a cyclopentanediyl group, a cyclohexanediyl group, a cycloheptanediyl group, a cyclooctanediyl group and the like. Of these, a divalent monocyclic saturated alicyclic hydrocarbon group having 3 to 8 carbon atoms is preferable, a cyclopentanediyl group or a cyclohexanediyl group is more preferable, and a cyclopentanediyl group is still more preferable.

Examples of the hydrocarbon group for $R^2$ and $R^3$ include a chain hydrocarbon group such as an alkyl group, an alicyclic hydrocarbon group, an aromatic hydrocarbon group, and groups formed by combining these groups.

Examples of the alkyl group include alkyl groups such as a methyl group, an ethyl group, a propyl group, an isopropyl group, a butyl group, an isobutyl group, a tert-butyl group, a pentyl group, a hexyl group, an octyl group and a nonyl group. The number of carbon atoms of the alkyl group is preferably 1 to 12, more preferably 1 to 6, still more preferably 1 to 4, and yet more preferably 1 to 2.

The alicyclic hydrocarbon group may be any one of monocyclic, polycyclic and spiro rings, or may be either saturated or unsaturated. Examples of the alicyclic hydrocarbon group include the following groups. * represents a bonding site.

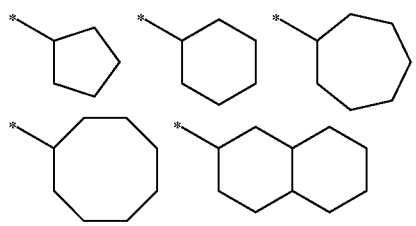

-continued

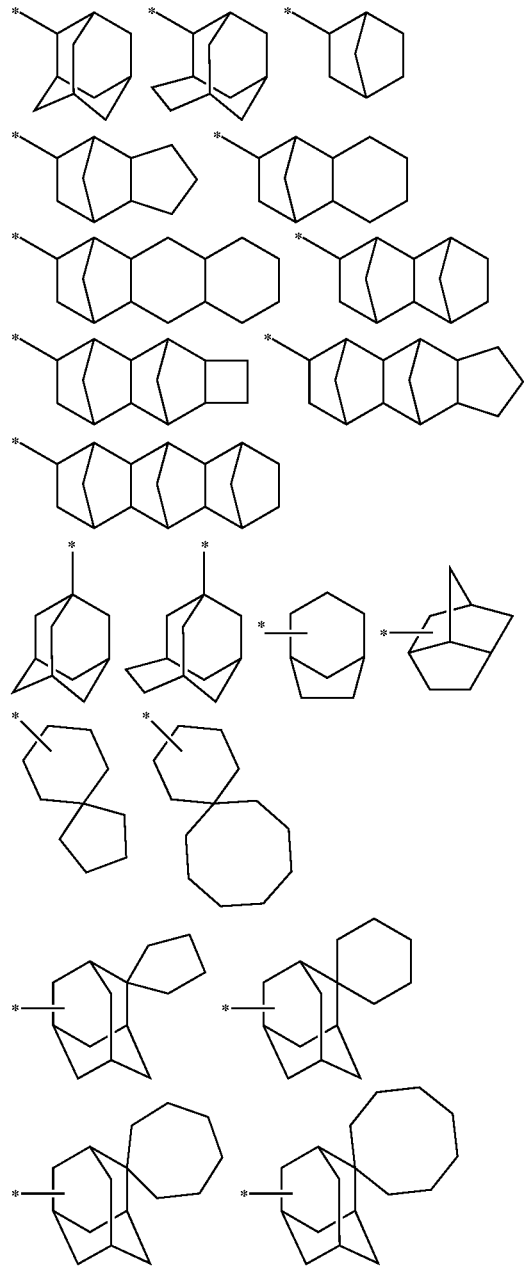

Specific examples thereof include monocyclic cycloalkyl groups such as a cyclopropyl group, a cyclobutyl group, a cyclopentyl group, a cyclohexyl group, a cyclooctyl group, a cyclononyl group, a cyclodecyl group and a cyclododecyl group; and polycyclic cycloalkyl groups such as a norbornyl group and an adamantyl group. The number of carbon atoms of the alicyclic hydrocarbon group is preferably 3 to 18, more preferably 3 to 16, and still more preferably 3 to 12.

Examples of the aromatic hydrocarbon group include a phenyl group, a naphthyl group and the like.

Examples of the group formed by combining these groups include groups formed by combining an alicyclic hydrocarbon group with a chain hydrocarbon group, such as a cyclopentylmethyl group and an adamantylmethyl group; and groups formed by combining an aromatic hydrocarbon group with a chain hydrocarbon group, such as a benzyl group and a phenethyl group.

In the case of groups formed by combination, groups having different valence in the above groups (a divalent or trivalent group (a chain hydrocarbon group, an alicyclic saturated hydrocarbon group, an aromatic hydrocarbon group)) may be included.

When —CH$_2$— included in the hydrocarbon group represented by R$^2$ and R$^3$, or the ring formed by bonding R$^2$ and R$^3$, or R$^2$, R$^3$ and R$^4$ each other is replaced by —O—, —S—, —CO— or —SO$_2$—, the number of carbon atoms before replacement is taken as the total number of the hydrocarbon group or the ring. When the ring formed by bonding R$^2$ and R$^3$, or R$^2$, R$^3$ and R$^4$ each other has an alkyl group, the number of carbon atoms excluding the number of carbon atoms of the alkyl group is taken as the total number of the ring.

Examples of the alkyl group which may be possessed when R$^2$ and R$^3$, or R$^2$, R$^3$ and R$^4$ are bonded each other to form a ring include the same group as mentioned above.

Examples of the group in which —CH$_2$— included in the alkyl group is replaced by —O—, —S—, —CO— or —SO$_2$— include a hydroxy group (group in which —CH$_2$— included in a methyl group is replaced by —O—), a carboxyl group (group in which —CH$_2$—CH$_2$-included in an ethyl group is replaced by —O—CO—), an alkoxy group having 1 to 11 carbon atoms (group in which —CH$_2$— included in an alkyl group having 2 to 12 carbon atoms is replaced by —O—), an alkoxycarbonyl group having 2 to 11 carbon atoms (group in which —CH$_2$—CH$_2$— included in an alkyl group having 3 to 12 carbon atoms is replaced by —O—CO—), an alkylcarbonyl group having 2 to 12 carbon atoms (group in which —CH$_2$— included in an alkyl group having 2 to 12 carbon atoms is replaced by —CO—), an alkylcarbonyloxy group having 2 to 11 carbon atoms (group in which —CH$_2$—CH$_2$— included in an alkyl group having 3 to 12 carbon atoms is replaced by —CO—O—), an alkylthio group having 1 to 11 carbon atoms (group in which —CH$_2$— included in an alkyl group having 2 to 12 carbon atoms is replaced by —S—) and the like.

Examples of the alkoxy group include a methoxy group, an ethoxy group, a propoxy group, a butoxy group, a pentyloxy group, a hexyloxy group, an octyloxy group, a 2-ethylhexyloxy group, a nonyloxy group, a decyloxy group, an undecyloxy group and the like.

The alkoxycarbonyl group, the alkylcarbonyl group and the alkylcarbonyloxy group represent a group in which a carbonyl group or a carbonyloxy group is bonded to the alkyl group or alkoxy group mentioned above.

Examples of the alkoxycarbonyl group include a methoxycarbonyl group, an ethoxycarbonyl group, a butoxycarbonyl group and the like; examples of the alkylcarbonyl group include an acetyl group, a propionyl group and a butyryl group; and examples of the alkylcarbonyloxy group include an acetyloxy group, a propionyloxy group, a butyryloxy group and the like.

Examples of the alkylthio group include a methylthio group, an ethylthio group and the like.

Examples of the group in which —CH$_2$— included in the alicyclic hydrocarbon group is replaced by —O—, —S—, —CO— or —SO$_2$— include the following groups. * represents a bonding site.

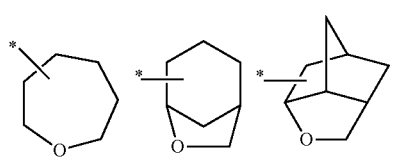

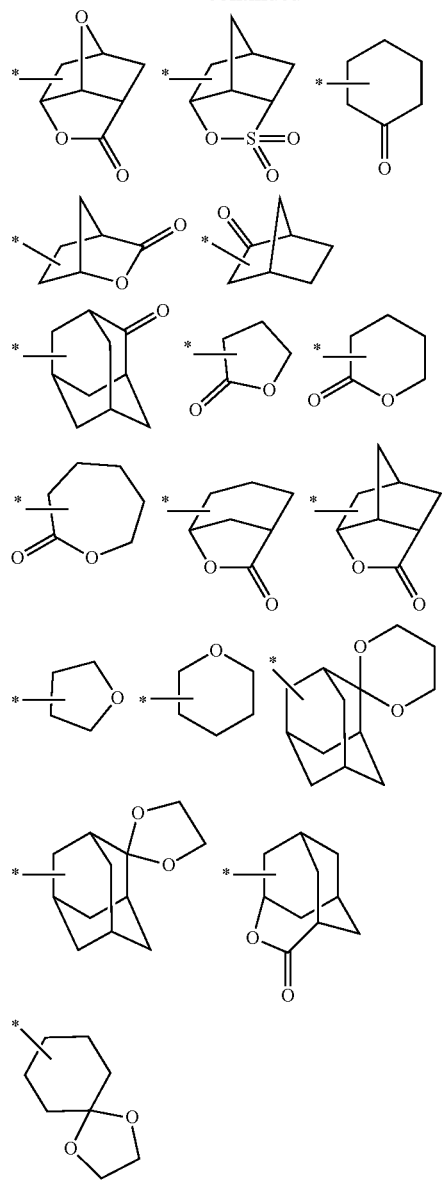

Examples of —C(R$^2$)(R$^3$)(R$^4$) when R$^2$ and R$^3$, or R$^2$, R$^3$ and R$^4$ are bonded each other to form a ring (the ring may have a fluorine atom or an alkyl group having 1 to 12 carbon atoms, —CH$_2$— included in the alkyl group may be replaced by —O— or —CO—, and —CH$_2$— included in the ring may be replaced by —O—, —S—, —CO— or —SO$_2$—) include the following groups. * represents a bonding site to —O—.

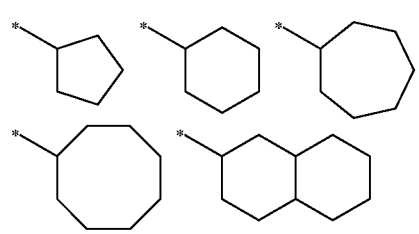

-continued
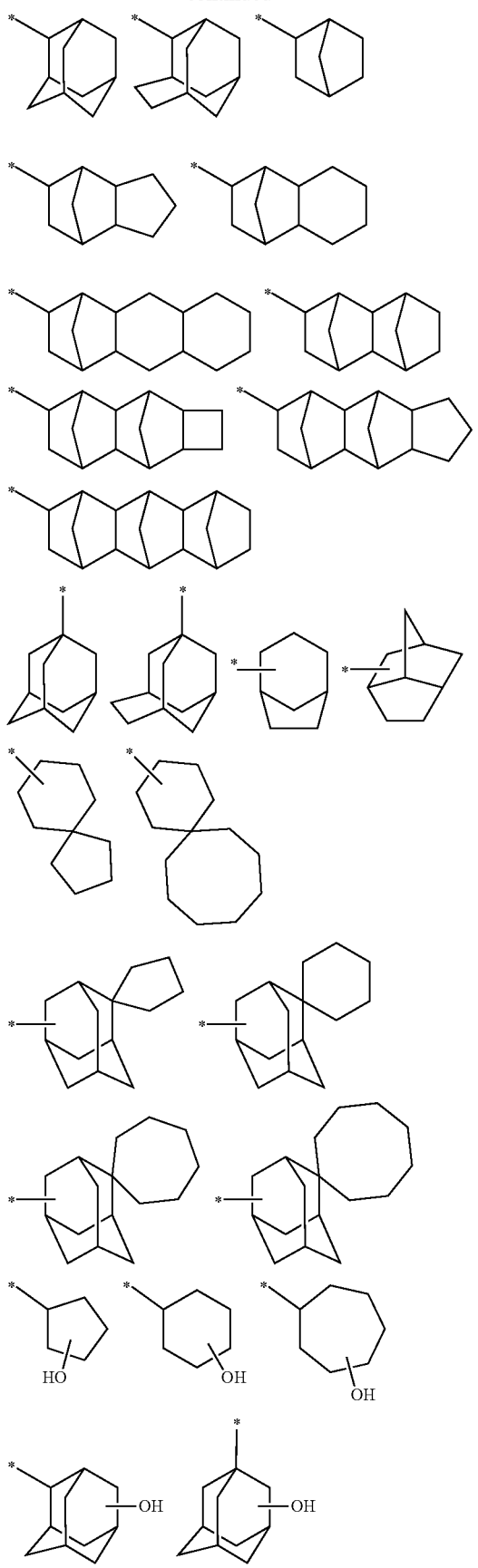
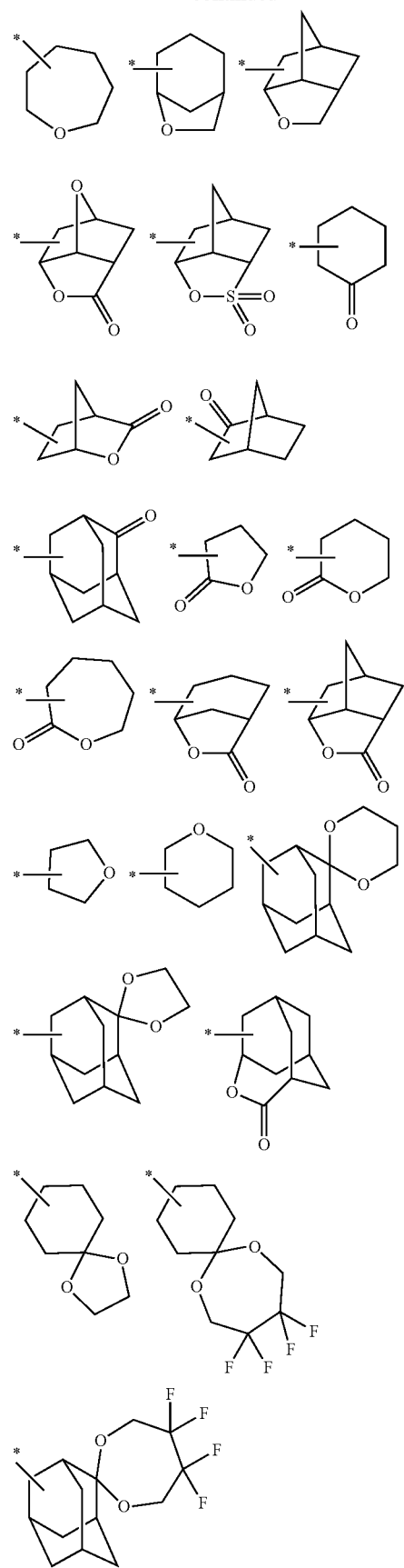

-continued

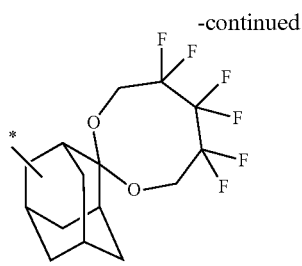

Preferably, $R^2$ and $R^3$ each independently represent a hydrogen atom or a hydrocarbon group having 1 to 14 carbon atoms which may have a fluorine atom (—$CH_2$— included in the hydrocarbon group may be replaced by —O—, —S—, —CO— or —$SO_2$—), or $R^2$ and $R^3$ are bonded each other to form a ring having 3 to 24 carbon atoms which may have a fluorine atom or an alkyl group having 1 to 12 carbon atoms (—$CH_2$— included in the alkyl group may be replaced by —O— or —CO—, and —$CH_2$— included in the ring may be replaced by —O—, —S—, —CO— or —$SO_2$—), more preferably, $R^2$ and $R^3$ each independently represent a hydrogen atom or a hydrocarbon group having 1 to 12 carbon atoms which may have a fluorine atom (—$CH_2$— included in the hydrocarbon group may be replaced by —O—, —S—, —CO— or —$SO_2$—), or $R^2$ and $R^3$ are bonded each other to form a ring having 3 to 16 carbon atoms which may have a fluorine atom or an alkyl group having 1 to 6 carbon atoms (—$CH_2$— included in the alkyl group may be replaced by —O— or —CO—, and —$CH_2$— included in the ring may be replaced by —O—, —S—, —CO— or —$SO_2$—), and still more preferably, $R^2$ and $R^3$ each independently represent a hydrogen atom or an alkyl group having 1 to 6 carbon atoms which may have a fluorine atom (—$CH_2$— included in the alkyl group may be replaced by —O—, —S—, —CO— or —$SO_2$—), or $R^2$ and $R^3$ are bonded each other to form a ring having 3 to 16 carbon atoms which may have a fluorine atom or an alkyl group having 1 to 4 carbon atoms (—$CH_2$— included in the alkyl group may be replaced by —O— or —CO—, and —$CH_2$— included in the ring may be replaced by —O—, —S—, —CO— or —$SO_2$—).

Preferably, $R^4$ is a hydrogen atom, or $R^2$, $R^3$ and $R^4$ are bonded each other to form a ring having 3 to 24 carbon atoms which may have a fluorine atom or an alkyl group having 1 to 12 carbon atoms (—$CH_2$— included in the alkyl group may be replaced by —O— or —CO—, and —$CH_2$— included in the ring may be replaced by —O—, —S—, —CO— or —$SO_2$—), more preferably, $R^4$ is a hydrogen atom, or $R^1$, $R^3$ and $R^4$ are bonded each other to form a ring having 3 to 16 carbon atoms which may have a fluorine atom or an alkyl group having 1 to 6 carbon atoms (—$CH_2$— included in the alkyl group may be replaced by —O— or —CO—, and —$CH_2$— included in the ring may be replaced by —O—, —S—, —CO— or —$SO_2$—), and still more preferably, $R^4$ is a hydrogen atom, or $R^1$, $R^3$ and $R^4$ are bonded each other to form a ring having 3 to 16 carbon atoms which may have a fluorine atom or an alkyl group having 1 to 4 carbon atoms (—$CH_2$— included in the alkyl group may be replaced by —O— or —CO—, and —$CH_2$— included in the ring may be replaced by —O—, —S—, —CO— or —$SO_2$—).

Examples of the compound (I) include the followings.

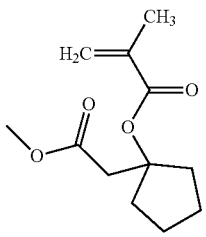
(I-1)

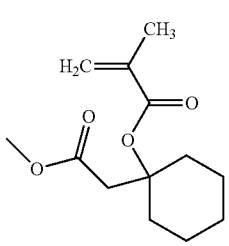
(I-2)

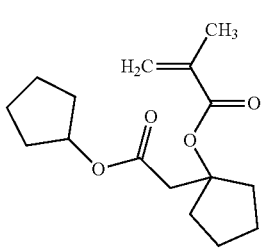
(I-3)

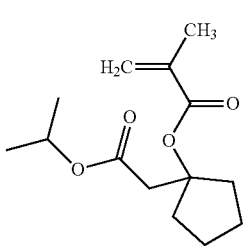
(I-4)

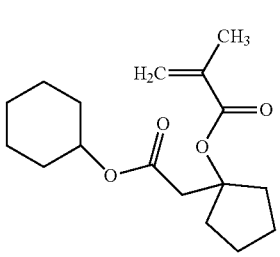
(I-5)

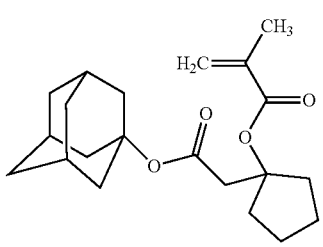
(I-6)

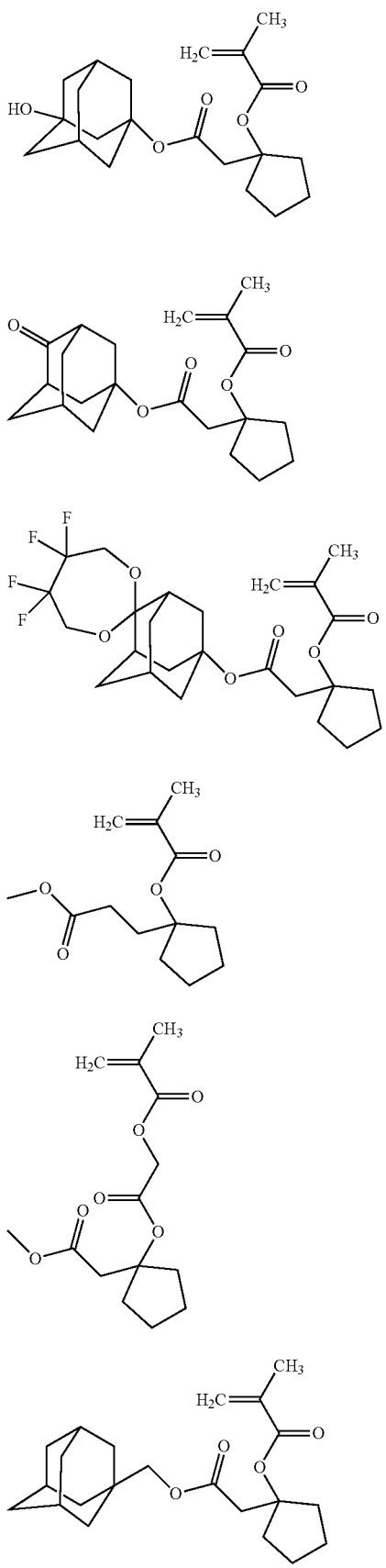
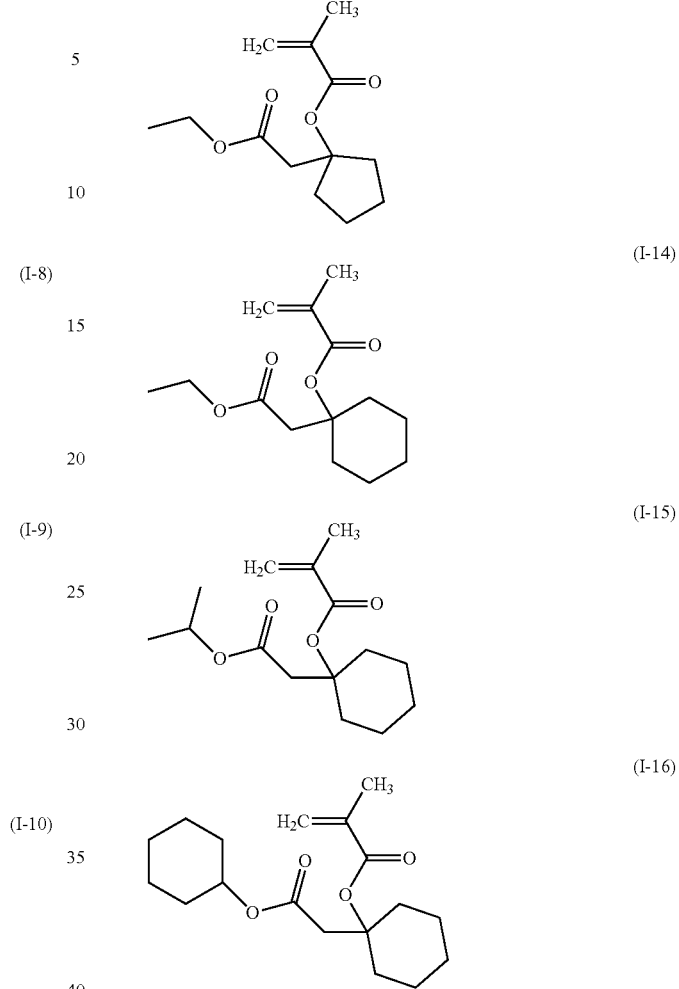

It is possible to exemplify compounds in which a methyl group corresponding to $R^1$ is substituted with a hydrogen atom or a halogen atom in compounds represented by formula (I-1) to formula (I-16) as specific examples of the compound (I).

<Method for Producing Compound (I)>

The compound represented by formula (I1) in which $A^1$ of the compound (I) is a single bond can be obtained by reacting a compound represented by formula (I1-a) with a compound represented by formula (I1-b) in the presence of a base catalyst in a solvent:

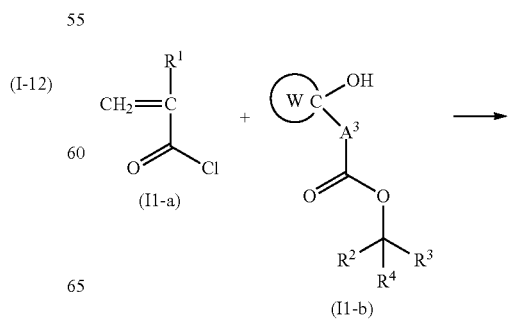

-continued

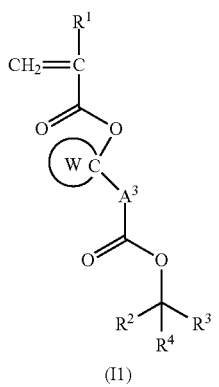
(I1)

wherein all symbols are the same as defined above.

Examples of the solvent include methyl isobutyl ketone, chloroform, tetrahydrofuran and toluene.

Examples of the base catalyst include pyridine, dimethylaminopyridine, N-methylpiperidine, N-methylpyrrolidine and the like.

Examples of the compound represented by formula (I1-a) include salts represented by the following formula and the like, which are easily available on the market.

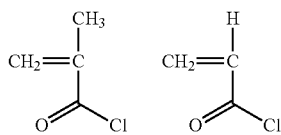

The compound represented by formula (I1-b) can be obtained by reacting a compound represented by formula (I1-c) with zinc in the presence of trimethylsilyl chloride in a solvent, followed by a reaction with a compound represented by formula (I1-d):

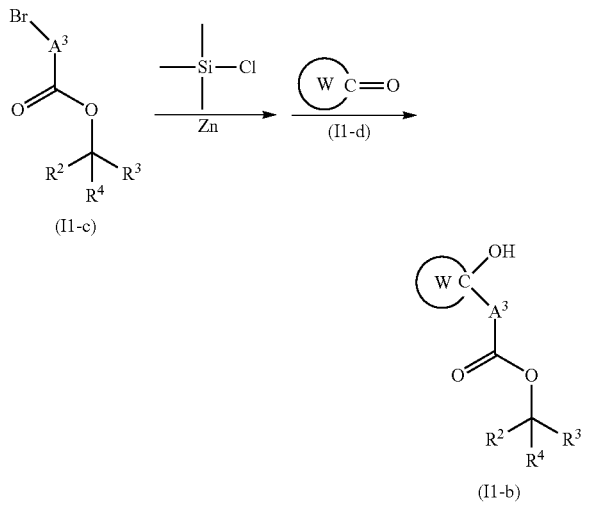

wherein all symbols are the same as defined above.

Examples of the solvent include tetrahydrofuran and the like.

Examples of the compound represented by formula (I1-c) include salts represented by the following formulas, which are easily available on the market and can also be synthesized easily by a known production process.

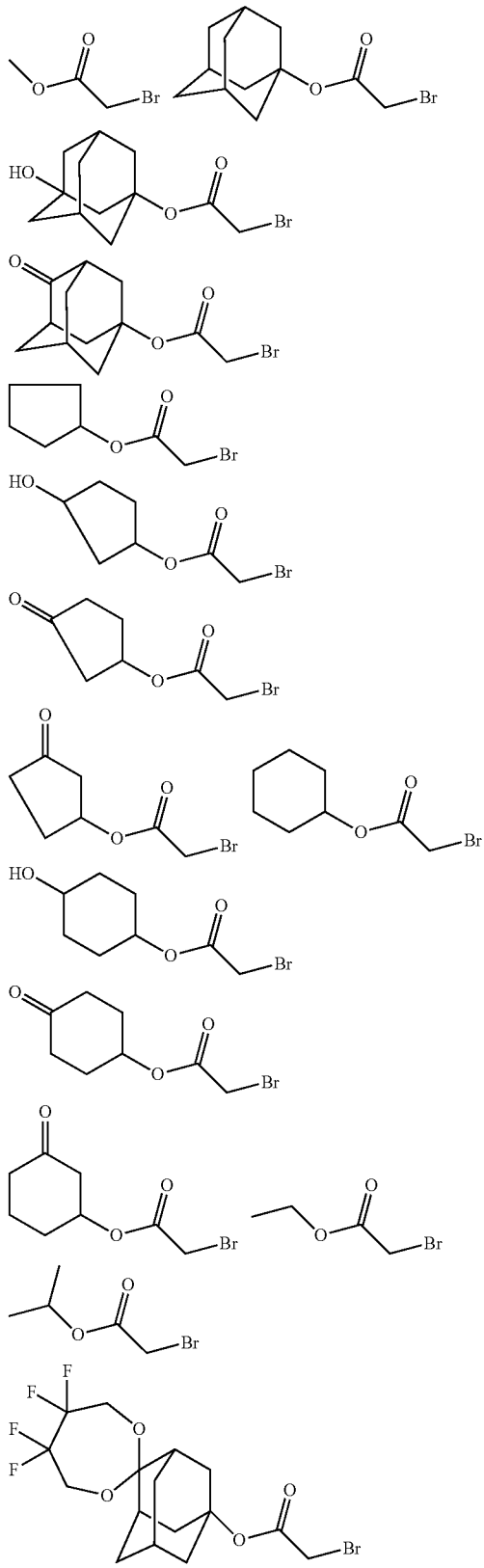

Examples of the compound represented by formula (I1-d) include salts represented by the following formulas, which are easily available on the market.

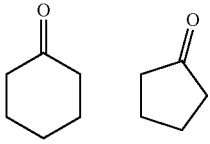 [SMILES: O=C1CCCCC1 ; O=C1CCCC1]

The compound represented by formula (I2) in which $A^1$ of the compound (I) is *-$A^2$-CO—O— can be obtained by reacting a compound represented by formula (I1-a) with a compound represented by formula (I2-b) in the presence of a base catalyst in a solvent:

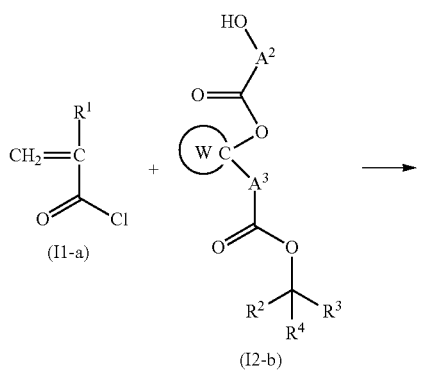

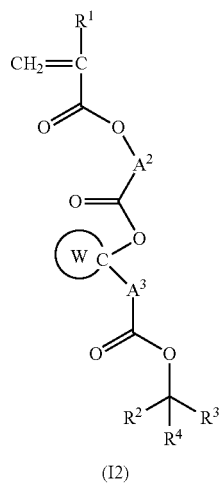

wherein all symbols are the same as defined above.

Examples of the solvent include methyl isobutyl ketone, chloroform, tetrahydrofuran and toluene.

Examples of the base catalyst include pyridine, dimethylaminopyridine, N-methylpiperidine, N-methylpyrrolidine and the like.

The compound represented by formula (I2-b) can be obtained by reacting a compound represented by formula (I1-b) with a compound represented by formula (I2-e) in the presence of a base catalyst in a solvent:

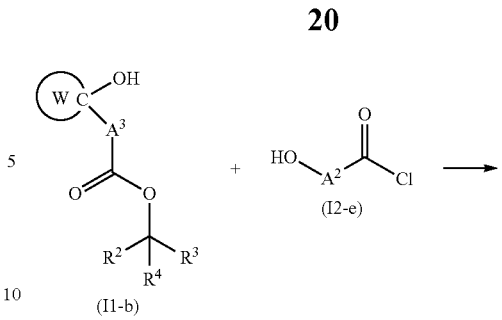

wherein all symbols are the same as defined above.

Examples of the solvent include methyl isobutyl ketone, chloroform, tetrahydrofuran and toluene.

Examples of the base catalyst include pyridine, dimethylaminopyridine, N-methylpiperidine, N-methylpyrrolidine and the like.

Examples of the compound represented by formula (I2-e) include a salt represented by the following formula, which is easily available on the market.

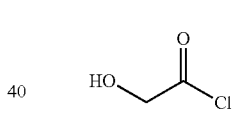

[Resin]

The resin of the present invention is a resin (hereinafter sometimes referred to as "resin (A)") including a structural unit derived from a compound (I) (hereinafter sometimes referred to as "structural unit (I)"). The resin (A) may be a homopolymer composed only of one structural unit (I), a copolymer composed of two or more structural units (I), or a polymer including one or more structural units other than the structural unit (I). Examples of the structural unit other than the structural unit (I) include a structural unit having an acid-labile group other than the structural unit (I) (hereinafter sometimes referred to as "structural unit (a1)"), a structural unit having a halogen atom other than the structural unit having an acid-labile group (hereinafter sometimes referred to as "structural unit (a4)"), a structural unit having no acid-labile group (hereinafter sometimes referred to as "structural unit (s)"), a structural unit having a non-leaving hydrocarbon group (hereinafter sometimes referred to as "structural unit (a5)") and the like. The "acid-labile group" means a group having a leaving group which is eliminated by contact with an acid, thus forming a hydrophilic group (e.g. a hydroxy group or a carboxy group). The resin (A) preferably includes, in addition to the structural unit (I), a structural unit (s) and/or a structural unit having an acid-labile group, more preferably includes at least one structural unit (s) and/or at least one structural unit (a1), and still more preferably includes at least one structural unit (s) and at least one structural unit (a1) or two or more structural units (a1).

The content of the structural unit (I) is usually 1 to 90 mol %, preferably 3 to 85 mol %, more preferably 5 to 80 mol %, still more preferably 7 to 75 mol %, and yet more preferably 10 to 70 mol %, based on all structural units in the resin (A).

When the resin (A) includes a structural unit (a4) and/or (a5) mentioned later (hereinafter sometimes referred to as "resin (AX)"), the content of the structural unit (I) in the resin (AX) of the present invention is preferably 5 to 75 mol %, more preferably 10 to 70 mol %, still more preferably 10 to 65 mol %, and particularly preferably 10 to 60 mol %, based on the total of all structural units of the resin (AX) of the present invention.

<Structural Unit (a1)>

The structural unit (a1) is derived from a monomer having an acid-labile group (hereinafter sometimes referred to as "monomer (a1)").

The acid-labile group contained in the resin (A) is preferably a group represented by formula (1) (hereinafter also referred to as group (1)) and/or a group represented by formula (2) (hereinafter also referred to as group (2)):

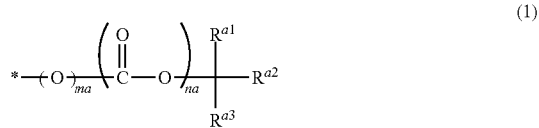

(1)

wherein, in formula (1), $R^{a1}$, $R^{a2}$ and $R^{a3}$ each independently represent an alkyl group having 1 to 8 carbon atoms, an alicyclic hydrocarbon group having 3 to 20 carbon atoms, or groups obtained by combining these groups, or $R^{a1}$ and $R^{a2}$ are bonded each other to form an alicyclic hydrocarbon group having 3 to 20 carbon atoms together with carbon atoms to which $R^{a1}$ and $R^{a2}$ are bonded, ma and na each independently represent 0 or 1, and at least one of ma and na represents 1, and

* represents a bonding site:

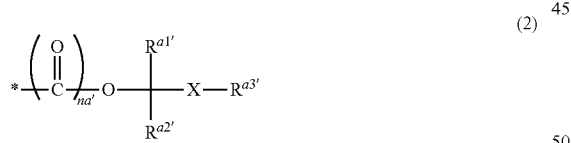

(2)

wherein, in formula (2), $R^{a1'}$ and $R^{a2'}$ each independently represent a hydrogen atom or a hydrocarbon group having 1 to 12 carbon atoms, $R^{a3'}$ represents a hydrocarbon group having 1 to 20 carbon atoms, or $R^{a2'}$ and $R^{a3'}$ are bonded each other to form a heterocyclic group having 3 to 20 carbon atoms together with carbon atoms and X to which $R^{a2'}$ and $R^{a3'}$ are bonded, and —CH$_2$— included in the hydrocarbon group and the heterocyclic group may be replaced by —O— or —S—, X represents an oxygen atom or a sulfur atom, na' represents 0 or 1, and

* represents a bonding site.

Examples of the alkyl group in $R^{a1}$, $R^{a2}$ and $R^{a3}$ include a methyl group, an ethyl group, a propyl group, a butyl group, a pentyl group, a hexyl group, a heptyl group, an octyl group and the like.

The alicyclic hydrocarbon group in $R^{a1}$, $R^{a2}$ and $R^{a3}$ may be either monocyclic or polycyclic. Examples of the monocyclic alicyclic hydrocarbon group include cycloalkyl groups such as a cyclopentyl group, a cyclohexyl group, a cycloheptyl group and a cyclooctyl group. Examples of the polycyclic alicyclic hydrocarbon group include a decahydronaphthyl group, an adamantyl group, a norbornyl group and the following groups (* represents a bonding site). The number of carbon atoms of the alicyclic hydrocarbon group for $R^{a1}$, $R^{a2}$ and $R^{a3}$ is preferably 3 to 16.

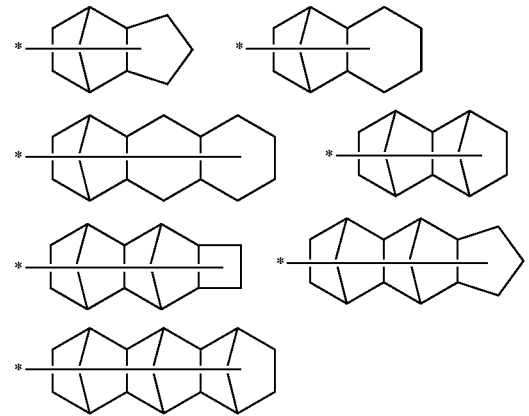

Examples of the group obtained by combining an alkyl group with an alicyclic hydrocarbon group include a methylcyclohexyl group, a dimethylcyclohexyl group, a methylnorbornyl group, a cyclohexylmethyl group, an adamantylmethyl group, an adamantyldimethyl group, a norbornylethyl group and the like.

Preferably, ma is 0 and na is 1.

When $R^{a1}$ and $R^{a2}$ are bonded each other to form an alicyclic hydrocarbon group, examples of —C($R^{a1}$)($R^{a2}$)($R^{a3}$) include the following groups. The alicyclic hydrocarbon group preferably has 3 to 12 carbon atoms. * represents a bonding site to —O—.

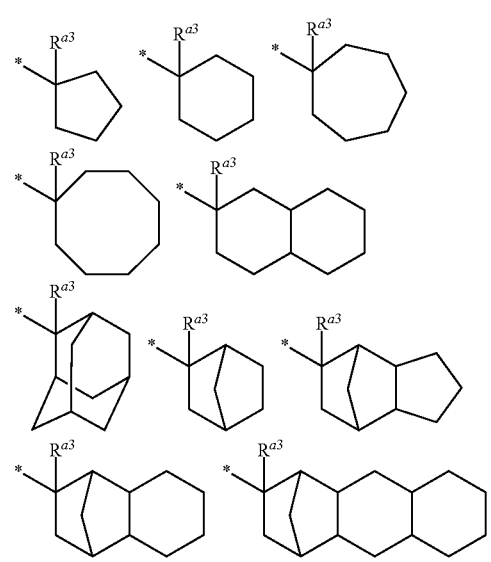

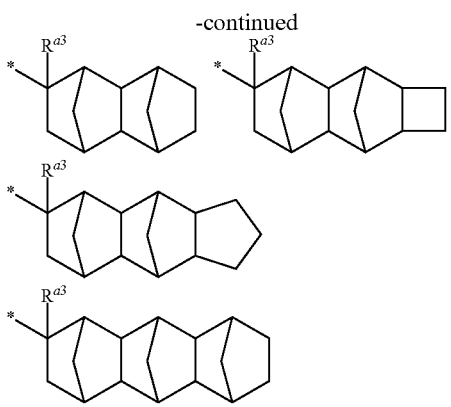

Examples of the hydrocarbon group in $R^{a1'}$, $R^{a2'}$ and $R^{a3'}$ include an alkyl group, an alicyclic hydrocarbon group, an aromatic hydrocarbon group, and groups obtained by combining these groups.

Examples of the alkyl group and the alicyclic hydrocarbon group include those which are the same as mentioned for $R^{a1}$, $R^{a2}$ and $R^{a3}$.

Examples of the aromatic hydrocarbon group include aryl groups such as a phenyl group, a naphthyl group, an anthryl group, a biphenyl group and a phenanthryl group.

Examples of the combined group include a group obtained by combining the above-mentioned alkyl group and alicyclic hydrocarbon group (e.g., a cycloalkylalkyl group), an aralkyl group such as a benzyl group, an aromatic hydrocarbon group having an alkyl group (a p-methylphenyl group, a p-tert-butylphenyl group, a tolyl group, a xylyl group, a cumenyl group, a mesityl group, a 2,6-diethylphenyl group, a 2-methyl-6-ethylphenyl group, etc.), an aromatic hydrocarbon group having an alicyclic hydrocarbon group (a p-cyclohexylphenyl group, a p-adamantylphenyl group, etc.), an aryl-cycloalkyl group such as a phenylcyclohexyl group and the like.

When $R^{a2'}$ and $R^{a3'}$ are bonded each other to form a heterocyclic ring together with carbon atoms and X to which $R^{a2'}$ and $R^{a3'}$ are bonded, examples of —C($R^{a1'}$) ($R^{a2'}$)— X—$R^{a3'}$ include the following rings. * represents a bonding site.

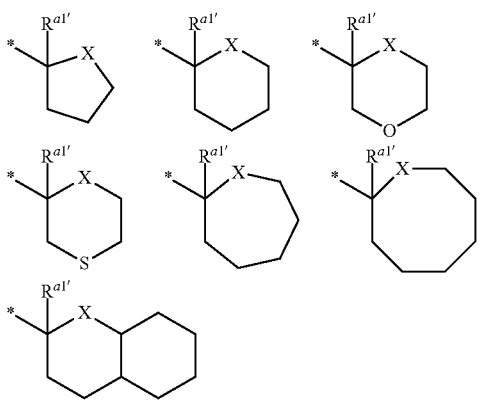

Of $R^{a1'}$ and $R^{a2'}$, at least one is preferably a hydrogen atom.

na' is preferably 0.

Examples of the group (1) include the following groups.

A group wherein, in formula (1), $R^{a1}$, $R^{a2}$ and $R^{a3}$ are alkyl groups, ma=0 and na=1. The group is preferably a tert-butoxycarbonyl group.

A group wherein, in formula (1), $R^{a1}$ and $R^{a2}$ are bonded each other to form an adamantyl group together with carbon atoms to which $R^{a1}$ and $R^{a2}$ are bonded, $R^{a3}$ is an alkyl group, ma=0 and na=1.

A group wherein, in formula (1), $R^{a1}$ and $R^{a2}$ are each independently an alkyl group, $R^{a3}$ is an adamantyl group, ma=0 and na=1.

Specific examples of the group (1) include the following groups. * represents a bonding site.

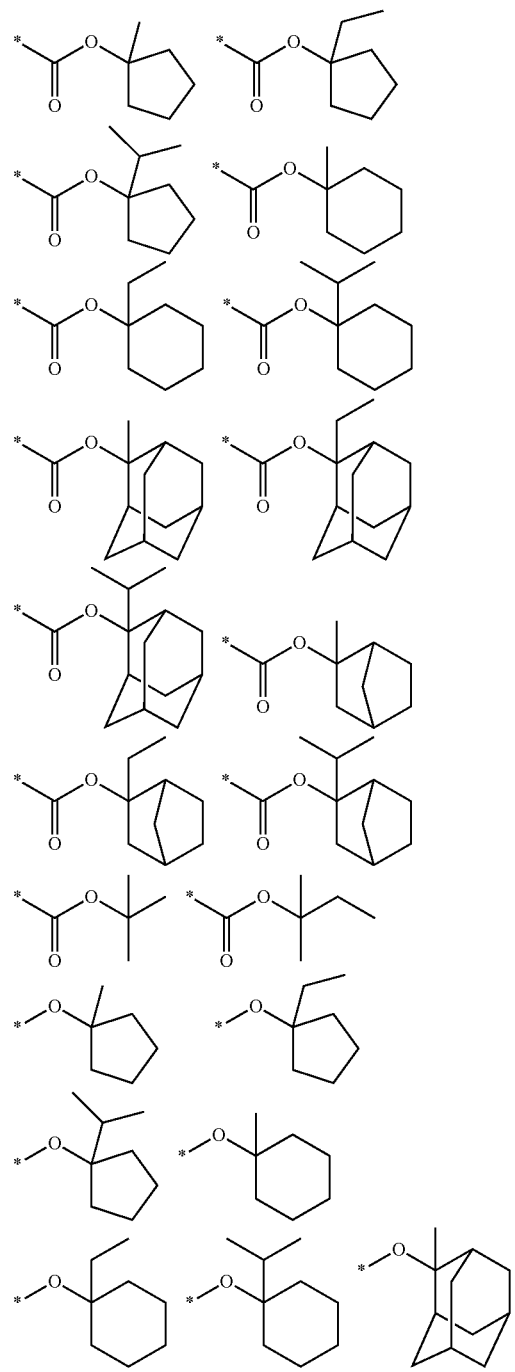

-continued
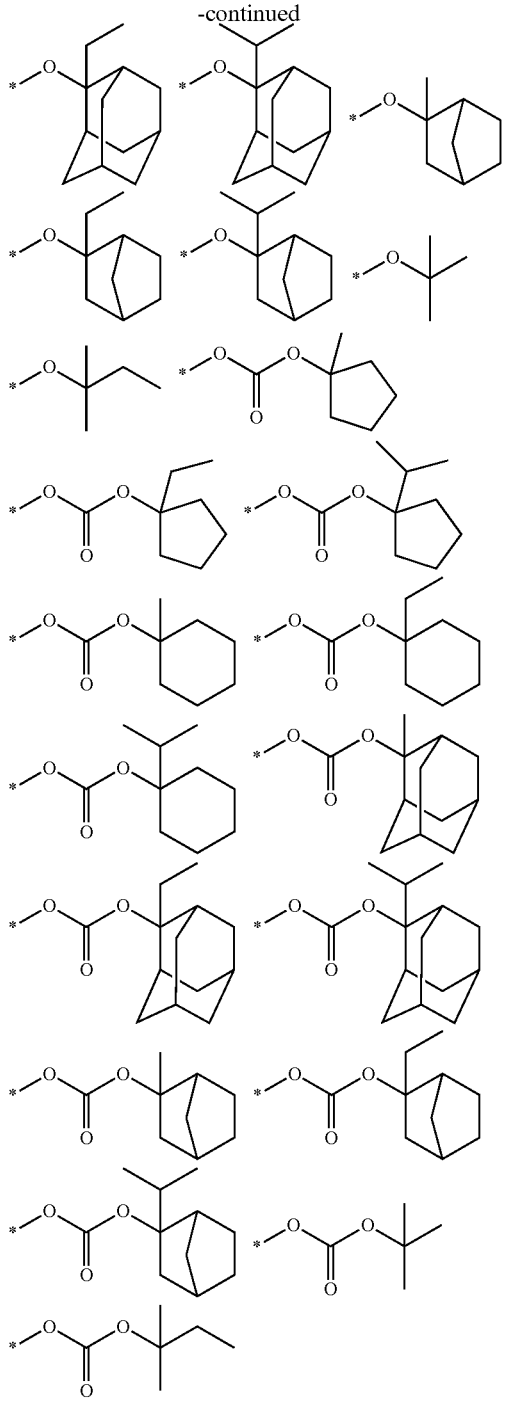
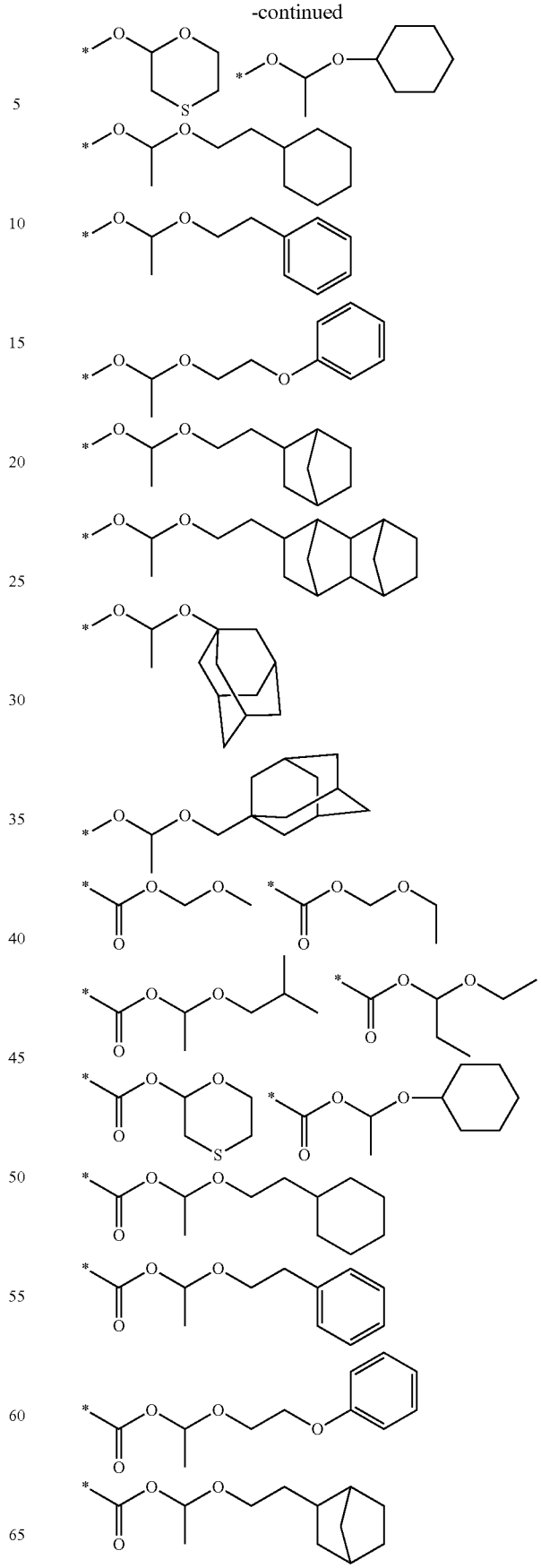
Specific examples of the group (2) include the following groups. * represents a bonding site.
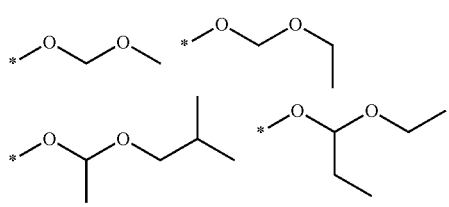

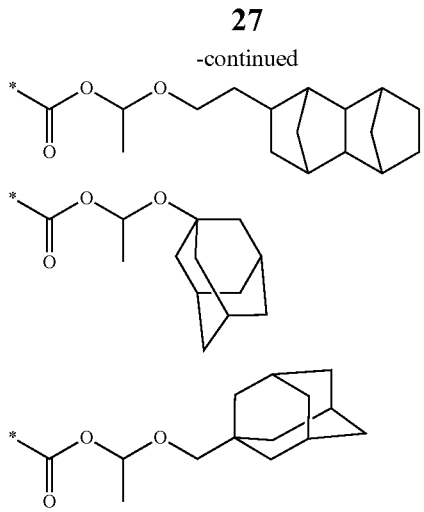

The monomer (a1) is preferably a monomer having an acid-labile group and an ethylenic unsaturated bond, and more preferably a (meth)acrylic monomer having an acid-labile group.

Of the (meth)acrylic monomers having an acid-labile group, those having an alicyclic hydrocarbon group having 5 to 20 carbon atoms are preferably exemplified. When a resin (A) including a structural unit derived from a monomer (a1) having a bulky structure such as an alicyclic hydrocarbon group is used in a resist composition, it is possible to improve the resolution of a resist pattern.

The structural unit derived from a (meth)acrylic monomer having a group (1) is a structural unit represented by formula (a1-0) (hereinafter sometimes referred to as structural unit (a1-0)), a structural unit represented by formula (a1-1) (hereinafter sometimes referred to as structural unit (a1-1)) or a structural unit represented by formula (a1-2) (hereinafter sometimes referred to as structural unit (a1-2)). Preferably, the structural unit is at least one structural unit selected from the group consisting of a structural unit (a1-1) and a structural unit (a1-2). These structural units may be used alone, or two or more structural units may be used in combination:

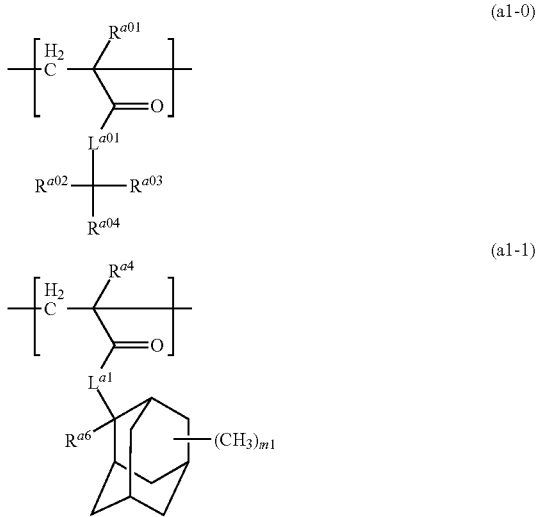

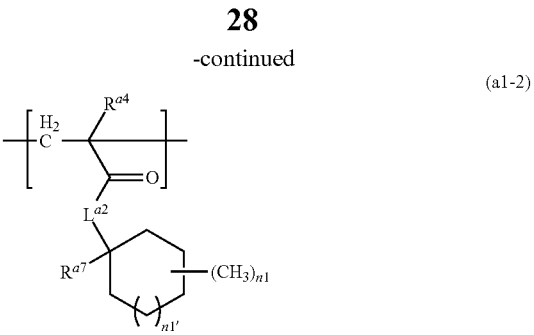

In formula (a1-0), formula (a1-1) and formula (a1-2), $L^{a01}$, $L^{a1}$ and $L^{a2}$ each independently represent —O— or *—O—$(CH_2)_{k1}$—CO—O—, k1 represents an integer of 1 to 7, and * represents a bonding site to —CO—, $R^{a01}$, $R^{a4}$ and $R^{a5}$ each independently represent a hydrogen atom or a methyl group, $R^{a02}$, $R^{a03}$ and $R^{a04}$ each independently represent an alkyl group having 1 to 8 carbon atoms, an alicyclic hydrocarbon group having 3 to 18 carbon atoms, or groups obtained by combining these groups, $R^{a6}$ and $R^{a7}$ each independently represent an alkyl group having 1 to 8 carbon atoms, an alicyclic hydrocarbon group having 3 to 18 carbon atoms, or groups obtained by combining these groups, m1 represents an integer of 0 to 14, n1 represents an integer of 0 to 10, and n1' represents an integer of 0 to 3.

$R^{a01}$, $R^{a4}$ and $R^{s5}$ are preferably a methyl group.

$L^{a01}$, $L^{a1}$ and $L^{a2}$ are preferably an oxygen atom or *—O—$(CH_2)_{k01}$—CO—O— (in which k01 is preferably an integer of 1 to 4, and more preferably 1), and more preferably an oxygen atom.

Examples of the alkyl group, the alicyclic hydrocarbon group, and groups obtained by combining these groups in $R^{a02}$, $R^{a03}$, $R^{a004}$, $R^{a6}$ and $R^{a7}$ include the same groups as mentioned for $R^{a1}$, $R^{a2}$ and $R^{a3}$ of formula (1).

The alkyl group in $R^{a02}$, $R^{a03}$ and $R^{a04}$ is preferably an alkyl group having 1 to 6 carbon atoms, more preferably a methyl group or an ethyl group, and still more preferably a methyl group.

The alkyl group in $R^{a6}$ and $R^{a7}$ is preferably an alkyl group having 1 to 6 carbon atoms, more preferably a methyl group, an ethyl group or an isopropyl group, and still more preferably an ethyl group or an isopropyl group.

The number of carbon atoms of the alicyclic hydrocarbon group in $R^{a02}$, $R^{a03}$, $R^{a04}$, $R^{a6}$ and $R^{a7}$ is preferably 5 to 12, and more preferably 5 to 10.

The total number of carbon atoms of the group obtained by combining the alkyl group with the alicyclic hydrocarbon group is preferably 18 or less.

Preferably, $R^{a02}$ and $R^{a03}$ each independently are an alkyl group having 1 to 6 carbon atoms, and more preferably a methyl group or an ethyl group.

$R^{a04}$ is preferably an alkyl group having 1 to 6 carbon atoms or an alicyclic hydrocarbon group having 5 to 12 carbon atoms, and more preferably a methyl group, an ethyl group, a cyclohexyl group or an adamantyl group.

Preferably, $R^{a6}$ and $R^{a7}$ each independently are an alkyl group having 1 to 6 carbon atoms, more preferably a methyl group, an ethyl group or an isopropyl group, and still more preferably an ethyl group or an isopropyl group.

m1 is preferably an integer of 0 to 3, and more preferably 0 or 1.

n1 is preferably an integer of 0 to 3, and more preferably 0 or 1.

n1' is preferably 0 or 1.

The structural unit (a1-0) includes, for example, a structural unit represented by any one of formula (a1-0-1) to formula (a1-0-12) and a structural unit in which a methyl group corresponding to $R^{a01}$ in the structural unit (a1-0) is substituted with a hydrogen atom and is preferably a structural unit represented by any one of formula (a1-0-1) to formula (a1-0-10)

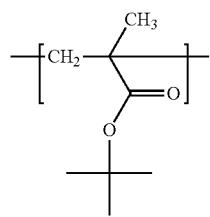
(a1-0-1)

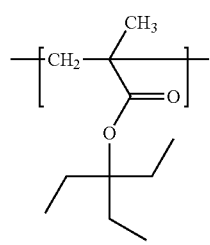
(a1-0-2)

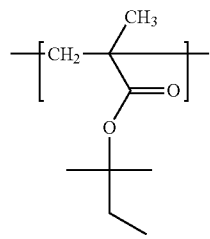
(a1-0-3)

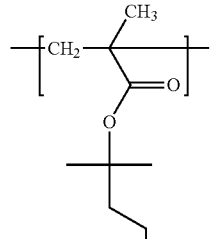
(a1-0-4)

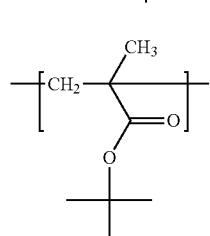
(a1-0-5)

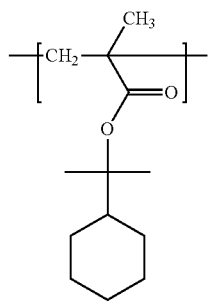
(a1-0-6)

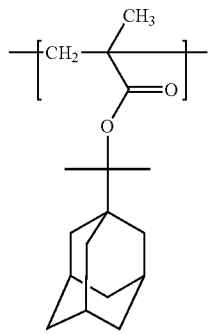
(a1-0-7)

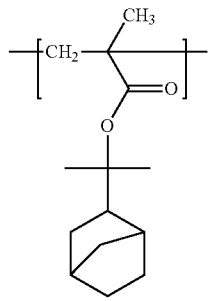
(a1-0-8)

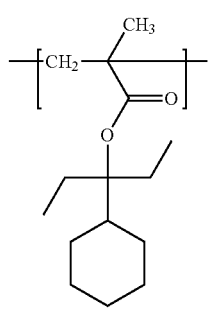
(a1-0-9)

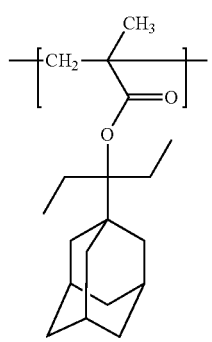
(a1-0-10)

(a1-0-11)

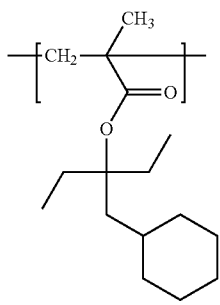

(a1-0-12)

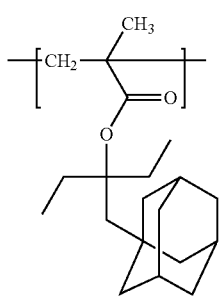

The structural unit (a1-1) includes, for example, structural units derived from the monomers mentioned in JP 2010-204646 A. Of these structural units, a structural unit represented by any one of formula (a1-1-1) to formula (a1-1-4) and a structural unit in which a methyl group corresponding to $R^{a4}$ in the structural unit (a1-1) is substituted with a hydrogen atom are preferable, and a structural unit represented by any one of formula (a1-1-1) to formula (a1-1-4) is more preferable.

(a1-1-1)

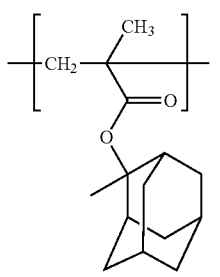

(a1-1-2)

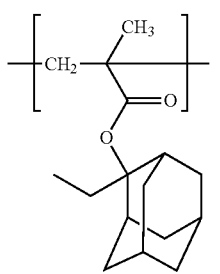

(a1-1-3)

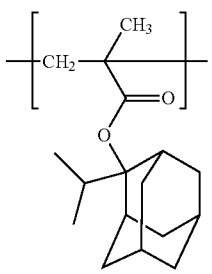

(a1-1-4)

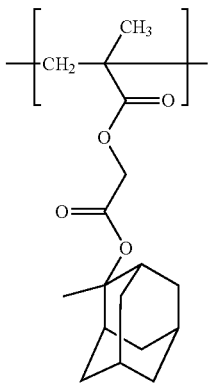

Examples of the structural unit (a1-2) include a structural unit represented by any one of formula (a1-2-1) to formula (a1-2-6) and a structural unit in which a methyl group corresponding to $R^{a5}$ in the structural unit (a1-2) is substituted with a hydrogen atom, and a structural unit represented by any one of formula (a1-2-2), formula (a1-2-5) and formula (a1-2-6) is preferable.

(a1-2-1)

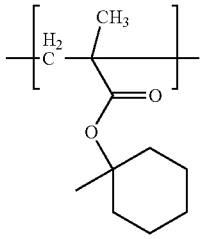

(a1-2-2)

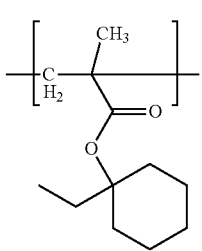

-continued

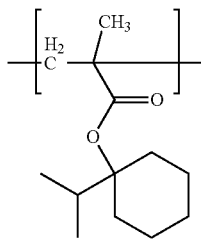
(a1-2-3)

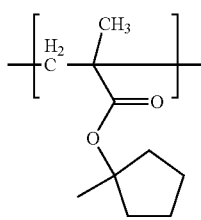
(a1-2-4)

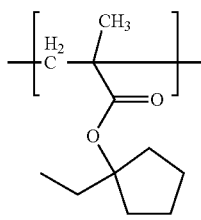
(a1-2-5)

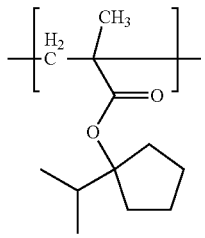
(a1-2-6)

When the resin (A) includes a structural unit (a1-0), the content is usually 5 to 60 mol %, preferably 5 to 50 mol %, and more preferably 10 to 40 mol %, based on all structural units of the resin (A).

When the resin (A) includes a structural unit (a1-1) and/or a structural unit (a1-2), the total content thereof is usually 3 to 80 mol %, preferably 5 to 75 mol %, more preferably 7 to 70 mol %, still more preferably 7 to 65 mol %, and yet more preferably 10 to 60 mol %, based on all structural units of the resin (A).

In the structural unit (a1), examples of the structural unit having a group (2) include a structural unit represented by formula (a1-4) (hereinafter sometimes referred to as "structural unit (a1-4)"):

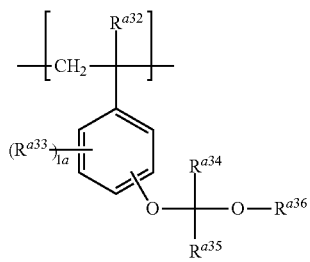
(a1-4)

wherein, in formula (a1-4), $R^{a32}$ represents a hydrogen atom, a halogen atom or an alkyl group having 1 to 6 carbon atoms which may have a halogen atom, $R^{a33}$ represents a halogen atom, a hydroxy group, an alkyl group having 1 to 6 carbon atoms, an alkoxy group having 1 to 6 carbon atoms, an alkylcarbonyl group having 2 to 4 carbon atoms, an alkylcarbonyloxy group having 2 to 4 carbon atoms, an acryloyloxy group or a methacryloyloxy group.

1a represents an integer of 0 to 4, and when 1a is 2 or more, a plurality of $R^{a33}$ may be the same or different from each other, and $R^{a34}$ and $R^{a35}$ each independently represent a hydrogen atom or a hydrocarbon group having 1 to 12 carbon atoms, $R^{a36}$ represents a hydrocarbon group having 1 to 20 carbon atoms, or $R^{a35}$ and $R^{a36}$ are bonded each other to form a divalent hydrocarbon group having 2 to 20 carbon atoms together with —C—O— to which $R^{a35}$ and $R^{a36}$ are bonded, and —CH$_2$— included in the hydrocarbon group and the divalent hydrocarbon group may be replaced by —O— or —S—.

Examples of the alkyl group in $R^{a32}$ and $R^{a33}$ include a methyl group, an ethyl group, a propyl group, an isopropyl group, a butyl group, a pentyl group and a hexyl group. The alkyl group is preferably an alkyl group having 1 to 4 carbon atoms, more preferably a methyl group or an ethyl group, and still more preferably a methyl group.

Examples of the halogen atom in $R^{a32}$ and $R^{a33}$ include a fluorine atom, a chlorine atom and a bromine atom.

Examples of the alkyl group having 1 to 6 carbon atoms which may have a halogen atom include a trifluoromethyl group, a difluoromethyl group, a methyl group, a perfluoroethyl group, a 2,2,2-trifluoroethyl group, a 1,1,2,2-tetrafluoroethyl group, an ethyl group, a perfluoropropyl group, a 2,2,3,3,3-pentafluoropropyl group, a propyl group, a perfluorobutyl group, a 1,1,2,2,3,3,4,4-octafluorobutyl group, a butyl group, a perfluoropentyl group, a 2,2,3,3,4,4,5,5,5-nonafluoropentyl group, a pentyl group, a hexyl group, a perfluorohexyl group and the like.

Examples of the alkoxy group include a methoxy group, an ethoxy group, a propoxy group, a butoxy group, a pentyloxy group and a hexyloxy group. Of these groups, an alkoxy group having 1 to 4 carbon atoms is preferable, a methoxy group or an ethoxy group is more preferable, and a methoxy group is still more preferable.

Examples of the alkylcarbonyl group include an acetyl group, a propionyl group and a butyryl group.

Examples of the alkylcarbonyloxy group include an acetyloxy group, a propionyloxy group, a butyryloxy group and the like.

Examples of the hydrocarbon group in $R^{a34}$, $R^{a35}$ and $R^{a36}$ include an alkyl group, an alicyclic hydrocarbon group, an aromatic hydrocarbon group, and groups obtained by combining these groups.

Examples of the alkyl group include a methyl group, an ethyl group, a propyl group, a butyl group, a pentyl group, a hexyl group, a heptyl group, an octyl group and the like.

The alicyclic hydrocarbon group may be either monocyclic or polycyclic. Examples of the monocyclic alicyclic hydrocarbon group include cycloalkyl groups such as a cyclopentyl group, a cyclohexyl group, a cycloheptyl group and a cyclooctyl group. Examples of the polycyclic alicyclic hydrocarbon group include a decahydronaphthyl group, an adamantyl group, a norbornyl group, and the following groups (* represents a bonding site).

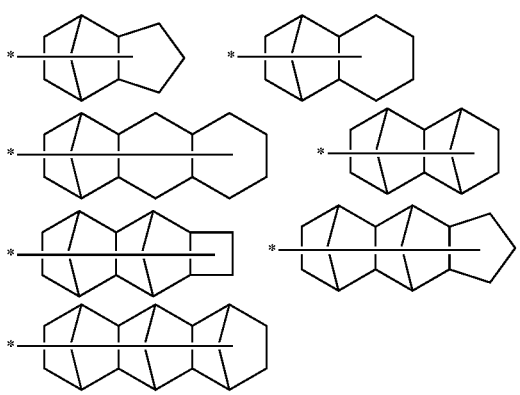

Examples of the aromatic hydrocarbon group include aryl groups such as a phenyl group, a naphthyl group, an anthryl group, a biphenyl group and a phenanthryl group.

Examples of the combined group include a group obtained by combining the above-mentioned alkyl group and alicyclic hydrocarbon group (e.g. a cycloalkylalkyl group), an aralkyl group such as a benzyl group, an aromatic hydrocarbon group having an alkyl group (a p-methylphenyl group, a p-tert-butylphenyl group, a tolyl group, a xylyl group, a cumenyl group, a mesityl group, a 2,6-diethylphenyl group, a 2-methyl-6-ethylphenyl group, etc.), an aromatic hydrocarbon group having an alicyclic hydrocarbon group (a p-cyclohexylphenyl group, a p-adamantylphenyl group, etc.), an aryl-cycloalkyl group such as a phenylcyclohexyl group and the like. Particularly, examples of $R^{a36}$ include an alkyl group having 1 to 18 carbon atoms, an alicyclic hydrocarbon group having 3 to 18 carbon atoms, an aromatic hydrocarbon group having 6 to 18 carbon atoms, or groups obtained by combining these groups.

In formula (a1-4), $R^{a32}$ is preferably a hydrogen atom, $R^{a33}$ is preferably an alkoxy group having 1 to 4 carbon atoms, more preferably a methoxy group and an ethoxy group, and still more preferably a methoxy group, 1a is preferably 0 or 1, and more preferably 0, $R^{a34}$ is preferably a hydrogen atom, and $R^{a35}$ is preferably an alkyl group having 1 to 12 carbon atoms or an alicyclic hydrocarbon group, and more preferably a methyl group or an ethyl group.

The hydrocarbon group for $R^{a36}$ is preferably an alkyl group having 1 to 18 carbon atoms, an alicyclic hydrocarbon group having 3 to 18 carbon atoms, an aromatic hydrocarbon group having 6 to 18 carbon atoms or groups formed by combining these groups, and more preferably an alkyl group having 1 to 18 carbon atoms, an alicyclic aliphatic hydrocarbon group having 3 to 18 carbon atoms or an aralkyl group having 7 to 18 carbon atoms. The alkyl group and the alicyclic hydrocarbon group in $R^{a36}$ are preferably unsubstituted. The aromatic hydrocarbon group in $R^{a36}$ is preferably an aromatic ring having an aryloxy group having 6 to 10 carbon atoms.

—OC($R^{a34}$)($R^{a35}$)—O—$R^{a36}$ in the structural unit (a1-4) is eliminated by contacting with an acid (e.g., p-toluenesulfonic acid) to form a hydroxy group.

The structural unit (a1-4) includes, for example, structural units derived from the monomers mentioned in JP 2010-204646 A. The structural unit preferably includes structural units represented by formula (a1-4-1) to formula (a1-4-12) and a structural unit in which a hydrogen atom corresponding to $R^{a32}$ in the structural unit (a1-4) is substituted with a methyl group, and more preferably structural units represented by formula (a1-4-1) to formula (a1-4-5) and formula (a1-4-10).

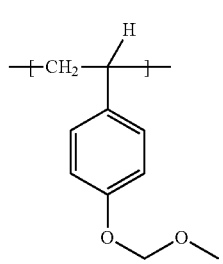

(a1-4-1)

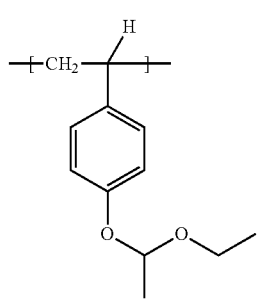

(a1-4-2)

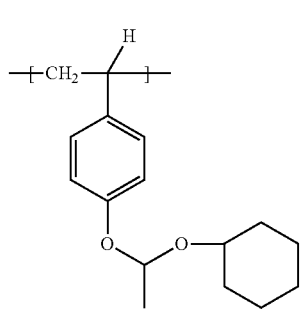

(a1-4-3)

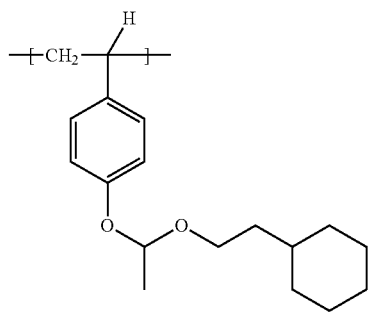

(a1-4-4)

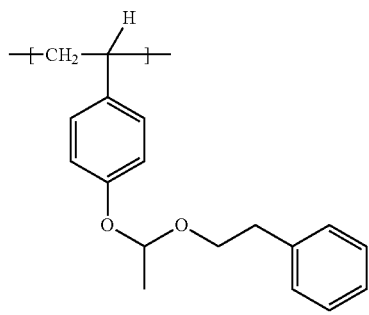

(a1-4-5)

(a1-4-6) 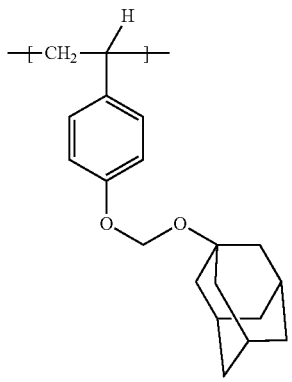

(a1-4-7) 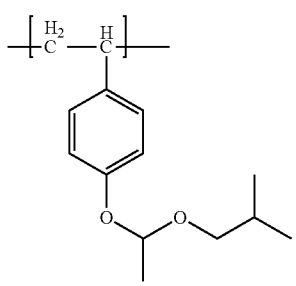

(a1-4-8) 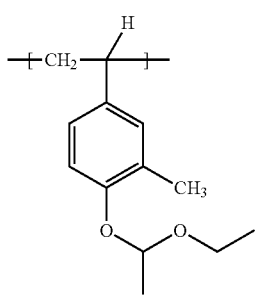

(a1-4-9), (a1-4-10), (a1-4-11), (a1-4-12) 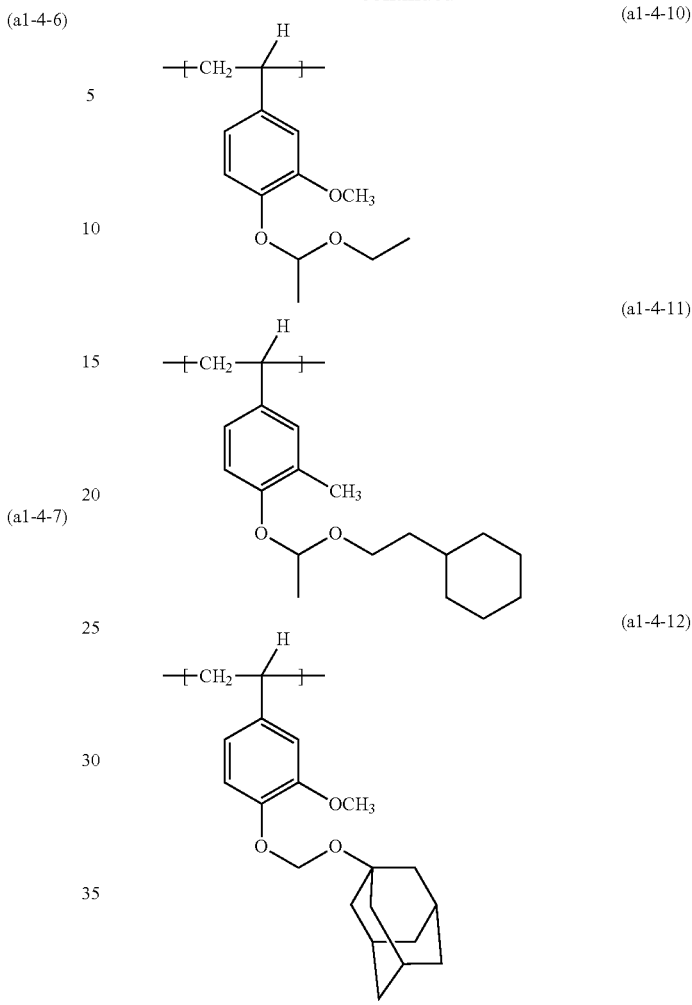

When the resin (A) includes the structural unit (a1-4), the content is preferably 3 to 80 mol %, more preferably 5 to 75 mol %, still more preferably 7 to 70 mol %, yet more preferably 7 to 65 mol %, and particularly preferably 10 to 60 mol %, based on the total of all structural units of the resin (A).

The structural unit derived from a (meth)acrylic monomer having a group (2) also includes a structural unit represented by formula (a1-5) (hereinafter sometimes referred to as "structural unit (a1-5)").

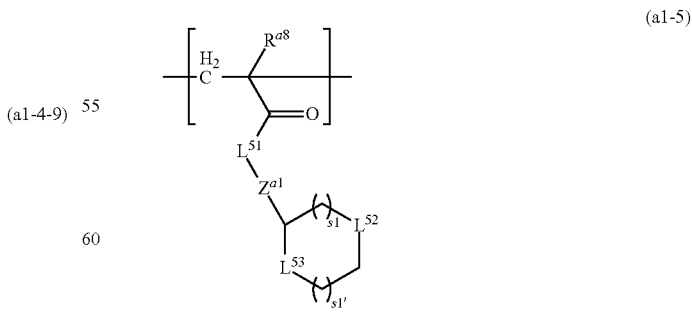

(a1-5)

In formula (a1-5), $R^{a8}$ represents an alkyl group having 1 to 6 carbon atoms which may have a halogen atom, a hydrogen atom or a halogen atom, $Z^{a1}$ represents a single bond or *—$(CH_2)_{h3}$—CO-$L^{54}$-, h3 represents an integer of 1 to 4, and * represents a bonding site to $L^{51}$, $L^{51}$, $L^{52}$, $L^{53}$ and $L^{54}$ each independently represent —O— or —S—, s1 represents an integer of 1 to 3, and s1' represents an integer of 0 to 3.

The halogen atom includes a fluorine atom and a chlorine atom and is preferably a fluorine atom. Examples of the alkyl group having 1 to 6 carbon atoms which may have a halogen atom include a methyl group, an ethyl group, a propyl group, a butyl group, a pentyl group, a hexyl group, a heptyl group, an octyl group, a fluoromethyl group and a trifluoromethyl group.

In formula (a1-5), $R^{a8}$ is preferably a hydrogen atom, a methyl group or a trifluoromethyl group, $L^{51}$ is preferably an oxygen atom, one of $L^{52}$ and $L^{53}$ is preferably —O— and the other one is preferably —S—, s1 is preferably 1, s1' is preferably an integer of 0 to 2, and $Z^{a1}$ is preferably a single bond or *—$CH_2$—CO—O—.

The structural unit (a1-5) includes, for example, structural units derived from the monomers mentioned in JP 2010-61117 A. Of these structural units, structural units represented by formula (a1-5-1) to formula (a1-5-4) are preferable, and structural units represented by formula (a1-5-1) or formula (a1-5-2) are more preferable.

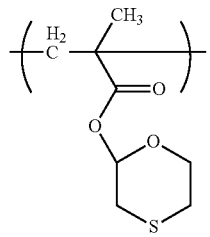

(a1-5-1)

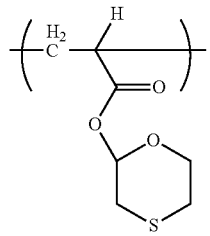

(a1-5-2)

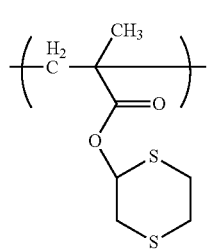

(a1-5-3)

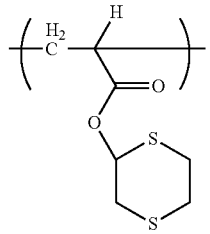

(a1-5-4)

When the resin (A) includes the structural unit (a1-5), the content is preferably 1 to 50 mol %, more preferably 3 to 45 mol %, still more preferably 5 to 40 mol %, and yet more preferably 5 to 30 mol %, based on all structural units of the resin (A).

The structural unit (a1) also includes, for example, a structural unit represented by formula (a1-0X) (hereinafter sometimes referred to as structural unit (a1-0X)):

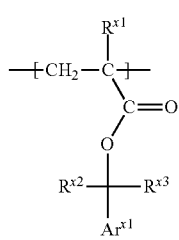

(a1-0X)

wherein, in formula (a1-0X), $R^{x1}$ represents a hydrogen atom or a methyl group, $R^{x2}$ and $R^{x3}$ each independently represent a saturated hydrocarbon group having 1 to 6 carbon atoms, and $Ar^{x1}$ represents an aromatic hydrocarbon group having 6 to 36 carbon atoms.

Examples of the saturated hydrocarbon group for $R^{x2}$ and $R^{x3}$ include an alkyl group, an alicyclic hydrocarbon group, and groups formed by combining these groups.

Examples of the alkyl group include a methyl group, an ethyl group, an n-propyl group, an isopropyl group, an n-butyl group, a sec-butyl group, a tert-butyl group, a pentyl group, a hexyl group and the like.

The alicyclic hydrocarbon group may be either monocyclic or polycyclic, and examples of the monocyclic alicyclic hydrocarbon group include a cyclopropyl group, a cyclobutyl group, a cyclopentyl group, a cyclohexyl group and the like.

Examples of the aromatic hydrocarbon group for $Ar^{x1}$ include aryl groups having 6 to 36 carbon atoms, such as a phenyl group, a naphthyl group and an anthryl group.

The aromatic hydrocarbon group preferably has 6 to 24 carbon atoms and more preferably has 6 to 18 carbon atoms, and is still more preferably a phenyl group.

$Ar^{x1}$ is preferably an aromatic hydrocarbon group having 6 to 18 carbon atoms, more preferably a phenyl group or a naphthyl group, and still more preferably a phenyl group.

Preferably, $R^{x1}$, $R^{x2}$ and $R^{x3}$ each independently represent a methyl group or an ethyl group, and more preferably a methyl group.

Examples of the structural unit (a1-0X) include structural units mentioned below, and structural units in which a methyl group corresponding to $R^{x1}$ in the structural unit (a1-0X) is substituted with a hydrogen atom. The structural unit (a1-0X) is preferably a structural unit (a1-0X-1) to a structural unit (a1-0X-3).

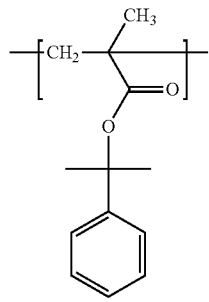

(a1-0X-1)

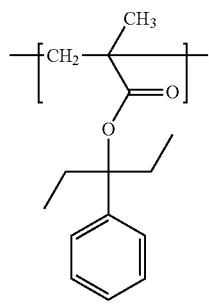

(a1-0X-2)

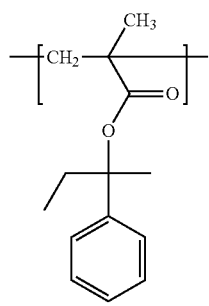

(a1-0X-3)

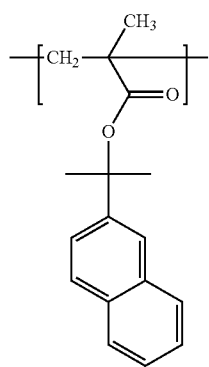

(a1-0X-4)

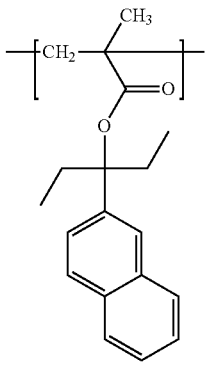

(a1-0X-5)

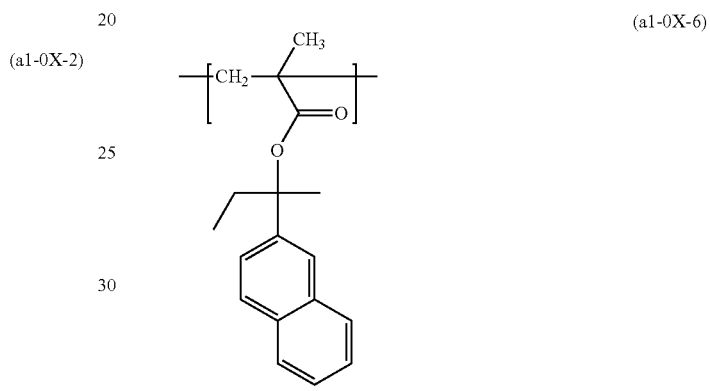

(a1-0X-6)

When the resin (A) includes a structural unit (a1-0X), the content is preferably 5 to 60 mol %, more preferably 5 to 50 mol %, and still more preferably 10 to 40 mol %, based on all monomers in the resin (A).

The resin (A) may include two or more structural units (a1-0X).

The structural unit (a1) also includes the following structural units.

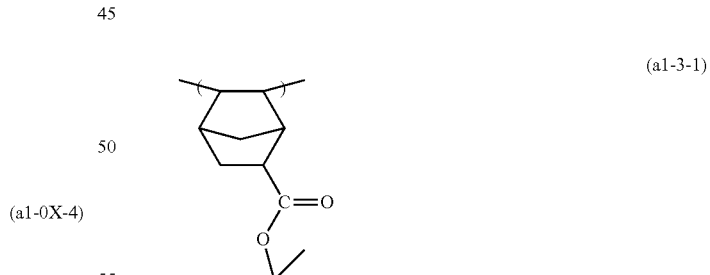

(a1-3-1)

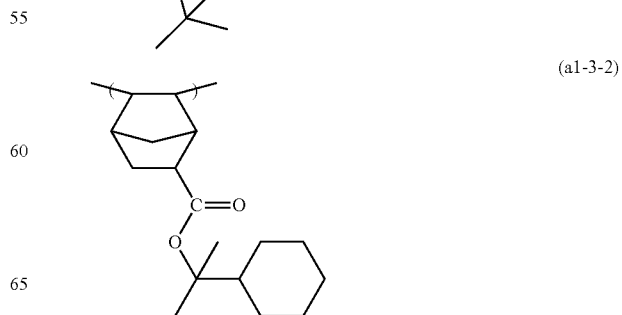

(a1-3-2)

(a1-3-3)
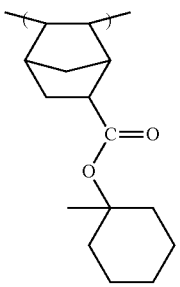

(a1-3-4)
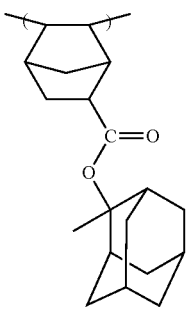

(a1-3-5)
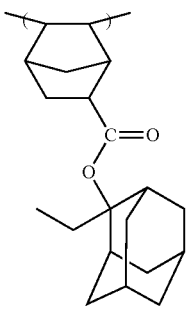

(a1-3-6)
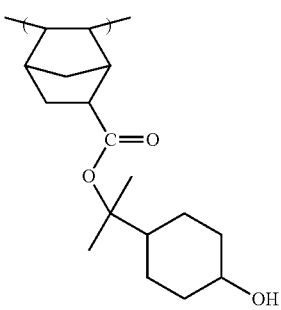

(a1-3-7)
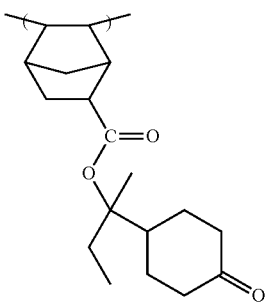

When the resin (A) includes the above structural units, the content is preferably 5 to 60 mol %, more preferably 5 to 50 mol %, and still more preferably 10 to 40 mol %, based on all structural units of the resin (A).

<Structural Unit (s)>

The structural unit (s) is derived from a monomer having no acid-labile group (hereinafter sometimes referred to as "monomer (s)"). The monomer, from which the structural unit (s) is derived, has no acid-labile group known in the resist field.

The structural unit (s) preferably has a hydroxy group or a lactone ring. When a resin including a structural unit having a hydroxy group and having no acid-labile group (hereinafter sometimes referred to as "structural unit (a2)") and/or a structural unit having a lactone ring and having no acid-labile group (hereinafter sometimes referred to as "structural unit (a3)") is used in the resist composition of the present invention, it is possible to improve the resolution of a resist pattern and the adhesion to a substrate.

<Structural Unit (a2)>

The hydroxy group possessed by the structural unit (a2) may be either an alcoholic hydroxy group or a phenolic hydroxy group.

When a resist pattern is produced from the resist composition of the present invention, in the case of using, as an exposure source, high energy rays such as KrF excimer laser (248 nm), electron beam or extreme ultraviolet light (EUV), a structural unit (a2) having a phenolic hydroxy group is preferably used as the structural unit (a2), and it is more preferably to use a structural unit (a2-A) mentioned below. When using ArF excimer laser (193 nm) or the like, a structural unit (a2) having an alcoholic hydroxy group is preferably used as the structural unit (a2), and it is more preferably to use a structural unit (a2-1) mentioned later. The structural unit (a2) may be included alone, or two or more structural units may be included.

In the structural unit (a2), examples of the structural unit having a phenolic hydroxy group include a structural unit represented by formula (a2-A) (hereinafter sometimes referred to as "structural unit (a2-A)"):

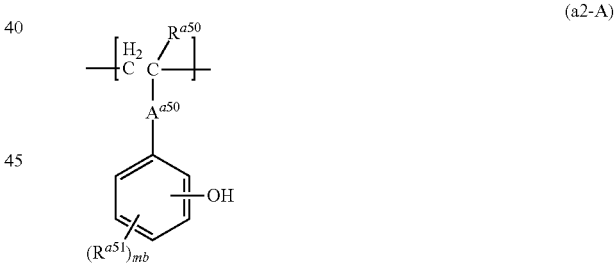

(a2-A)

wherein, in formula (a2-A), $R^{a50}$ represents a hydrogen atom, a halogen atom or an alkyl group having 1 to 6 carbon atoms which may have a halogen atom, $R^{a51}$ represents a halogen atom, a hydroxy group, an alkyl group having 1 to 6 carbon atoms, an alkoxy group having 1 to 6 carbon atoms, an alkylcarbonyl group having 2 to 4 carbon atoms, an alkylcarbonyloxy group having 2 to 4 carbon atoms, an acryloyloxy group or a methacryloyloxy group, $A^{a50}$ represents a single bond or *—$X^{a51}$-($A^{a52}$-$X^{a52}$)$_{nb}$—, and * represents a bonding site to carbon atoms to which —$R^{a50}$ is bonded, $A^{a52}$ represents an alkanediyl group having 1 to 6 carbon atoms, $X^{a51}$ and $X^{a52}$ each independently represent —O—, —CO—O— or —O—CO—, nb represents 0 or 1, and mb represents an integer of 0 to 4, and when mb is an integer of 2 or more, a plurality of $R^{a51}$ may be the same or different from each other.

Examples of the halogen atom in $R^{a50}$ include a fluorine atom, a chlorine atom and a bromine atom.

Examples of the alkyl group having 1 to 6 carbon atoms which may have a halogen atom in $R^{a50}$ include a trifluoromethyl group, a difluoromethyl group, a methyl group, a perfluoroethyl group, a 2,2,2-trifluoroethyl group, a 1,1,2,2-tetrafluoroethyl group, an ethyl group, a perfluoropropyl group, a 2,2,3,3,3-pentafluoropropyl group, a propyl group, a perfluorobutyl group, a 1,1,2,2,3,3,4,4-octafluorobutyl group, a butyl group, a perfluoropentyl group, a 2,2,3,3,4,4,5,5,5-nonafluoropentyl group, a pentyl group, a hexyl group and a perfluorohexyl group.

$R^{a50}$ is preferably a hydrogen atom or an alkyl group having 1 to 4 carbon atoms, more preferably a hydrogen atom, a methyl group or an ethyl group, and still more preferably a hydrogen atom or a methyl group.

Examples of the alkyl group in $R^{a51}$ include a methyl group, an ethyl group, a propyl group, an isopropyl group, a butyl group, a sec-butyl group, a tert-butyl group, a pentyl group and a hexyl group.

Examples of the alkoxy group in $R^{a51}$ include a methoxy group, an ethoxy group, a propoxy group, an isopropoxy group, a butoxy group, a sec-butoxy group and a tert-butoxy group. An alkoxy group having 1 to 4 carbon atoms is preferable, a methoxy group or an ethoxy group is more preferable, and a methoxy group is still more preferable.

Examples of the alkylcarbonyl group in $R^{a51}$ include an acetyl group, a propionyl group and a butyryl group.

Examples of the alkylcarbonyloxy group in $R^{a51}$ include an acetyloxy group, a propionyloxy group and a butyryloxy group.

$R^{a51}$ is preferably a methyl group.

Examples of *—$X^{a51}$-($A^{a52}$-$X^{a52}$)$_{nb}$— include *—O—, *—CO—O—, *—O—CO—, *—CO—O-$A^{a52}$-CO—O—, *—O—CO-$A^{a52}$-O—, *—O-$A^{a52}$-CO—O—, *—CO-O-$A^{a52}$-O—CO— and *—O—CO-$A^{a52}$-O—CO—. Of these, *—CO—O—, *—CO—O-$A^{a52}$-CO—O— or *—O-$A^{a52}$-CO—O— is preferable.

Examples of the alkanediyl group include a methylene group, an ethylene group, a propane-1,3-diyl group, a propane-1,2-diyl group, a butane-1,4-diyl group, a pentane-1,5-diyl group, a hexane-1,6-diyl group, a butane-1,3-diyl group, a 2-methylpropane-1,3-diyl group, a 2-methylpropane-1,2-diyl group, a pentane-1,4-diyl group and a 2-methylbutane-1,4-diyl group.

$A^{a52}$ is preferably a methylene group or an ethylene group.

$A^{a50}$ is preferably a single bond, *—CO—O— or *—CO—O-$A^{52}$-CO—O—, more preferably a single bond, *—CO—O— or *—CO—O—CH$_2$—CO—O—, and still more preferably a single bond or *—CO—O—.

mb is preferably 0, 1 or 2, more preferably 0 or 1, and particularly preferably 0.

The hydroxy group is preferably bonded to the ortho-position or the para-position of a benzene ring, and more preferably the para-position.

Examples of the structural unit (a2-A) include structural units derived from the monomers mentioned in JP 2010-204634 A and JP 2012-12577 A.

Examples of the structural unit (a2-A) include structural units represented by formula (a2-2-1) to formula (a2-2-6), and a structural unit in which a methyl group corresponding to $R^{s50}$ in the structural unit (a2-A) is substituted with a hydrogen atom in structural units represented by formula (a2-2-1) to formula (a2-2-6). The structural unit (a2-A) is preferably a structural unit represented by formula (a2-2-1), a structural unit represented by formula (a2-2-3), a structural unit represented by formula (a2-2-6), and a structural unit in which a methyl group corresponding to $R^{50}$ in the structural unit (a2-A) is substituted with a hydrogen atom in the structural unit represented by formula (a2-2-1), formula (a2-2-3) or formula (a2-2-6).

(a2-2-1)

(a2-2-2)

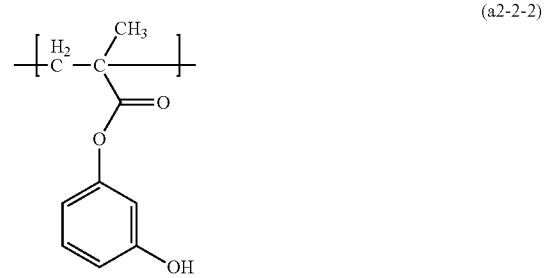

(a2-2-3)

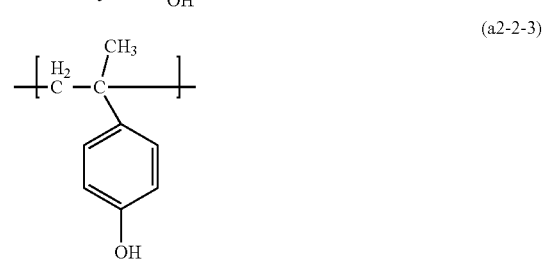

(a2-2-4)

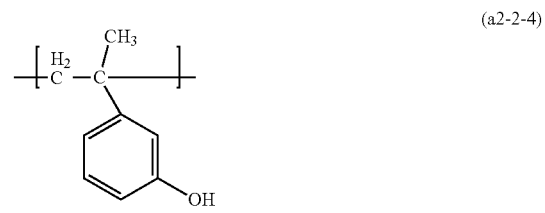

(a2-2-5)

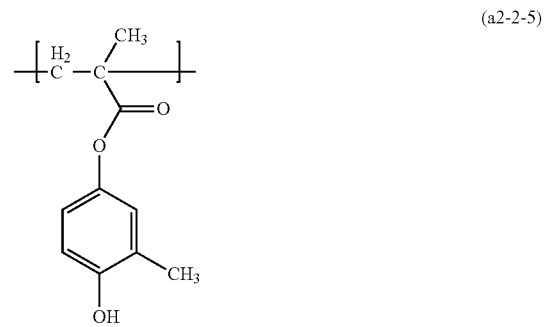

(a2-2-6)

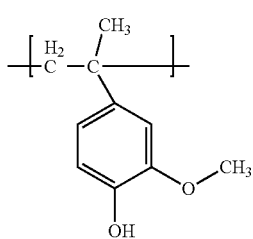

When the structural unit (a2-A) is included in the resin (A), the content of the structural unit (a2-A) is preferably 5 to 80 mol %, more preferably 10 to 70 mol %, still more preferably 10 to 60 mol %, and yet more preferably 10 to 50 mol %, based on all structural units.

The structural unit (a2-A) can be included in a resin (A) by polymerizing, for example, with a structural unit (a1-4) and treating with an acid such as p-toluenesulfonic acid. The structural unit (a2-A) can also be included in the resin (A) by polymerizing with acetoxystyrene and treating with an alkali such as tetramethylammonium hydroxide.

Examples of the structural unit having an alcoholic hydroxy group in the structural unit (a2) include a structural unit represented by formula (a2-1) (hereinafter sometimes referred to as "structural unit (a2-1)").

(a2-1)

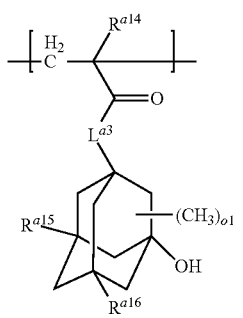

In formula (a2-1), $L^{a3}$ represents —O— or *—O—$(CH_2)_{k2}$—CO—O—, k2 represents an integer of 1 to 7, and * represents a bonding site to —CO—, $R^{a14}$ represents a hydrogen atom or a methyl group, $R^{a15}$ and $R^{a16}$ each independently represent a hydrogen atom, a methyl group or a hydroxy group, and o1 represents an integer of 0 to 10.

In formula (a2-1), $L^{a3}$ is preferably —O— or —O—$(CH_2)_{f1}$—CO—O— (f1 represents an integer of 1 to 4), and more preferably —O—, $R^{a14}$ is preferably a methyl group, $R^{a15}$ is preferably a hydrogen atom, $R^{a16}$ is preferably a hydrogen atom or a hydroxy group, and o1 is preferably an integer of 0 to 3, and more preferably 0 or 1.

The structural unit (a2-1) includes, for example, structural units derived from the monomers mentioned in JP 2010-204646 A. A structural unit represented by any one of formula (a2-1-1) to formula (a2-1-6) is preferable, a structural unit represented by any one of formula (a2-1-1) to formula (a2-1-4) is more preferable, and a structural unit represented by formula (a2-1-1) or formula (a2-1-3) is still more preferable.

(a2-1-1)

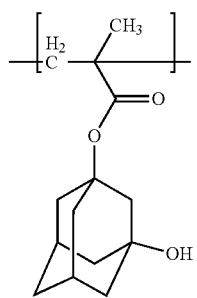

(a2-1-2)

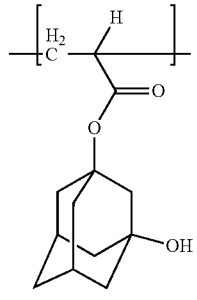

(a2-1-3)

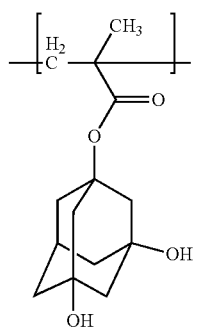

(a2-1-4)

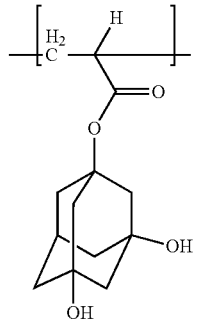

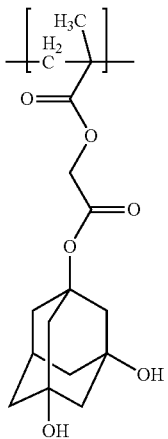

(a2-1-5)

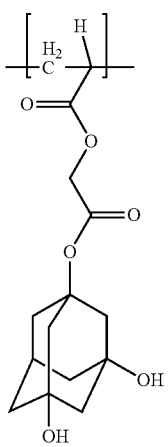

(a2-1-6)

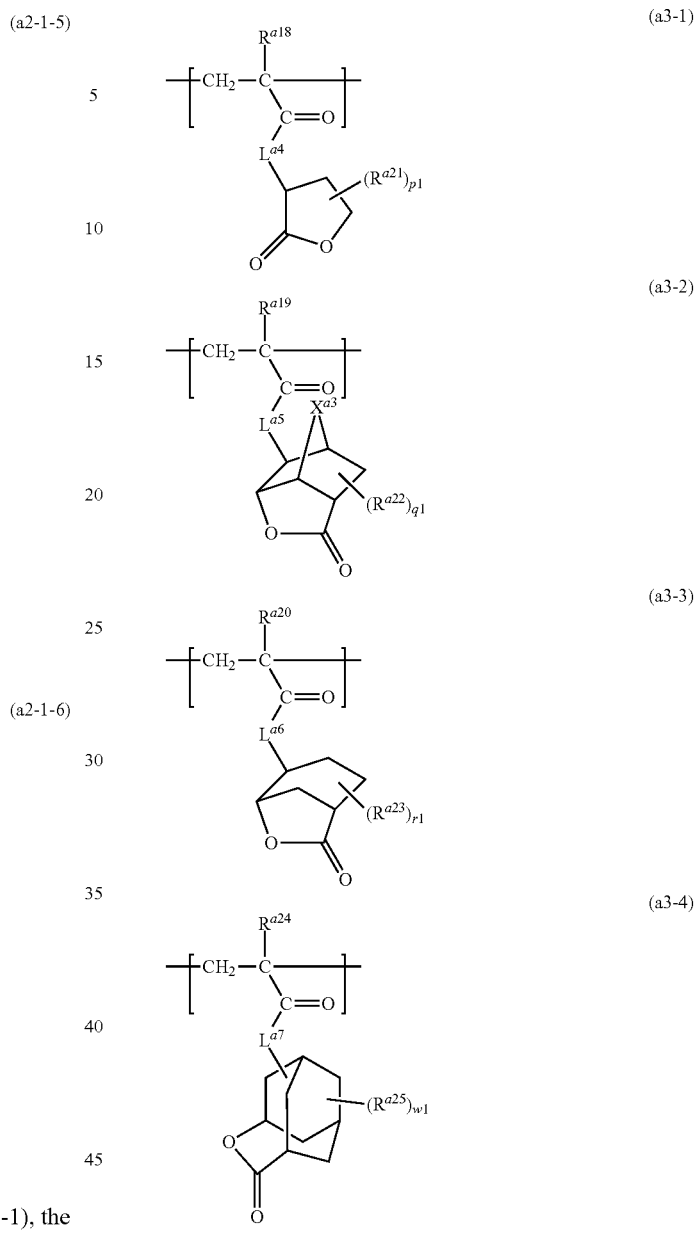

When the resin (A) includes the structural unit (a2-1), the content is usually 1 to 45 mol %, preferably 1 to 40 mol %, more preferably 1 to 35 mol %, still more preferably 1 to 20 mol %, and yet more preferably 1 to 10 mol %, based on all structural units of the resin (A).

<Structural Unit (a3)>

The lactone ring possessed by the structural unit (a3) may be a monocyclic ring such as a β-propiolactone ring, a γ-butyrolactone ring or a δ-valerolactone ring, or a condensed ring of a monocyclic lactone ring and the other ring. Preferably, a γ-butyrolactone ring, an adamantanelactone ring or a bridged ring including a γ-butyrolactone ring structure (e.g., a structural unit represented by the following formula (a3-2)) is exemplified.

The structural unit (a3) is preferably a structural unit represented by formula (a3-1), formula (a3-2), formula (a3-3) or formula (a3-4). These structural units may be included alone, or two or more structural units may be included:

wherein, in formula (a3-1), formula (a3-2), formula (a3-3) and formula (a3-4), $L^{a4}$, $L^{a5}$ and $L^{a6}$ each independently represent —O— or a group represented by *—O—(CH$_2$)$_{k3}$—CO—O— (k3 represents an integer of 1 to 7), $L^{a7}$ represents —O—, *—O-$L^{a8}$-O—, *—O-$L^{a8}$-CO—O—, *—O-$L^{as}$-CO—O-$L^{a9}$-CO—O— or *—O-$L^{a8}$-O—CO-$L^{a9}$-O—, $L^{a8}$ and $L^{a9}$ each independently represent an alkanediyl group having 1 to 6 carbon atoms,

* represents a bonding site to a carbonyl group, $R^{a18}$, $R^{a19}$ and $R^{a20}$ each independently represent a hydrogen atom or a methyl group, $R^{a24}$ represents an alkyl group having 1 to 6 carbon atoms which may have a halogen atom, a hydrogen atom or a halogen atom, $X^{a3}$ represents —CH$_2$— or an oxygen atom, $R^{a21}$ represents an aliphatic hydrocarbon group having 1 to 4 carbon atoms, $R^{a22}$, $R^{a23}$ and $R^{a25}$ each independently represent a carboxy group, a cyano group or an aliphatic hydrocarbon group having 1 to 4 carbon atoms, p1 represents an integer of 0 to 5, q1 represents an integer of 0 to 3, r1 represents an integer of 0 to 3, w1 represents an integer of 0 to 8, and when p1, q1, r1 and/or w1 is/are 2 or more, a plurality of $R^{a21}$, $R^{a22}$, $R^{a23}$ and/or $R^{a25}$ may be the same or different from each other.

Examples of the aliphatic hydrocarbon group in $R^{a21}$, $R^{a22}$, $R^{a23}$ and $R^{a25}$ include alkyl groups such as a methyl group, an ethyl group, a propyl group, an isopropyl group, a butyl group, a sec-butyl group and a tert-butyl group.

Examples of the halogen atom in $R^{a24}$ include a fluorine atom, a chlorine atom, a bromine atom and an iodine atom.

Examples of the alkyl group in $R^{a24}$ include a methyl group, an ethyl group, a propyl group, an isopropyl group, a butyl group, a sec-butyl group, a tert-butyl group, a pentyl group and a hexyl group, and the alkyl group is preferably an alkyl group having 1 to 4 carbon atoms, and more preferably a methyl group or an ethyl group.

Examples of the alkyl group having a halogen atom in $R^{a24}$ include a trifluoromethyl group, a perfluoroethyl group, a perfluoropropyl group, a perfluoroisopropyl group, a perfluorobutyl group, a perfluorosec-butyl group, a perfluoro-tert-butyl group, a perfluoropentyl group, a perfluorohexyl group, a trichloromethyl group, a tribromomethyl group, a triiodomethyl group and the like.

Examples of the alkanediyl group in $L^{a8}$ and $L^{a9}$ include a methylene group, an ethylene group, a propane-1,3-diyl group, a propane-1,2-diyl group, a butane-1,4-diyl group, a pentane-1,5-diyl group, a hexane-1,6-diyl group, a butane-1,3-diyl group, a 2-methylpropane-1,3-diyl group, a 2-methylpropane-1,2-diyl group, a pentane-1,4-diyl group and a 2-methylbutane-1,4-diyl group.

In formula (a3-1) to formula (a3-3), preferably, $L^{a4}$ to $L^{a6}$ are each independently —O— or a group in which k3 is an integer of 1 to 4 in *—O—(CH$_2$)$_{k3}$—CO—O—, more preferably —O— and *—O—CH$_2$—CO—O—, and still more preferably an oxygen atom, $R^{a18}$ to $R^{a21}$ are preferably a methyl group, preferably, $R^{a22}$ and $R^{a23}$ are each independently a carboxy group, a cyano group or a methyl group, and preferably, p1, q1 and r1 are each independently an integer of 0 to 2, and more preferably 0 or 1.

In formula (a3-4), $R^{a24}$ is preferably a hydrogen atom or an alkyl group having 1 to 4 carbon atoms, more preferably a hydrogen atom, a methyl group or an ethyl group, and still more preferably a hydrogen atom or a methyl group, $R^{a25}$ is preferably a carboxy group, a cyano group or a methyl group, $L^{a7}$ is preferably —O— or *—O-$L^{a8}$-CO—O—, and more preferably —O—, —O—CH$_2$—CO—O— or —O—C$_2$H$_4$—CO—O—, and w1 is preferably an integer of 0 to 2, and more preferably 0 or 1.

Particularly, formula (a3-4) is preferably formula (a3-4)':

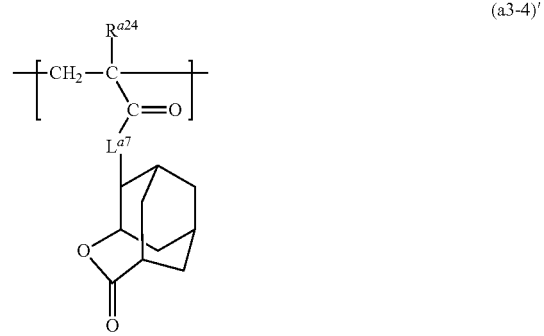

(a3-4)' wherein $R^{a24}$ and $L^{a7}$ are the same as defined above.

Examples of the structural unit (a3) include structural units derived from the monomers mentioned in JP 2010-204646 A, the monomers mentioned in JP 2000-122294 A and the monomers mentioned in JP 2012-41274 A. The structural unit (a3) is preferably a structural unit represented by any one of formula (a3-1-1), formula (a3-1-2), formula (a3-2-1), formula (a3-2-2), formula (a3-3-1), formula (a3-3-2) and formula (a3-4-1) to formula (a3-4-12), and structural units in which methyl groups corresponding to $R^{a18}$, $R^{a19}$, $R^{a20}$ and $R^{a24}$ in formula (a3-1) to formula (a3-4) are substituted with hydrogen atoms in the above structural units.

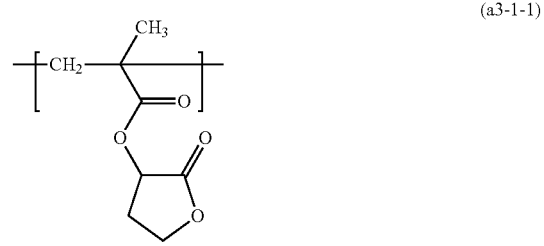

(a3-1-1)

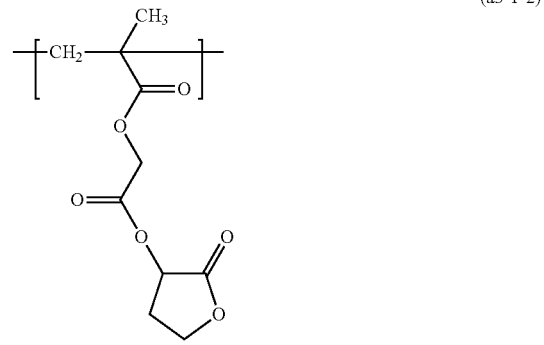

(a3-1-2)

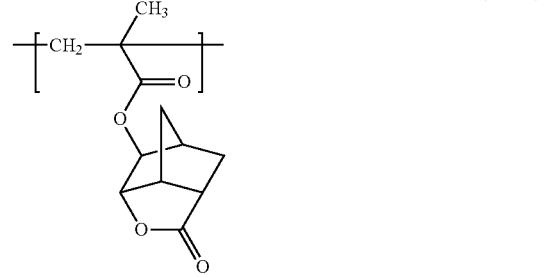

(a3-2-1)

(a3-2-2)
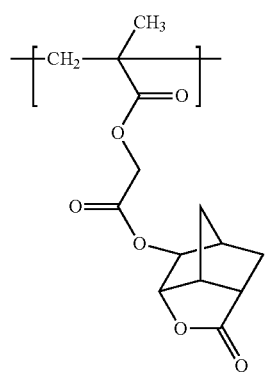
(a3-2x-1)
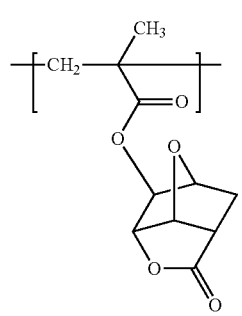
(a3-2x-2)
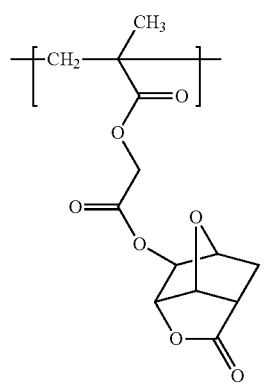
(a3-3-1)
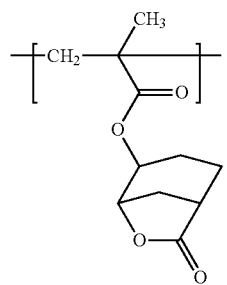
(a3-3-2)
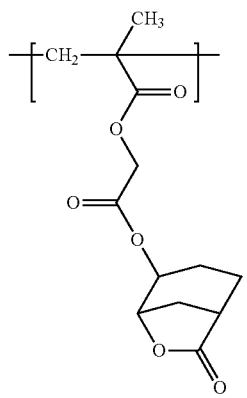
(a3-4-1)
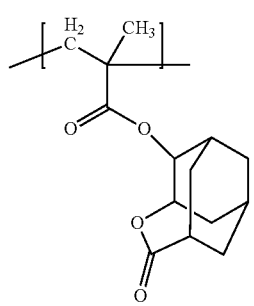
(a3-4-2)
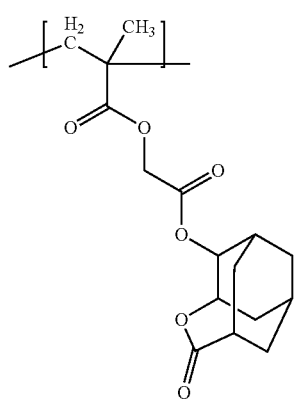
(a3-4-3)
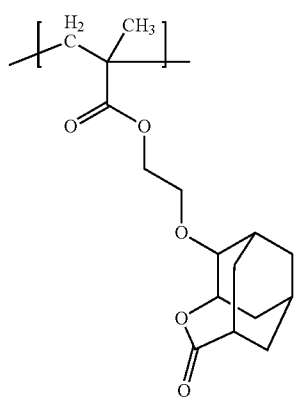

(a3-4-4)
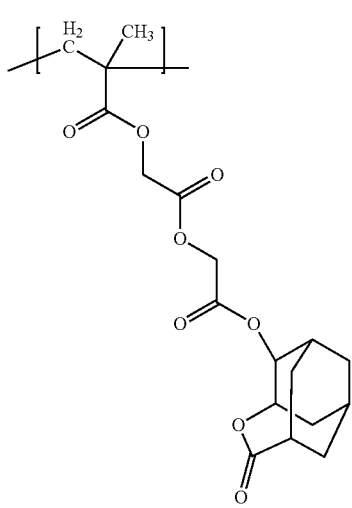
(a3-4-5)
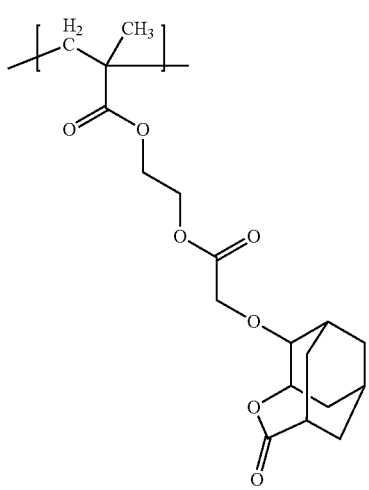
(a3-4-6)
(a3-4-7)
(a3-4-8)
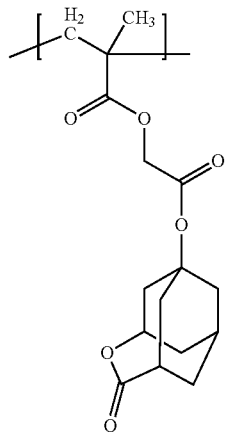
(a3-4-9)
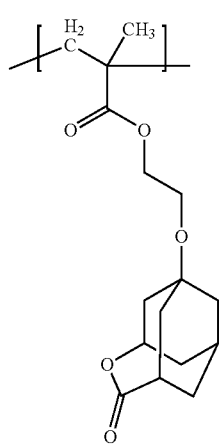
(a3-4-10)
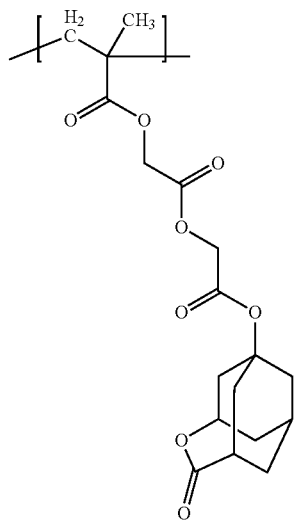

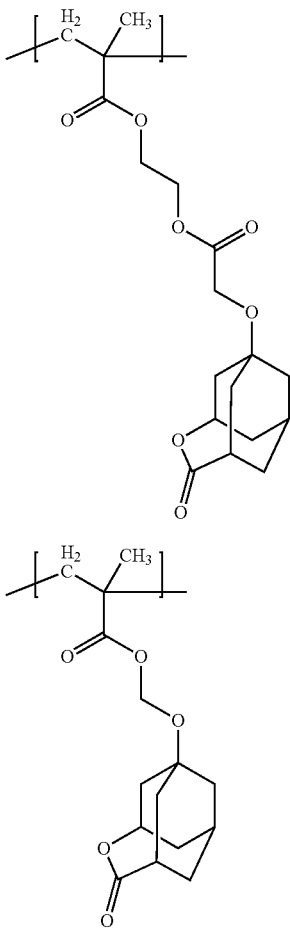

(a3-4-11)

(a3-4-12)

When the resin (A) includes the structural unit (a3), the total content is usually 5 to 70 mol %, preferably 5 to 60 mol %, and more preferably 7 to 50 mol %, based on all structural units of the resin (A).

Each content of the structural unit (a3-1), the structural unit (a3-2), the structural unit (a3-3) or the structural unit (a3-4) is preferably 5 to 60 mol %, more preferably 5 to 50 mol %, and still more preferably 7 to 40 mol %, based on all structural units of the resin (A).

<Structural Unit (a4)>

Examples of the structural unit (a4) include the following structural unit:

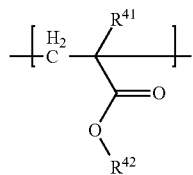

(a4)

wherein, in formula (a4), $R^{41}$ represents a hydrogen atom or a methyl group, and $R^{42}$ represents a saturated hydrocarbon group having 1 to 24 carbon atoms having a fluorine atom, and —$CH_2$— included in the saturated hydrocarbon group may be replaced by —O— or —CO—.

Examples of the saturated hydrocarbon group represented by $R^{42}$ include a chain hydrocarbon group and a monocyclic or polycyclic alicyclic hydrocarbon group, and groups formed by combining these groups.

Examples of the chain hydrocarbon group include a methyl group, an ethyl group, a propyl group, a butyl group, a pentyl group, a hexyl group, a heptyl group, an octyl group, a decyl group, a dodecyl group, a pentadecyl group, a hexadecyl group, a heptadecyl group and an octadecyl group. Examples of the monocyclic or polycyclic alicyclic hydrocarbon group include cycloalkyl groups such as a cyclopentyl group, a cyclohexyl group, a cycloheptyl group and a cyclooctyl group; and polycyclic alicyclic saturated hydrocarbon groups such as a decahydronaphthyl group, an adamantyl group, a norbornyl group and the following groups (* represents a bonding site).

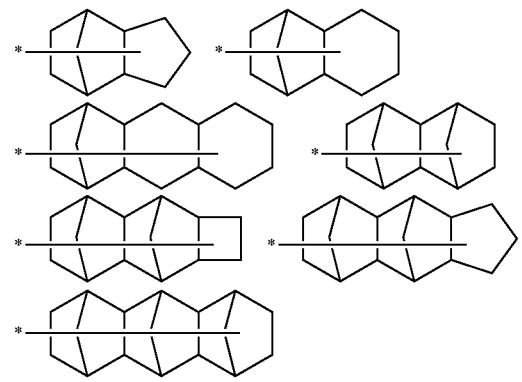

Examples of the group formed by combination include groups formed by combining one or more alkyl groups or one or more alkanediyl groups with one or more alicyclic hydrocarbon groups, and include an alkanediyl group-alicyclic hydrocarbon group, an alicyclic hydrocarbon group-alkyl group, an alkanediyl group-alicyclic hydrocarbon group-alkyl group and the like.

Examples of the structural unit (a4) include a structural unit represented by at least one selected from the group consisting of formula (a4-0), formula (a4-1), formula (a4-2), formula (a4-3) and formula (a4-4):

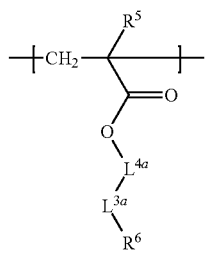

(a4-0)

wherein, in formula (a4-0), $R^5$ represents a hydrogen atom or a methyl group, $L^{4a}$ represents a single bond or a divalent aliphatic saturated hydrocarbon group having 1 to 4 carbon atoms, $L^{3a}$ represents a perfluoroalkanediyl group having 1 to 8 carbon atoms or a perfluorocycloalkanediyl group having 3 to 12 carbon atoms, and $R^6$ represents a hydrogen atom or a fluorine atom.

Examples of the divalent aliphatic saturated hydrocarbon group in $L^{4a}$ include linear alkanediyl groups such as a methylene group, an ethylene group, a propane-1,3-diyl group and a butane-1,4-diyl group; and branched alkanediyl groups such as an ethane-1,1-diyl group, a propane-1,2-diyl group, a butane-1,3-diyl group, a 2-methylpropane-1,3-diyl group and a 2-methylpropane-1,2-diyl group.

Examples of the perfluoroalkanediyl group in $L^{3a}$ include a difluoromethylene group, a perfluoroethylene group, a perfluoropropane-1,1-diyl group, a perfluoropropane-1,3-diyl group, a perfluoropropane-1,2-diyl group, a perfluoropropane-2,2-diyl group, a perfluorobutane-1,4-diyl group, a perfluorobutane-2,2-diyl group, a perfluorobutane-1,2-diyl group, a perfluoropentane-1,5-diyl group, a perfluoropentane-2,2-diyl group, a perfluoropentane-3,3-diyl group, a perfluorohexane-1,6-diyl group, a perfluorohexane-2,2-diyl group, a perfluorohexane-3,3-diyl group, a perfluoroheptane-1,7-diyl group, a perfluoroheptane-2,2-diyl group, a perfluoroheptane-3,4-diyl group, a perfluoroheptane-4,4-diyl group, a perfluorooctane-1,8-diyl group, a perfluorooctane-2,2-diyl group, a perfluorooctane-3,3-diyl group, a perfluorooctane-4,4-diyl group and the like.

Examples of the perfluorocycloalkanediyl group in $L^{3a}$ include a perfluorocyclohexanediyl group, a perfluorocyclopentanediyl group, a perfluorocycloheptanediyl group, a perfluoroadamantanediyl group and the like.

$L^{4a}$ is preferably a single bond, a methylene group or an ethylene group, and more preferably a single bond or a methylene group.

$L^{3a}$ is preferably a perfluoroalkanediyl group having 1 to 6 carbon atoms, and more preferably a perfluoroalkanediyl group having 1 to 3 carbon atoms.

Examples of the structural unit (a4-0) include the following structural units, and structural units in which a methyl group corresponding to $R^5$ in the structural unit (a4-0) in the following structural units is substituted with a

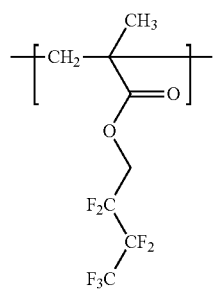

(a4-0-1)

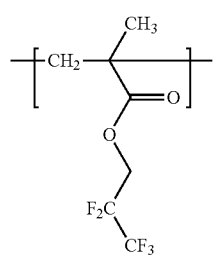

(a4-0-2)

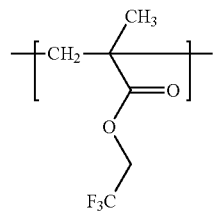

(a4-0-3)

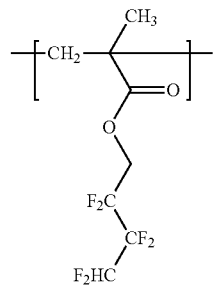

(a4-0-4)

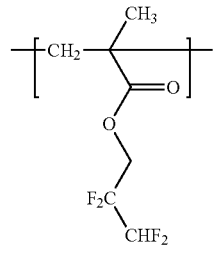

(a4-0-5)

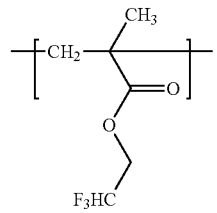

(a4-0-6)

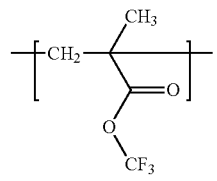

(a4-0-7)

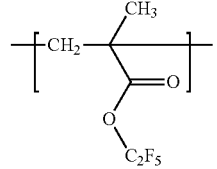

(a4-0-8)

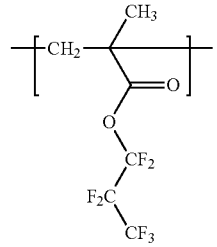

(a4-0-9)

-continued

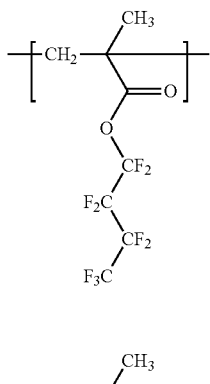
(a4-O-10)

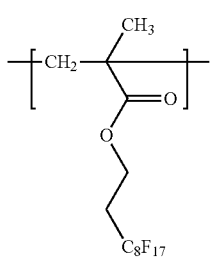
(a4-O-11)

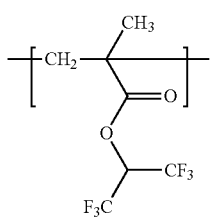
(a4-O-12)

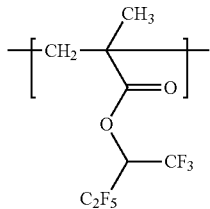
(a4-O-13)

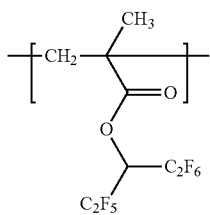
(a4-O-14)

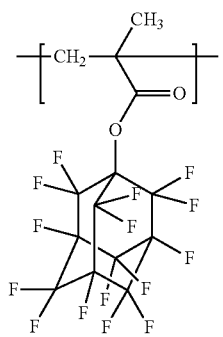
(a4-O-15)

-continued

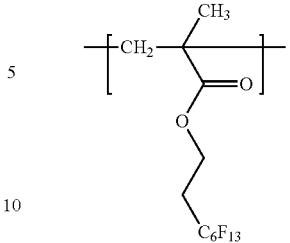
(a4-O-16)

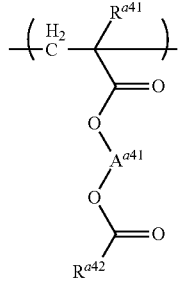
(a4-1)

hydrogen atom:
wherein, in formula (a4-1),
$R^{a41}$ represents a hydrogen atom or a methyl group,
$R^{a42}$ represents a saturated hydrocarbon group having 1 to 20 carbon atoms which may have a substituent, and —$CH_2$— included in the saturated hydrocarbon group may be replaced by —O— or —CO—,
$A^{a41}$ represents an alkanediyl group having 1 to 6 carbon atoms which may have a substituent or a group represented by formula (a-g1), in which at least one of $A^{a41}$ and $R^{a42}$ has, as a substituent, a halogen atom (preferably a fluorine atom):

$$*\text{—}A^{a42}\text{—}(X^{a41}\text{—}A^{a43})_s\text{—}X^{a42}\text{—}A^{a44}\text{—}* \qquad (a\text{-}g1)$$

[wherein, in formula (a-g1),
s represents 0 or 1,
$A^{a42}$ and $A^{a44}$ each independently represent a divalent saturated hydrocarbon group having 1 to 5 carbon atoms which may have a substituent,
$A^{a43}$ represents a single bond or a divalent aliphatic hydrocarbon group having 1 to 5 carbon atoms which may have a substituent,
$X^{a41}$ and $X^{a42}$ each independently represent —O—, —CO—, —CO—O— or —O—CO—, in which the total number of carbon atoms of $A^{a42}$, $A^{a43}$, $A^{a44}$, $X^{a41}$ and $X^{a42}$ is 7 or less], and
* is a bonding site and * at the right side is a bonding site to —O—CO—$R^{a42}$.

Examples of the saturated hydrocarbon group in $R^{a42}$ include a chain saturated hydrocarbon group and a monocyclic or polycyclic alicyclic saturated hydrocarbon group, and groups formed by combining these groups.

Examples of the chain saturated hydrocarbon group include a methyl group, an ethyl group, a propyl group, a butyl group, a pentyl group, a hexyl group, a heptyl group, an octyl group, a decyl group, a dodecyl group, a pentadecyl group, a hexadecyl group, a heptadecyl group and an octadecyl group.

Examples of the monocyclic or polycyclic alicyclic saturated hydrocarbon group include cycloalkyl groups such as a cyclopentyl group, a cyclohexyl group, a cycloheptyl group and a cyclooctyl group; and polycyclic alicyclic saturated hydrocarbon groups such as a decahydronaphthyl group, an adamantyl group, a norbornyl group and the following groups (* represents a bonding site).

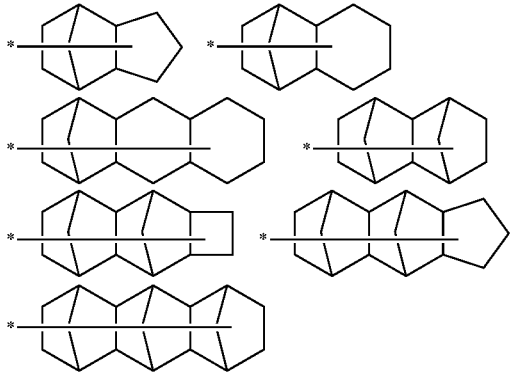

Examples of the group formed by combination include groups formed by combining one or more alkyl groups or one or more alkanediyl groups with one or more alicyclic saturated hydrocarbon groups, and include an -alkanediyl group-alicyclic saturated hydrocarbon group, an -alicyclic saturated hydrocarbon group-alkyl group, an -alkanediyl group-alicyclic saturated hydrocarbon group-alkyl group and the like.

Examples of the substituent possessed by $R^{a42}$ include at least one selected from the group consisting of a halogen atom and a group represented by formula (a-g3). Examples of the halogen atom include a fluorine atom, a chlorine atom, a bromine atom and an iodine atom, and the halogen atom is preferably a fluorine atom:

$$*-X^{a43}-A^{a45} \tag{a-g3}$$

wherein, in formula (a-g3), $X^{a43}$ represents an oxygen atom, a carbonyl group, *—O—CO— or *—CO—O—, $A^{a45}$ represents an aliphatic hydrocarbon group having 1 to 17 carbon atoms which may have a halogen atom, and

* represents a bonding site to $R^{a42}$.

In $R^{a42}$—$X^{a43}$-$A^{a45}$, when $R^{a42}$ has no halogen atom, $A^{a45}$ represents an aliphatic hydrocarbon group having 1 to 17 carbon atoms which has at least one halogen atom.

Examples of the aliphatic hydrocarbon group in $A^{a45}$ include alkyl groups such as a methyl group, an ethyl group, a propyl group, a butyl group, a pentyl group, a hexyl group, a heptyl group, an octyl group, a decyl group, a dodecyl group, a pentadecyl group, a hexadecyl group, a heptadecyl group and an octadecyl group;
monocyclic alicyclic hydrocarbon groups such as a cyclopentyl group, a cyclohexyl group, a cycloheptyl group and a cyclooctyl group; and polycyclic alicyclic hydrocarbon groups such as a decahydronaphthyl group, an adamantyl group, a norbornyl group and the following groups (* represents a bonding site).

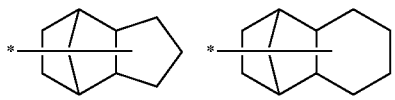

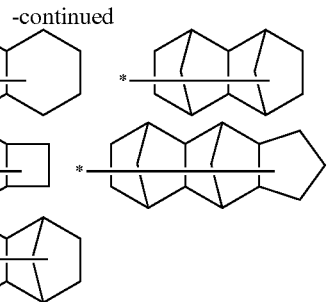

Examples of the group formed by combination include groups formed by combining one or more alkyl groups or one or more alkanediyl groups with one or more alicyclic hydrocarbon groups, and include an -alkanediyl group-alicyclic hydrocarbon group, an -alicyclic hydrocarbon group-alkyl group, an -alkanediyl group-alicyclic hydrocarbon group-alkyl group and the like.

$R^{a42}$ is preferably an aliphatic hydrocarbon group which may have a halogen atom, and more preferably an alkyl group having a halogen atom and/or an aliphatic hydrocarbon group having a group represented by formula (a-g3).

When $R^{a42}$ is an aliphatic hydrocarbon group which has a halogen atom, an aliphatic hydrocarbon group having a fluorine atom is preferable, a perfluoroalkyl group or a perfluorocycloalkyl group is more preferable, a perfluoroalkyl group having 1 to 6 carbon atoms is still more preferable, and a perfluoroalkyl group having 1 to 3 carbon atoms is particularly preferable. Examples of the perfluoroalkyl group include a perfluoromethyl group, a perfluoroethyl group, a perfluoropropyl group, a perfluorobutyl group, a perfluoropentyl group, a perfluorohexyl group, a perfluoroheptyl group and a perfluorooctyl group. Examples of the perfluorocycloalkyl group include a perfluorocyclohexyl group and the like.

When $R^{a42}$ is an aliphatic hydrocarbon group having a group represented by formula (a-g3), the total number of carbon atoms of $R^{a42}$ is preferably 15 or less, and more preferably 12 or less, including the number of carbon atoms included in the group represented by formula (a-g3). When having the group represented by formula (a-g3) as the substituent, the number thereof is preferably 1.

When $R^{a42}$ is a saturated hydrocarbon group having the group represented by formula (a-g3), $R^{a42}$ is still more preferably a group represented by formula (a-g2):

$$*-A^{a46}-X^{a44}-A^{a47} \tag{a-g2}$$

wherein, in formula (a-g2), $A^{a46}$ represents a divalent aliphatic hydrocarbon group having 1 to 17 carbon atoms which may have a halogen atom, $X^{a44}$ represents —O—CO— or —CO—O— (** represents a bonding site to $A^{a46}$), $A^{a47}$ represents an aliphatic hydrocarbon group having 1 to 17 carbon atoms which may have a halogen atom, the total number of carbon atoms of $A^{a46}$, $A^{a47}$ and $X^{a44}$ is 18 or less, and at least one of $A^{a46}$ and $A^{a47}$ has at least one halogen atom, and

* represents a bond to a bonding site to a carbonyl group.

The number of carbon atoms of the aliphatic hydrocarbon group for $A^{a46}$ is preferably 1 to 6, and more preferably 1 to 3.

The number of carbon atoms of the aliphatic hydrocarbon group for $A^{a47}$ is preferably 4 to 15, and more preferably 5 to 12, and $A^{a47}$ is still more preferably a cyclohexyl group or an adamantyl group.

Preferred structure of the group represented by formula (a-g2) is the following structure (* is a bonding site to a carbonyl group).

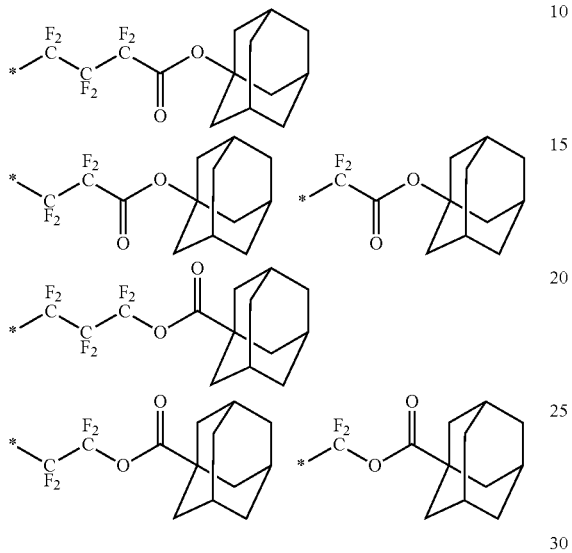

Examples of the alkanediyl group in $A^{a41}$ include linear alkanediyl groups such as a methylene group, an ethylene group, a propane-1,3-diyl group, a butane-1,4-diyl group, a pentane-1,5-diyl group and a hexane-1,6-diyl group; and branched alkanediyl groups such as a propane-1,2-diyl group, a butane-1,3-diyl group, a 2-methylpropane-1,2-diyl group, a 1-methylbutane-1,4-diyl group and a 2-methylbutane-1,4-diyl group.

Examples of the substituent in the alkanediyl group for $A^{a41}$ include a hydroxy group and an alkoxy group having 1 to 6 carbon atoms.

$A^{a41}$ is preferably an alkanediyl group having 1 to 4 carbon atoms, more preferably an alkanediyl group having 2 to 4 carbon atoms, and still more preferably an ethylene group.

Examples of the divalent saturated hydrocarbon group represented by $A^{a42}$, $A^{a43}$ and $A^{a44}$ in the group represented by formula (a-g1) include a linear or branched alkanediyl group and a monocyclic divalent alicyclic hydrocarbon group, and groups formed by combining an alkanediyl group and a divalent alicyclic hydrocarbon group. Specific examples thereof include a methylene group, an ethylene group, a propane-1,3-diyl group, a propane-1,2-diyl group, a butane-1,4-diyl group, a 1-methylpropane-1,3-diyl group, a 2-methylpropane-1,3-diyl group, a 2-methylpropane-1,2-diyl group and the like.

Examples of the substituent of the divalent saturated hydrocarbon group represented by $A^{a42}$, $A^{a43}$ and $A^{a44}$ include a hydroxy group and an alkoxy group having 1 to 6 carbon atoms.

s is preferably 0.

In a group represented by formula (a-g1), examples of the group in which $X^{a42}$ is —O—, —CO—, —CO—O— or —O—CO— include the following groups. In the following exemplification, * and  each represent a bonding site, and  is a bonding site to —O—CO—$R^{a42}$.

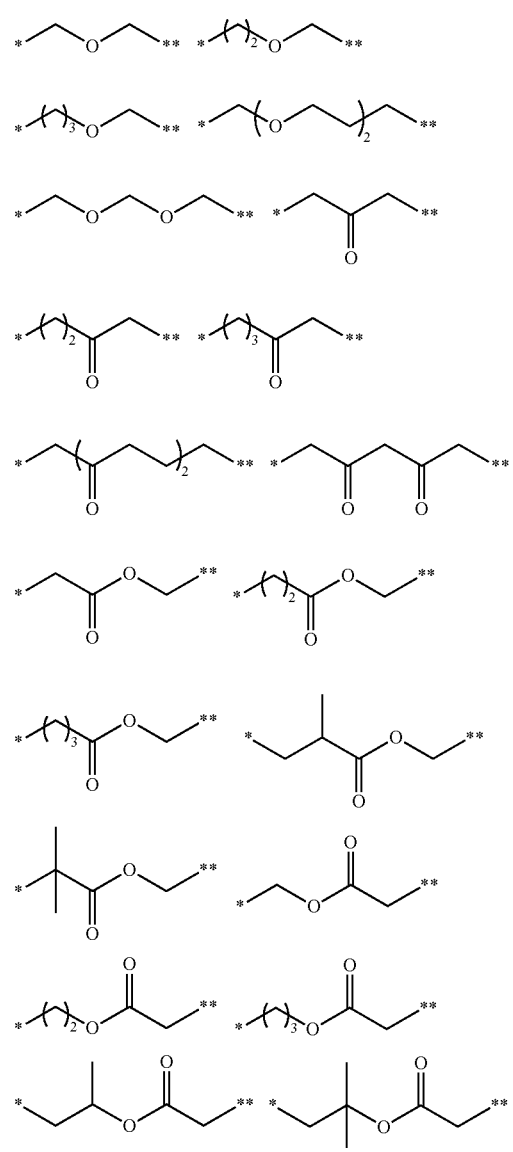

Examples of the structural unit represented by formula (a4-1) include the following structural units, and structural units in which a methyl group corresponding to $R^{a41}$ in the structural unit represented by formula (a4-1) in the following structural units is substituted with a hydrogen atom.

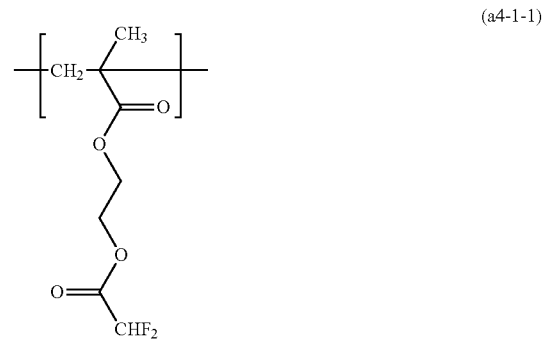

(a4-1-1)

-continued
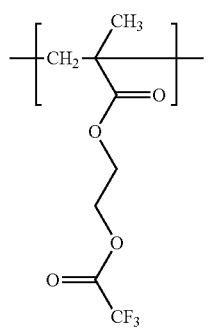
(a4-1-2)
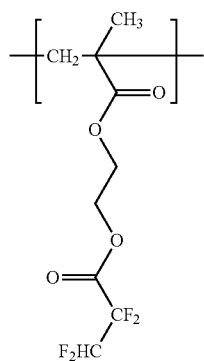
(a4-1-3)
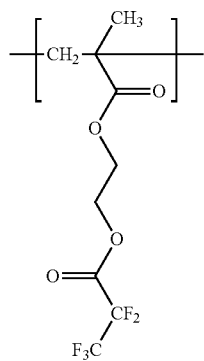
(a4-1-4)
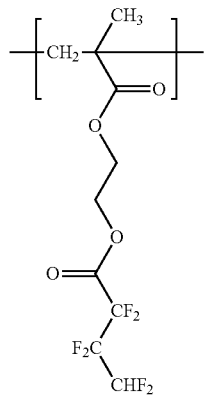
(a4-1-5)
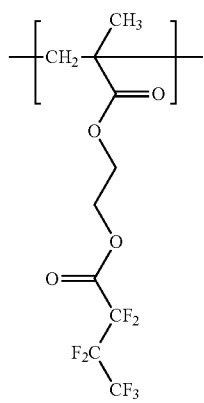
(a4-1-6)
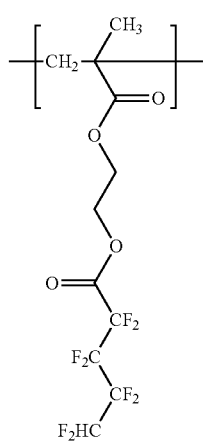
(a4-1-7)
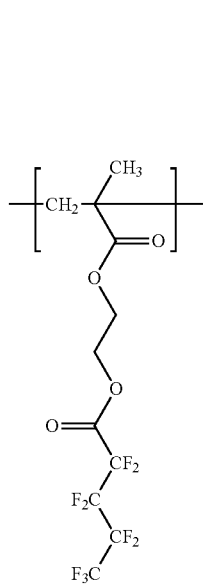
(a4-1-8)

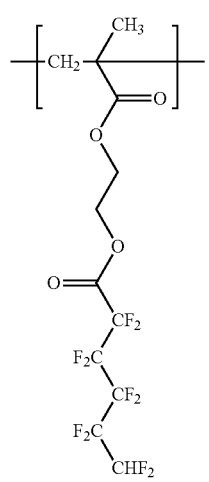 (a4-1-9)
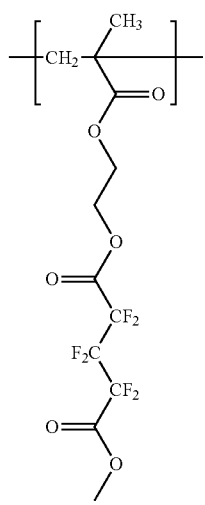 (a4-1'-1)
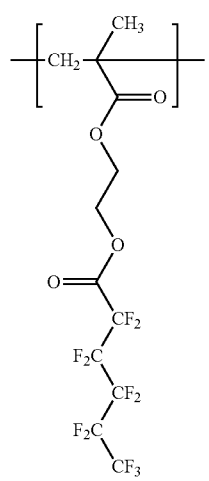 (a4-1-10)
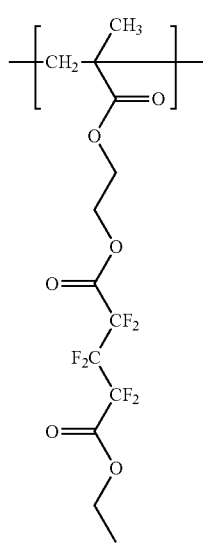 (a4-1'-2)
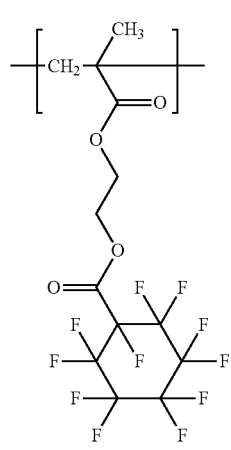 (a4-1-11)
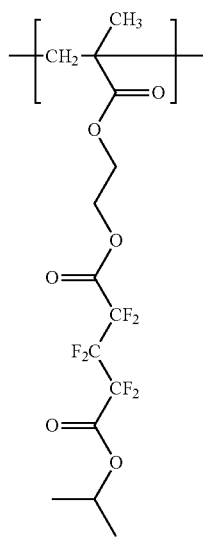 (a4-1'-3)

(a4-1'-4)
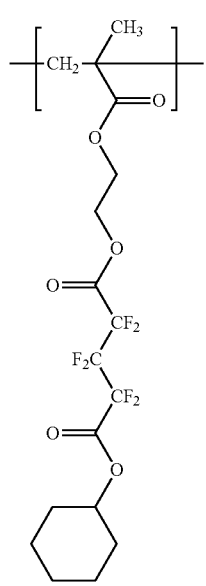
(a4-1'-5)
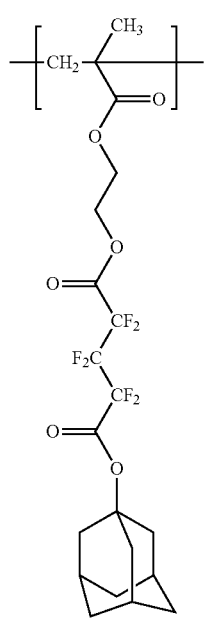
(a4-1'-6)
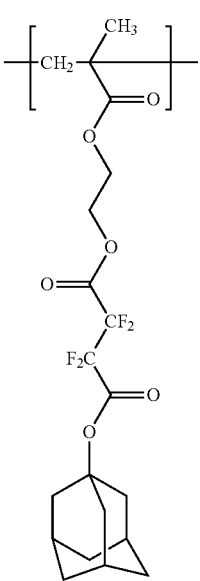
(a4-1'-7)
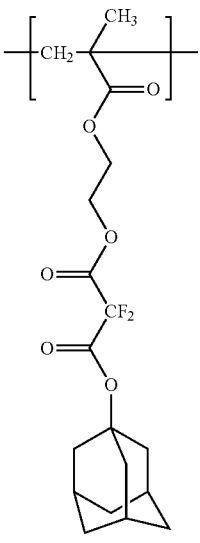

(a4-1'-8)

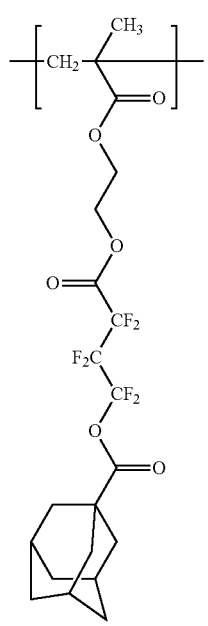

(a4-1'-9)

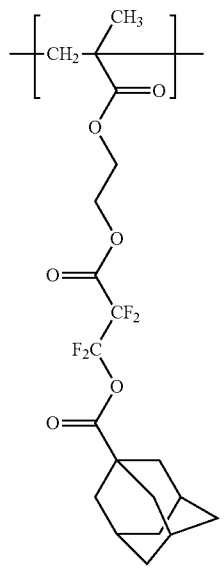

(a4-1'-10)

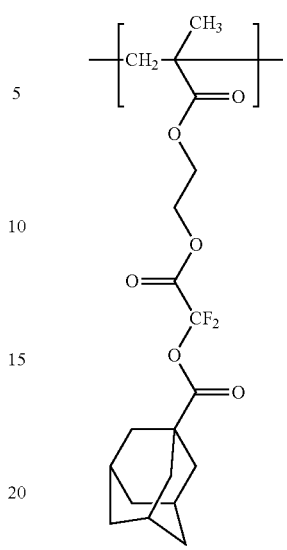

(a4-1'-11)

The structural unit represented by formula (a4-1) is preferably a structural unit represented by formula (a4-2):

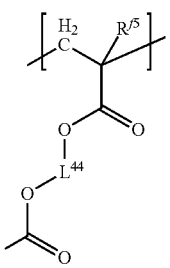

(a4-2)

wherein, in formula (a4-2), $R^{f5}$ represents a hydrogen atom or a methyl group, $L^{44}$ represents an alkanediyl group having 1 to 6 carbon atoms, and the —CH$_2$— included in the alkanediyl group may be replaced by —O— or —CO—, $R^{f6}$ represents a saturated hydrocarbon group having 1 to 20 carbon atoms having a fluorine atom, and the upper limit of the total number of carbon atoms of $L^{44}$ and $R^{f6}$ is 21.

Examples of the alkanediyl group having 1 to 6 carbon atoms for $L^{44}$ include the same groups as mentioned in the alkanediyl group for $A^{a41}$.

Examples of the saturated hydrocarbon group for $R^{f6}$ include the same groups as mentioned for $R^{a42}$.

The alkanediyl group having 1 to 6 carbon atoms in $L^{44}$ is preferably an alkanediyl group having 2 to 4 carbon atoms, and more preferably an ethylene group.

Examples of the structural unit represented by formula (a4-2) include structural units each represented by formula (a4-1-1) to formula (a4-1-11). Examples of the structural unit represented by formula (a4-2) also include a structural unit in which a methyl group corresponding to $R^{f5}$ in a structural unit (a4-2) is substituted with a hydrogen atom.

Examples of the structural unit (a4) include a structural unit represented by formula (a4-3):

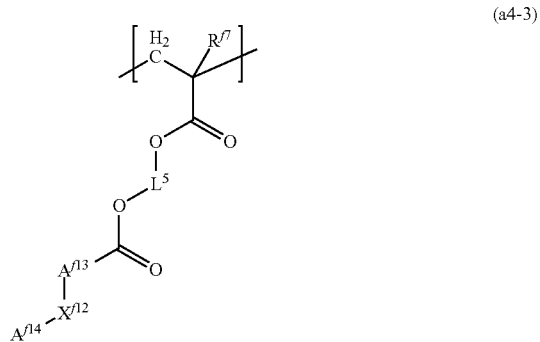

(a4-3)

wherein, in formula (a4-3), $R^{f7}$ represents a hydrogen atom or a methyl group, $L^5$ represents an alkanediyl group having 1 to 6 carbon atoms, $A^{f13}$ represents a divalent saturated hydrocarbon group having 1 to 18 carbon atoms which may have a fluorine atom, $X^{f12}$ represents *—O—CO— or *—CO—O— (* represents a bonding site to $A^{f13}$), $A^{f14}$ represents a saturated hydrocarbon group having 1 to 17 carbon atoms which may have a fluorine atom, and at least one of $A^{f13}$ and $A^{f14}$ has a fluorine atom, and the upper limit of the total number of carbon atoms of $L^5$, $A^{f13}$ and $A^{f14}$ is 20.

Examples of the alkanediyl group in $L^5$ include those which are the same as mentioned in the alkanediyl group for $A^{a41}$.

The divalent saturated hydrocarbon group which may have a fluorine atom in $A^{f13}$ is preferably a divalent saturated hydrocarbon group which may have a fluorine atom and a divalent alicyclic saturated hydrocarbon group which may have a fluorine atom, and more preferably a perfluoroalkanediyl group.

Examples of the divalent saturated hydrocarbon group which may have a fluorine atom include alkanediyl groups such as a methylene group, an ethylene group, a propanediyl group, a butanediyl group and a pentanediyl group; and perfluoroalkanediyl groups such as a difluoromethylene group, a perfluoroethylene group, a perfluoropropanediyl group, a perfluorobutanediyl group and a perfluoropentanediyl group.

The divalent alicyclic hydrocarbon group which may have a fluorine atom may be either monocyclic or polycyclic. Examples of the monocyclic group include a cyclohexanediyl group and a perfluorocyclohexanediyl group. Examples of the polycyclic group include an adamantanediyl group, a norbornanediyl group, a perfluoroadamantanediyl group and the like.

Examples of the saturated hydrocarbon group and the saturated hydrocarbon group which may have a fluorine atom for $A^{f14}$ include the same groups as mentioned for $R^{a42}$. Of these groups, preferable are fluorinated alkyl groups such as a trifluoromethyl group, a difluoromethyl group, a methyl group, a perfluoroethyl group, a 2,2,2-trifluoroethyl group, a 1,1,2,2-tetrafluoroethyl group, an ethyl group, a perfluoropropyl group, a 2,2,3,3,3-pentafluoropropyl group, a propyl group, a perfluorobutyl group, a 1,1,2,2,3,3,4,4-octafluorobutyl group, a butyl group, a perfluoropentyl group, a 2,2,3,3,4,4,5,5,5-nonafluoropentyl group, a pentyl group, a hexyl group, a perfluorohexyl group, a heptyl group, a perfluoroheptyl group, an octyl group and a perfluorooctyl group; a cyclopropylmethyl group, a cyclopropyl group, a cyclobutylmethyl group, a cyclopentyl group, a cyclohexyl group, a perfluorocyclohexyl group, an adamantyl group, an adamantylmethyl group, an adamantyldimethyl group, a norbornyl group, a norbornylmethyl group, a perfluoroadamantyl group, a perfluoroadamantylmethyl group and the like.

In formula (a4-3), $L^5$ is preferably an ethylene group.

The divalent saturated hydrocarbon group for $A^{f13}$ is preferably a group including a divalent chain hydrocarbon group having 1 to 6 carbon atoms and a divalent alicyclic hydrocarbon group having 3 to 12 carbon atoms, and more preferably a divalent chain hydrocarbon group having 2 to 3 carbon atoms.

The saturated hydrocarbon group for $A^{f14}$ is preferably a group including a chain hydrocarbon group having 3 to 12 carbon atoms and an aliphatic hydrocarbon group having 3 to 12 carbon atoms, and more preferably a group including a chain hydrocarbon group having 3 to 10 carbon atoms and an alicyclic hydrocarbon group having 3 to 10 carbon atoms. Of these groups, $A^{f14}$ is preferably a group including an alicyclic hydrocarbon group having 3 to 12 carbon atoms, and more preferably a cyclopropylmethyl group, a cyclopentyl group, a cyclohexyl group, a norbornyl group and an adamantyl group.

Examples of the structural unit represented by formula (a4-3) include structural units each represented by formula (a4-1'-1) to formula (a4-1'-11). Examples of the structural unit represented by formula (a4-3) also include a structural unit in which a methyl group corresponding to $R^{f7}$ in a structural unit (a4-3) is substituted with a hydrogen atom.

The structural unit (a4) also includes a structural unit represented by formula (a4-4):

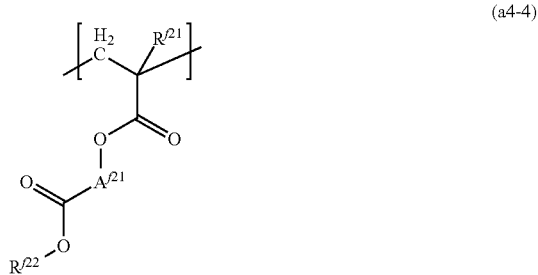

(a4-4)

wherein, in formula (a4-4),

R′²¹ represents a hydrogen atom or a methyl group,

A′²¹ represents —(CH$_2$)$_{j1}$—, —(CH$_2$)$^{j2}$—O—(CH$_2$)$_{j3}$— or —(CH$_2$)$_{j4}$—CO—O—(CH$_2$)$_{j5}$—, j1 to j5 each independently represent an integer of 1 to 6, and R′²² represents a saturated hydrocarbon group having 1 to 10 carbon atoms having a fluorine atom.

Examples of the saturated hydrocarbon group for R′²² include those which are the same as the saturated hydrocarbon group represented by R$^{a42}$. R′²² is preferably an alkyl group having 1 to 10 carbon atoms having a fluorine atom or an alicyclic hydrocarbon group having 1 to 10 carbon atoms having a fluorine atom, more preferably an alkyl group having 1 to 10 carbon atoms having a fluorine atom, and still more preferably an alkyl group having 1 to 6 carbon atoms having a fluorine atom.

In formula (a4-4), A′²¹ is preferably —(CH$_2$)$_{j1}$—, more preferably an ethylene group or a methylene group, and still more preferably a methylene group.

The structural unit represented by formula (a4-4) includes, for example, the following structural units and structural units in which a methyl group corresponding to R′²¹ in the structural unit (a4-4) is substituted with a hydrogen atom in structural units represented by the following formulas.

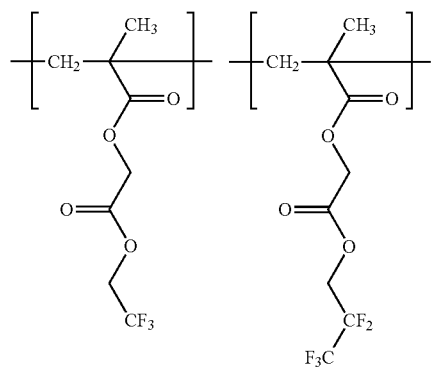

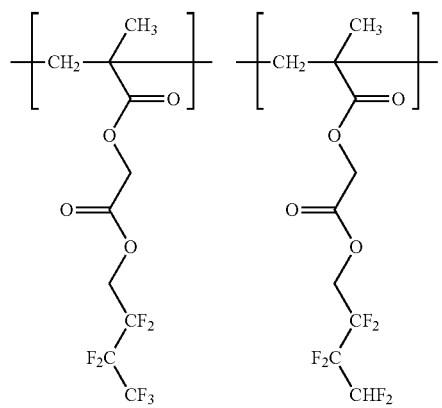

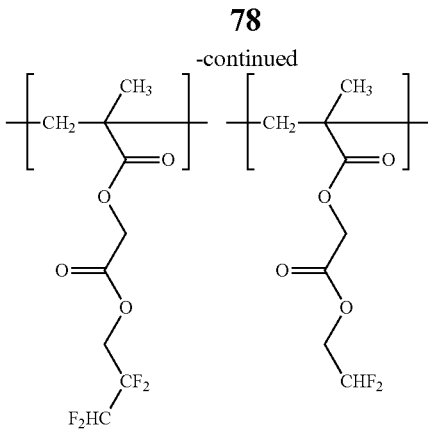

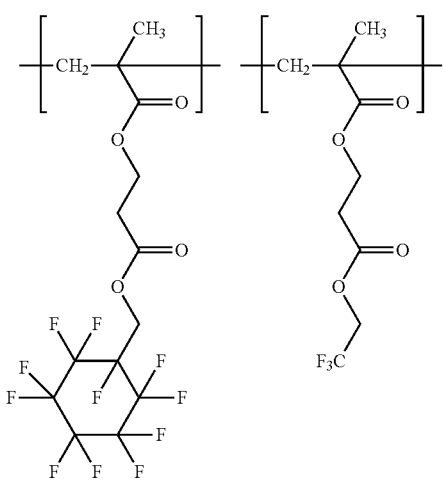

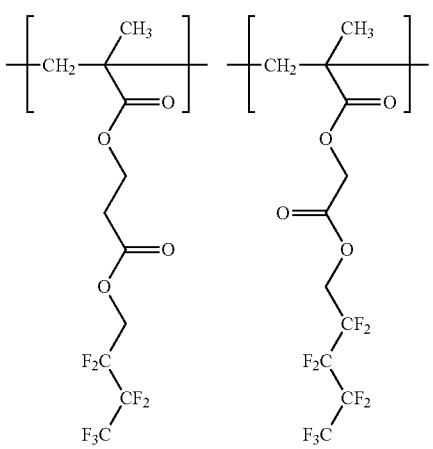

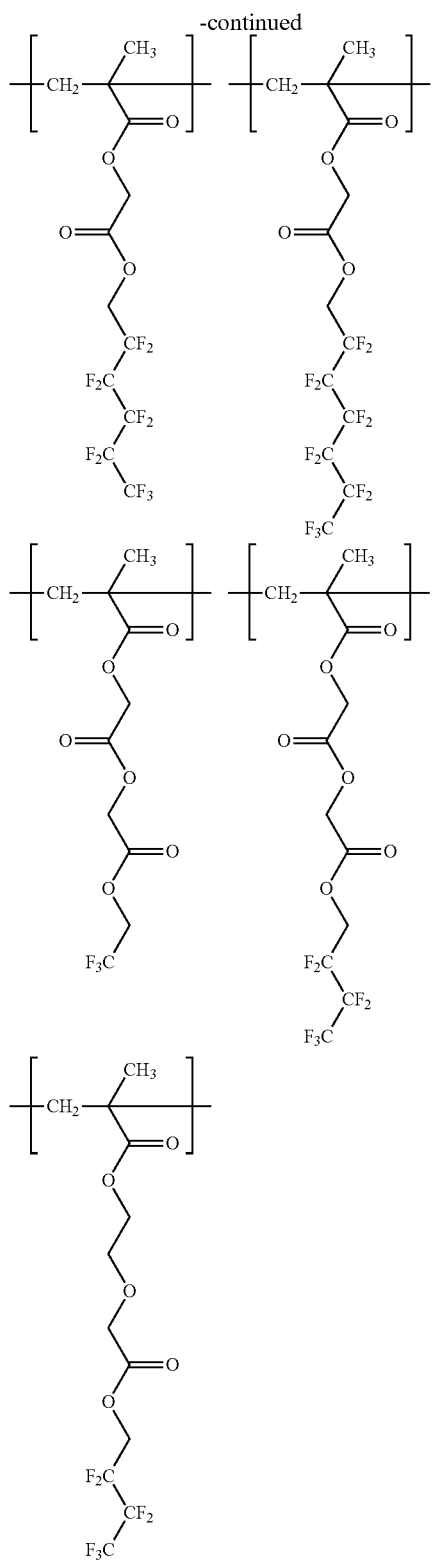

When the resin (A) includes the structural unit (a4), the content is preferably 1 to 20 mol %, more preferably 2 to 15 mol %, and still more preferably 3 to 10 mol %, based on all structural units of the resin (A).

<Structural Unit (a5)>

Examples of a non-leaving hydrocarbon group possessed by the structural unit (a5) include groups having a linear, branched or cyclic hydrocarbon group. Of these, the structural unit (a5) is preferably a group having an alicyclic hydrocarbon group.

The structural unit (a5) includes, for example, a structural unit represented by formula (a5-1):

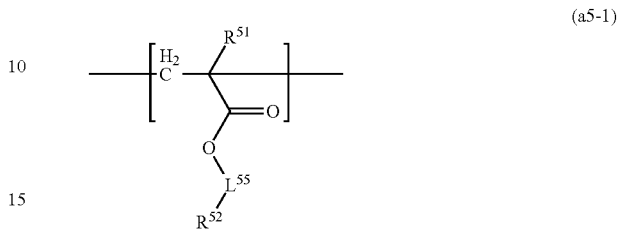

wherein, in formula (a5-1), $R^{51}$ represents a hydrogen atom or a methyl group, $R^{52}$ represents an alicyclic hydrocarbon group having 3 to 18 carbon atoms, and a hydrogen atom included in the alicyclic hydrocarbon group may be substituted with an aliphatic hydrocarbon group having 1 to 8 carbon atoms, and $L^{55}$ represents a single bond or a divalent saturated hydrocarbon group having 1 to 18 carbon atoms, and —CH$_2$— included in the saturated hydrocarbon group may be replaced by —O— or —CO—.

The alicyclic hydrocarbon group in $R^{52}$ may be either monocyclic or polycyclic. The monocyclic alicyclic hydrocarbon group includes, for example, a cyclopropyl group, a cyclobutyl group, a cyclopentyl group and a cyclohexyl group. The polycyclic alicyclic hydrocarbon group includes, for example, an adamantyl group and a norbornyl group.

The aliphatic hydrocarbon group having 1 to 8 carbon atoms includes, for example, alkyl groups such as a methyl group, an ethyl group, a propyl group, an isopropyl group, a butyl group, a sec-butyl group, a tert-butyl group, a pentyl group, a hexyl group, an octyl group and a 2-ethylhexyl group.

Examples of the alicyclic hydrocarbon group having a substituent includes a 3-methyladamantyl group and the like.

$R^{52}$ is preferably an unsubstituted alicyclic hydrocarbon group having 3 to 18 carbon atoms, and more preferably an adamantyl group, a norbornyl group or a cyclohexyl group.

Examples of the divalent saturated hydrocarbon group in $L^{55}$ include a divalent chain saturated hydrocarbon group and a divalent alicyclic saturated hydrocarbon group, and a divalent chain saturated hydrocarbon group is preferable.

The divalent chain saturated hydrocarbon group includes, for example, alkanediyl groups such as a methylene group, an ethylene group, a propanediyl group, a butanediyl group and a pentanediyl group.

The divalent alicyclic saturated hydrocarbon group may be either monocyclic or polycyclic. Examples of the monocyclic alicyclic saturated hydrocarbon group include cycloalkanediyl groups such as a cyclopentanediyl group and a cyclohexanediyl group. Examples of the polycyclic divalent alicyclic saturated hydrocarbon group include an adamantanediyl group and a norbornanediyl group.

Examples of the group in which —CH$_2$— included in the divalent saturated hydrocarbon group represented by $L^{55}$ is replaced by —O— or —CO— include groups represented by formula (L1-1) to formula (L1-4). In the following formulas, * and ** each represent a bonding site, and * represents a bonding site to an oxygen atom.

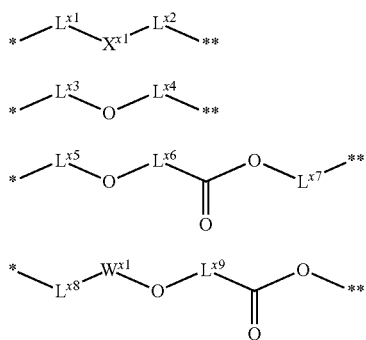

(L1-1)
(L1-2)
(L1-3)
(L1-4)

In formula (L1-1),
$X^{x1}$ represents *—O—CO— or *—CO—O— (* represents a bonding site to $L^{x1}$),
$L^{x1}$ represents a divalent aliphatic saturated hydrocarbon group having 1 to 16 carbon atoms,
$L^{x2}$ represents a single bond or a divalent aliphatic saturated hydrocarbon group having 1 to 15 carbon atoms, and
the total number of carbon atoms of $L^{x1}$ and $L^{x2}$ is 16 or less.
In formula (L1-2),
$L^{x3}$ represents a divalent aliphatic saturated hydrocarbon group having 1 to 17 carbon atoms,
$L^{x4}$ represents a single bond or a divalent aliphatic saturated hydrocarbon group having 1 to 16 carbon atoms, and
the total number of carbon atoms of $L^{x3}$ and $L^{x4}$ is 17 or less.
In formula (L1-3),
$L^{x5}$ represents a divalent aliphatic saturated hydrocarbon group having 1 to 15 carbon atoms,
$L^{x6}$ and $L^{x7}$ each independently represent a single bond or a divalent aliphatic saturated hydrocarbon group having 1 to 14 carbon atoms, and
the total number of carbon atoms of $L^{x5}$, $L^{x6}$ and $L^{x7}$ is 15 or less.
In formula (L1-4),
$L^{x8}$ and $L^{x9}$ represent a single bond or a divalent aliphatic saturated hydrocarbon group having 1 to 12 carbon atoms,
$W^{x1}$ represents a divalent alicyclic saturated hydrocarbon group having 3 to 15 carbon atoms, and
the total number of carbon atoms of $L^{x8}$, $L^{x9}$ and $W^{x1}$ is 15 or less.
$L^{x1}$: is preferably a divalent aliphatic saturated hydrocarbon group having 1 to 8 carbon atoms, and more preferably a methylene group or an ethylene group.
$L^{x2}$ is preferably a single bond or a divalent aliphatic saturated hydrocarbon group having 1 to 8 carbon atoms, and more preferably a single bond.
$L^{x3}$ is preferably a divalent aliphatic saturated hydrocarbon group having 1 to 8 carbon atoms.
$L^{x4}$ is preferably a single bond or a divalent aliphatic saturated hydrocarbon group having 1 to 8 carbon atoms.
$L^{x5}$ is preferably a divalent aliphatic saturated hydrocarbon group having 1 to 8 carbon atoms, and more preferably a methylene group or an ethylene group.
$L^{x6}$ is preferably a single bond or a divalent aliphatic saturated hydrocarbon group having 1 to 8 carbon atoms, and more preferably a methylene group or an ethylene group.
$L^{x7}$ is preferably a single bond or a divalent aliphatic saturated hydrocarbon group having 1 to 8 carbon atoms.

$L^{x8}$ is preferably a single bond or a divalent aliphatic saturated hydrocarbon group having 1 to 8 carbon atoms, and more preferably a single bond or a methylene group.
$L^{x9}$ is preferably a single bond or a divalent aliphatic saturated hydrocarbon group having 1 to 8 carbon atoms, and more preferably a single bond or a methylene group.
$W^{x1}$ is preferably a divalent alicyclic saturated hydrocarbon group having 3 to 10 carbon atoms, and more preferably a cyclohexanediyl group or an adamantanediyl group.

The group represented by formula (L1-1) includes, for example, the following divalent groups.

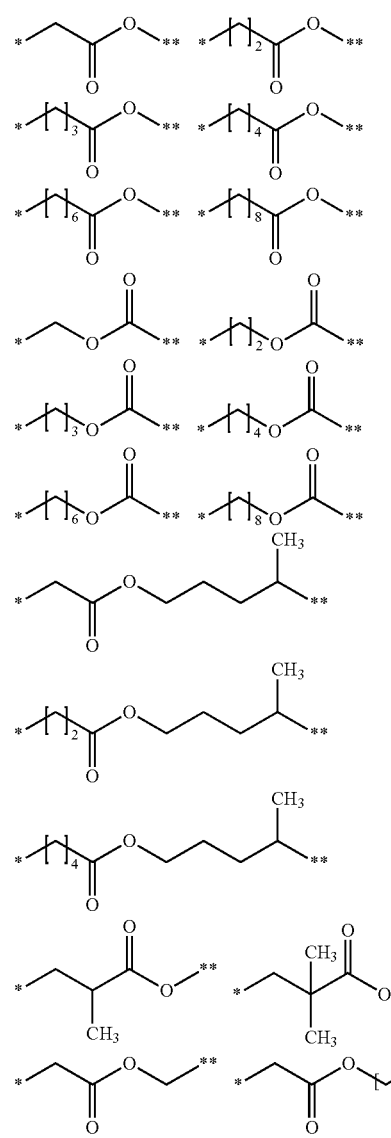

The group represented by formula (L1-2) includes, for example, the following divalent groups.

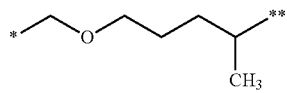

-continued

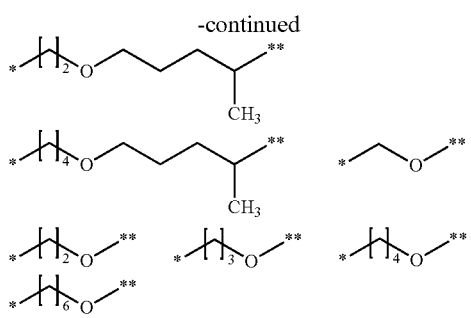

The group represented by formula (L1-3) includes, for example, the following divalent groups.

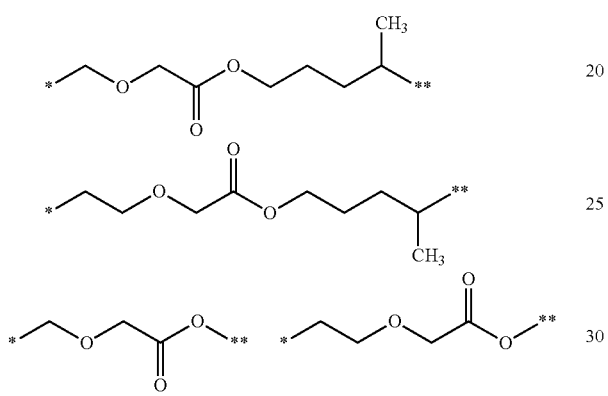

The group represented by formula (L1-4) includes, for example, the following divalent groups.

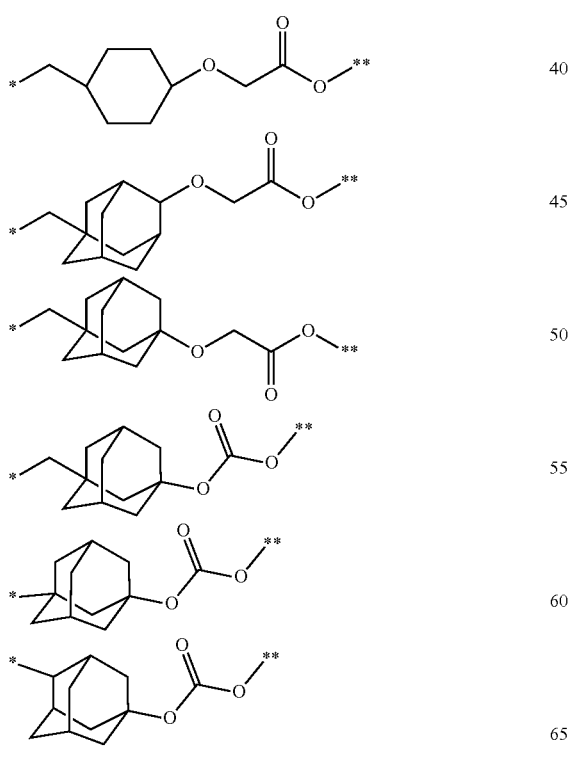

$L^{55}$ is preferably a single bond or a group represented by formula (L1-1).

Examples of the structural unit (a5-1) include the following structural units and structural units in which a methyl group corresponding to $R^{51}$ in the structural unit (a5-1) in the following structural units is substituted with a hydrogen atom.

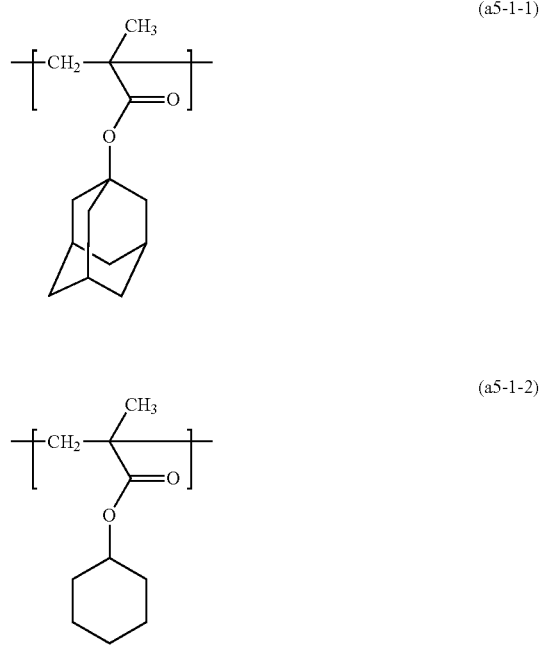

(a5-1-1)

(a5-1-2)

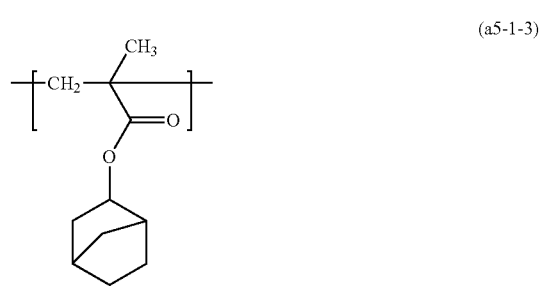

(a5-1-3)

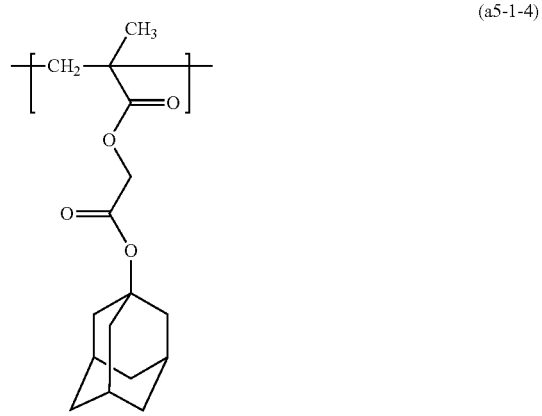

(a5-1-4)

(a5-1-5) 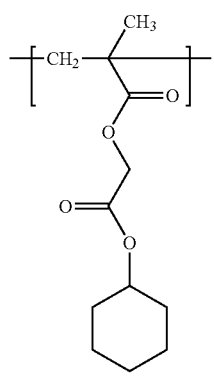
(a5-1-6) 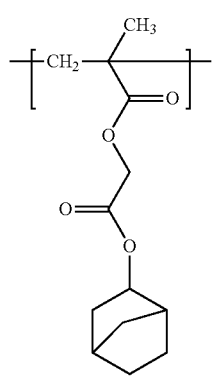
(a5-1-7) 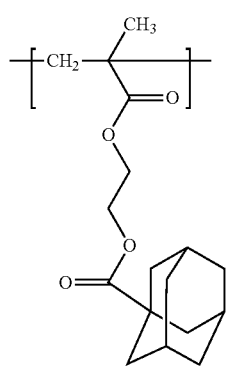
(a5-1-8) 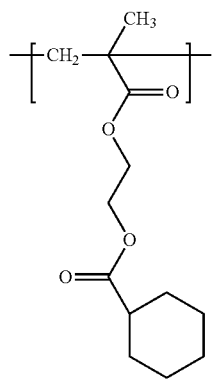
(a5-1-9) 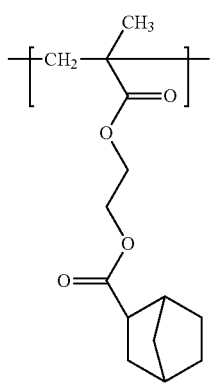
(a5-1-10) 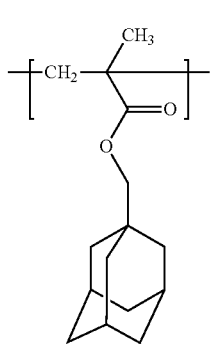
(a5-1-11) 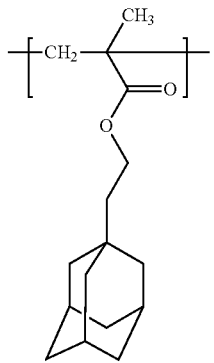
(a5-1-12) 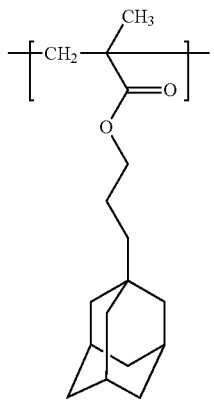

(a5-1-13)
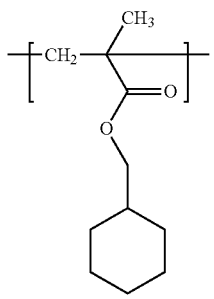

(a5-1-14)
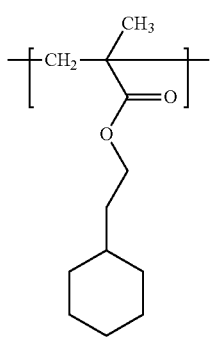

(a5-1-15)
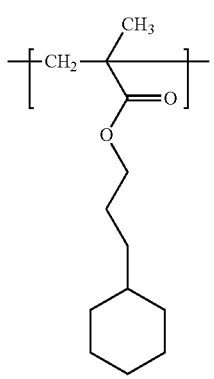

(a5-1-16)
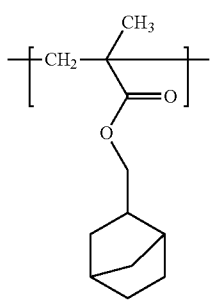

(a5-1-17)
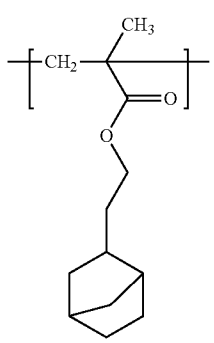

(a5-1-18)
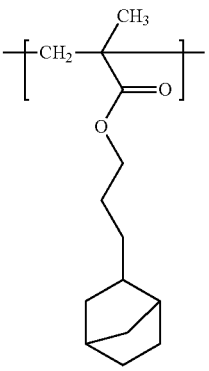

When the resin (A) includes the structural unit (a5), the content is preferably 1 to 30 mol %, more preferably 2 to 20 mol %, and still more preferably 3 to 15 mol %, based on all structural units of the resin (A).

<Structural Unit (II)>

The resin (A) may further include a structural unit which is decomposed upon exposure to radiation to generate an acid (hereinafter sometimes referred to as "structural unit (II)"). Specific examples of the structural unit (II) include the structural units mentioned in JP 2016-79235 A, and a structural unit having a sulfonate group or a carboxylate group and an organic cation in a side chain or a structural unit having a sulfonio group and an organic anion in a side chain are preferable.

The structural unit having a sulfonate group or a carboxylate group in a side chain is preferably a structural unit represented by formula (II-2-A'):

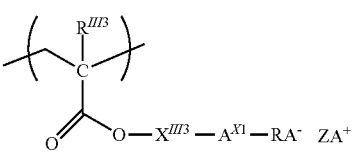

(II-2-A')

wherein, in formula (II-2-A'), $X^{III3}$ represents a divalent saturated hydrocarbon group having 1 to 18 carbon atoms, —$CH_2$— included in the saturated hydrocarbon group may be replaced by —O—, —S— or —CO—, and a hydrogen atom included in the saturated hydrocarbon group may be substituted with a halogen atom, an alkyl group having 1 to 6 carbon atoms which may have a halogen atom, or a hydroxy group, $A^{x1}$ represents an alkanediyl group having 1 to 8 carbon atoms, and a hydrogen atom included in the alkanediyl group may be substituted with a fluorine atom or a perfluoroalkyl group having 1 to 6 carbon atoms, $RA^-$ represents a sulfonate group or a carboxylate group, $R^{III3}$ represents a hydrogen atom, a halogen atom or an alkyl group having 1 to 6 carbon atoms which may have a halogen atom, and $ZA^+$ represents an organic cation.

Examples of the halogen atom represented by $R^{III3}$ include a fluorine atom, a chlorine atom, a bromine atom and an iodine atom.

Examples of the alkyl group having 1 to 6 carbon atoms which may have a halogen atom represented by $R^{III3}$ include those which are the same as the alkyl group having 1 to 6 carbon atoms which may have a halogen atom represented by $R^{a8}$.

Examples of the alkanediyl group having 1 to 8 carbon atoms represented by $A^{x1}$ include a methylene group, an ethylene group, a propane-1,3-diyl group, a butane-1,4-diyl group, a pentane-1,5-diyl group, a hexane-1,6-diyl group, an ethane-1,1-diyl group, a propane-1,1-diyl group, a propane-1,2-diyl group, a propane-2,2-diyl group, a pentane-2,4-diyl group, a 2-methylpropane-1,3-diyl group, a 2-methylpropane-1,2-diyl group, a pentane-1,4-diyl group, a 2-methylbutane-1,4-diyl group and the like.

Examples of the perfluoroalkyl group having 1 to 6 carbon atoms which may be substituted in $A^{x1}$ include a trifluoromethyl group, a perfluoroethyl group, a perfluoropropyl group, a perfluoroisopropyl group, a perfluorobutyl group, a perfluorosec-butyl group, a perfluorotert-butyl group, a perfluoropentyl group, a perfluorohexyl group and the like.

Examples of the divalent saturated hydrocarbon group having 1 to 18 carbon atoms represented by $X^{III3}$ include a linear or branched alkanediyl group, a monocyclic or polycyclic divalent alicyclic saturated hydrocarbon group, or a combination thereof.

Specific examples thereof include linear alkanediyl groups such as a methylene group, an ethylene group, a propane-1,3-diyl group, a propane-1,2-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group and a dodecane-1,12-diyl group; branched alkanediyl groups such as a butane-1,3-diyl group, a 2-methylpropane-1,3-diyl group, a 2-methylpropane-1,2-diyl group, a pentane-1,4-diyl group and a 2-methylbutane-1,4-diyl group; cycloalkanediyl groups such as a cyclobutane-1,3-diyl group, a cyclopentane-1,3-diyl group, a cyclohexane-1,4-diyl group and a cyclooctane-1,5-diyl group; and divalent polycyclic alicyclic saturated hydrocarbon groups such as a norbornane-1,4-diyl group, a norbornane-2,5-diyl group, an adamantane-1,5-diyl group and an adamantane-2,6-diyl group.

Those in which —$CH_2$— included in the saturated hydrocarbon group are replaced by —O—, —S— or —CO— include, for example, divalent groups represented by formula (X1) to formula (X53). Before replacing —$CH_2$— included in the saturated hydrocarbon group by —O—, —S— or —CO—, the number of carbon atoms is 17 or less. In the following formulas, * and ** represent a bonding site, and * represents a bonding site to $A^{x1}$.

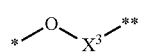 (X1)

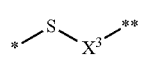 (X2)

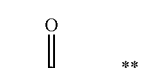 (X3)

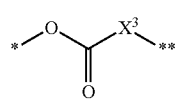 (X4)

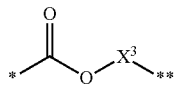 (X5)

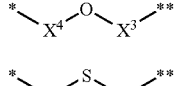 (X6)

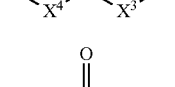 (X7)

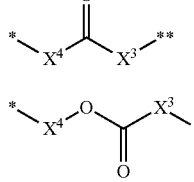 (X8)

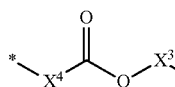 (X9)

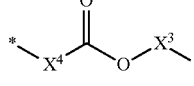 (X10)

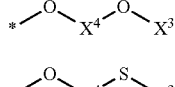 (X11)

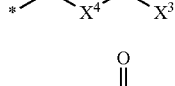 (X12)

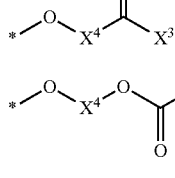 (X13)

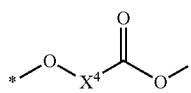 (X14)

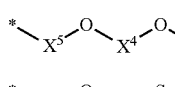 (X15)

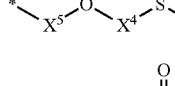 (X16)

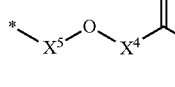 (X17)

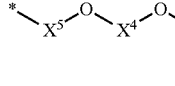 (X18)

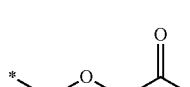 (X19)

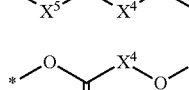 (X20)

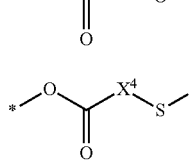 (X21)

(X22)

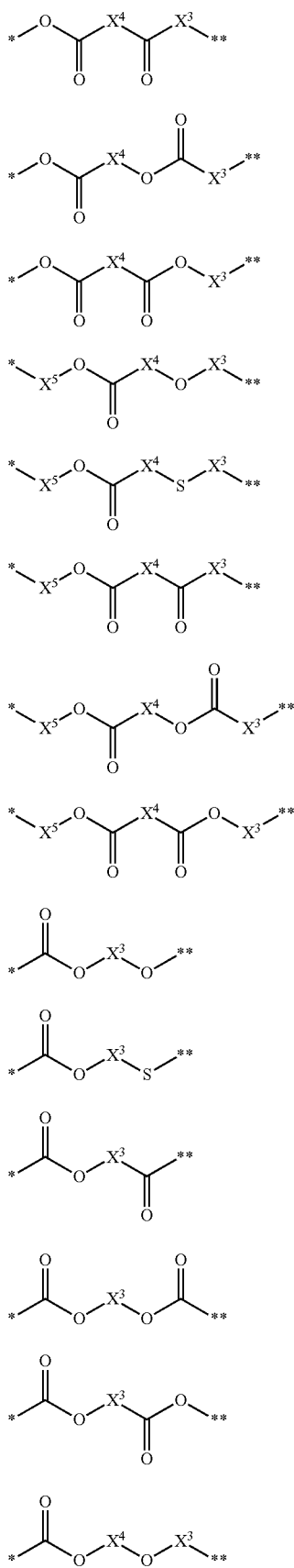
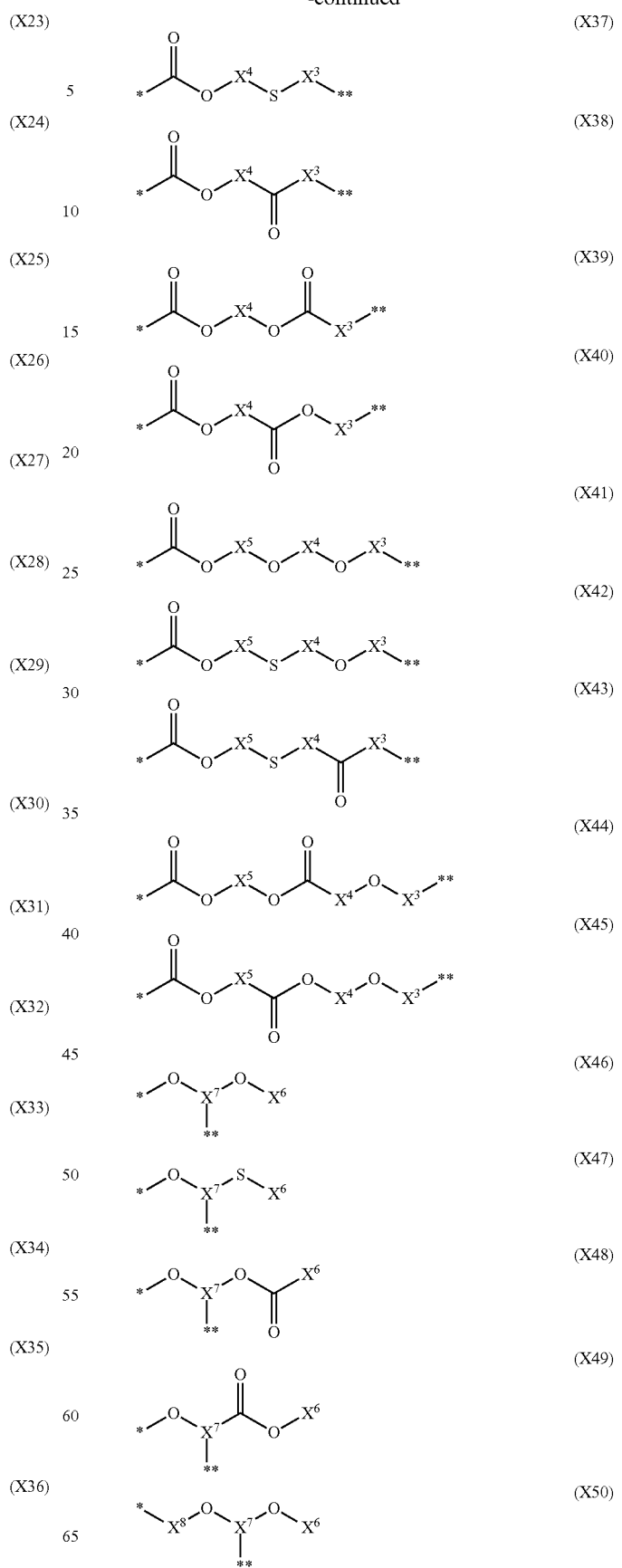

(X51)

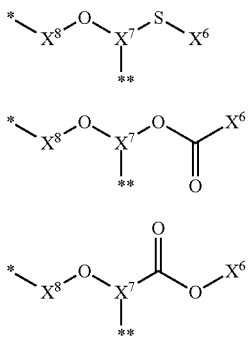

(X52)

(X53)

$X^3$ represents a divalent saturated hydrocarbon group having 1 to 16 carbon atoms.

$X^4$ represents a divalent saturated hydrocarbon group having 1 to 15 carbon atoms.

$X^5$ represents a divalent saturated hydrocarbon group having 1 to 13 carbon atoms.

$X^6$ represents a divalent saturated hydrocarbon group having 1 to 14 carbon atoms.

$X^7$ represents a divalent saturated hydrocarbon group having 1 to 14 carbon atoms.

$X^8$ represents a divalent saturated hydrocarbon group having 1 to 13 carbon atoms.

Examples of $ZA^+$ in formula (II-2-A') include those which are the same as the cation $Z^+$ in the salt represented by formula (B1) mentioned later.

The structural unit represented by formula (II-2-A') is preferably a structural unit represented by formula (II-2-A):

(II-2-A)

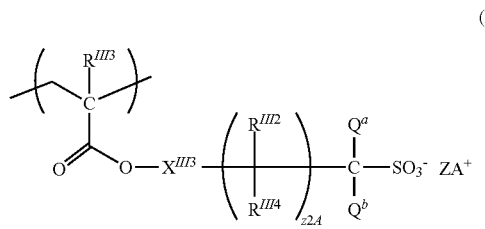

wherein, in formula (II-2-A), $R^{III3}$, $X^{III3}$ and $ZA^+$ are the same as defined above, z2A represents an integer of 0 to 6, $R^{III2}$ and $R^{III4}$ each independently represent a hydrogen atom, a fluorine atom or a perfluoroalkyl group having 1 to 6 carbon atoms, and when z2A is 2 or more, a plurality of $R^{III2}$ and $R^{III4}$ may be the same or different from each other, and $Q^a$ and $Q^b$ each independently represent a fluorine atom or a perfluoroalkyl group having 1 to 6 carbon atoms.

Examples of the perfluoroalkyl group having 1 to 6 carbon atoms represented by $R^{III2}$, $R^{III4}$, $Q^a$ and $Q^b$ include those which are the same as the perfluoroalkyl group having 1 to 6 carbon atoms represented by the below-mentioned $Q^{b1}$.

The structural unit represented by formula (II-2-A) is preferably a structural unit represented by formula (II-2-A-1):

(II-2-A-1)

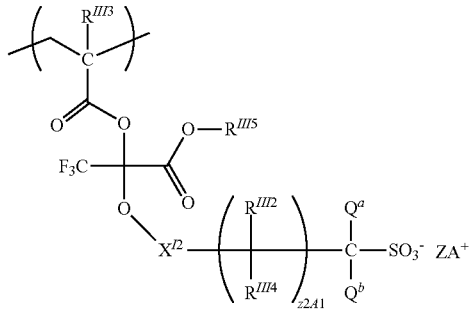

wherein, in formula (II-2-A-1), $R^{III2}$, $R^{III3}$, $R^{III4}$, $Q^a$, $Q^b$ and $ZA^+$ are the same as defined above, $R^{III5}$ represents a saturated hydrocarbon group having 1 to 12 carbon atoms, z2A1 represents an integer of 0 to 6, and $X^{12}$ represents a divalent saturated hydrocarbon group having 1 to 11 carbon atoms, —$CH_2$— included in the saturated hydrocarbon group may be replaced by —O—, —S— or —CO—, and a hydrogen atom included in the saturated hydrocarbon group may be substituted with a halogen atom or a hydroxy group.

Examples of the saturated hydrocarbon group having 1 to 12 carbon atoms represented by $R^{III5}$ include linear or branched alkyl groups such as a methyl group, an ethyl group, a propyl group, an isopropyl group, a butyl group, a sec-butyl group, a tert-butyl group, a pentyl group, a hexyl group, a heptyl group, an octyl group, a nonyl group, a decyl group, an undecyl group and a dodecyl group.

Examples of the divalent saturated hydrocarbon group represented by $X^{12}$ include the same as those of the divalent saturated hydrocarbon group represented by $X^{III3}$, The structural unit represented by formula (II-2-A-1) is more preferably a structural unit represented by formula (II-2-A-2):

(II-2-A-2)

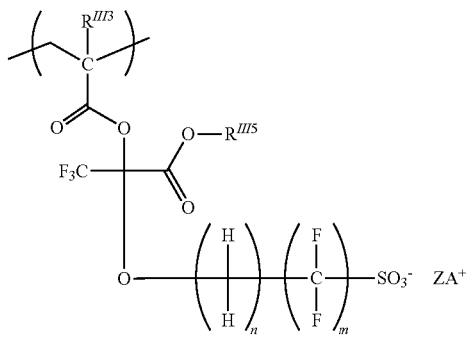

wherein, in formula (II-2-A-2), $R^{III3}$, $R^{III5}$ and $ZA^+$ are the same as defined above, and m and n each independently represent 1 or 2.

Examples of structural unit represented by the formula (II-2-A') include the following structural units, structural units in which a group corresponding to a methyl group of $R^{III3}$ is substituted with a hydrogen atom, a halogen atom (e.g., a fluorine atom) or an alkyl group having 1 to 6 carbon atoms which may have a halogen atom (e.g., a trifluoromethyl group, etc.), and the structural units mentioned in WO 2012/050015 A. ZA+ represents an organic cation.
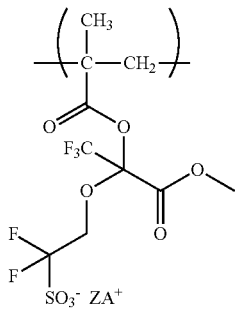
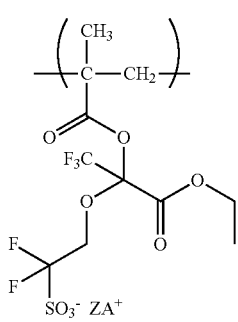
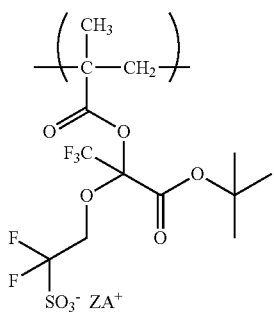
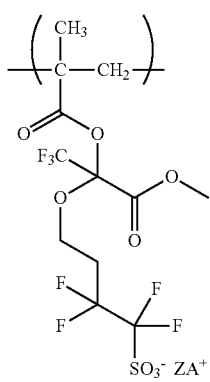
-continued
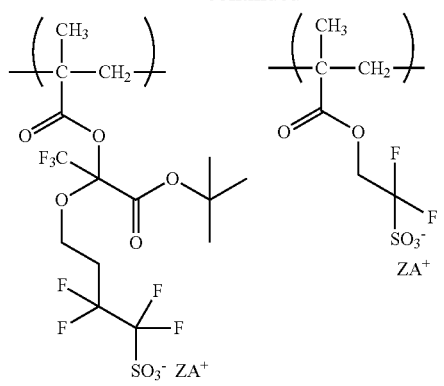
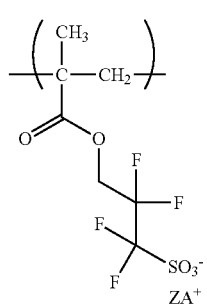
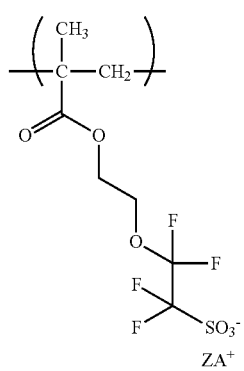
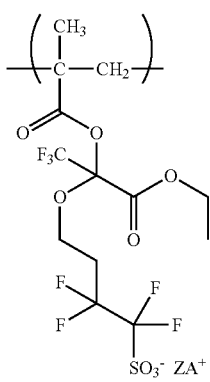
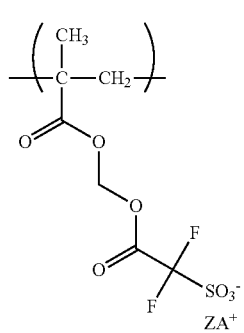

-continued

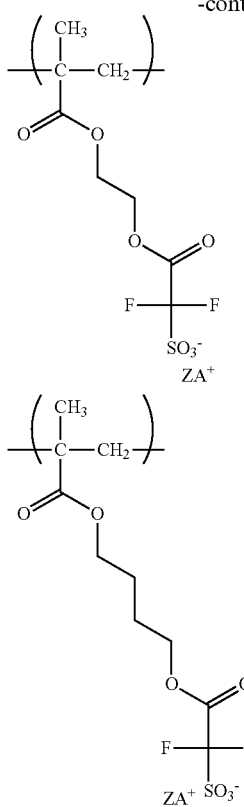

The structural unit having a sulfonio group and an organic anion in a side chain is preferably a structural unit represented by formula (II-1-1)

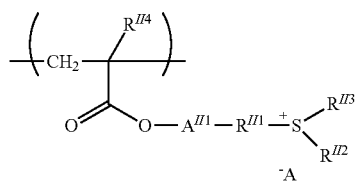
(II-1-1)

wherein, in formula (II-1-1), $A^{II1}$ represents a single bond or a divalent linking group, $R^{II1}$ represents a divalent aromatic hydrocarbon group having 6 to 18 carbon atoms, $R^{II2}$ and $R^{II3}$ each independently represent a hydrocarbon group having 1 to 18 carbon atoms, and $R^{II2}$ and $R^{II3}$ may be bonded each other to form a ring together with a sulfur atom to which $R^{II2}$ and $R^{II3}$ are bonded, $R^{II4}$ represents a hydrogen atom, a halogen atom or an alkyl group having 1 to 6 carbon atoms which may have a halogen atom, and $A^-$ represents an organic anion.

Examples of the divalent aromatic hydrocarbon group having 6 to 18 carbon atoms represented by $R^{II1}$ include a phenylene group and a naphthylene group.

Examples of the hydrocarbon group represented by $R^{II2}$ and $R^{II3}$ include an alkyl group, an alicyclic hydrocarbon group, an aromatic hydrocarbon group, and groups formed by combining these groups.

Examples of the halogen atom represented by $R^{II4}$ include a fluorine atom, a chlorine atom, a bromine atom and an iodine atom.

Examples of the alkyl group having 1 to 6 carbon atoms which may have a halogen atom represented by $R^{II4}$ include those which are the same as the alkyl group having 1 to 6 carbon atoms which may have a halogen atom represented by $R^{a8}$.

Examples of the divalent linking group represented by $A^{II1}$ include a divalent saturated hydrocarbon group having 1 to 18 carbon atoms, and —$CH_2$— included in the divalent saturated hydrocarbon group may be replaced by —O—, —S— or —CO—. Specific examples thereof include those which are the same as the divalent saturated hydrocarbon group having 1 to 18 carbon atoms represented by $X^{III3}$.

Examples of the structural unit including a cation in formula (II-1-1) include the following structural units and structural units in which a group corresponding to a methyl group of $R^{II4}$ is substituted with a hydrogen atom, a fluorine atom, a trifluoromethyl group or the like.

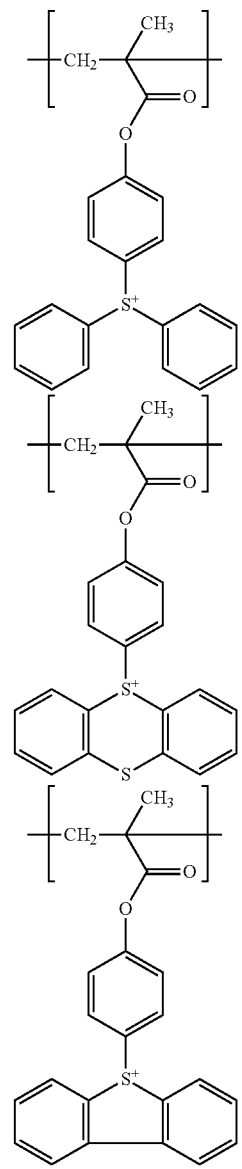

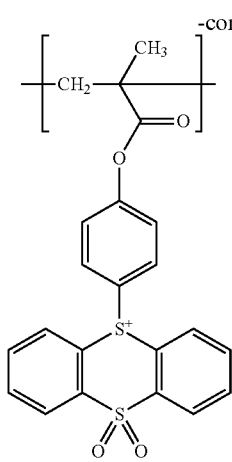
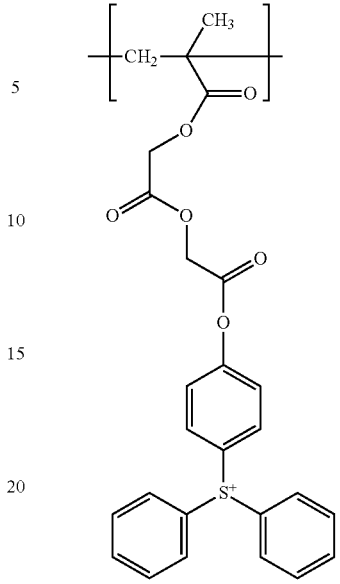
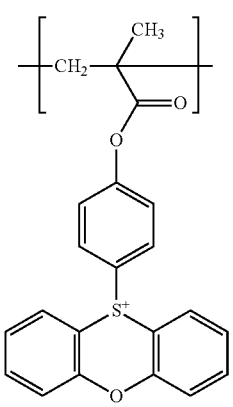
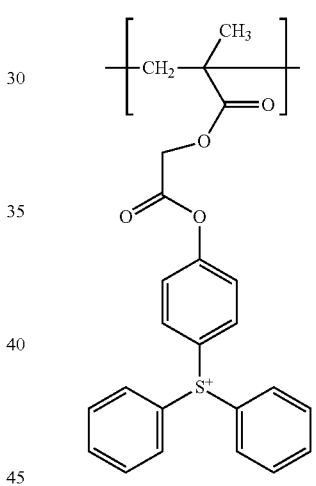
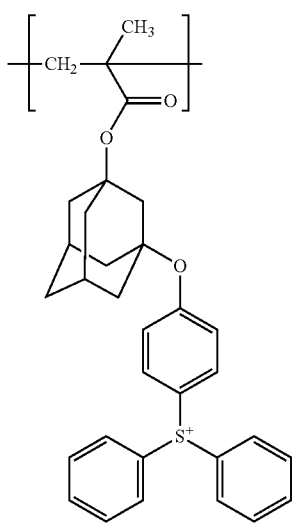

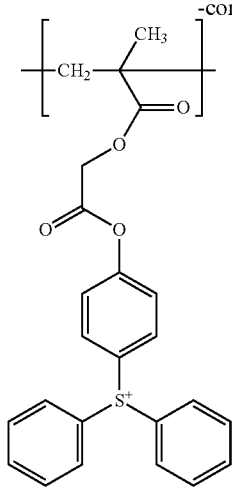

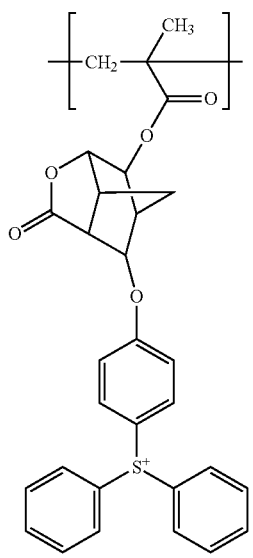

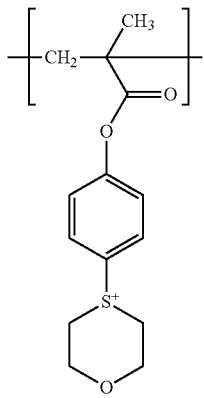

Examples of the organic anion represented by A⁻ include a sulfonic acid anion, a sulfonylimide anion, a sulfonylmethide anion and a carboxylic acid anion. The organic anion represented by A is preferably a sulfonic acid anion, and the sulfonic acid anion is more preferably an anion included in the above-mentioned salt represented by formula (B1).

Examples of the sulfonylimide anion represented by A⁻ include the followings.

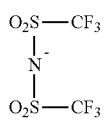 (I-b-1)

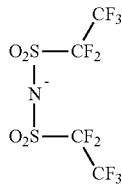 (I-b-2)

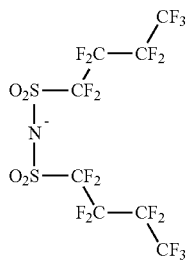 (I-b-3)

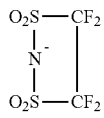 (I-b-4)

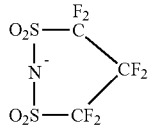 (I-b-5)

Examples of the sulfonylmethide anion include the followings.

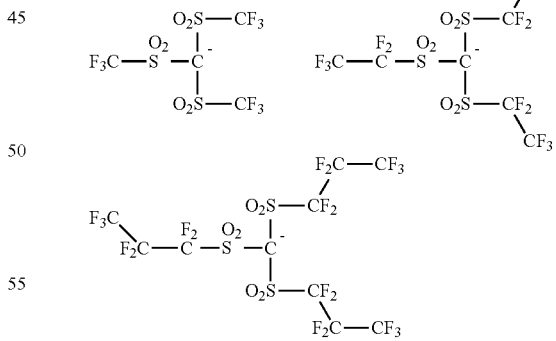

Examples of the carboxylic acid anion include the followings.

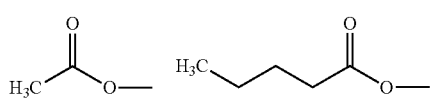

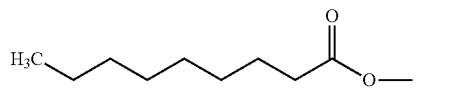
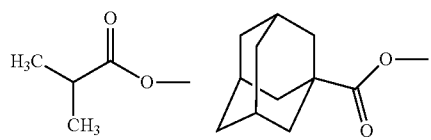
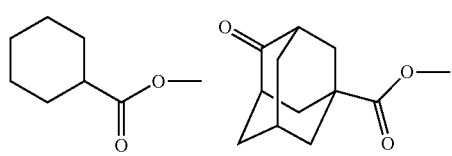
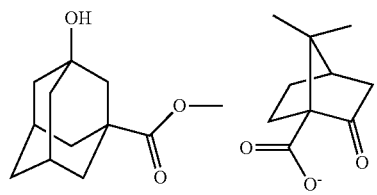
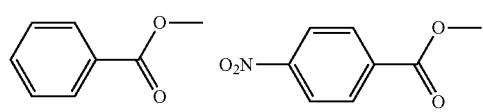
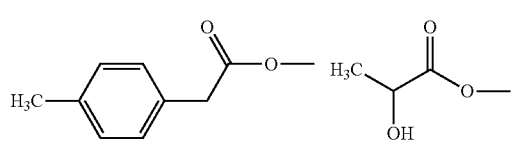
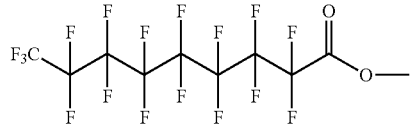
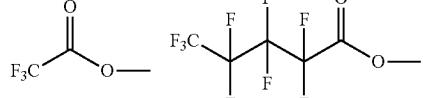
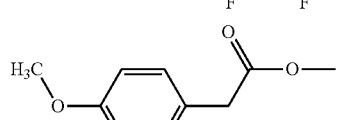
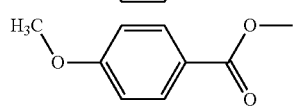
Examples of the structural unit represented by formula (II-1-1) include the following structural units.
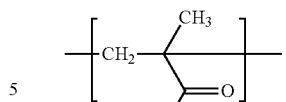
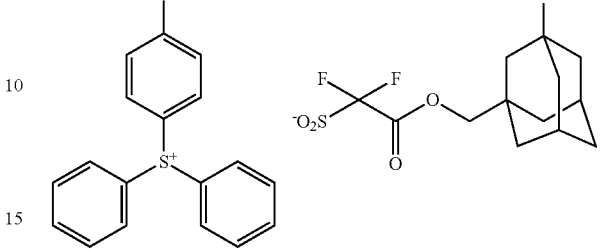
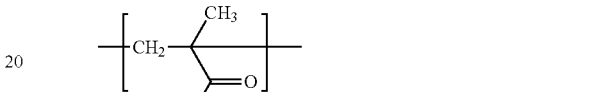
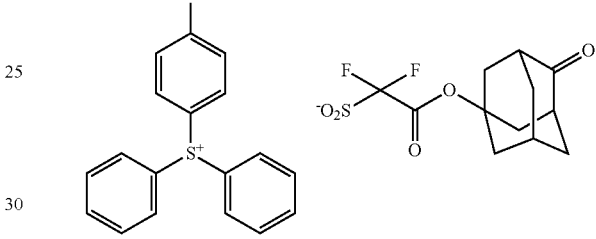
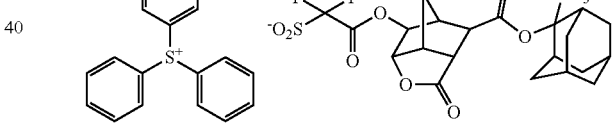
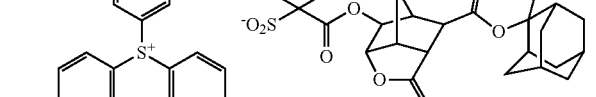
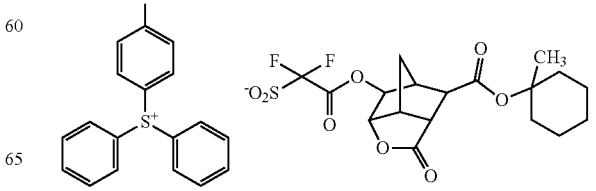

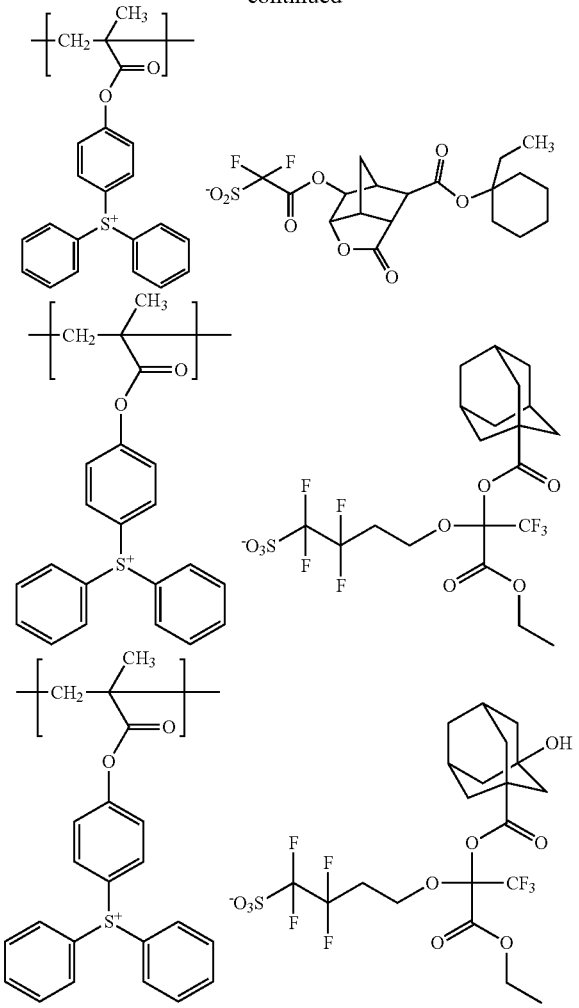

When the structural unit (II) is included in the resin (A), the content of the structural unit (II) is preferably 1 to 20 mol %, more preferably 2 to 15 mol %, and still more preferably 3 to 10 mol %, based on all structural units of the resin (A).

The resin (A) may include a structural unit other than the above-mentioned structural units, and examples of the structural unit include structural units well-known in this technical field.

The resin (A) is preferably a resin composed of a structural unit (I) and a structural unit (a1), a resin composed of a structural unit (I) and a structural unit (s), a resin composed of a structural unit (I), a structural unit (a1) and a structural unit (s), a resin composed of a structural unit (I), a structural unit (a1), a structural unit (s), a structural unit (a4) and/or a structural unit (a5), a resin composed only of a structural unit (I), or a resin composed only of a structural unit (I) and a structural unit (a4), and more preferably a resin composed of a structural unit (I) and a structural unit (a1), a resin composed of a structural unit (I) and a structural unit (s) or a resin composed of a structural unit (I), a structural unit (a1) and a structural unit (s).

The structural unit (a1) is preferably at least one selected from the group consisting of a structural unit (a1-0), a structural unit (a1-0X), a structural unit (a1-1) and a structural unit (a1-2) (preferably a structural unit having a cyclohexyl group or a cyclopentyl group), and more preferably at least two selected from the group consisting of a structural unit (a1-0), a structural unit (a1-0X), a structural unit (a1-1) and a structural unit (a1-2) (preferably a structural unit having a cyclohexyl group or a cyclopentyl group).

The structural unit (s) is preferably at least one selected from the group consisting of a structural unit (a2) and a structural unit (a3). The structural unit (a2) is preferably a structural unit (a2-1) or a structural unit (a2-A). The structural unit (a3) is preferably at least one selected from the group consisting of a structural unit represented by formula (a3-1), a structural unit represented by formula (a3-2) and a structural unit represented by formula (a3-4).

The respective structural units constituting the resin (A) may be used alone, or two or more structural units may be used in combination. Using a monomer from which these structural units are derived, it is possible to produce by a known polymerization method (e.g., radical polymerization method). The content of the respective structural units included in the resin (A) can be adjusted according to the amount of the monomer used in the polymerization.

The weight-average molecular weight of the resin (A) is preferably 2,000 or more (more preferably 2,500 or more, and still more preferably 3,000 or more), and 50,000 or less (more preferably 30,000 or less, and still more preferably 15,000 or less).

In the present specification, the weight-average molecular weight is a value determined by gel permeation chromatography. The gel permeation chromatography can be measured under the analysis conditions mentioned in Examples.

[Resist Composition]

The resist composition of the present invention preferably includes a resin (A) and an acid generator known in a resist field (hereinafter sometimes referred to as "acid generator (B)").

The resist composition of the present invention may further include a resin other than resin (A).

The resist composition of the present invention preferably includes a quencher such as a salt generating an acid having an acidity lower than that of an acid generated from an acid generator (hereinafter sometimes referred to as "quencher (C)"), and preferably includes a solvent (hereinafter sometimes referred to as "solvent (E)").

<Resin Other than Resin (A)>

In the resist composition of the present invention, a resin other than resin (A) may be used in combination. The resin other than resin (A) is a resin including no structural unit (I), and examples of the resin include a resin including a structural unit having an acid-labile group and including no structural unit (I) (hereinafter sometimes referred to as "resin (AY)"), a resin composed only of a structural unit (a4), and a resin composed of a structural unit (a4) and a structural unit (a5) (hereinafter, a resin composed only of a structural unit (a4) and a resin composed of a structural unit (a4) and a structural unit (a5) may be sometimes referred collectively as resin (X)).

In the resin (X), the content of the structural unit (a4) is preferably 30 mol % or more, more preferably 40 mol % or more, and still more preferably 45 mol % or more, based on the total of all structural units of the resin X).

The respective structural unit constituting the resin (X) may be used alone, or two or more structural units may be used in combination. Using a monomer from which these structural units are derived, it is possible to produce by a known polymerization method (e.g., radical polymerization method). The content of the respective structural units included in the resin (X) can be adjusted according to the amount of the monomer used in the polymerization.

Each weight-average molecular weight of the resin (AY) and the resin (X) is preferably 6,000 or more (more preferably 7,000 or more), and 80,000 or less (more preferably 60,000 or less). The measurement means of the weight-average molecular weight of the resin (AY) and the resin (X) is the same as in the case of the resin (A).

When the resist composition of the present invention includes the resin (AY), the content is usually 1 to 2,500 parts by mass (more preferably 10 to 1,000 parts by mass) based on 100 parts by mass of the resin (A).

When the resist composition includes the resin (X), the content is preferably 1 to 60 parts by mass, more preferably 1 to 50 parts by mass, still more preferably 1 to 40 parts by mass, particularly preferably 1 to 30 parts by mass, and particularly preferably 1 to 8 parts by mass, based on 100 parts by mass of the resin (A).

The content of the resin (A) in the resist composition is preferably 80% by mass or more and 99% by mass or less, and more preferably 90% by mass or more and 99% by mass or less, based on the solid component of the resist composition. When including the resin other than the resin (A), the total content of the resin (A) and the resin other than the resin (A) is preferably 80% by mass or more and 99% by mass or less, and more preferably 90% by mass or more and 99% by mass or less, based on the solid component of the resist composition. The solid component of the resist composition and the content of the resin thereto can be measured by a known analysis means such as liquid chromatography or gas chromatography.

<Acid Generator (B)>

Either nonionic or ionic acid generator may be used as the acid generator (B). Examples of the nonionic acid generator include sulfonate esters (e.g., 2-nitrobenzyl ester, aromatic sulfonate, oxime sulfonate, N-sulfonyloxyimide, sulfonyloxyketone, diazonaphthoquinone 4-sulfonate), sulfones (e.g., disulfone, ketosulfone, sulfonyldiazomethane) and the like. Typical examples of the ionic acid generator include onium salts containing an onium cation (e.g., diazonium salt, phosphonium salt, sulfonium salt, iodonium salt). Examples of the anion of the onium salt include sulfonic acid anion, sulfonylimide anion, sulfonylmethide anion and the like.

Specific examples of the acid generator (B) include compounds generating an acid upon exposure to radiation mentioned in JP 63-26653 A, JP 55-164824 A, JP 62-69263 A, JP 63-146038 A, JP 63-163452 A, JP 62-153853 A, JP 63-146029 A, U.S. Pat. Nos. 3,779,778, 3,849,137, DE Patent No. 3914407 and EP Patent No. 126,712. Compounds produced by a known method may also be used. Two or more acid generators (B) may also be used in combination.

The acid generator (B) is preferably a fluorine-containing acid generator, and more preferably a salt represented by formula (B1) (hereinafter sometimes referred to as "acid generator (B1)"):

(B1)

wherein, in formula (B1), $Q^{b1}$ and $Q^{b2}$ each independently represent a fluorine atom or a perfluoroalkyl group having 1 to 6 carbon atoms, $L^{b1}$ represents a divalent saturated hydrocarbon group having 1 to 24 carbon atoms, —$CH_2$— included in the divalent saturated hydrocarbon group may be replaced by —O— or —CO—, and a hydrogen atom included in the saturated hydrocarbon group may be substituted with a fluorine atom or a hydroxy group, Y represents a methyl group which may have a substituent or an alicyclic hydrocarbon group having 3 to 18 carbon atoms which may have a substituent, and —$CH_2$— included in the alicyclic hydrocarbon group may be replaced by —O—, —$S(O)_2$— or —CO—, and $Z^+$ represents an organic cation.

Examples of the perfluoroalkyl group represented by $Q^{b1}$ and $Q^{b2}$ include a trifluoromethyl group, a perfluoroethyl group, a perfluoropropyl group, a perfluoroisopropyl group, a perfluorobutyl group, a perfluorosec-butyl group, a perfluorotert-butyl group, a perfluoropentyl group and a perfluorohexyl group.

Preferably, $Q^{b1}$ and $Q^{b2}$ are each independently a fluorine atom or trifluoromethyl group, and more preferably, both are fluorine atoms.

Examples of the divalent saturated hydrocarbon group in $L^{b1}$ include a linear alkanediyl group, a branched alkanediyl group, and a monocyclic or polycyclic divalent alicyclic saturated hydrocarbon group, or the divalent saturated hydrocarbon group may be a group formed by using two or more of these groups in combination.

Specific examples thereof include linear alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group;

branched alkanediyl groups such as an ethane-1,1-diyl group, a propane-1,1-diyl group, a propane-1,2-diyl group, a propane-2,2-diyl group, a pentane-2,4-diyl group, a 2-methylpropane-1,3-diyl group, a 2-methylpropane-1,2-diyl group, a pentane-1,4-diyl group and a 2-methylbutane-1,4-diyl group;

monocyclic divalent alicyclic saturated hydrocarbon groups which are cycloalkanediyl groups such as a cyclobutane-1,3-diyl group, a cyclopentane-1,3-diyl group, a cyclohexane-1,4-diyl group and a cyclooctane-1,5-diyl group; and polycyclic divalent alicyclic saturated hydrocarbon groups such as a norbornane-1,4-diyl group, a norbornane-2,5-diyl group, an adamantane-1,5-diyl group and an adamantane-2,6-diyl group.

The group in which —$CH_2$— included in the divalent saturated hydrocarbon group represented by $L^{b1}$ is replaced by —O— or —CO— includes, for example, a group represented by any one of formula (b1-1) to formula (b1-3). In groups represented by formula (b1-1) to formula (b1-3) and groups represented by formula (b1-4) to formula (b1-11) which are specific examples thereof, * and ** represent a bonding site, and * represents a bonding site to —Y.

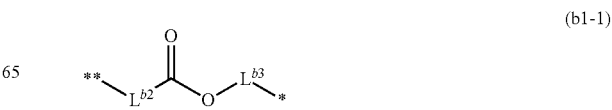

(b1-1)

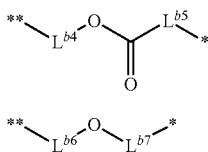
(b1-2)

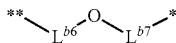
(b1-3)

In formula (b1-1), $L^{b2}$ represents a single bond or a divalent saturated hydrocarbon group having 1 to 22 carbon atoms, and a hydrogen atom included in the saturated hydrocarbon group may be substituted with a fluorine atom, $L^{b3}$ represents a single bond or a divalent saturated hydrocarbon group having 1 to 22 carbon atoms, a hydrogen atom included in the saturated hydrocarbon group may be substituted with a fluorine atom or a hydroxy group, and —$CH_2$— included in the saturated hydrocarbon group may be replaced by —O— or —CO—, and the total number of carbon atoms of $L^{b2}$ and $L^{b3}$ is 22 or less.

In formula (b1-2), $L^{b4}$ represents a single bond or a divalent saturated hydrocarbon group having 1 to 22 carbon atoms, and a hydrogen atom included in the saturated hydrocarbon group may be substituted with a fluorine atom, $L^{b5}$ represents a single bond or a divalent saturated hydrocarbon group having 1 to 22 carbon atoms, a hydrogen atom included in the saturated hydrocarbon group may be substituted with a fluorine atom or a hydroxy group, and —$CH_2$— included in the saturated hydrocarbon group may be replaced by —O— or —CO—, and the total number of carbon atoms of $L^{b4}$ and $L^{b5}$ is 22 or less.

In formula (b1-3), $L^{b6}$ represents a single bond or a divalent saturated hydrocarbon group having 1 to 23 carbon atoms, and a hydrogen atom included in the saturated hydrocarbon group may be substituted with a fluorine atom or a hydroxy group, $L^{b7}$ represents a single bond or a divalent saturated hydrocarbon group having 1 to 23 carbon atoms, a hydrogen atom included in the saturated hydrocarbon group may be substituted with a fluorine atom or a hydroxy group, and —$CH_2$— included in the saturated hydrocarbon group may be replaced by —O— or —CO—, and the total number of carbon atoms of $L^{b6}$ and $L^{b7}$ is 23 or less.

In groups represented by formula (b1-1) to formula (b1-3), when —$CH_2$— included in the saturated hydrocarbon group is replaced by —O— or —CO—, the number of carbon atoms before replacement is taken as the number of carbon atoms of the saturated hydrocarbon group.

Examples of the divalent saturated hydrocarbon group include those which are the same as the saturated hydrocarbon group of $L^{b1}$.

$L^{b2}$ is preferably a single bond.

$L^{b3}$ is preferably a divalent saturated hydrocarbon group having 1 to 4 carbon atoms.

$L^{b4}$ is preferably a divalent saturated hydrocarbon group having 1 to 8 carbon atoms, and a hydrogen atom included in the divalent saturated hydrocarbon group may be substituted with a fluorine atom.

$L^{b5}$ is preferably a single bond or a divalent saturated hydrocarbon group having 1 to 8 carbon atoms.

$L^{b6}$ is preferably a single bond or a divalent saturated hydrocarbon group having 1 to 4 carbon atoms, a hydrogen atom included in the saturated hydrocarbon group may be substituted with a fluorine atom.

$L^{b7}$ is preferably a single bond or a divalent saturated hydrocarbon group having 1 to 18 carbon atoms, a hydrogen atom included in the saturated hydrocarbon group may be substituted with a fluorine atom or a hydroxy group, and —$CH_2$— included in the divalent saturated hydrocarbon group may be replaced by —O— or —CO—.

The group in which —$CH_2$— included in the divalent saturated hydrocarbon group represented by $L^{b1}$ is replaced by —O— or —CO— is preferably a group represented by formula (b1-1) or formula (b1-3).

Examples of the group represented by formula (b1-1) include groups represented by formula (b1-4) to formula (b1-8).

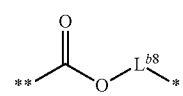
(b1-4)

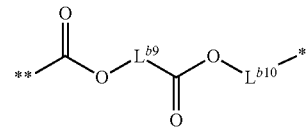
(b1-5)

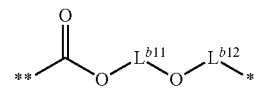
(b1-6)

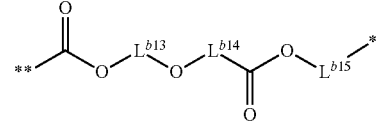
(b1-7)

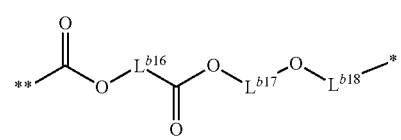
(b1-8)

In formula (b1-4), $L^{b8}$ represents a single bond or a divalent saturated hydrocarbon group having 1 to 22 carbon atoms, and a hydrogen atom included in the saturated hydrocarbon group may be substituted with a fluorine atom or a hydroxy group.

In formula (b1-5), $L^{b9}$ represents a divalent saturated hydrocarbon group having 1 to 20 carbon atoms, and —$CH_2$— included in the divalent saturated hydrocarbon group may be replaced by —O— or —CO—, $L^{b10}$ represents a single bond or a saturated hydrocarbon group having 1 to 19 carbon atoms, and a hydrogen atom included in the divalent saturated hydrocarbon group may be substituted with a fluorine atom or a hydroxy group, and the total number of carbon atoms of $L^{b9}$ and $L^{b10}$ is 20 or less.

In formula (b1-6), $L^{b11}$ represents a divalent saturated hydrocarbon group having 1 to 21 carbon atoms, $L^{b12}$ represents a single bond or a divalent saturated hydrocarbon group having 1 to 20 carbon atoms, and a hydrogen atom included in the divalent saturated hydrocarbon group may be substituted with a fluorine atom or a hydroxy group, and the total number of carbon atoms of $L^{b11}$ and $L^{b12}$ is 21 or less.

In formula (b1-7),
$L^{b13}$ represents a divalent saturated hydrocarbon group having 1 to 19 carbon atoms,
$L^{b14}$ represents a single bond or a divalent saturated hydrocarbon group having 1 to 18 carbon atoms, and —CH$_2$— included in the divalent saturated hydrocarbon group may be replaced by —O— or —CO—,
$L^{b15}$ represents a single bond or a divalent saturated hydrocarbon group having 1 to 18 carbon atoms, and a hydrogen atom included in the divalent saturated hydrocarbon group may be substituted with a fluorine atom or a hydroxy group, and
the total number of carbon atoms of $L^{b13}$ to $L^{b15}$ is 19 or less.

In formula (b1-8),
$L^{b16}$ represents a divalent saturated hydrocarbon group having 1 to 18 carbon atoms, and —CH$_2$— included in the divalent saturated hydrocarbon group may be replaced by —O— or —CO—,
$L^{b17}$ represents a divalent saturated hydrocarbon group having 1 to 18 carbon atoms,
$L^{b18}$ represents a single bond or a divalent saturated hydrocarbon group having 1 to 17 carbon atoms, and a hydrogen atom included in the divalent saturated hydrocarbon group may be substituted with a fluorine atom or a hydroxy group, and
the total number of carbon atoms of $L^{b16}$ to $L^{b18}$ is 19 or less.

$L^{b8}$ is preferably a divalent saturated hydrocarbon group having 1 to 4 carbon atoms.

$L^{b9}$ is preferably a divalent saturated hydrocarbon group having 1 to 8 carbon atoms.

$L^{b10}$ is preferably a single bond or a divalent saturated hydrocarbon group having 1 to 19 carbon atoms, and more preferably a single bond or a divalent saturated hydrocarbon group having 1 to 8 carbon atoms.

$L^{b11}$ is preferably a divalent saturated hydrocarbon group having 1 to 8 carbon atoms.

$L^{b12}$ is preferably a single bond or a divalent saturated hydrocarbon group having 1 to 8 carbon atoms.

$L^{b13}$ is preferably a divalent saturated hydrocarbon group having 1 to 12 carbon atoms.

$L^{b14}$ is preferably a single bond or a divalent saturated hydrocarbon group having 1 to 6 carbon atoms.

$L^{b15}$ is preferably a divalent saturated hydrocarbon group having 1 to 18 carbon atoms, and more preferably a single bond or a divalent saturated hydrocarbon group having 1 to 8 carbon atoms.

$L^{b16}$ is preferably a divalent saturated hydrocarbon group having 1 to 12 carbon atoms.

$L^{b17}$ is preferably a divalent saturated hydrocarbon group having 1 to 6 carbon atoms.

$L^{b18}$ is preferably a single bond or a divalent saturated hydrocarbon group having 1 to 17 carbon atoms, and more preferably a single bond or a divalent saturated hydrocarbon group having 1 to 4 carbon atoms.

Examples of the group represented by formula (b1-3) include groups represented by formula (b1-9) to formula (b1-11).

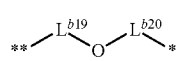
(b1-9)

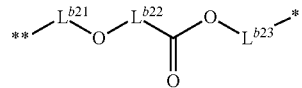
(b1-10)

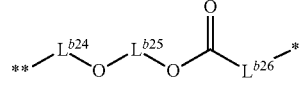
(b1-11)

In formula (b1-9),
$L^{b19}$ represents a single bond or a divalent saturated hydrocarbon group having 1 to 23 carbon atoms, and a hydrogen atom included in the saturated hydrocarbon group may be substituted with a fluorine atom,
$L^{b20}$ represents a single bond or a divalent saturated hydrocarbon group having 1 to 23 carbon atoms, and a hydrogen atom included in the saturated hydrocarbon group may be substituted with a fluorine atom, a hydroxy group or an alkylcarbonyloxy group, —CH$_2$— included in the alkylcarbonyloxy group may be replaced by —O— or —CO—, and a hydrogen atom included in the alkylcarbonyloxy group may be substituted with a hydroxy group, and
the total number of carbon atoms of $L^{b19}$ and $L^{b20}$ is 23 or less.

In formula (b1-10),
$L^{b21}$ represents a single bond or a divalent saturated hydrocarbon group having 1 to 21 carbon atoms, and a hydrogen atom included in the saturated hydrocarbon group may be substituted with a fluorine atom,
$L^{b22}$ represents a single bond or a divalent saturated hydrocarbon group having 1 to 21 carbon atoms,
$L^{b23}$ represents a single bond or a divalent saturated hydrocarbon group having 1 to 21 carbon atoms, and a hydrogen atom included in the saturated hydrocarbon group may be substituted with a fluorine atom, a hydroxy group or an alkylcarbonyloxy group, —CH$_2$— included in the alkylcarbonyloxy group may be replaced by —O— or —CO—, and a hydrogen atom included in the alkylcarbonyloxy group may be substituted with a hydroxy group, and
the total number of carbon atoms of $L^{b21}$, $L^{b22}$ and $L^{b23}$ is 21 or less.

In formula (b1-11),
$L^{b24}$ represents a single bond or a divalent saturated hydrocarbon group having 1 to 20 carbon atoms, and a hydrogen atom included in the saturated hydrocarbon group may be substituted with a fluorine atom,
$L^{b25}$ represents a divalent saturated hydrocarbon group having 1 to 21 carbon atoms,
$L^{b26}$ represents a single bond or a divalent saturated hydrocarbon group having 1 to 20 carbon atoms, a hydrogen atom included in the saturated hydrocarbon group may be substituted with a fluorine atom, a hydroxy group or an alkylcarbonyloxy group, —CH$_2$— included in the alkylcarbonyloxy group may be replaced by —O— or —CO—, and a hydrogen atom included in the alkylcarbonyloxy group may be substituted with a hydroxy group, and
the total number of carbon atoms of $L^{b24}$, $L^{b25}$ and $L^{b26}$ is 21 or less.

In the group represented by formula (b1-9) to the group represented by formula (b1-11), when a hydrogen atom included in the saturated hydrocarbon group is substituted with an alkylcarbonyloxy group, the number of carbon atoms before substitution is taken as the number of carbon atoms of the saturated hydrocarbon group.

Examples of the alkylcarbonyloxy group include an acetyloxy group, a propionyloxy group, a butyryloxy group, a cyclohexylcarbonyloxy group, an adamantylcarbonyloxy group and the like.

Examples of the group represented by formula (b1-4) include the followings:

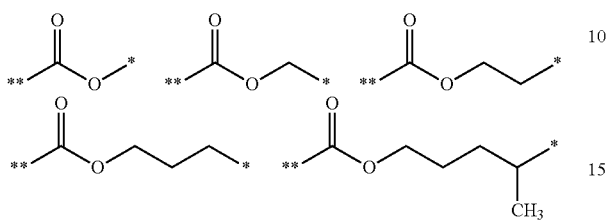

Examples of the group represented by formula (b1-5) include the followings:

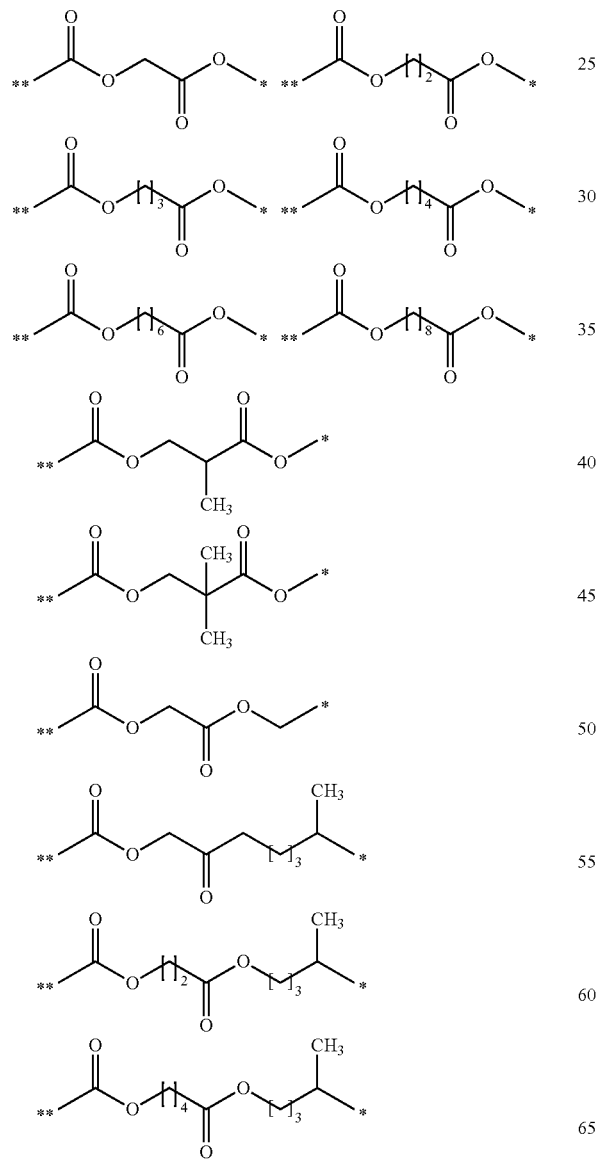

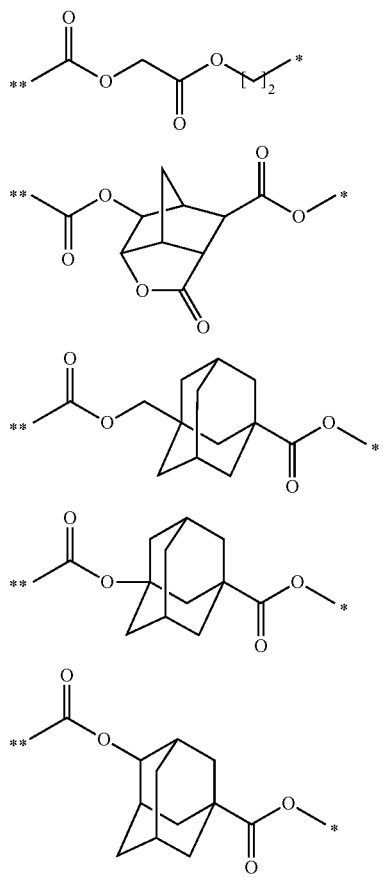

Examples of the group represented by formula (b1-6) include the followings:

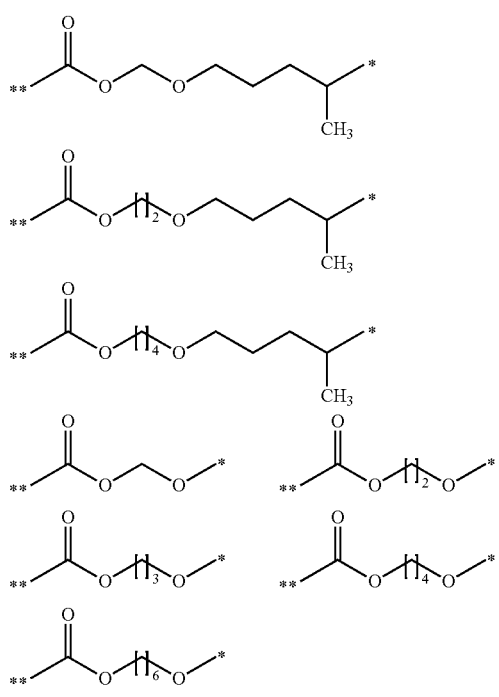

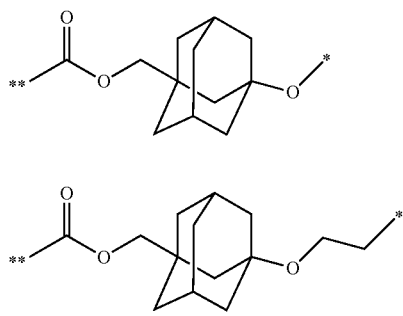
Examples of the group represented by formula (b1-7) include the followings:
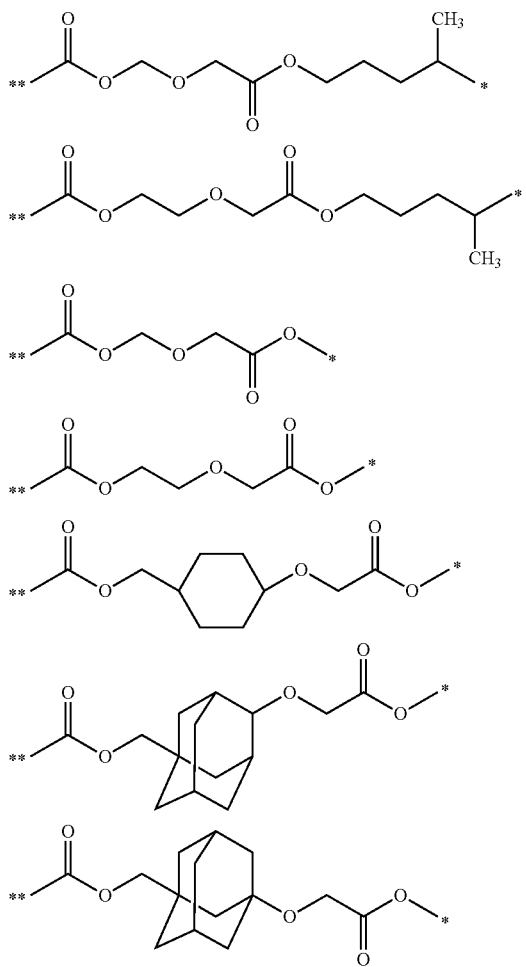
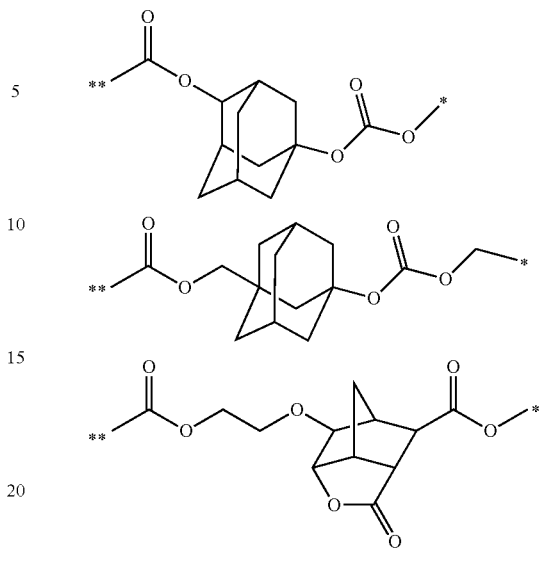
Examples of the group represented by formula (b1-8) include the followings:
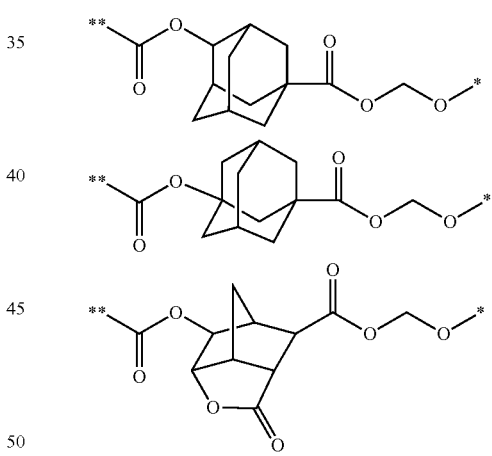
Examples of the group represented by formula (b1-2) include the followings:
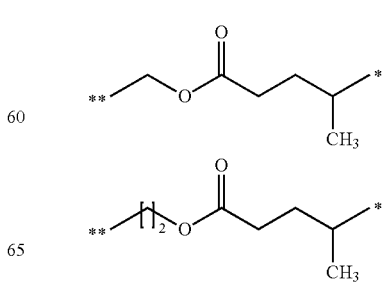

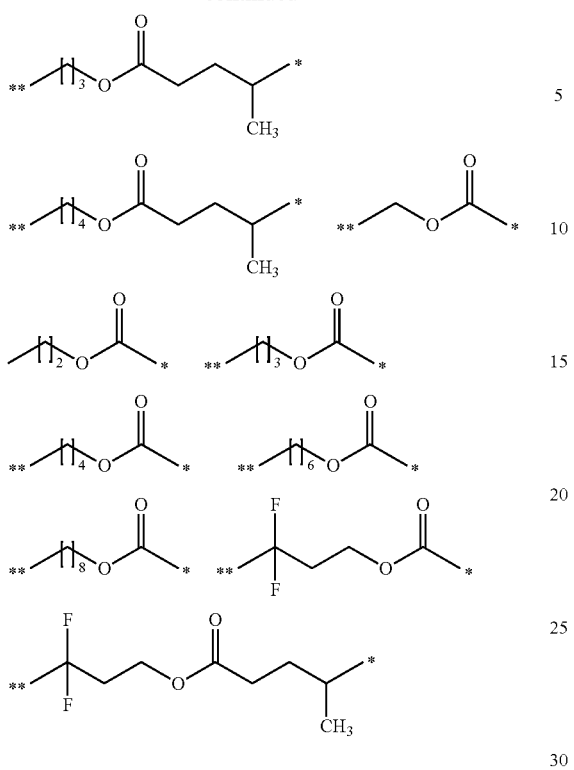
Examples of the group represented by formula (b1-9) include the followings:
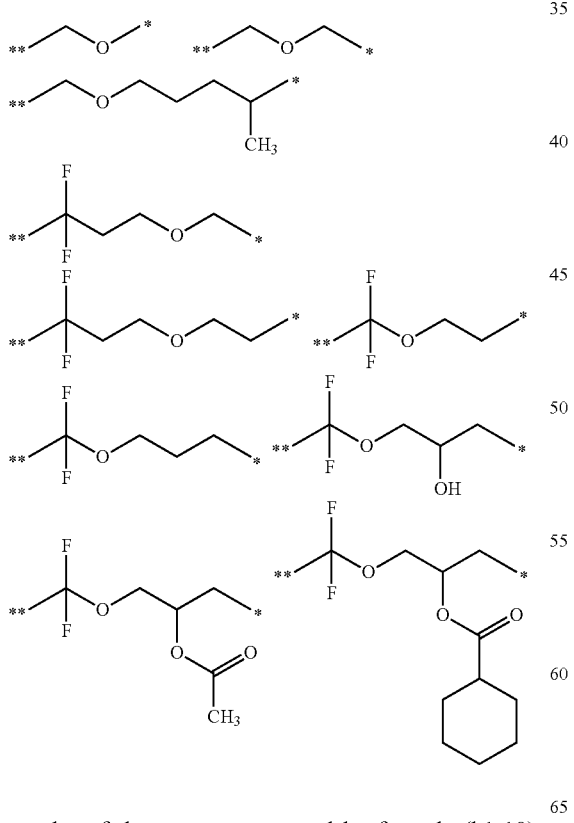
Examples of the group represented by formula (b1-10) include the followings:
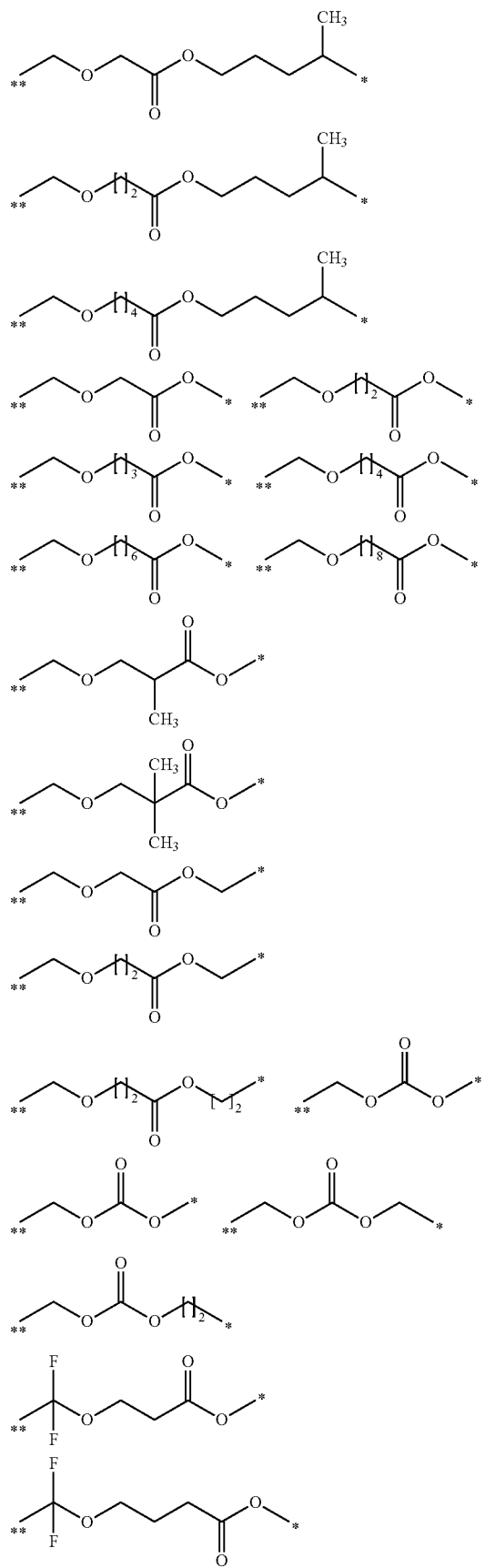

-continued
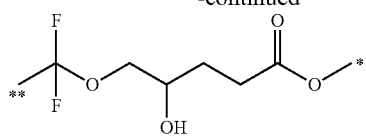
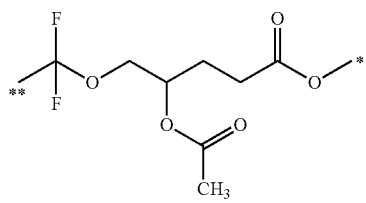
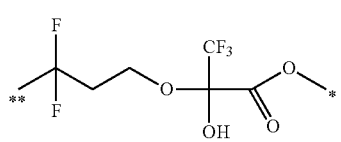
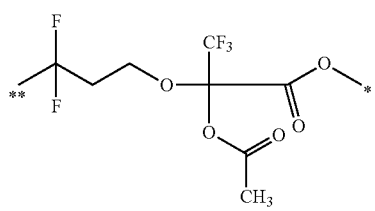
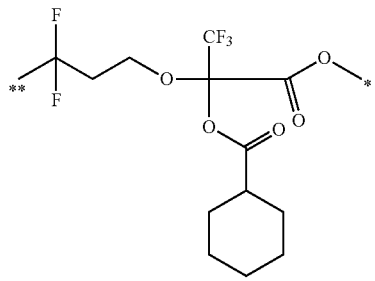
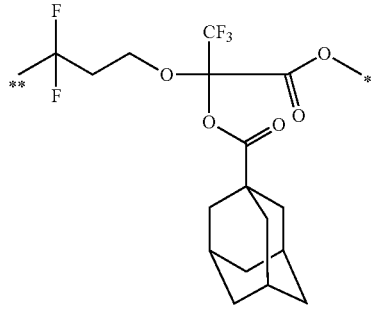
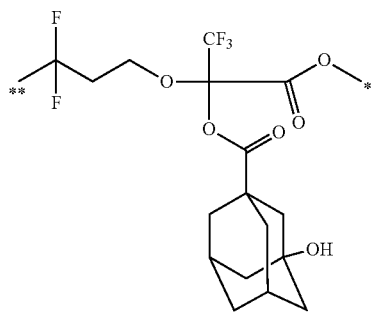
-continued
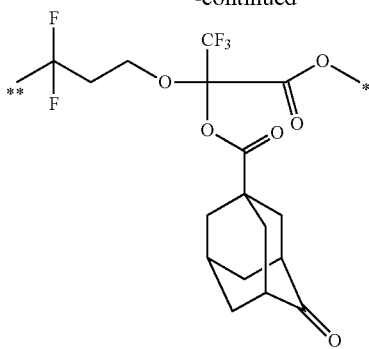
Examples of the group represented by formula (b1-11) include the followings:
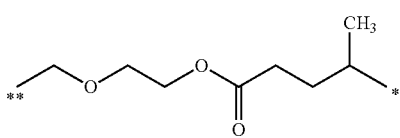
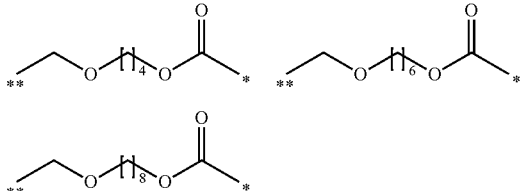
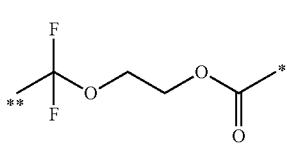
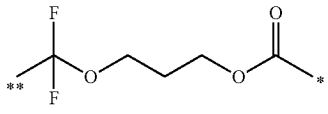
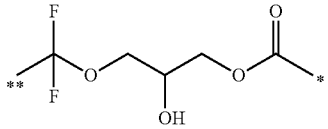
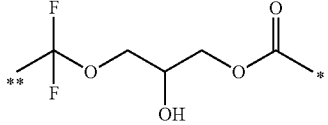
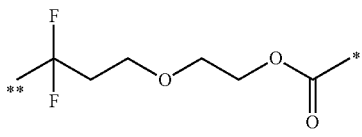
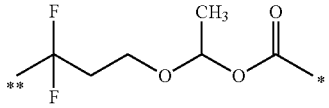

-continued

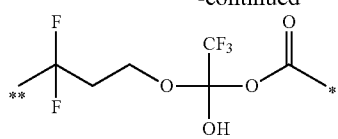
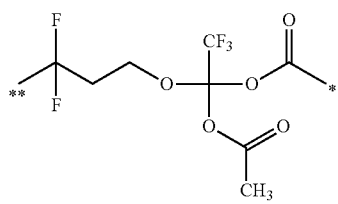
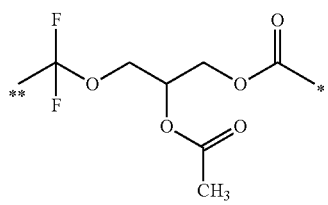
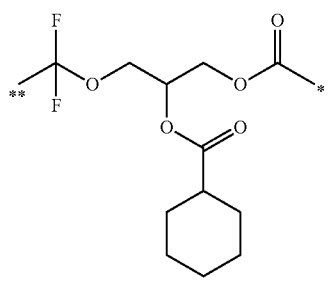
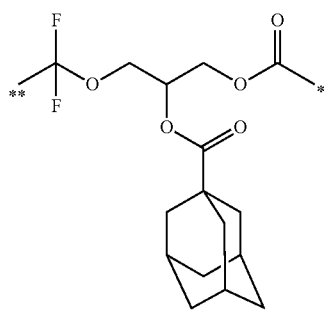
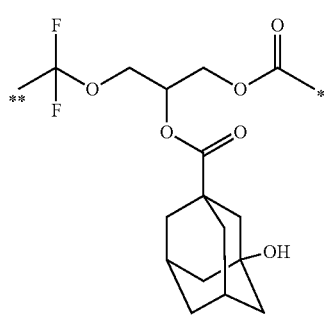

-continued

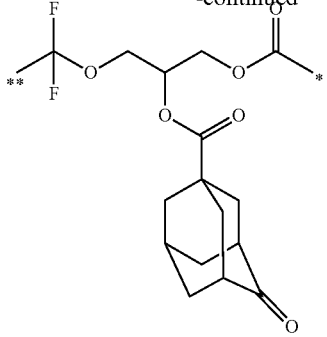

Examples of the alicyclic hydrocarbon group represented by Y include groups represented by formula (Y1) to formula (Y11) and formula (Y36) to formula (Y38).

When —CH$_2$— included in the alicyclic hydrocarbon group represented by Y is replaced by —O—, —S(O)$_2$— or —CO—, the number may be 1, or 2 or more. Examples of such group include groups represented by formula (Y12) to formula (Y35) and formula (Y39) and formula (Y41).

 (Y1)

 (Y2)

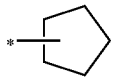 (Y3)

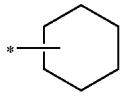 (Y4)

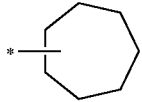 (Y5)

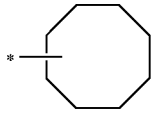 (Y6)

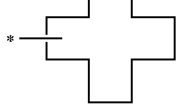 (Y7)

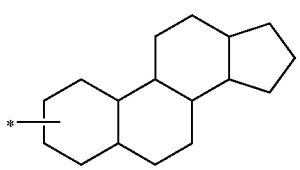 (Y8)

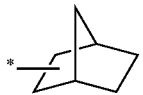 (Y9)

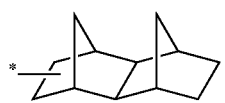 (Y10)
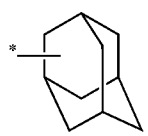 (Y11)
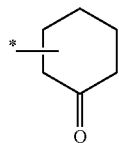 (Y12)
 (Y13)
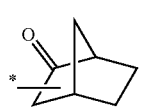 (Y14)
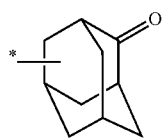 (Y15)
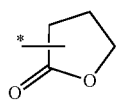 (Y16)
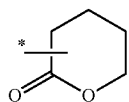 (Y17)
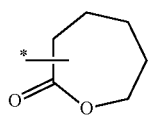 (Y18)
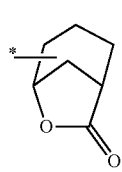 (Y19)
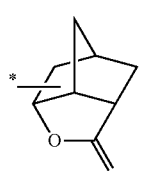 (Y20)
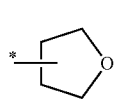 (Y21)
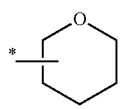 (Y22)
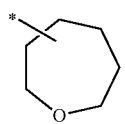 (Y23)
(Y24)
(Y25)
(Y26)
(Y27)
(Y28)
(Y29)
(Y30)

(Y31) 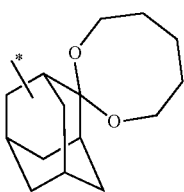

(Y32) 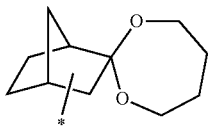

(Y33) 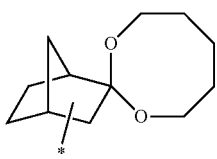

(Y34) 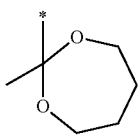

(Y35) 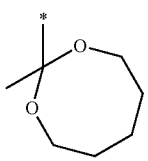

(Y36) 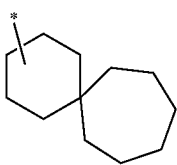

(Y37) 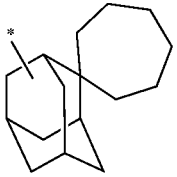

(Y38) 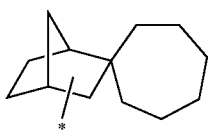

(Y39) 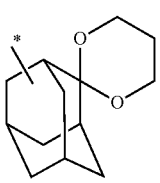

(Y40) 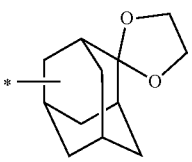

(Y41) 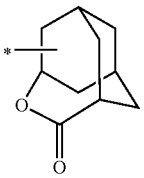

The alicyclic hydrocarbon group represented by Y is preferably a group represented by any one of formula (Y1) to formula (Y20), formula (Y26), formula (Y27), formula (Y30), formula (Y31) and formula (Y39) to formula (Y41), more preferably a group represented by formula (Y11), formula (Y15), formula (Y16), formula (Y20), formula (Y26), formula (Y27), formula (Y30), formula (Y31), formula (Y39) or formula (Y40), and still more preferably a group represented by formula (Y11), formula (Y15), formula (Y20), formula (Y26), formula (Y27), formula (Y30), formula (Y31), formula (Y39) or formula (Y40)

When the alicyclic hydrocarbon group represented by Y is a spiro ring containing an oxygen atom, such as formula (Y28) to formula (Y35) and formula (Y39) to formula (Y40), the alkanediyl group between two oxygen atoms preferably includes one or more fluorine atoms. Of alkanediyl groups included in a ketal structure, it is preferable that a methylene group adjacent to the oxygen atom is not substituted with a fluorine atom.

Examples of the substituent of the methyl group represented by Y include a halogen atom, a hydroxy group, an alicyclic hydrocarbon group having 3 to 16 carbon atoms, an aromatic hydrocarbon group having 6 to 18 carbon atoms, a glycidyloxy group, a —$(CH_2)_{ja}$—CO—O—$R^{b1}$ group or a —$(CH_2)_{ja}$—O—CO—$R^{b1}$ group (wherein $R^{b1}$ represents an alkyl group having 1 to 16 carbon atoms, an alicyclic hydrocarbon group having 3 to 16 carbon atoms, an aromatic hydrocarbon group having 6 to 18 carbon atoms, or groups obtained by combining these groups, ja represents an integer of 0 to 4, —$CH_2$— included in the alkyl group and the alicyclic hydrocarbon group may be replaced by —O—, —$S(O)_2$— or —CO—, and a hydrogen atom included in the alkyl group, the alicyclic hydrocarbon group and the aromatic hydrocarbon group may be substituted with a hydroxy group or a fluorine atom) and the like.

Examples of the substituent of the alicyclic hydrocarbon group represented by Y include a halogen atom, a hydroxy group, an alkyl group having 1 to 12 carbon atoms which may be substituted with a hydroxy group, an alicyclic hydrocarbon group having 3 to 16 carbon atoms, an alkoxy group having 1 to 12 carbon atoms, an aromatic hydrocarbon group having 6 to 18 carbon atoms, an aralkyl group having 7 to 21 carbon atoms, an alkylcarbonyl group having 2 to 4 carbon atoms, a glycidyloxy group, a —$(CH_2)_{ja}$—CO—O—$R^{b1}$ group or a —$(CH_2)_{ja}$—O—CO—$R^{b1}$ group (wherein $R^{b1}$ represents an alkyl group having 1 to 16 carbon atoms, an alicyclic hydrocarbon group having 3 to 16 carbon atoms, an aromatic hydrocarbon group having 6 to 18 carbon atoms or groups obtained by combining these groups, ja represents an integer of 0 to 4, and —$CH_2$— included in the alkyl group and the alicyclic hydrocarbon group may be replaced by —O—, —S(O)$_2$— or —CO—, a hydrogen atom included in the alkyl group, the alicyclic hydrocarbon group and the aromatic hydrocarbon group may be substituted with a hydroxy group or a fluorine atom) and the like.

Examples of the halogen atom include a fluorine atom, a chlorine atom, a bromine atom and an iodine atom.

Examples of the alicyclic hydrocarbon group include a cyclopentyl group, a cyclohexyl group, a methylcyclohexyl group, a dimethylcyclohexyl group, a cycloheptyl group, a cyclooctyl group, a norbornyl group, an adamantyl group and the like. The alicyclic hydrocarbon group may have a chain hydrocarbon group, and examples thereof include a methylcyclohexyl group, a dimethylcyclohexyl group and the like.

Examples of the aromatic hydrocarbon group include aryl groups such as a phenyl group, a naphthyl group, an anthryl group, a biphenyl group and a phenanthryl group. The aromatic hydrocarbon group may have a chain hydrocarbon group or an alicyclic hydrocarbon group, and examples of the aromatic hydrocarbon group having a chain hydrocarbon group include a tolyl group, a xylyl group, a cumenyl group, a mesityl group, a p-methylphenyl group, a p-ethylphenyl group, a p-tert-butylphenyl group, a 2,6-diethylphenyl group, a 2-methyl-6-ethylphenyl group and the like, and examples of the aromatic hydrocarbon group having an alicyclic hydrocarbon group include a p-adamantylphenyl group, a p-cyclohexylphenyl group and the like.

Examples of the alkyl group include a methyl group, an ethyl group, a propyl group, an isopropyl group, a butyl group, a sec-butyl group, a tert-butyl group, a pentyl group, a hexyl group, a heptyl group, a 2-ethylhexyl group, an octyl group, a nonyl group, a decyl group, an undecyl group, a dodecyl group and the like.

Examples of the alkyl group substituted with a hydroxy group include hydroxyalkyl groups such as a hydroxymethyl group and a hydroxyethyl group.

Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the aralkyl group include a benzyl group, a phenethyl group, a phenylpropyl group, a naphthylmethyl group and a naphthylethyl group.

Examples of the alkylcarbonyl group include an acetyl group, a propionyl group and a butyryl group.

Examples of Y include the followings.

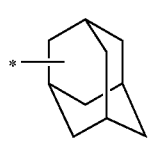
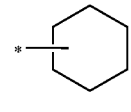
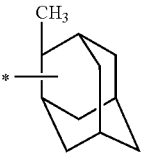
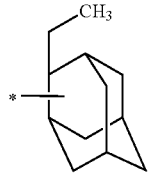
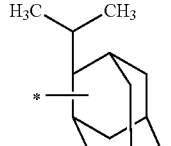
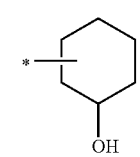

-continued

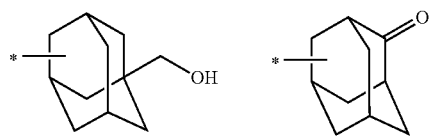

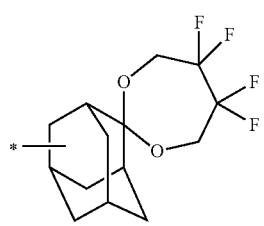

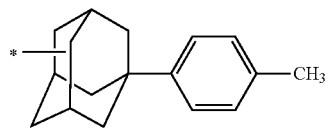

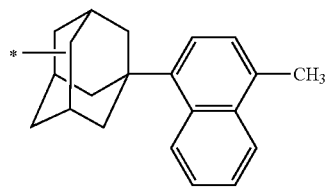

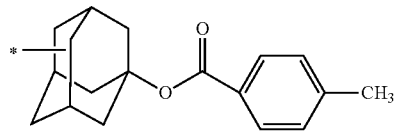

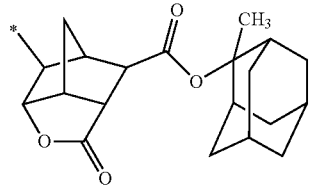

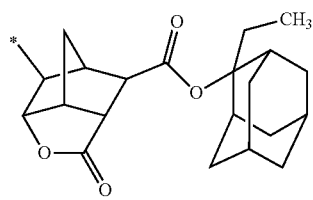

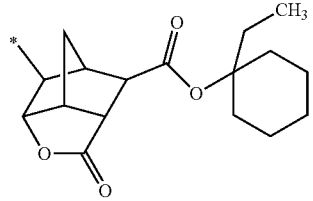

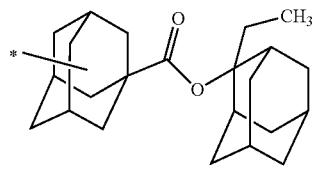

129
-continued
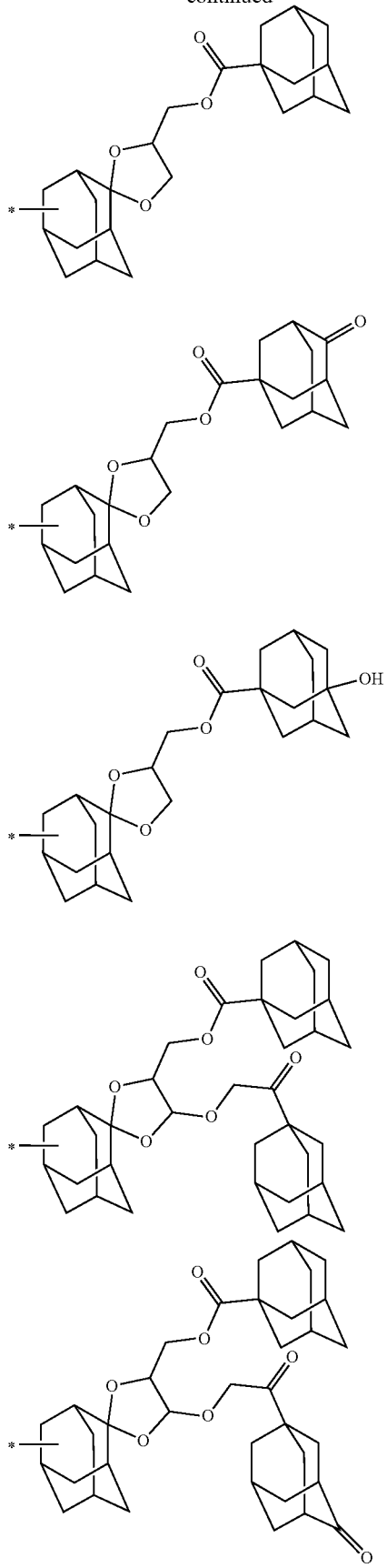
130
-continued
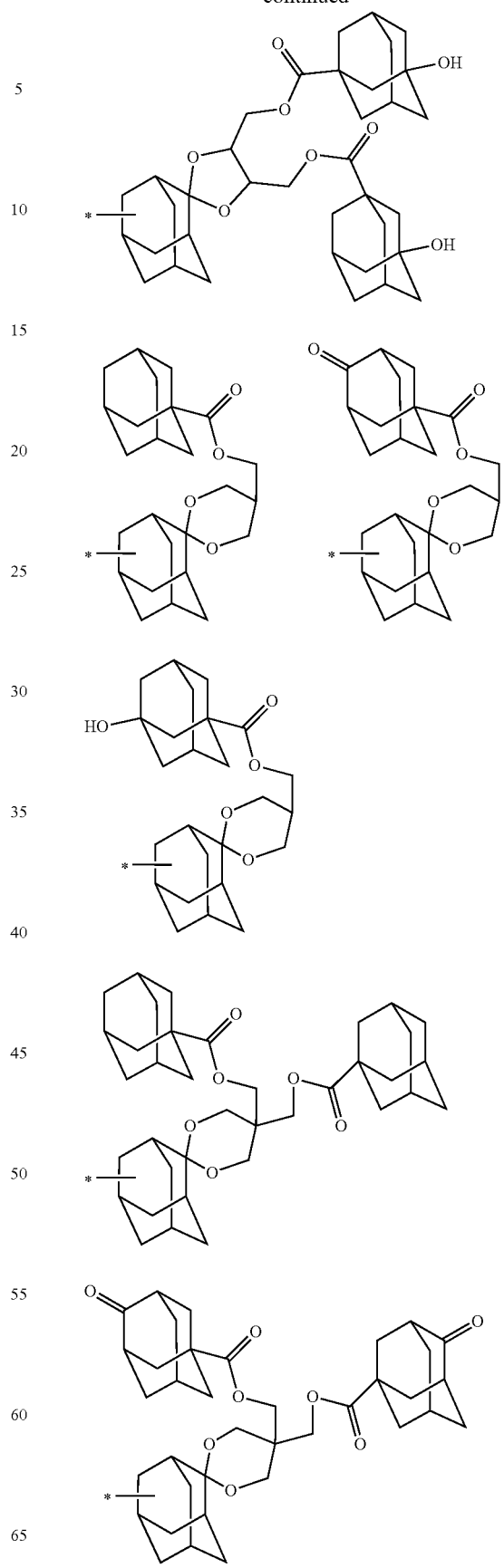

131
-continued

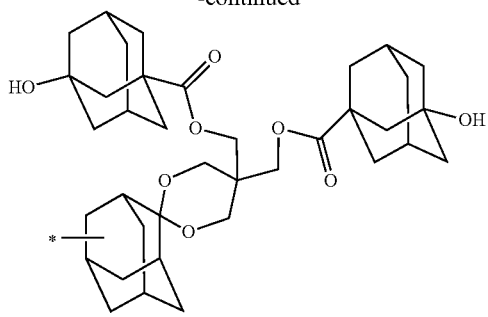

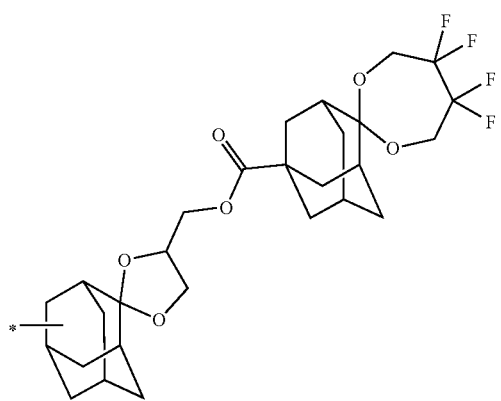

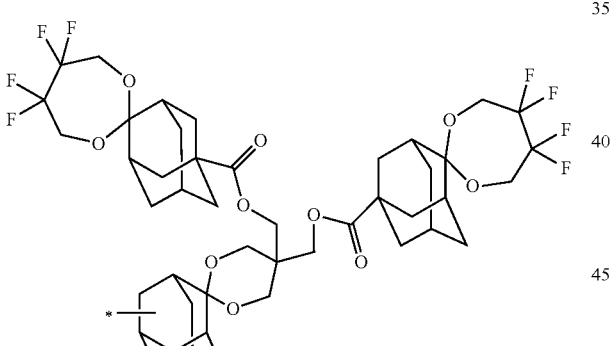

132
-continued

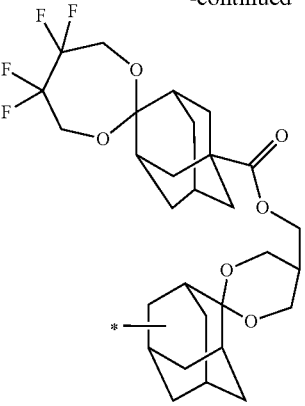

Y is preferably an alicyclic hydrocarbon group having 3 to 18 carbon atoms which may have a substituent, more preferably an adamantyl group which may have a substituent, and —CH$_2$— constituting the alicyclic hydrocarbon group or the adamantyl group may be replaced by —CO—, —S(O)$_2$— or —CO—. Y is still more preferably an adamantyl group, a hydroxyadamantyl group, an oxoadamantyl group, or groups represented by the followings.

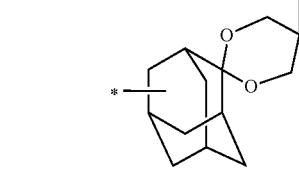

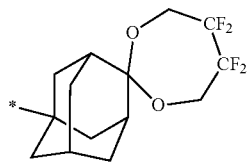

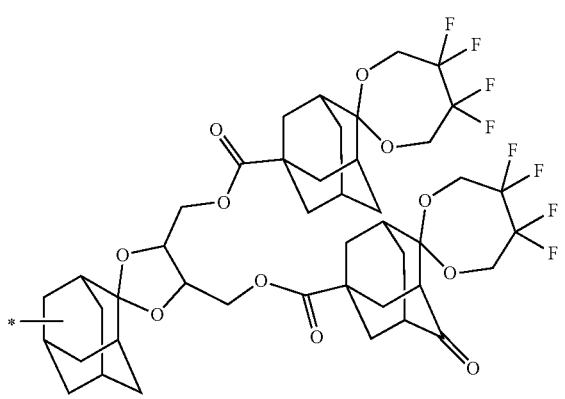

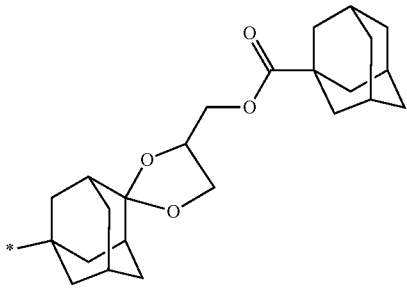

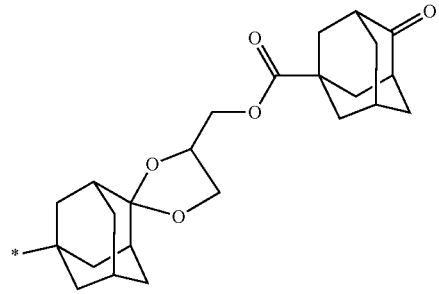

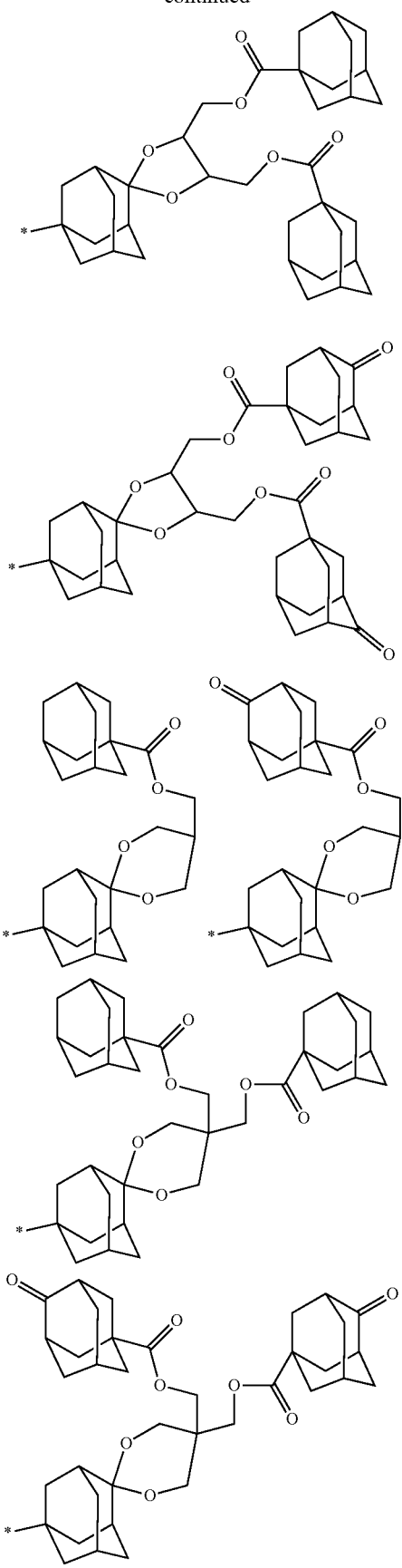
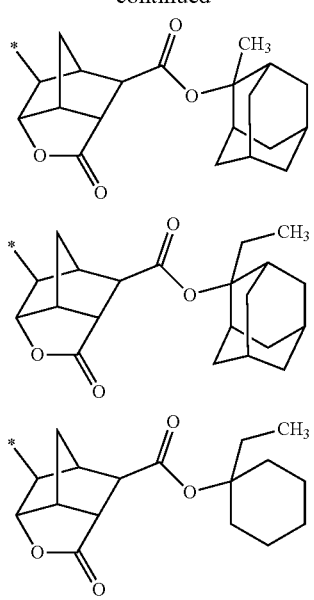

The anion in the salt represented by formula (B1) is preferably anions represented by formula (B1-A-1) to formula (B1-A-55) [hereinafter sometimes referred to as "anion (B1-A-1)" according to the number of formula], and more preferably an anion represented by any one of formula (B1-A-1) to formula (B1-A-4), formula (B1-A-9), formula (B1-A-10), formula (B1-A-24) to formula (B1-A-33), formula (B1-A-36) to formula (B1-A-40) and formula (B1-A-47) to formula (B1-A-55).

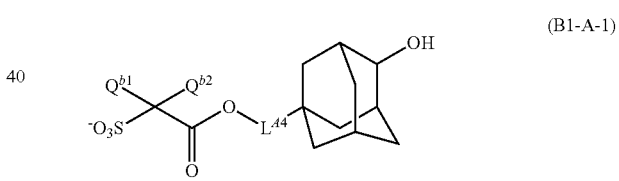
(B1-A-1)

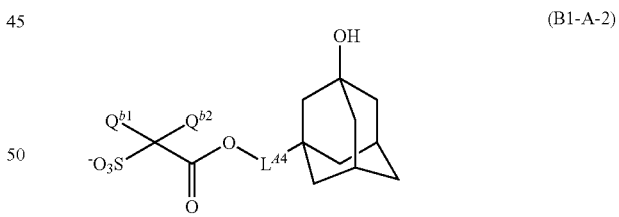
(B1-A-2)

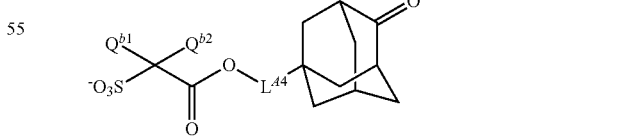
(B1-A-3)

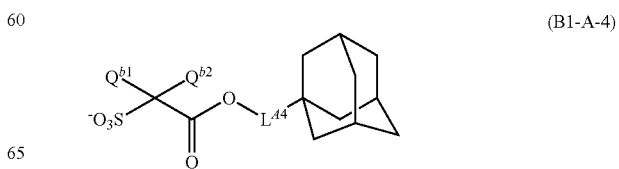
(B1-A-4)

-continued
(B1-A-5)
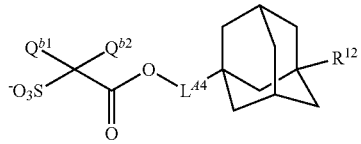
(B1-A-6)
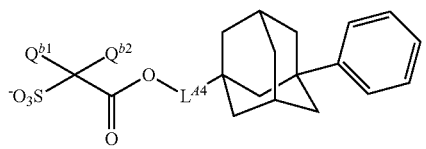
(B1-A-7)
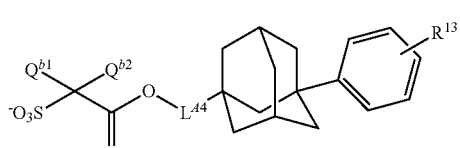
(B1-A-8)
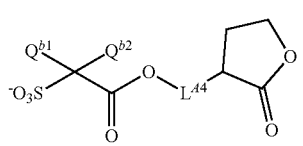
(B1-A-9)
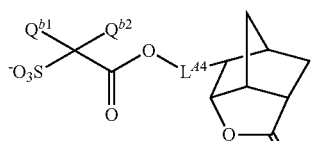
(B1-A-10)
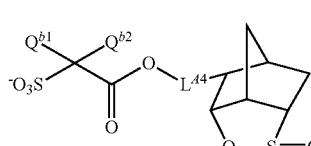
(B1-A-11)
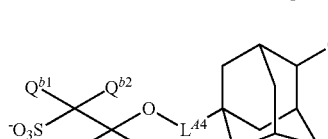
(B1-A-12)
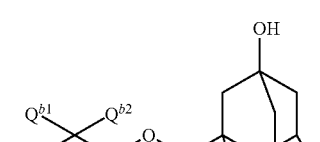
(B1-A-13)
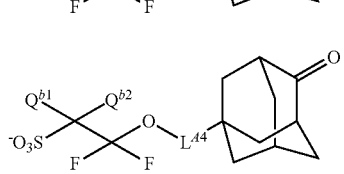
-continued
(B1-A-14)
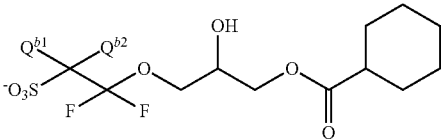
(B1-A-15)
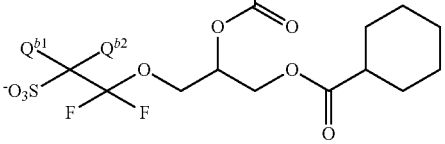
(B1-A-16)
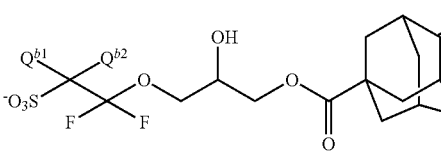
(B1-A-17)
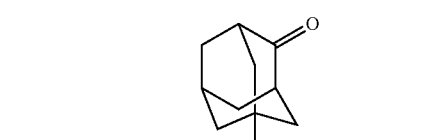
(B1-A-18)
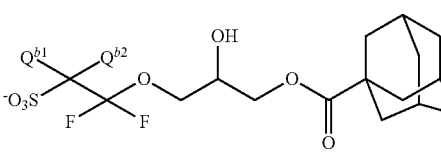
(B1-A-19)
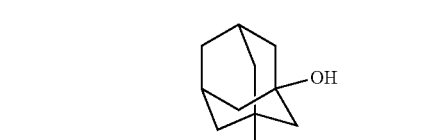
(B1-A-20)
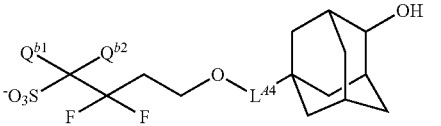

(B1-A-21)
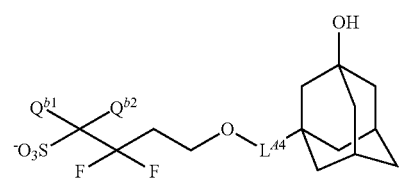
(B1-A-22)
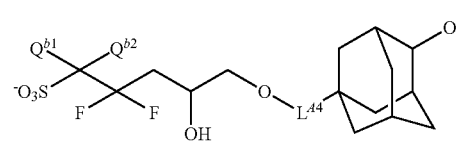
(B1-A-23)
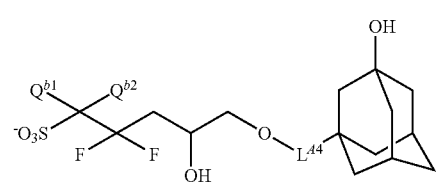
(B1-A-24)
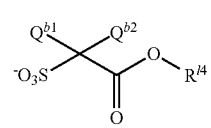
(B1-A-25)
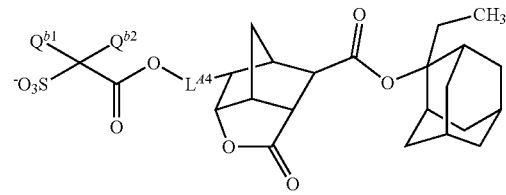
(B1-A-26)
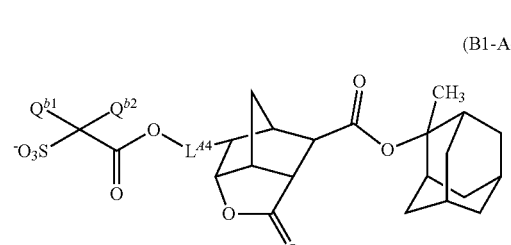
(B1-A-27)
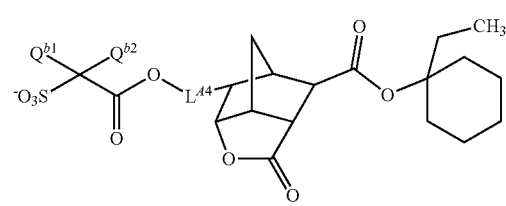
(B1-A-28)
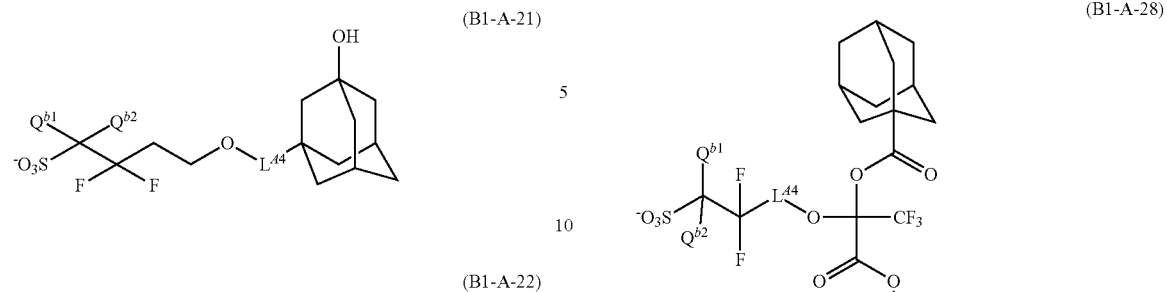
(B1-A-29)
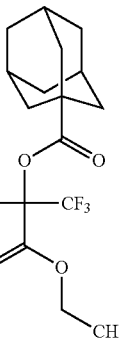
(B1-A-30)
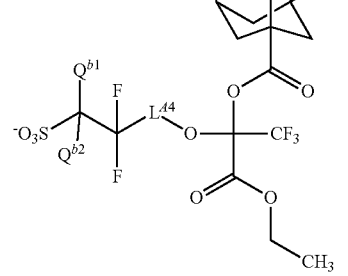
(B1-A-31)
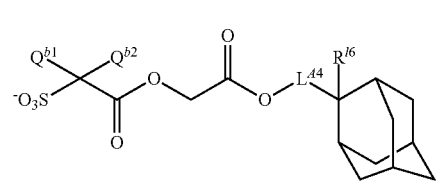
(B1-A-32)
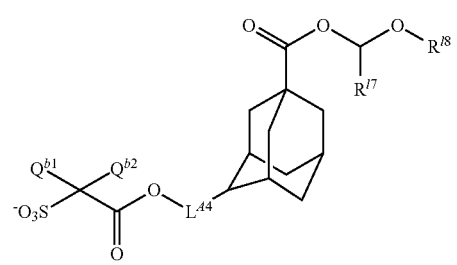
(B1-A-33)
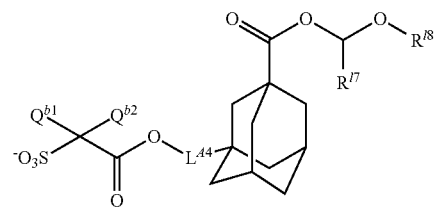

(B1-A-34)
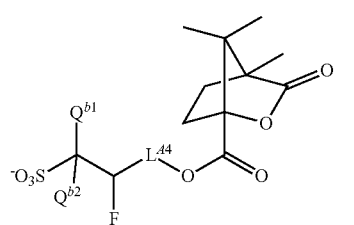
(B1-A-35)
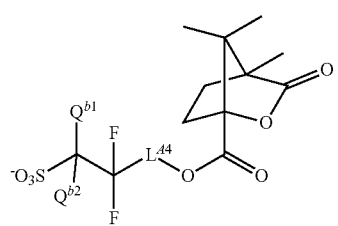
(B1-A-36)
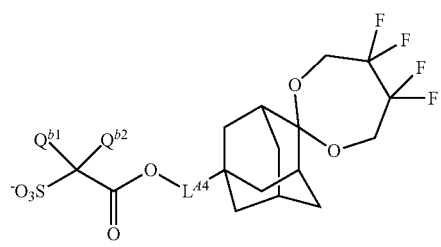
(B1-A-37)
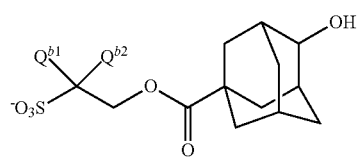
(B1-A-38)
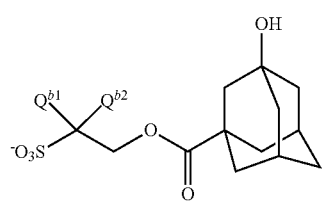
(B1-A-39)
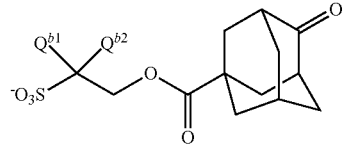
(B1-A-40)
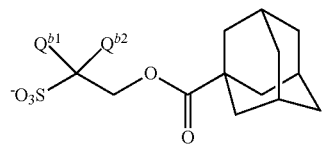
(B1-A-41)
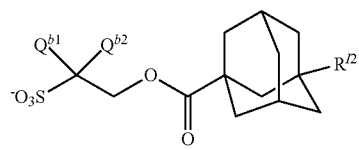
(B1-A-42)
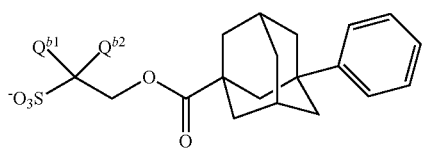
(B1-A-43)
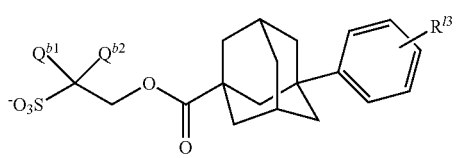
(B1-A-44)
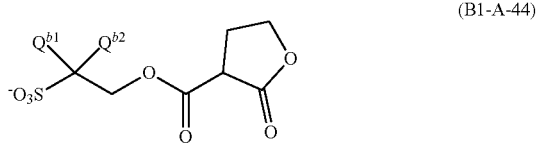
(B1-A-45)
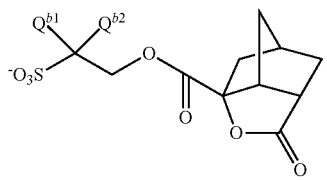
(B1-A-46)
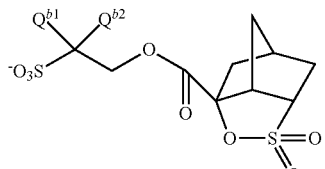
(B1-A-47)
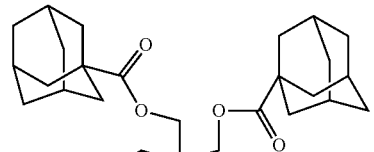
(B1-A-48)
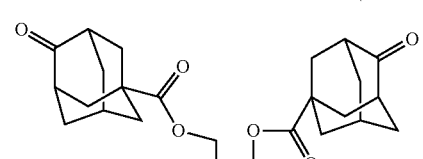
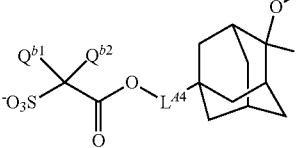

141
-continued (B1-A-49)
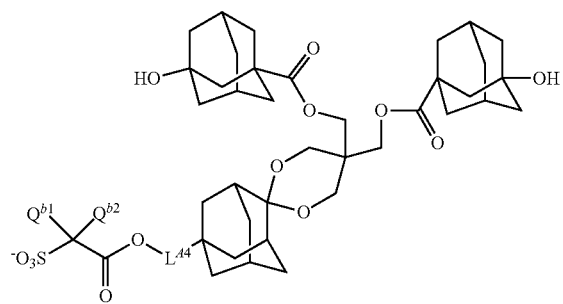

(B1-A-50)
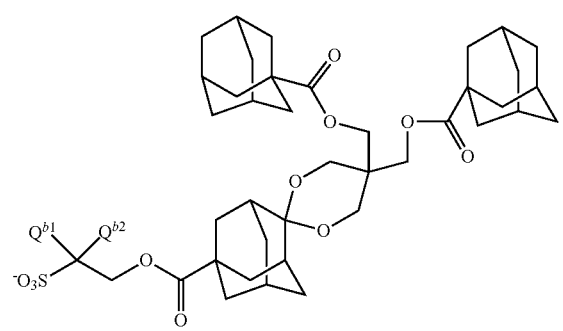

(B1-A-51)
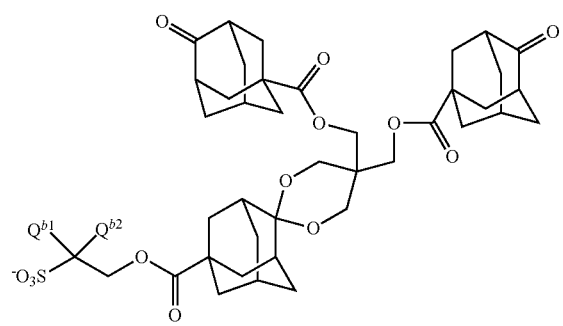

(B1-A-52)
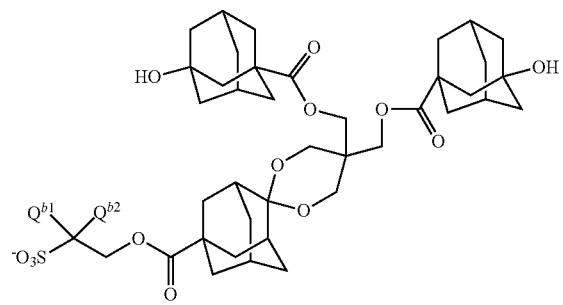

142
-continued (B1-A-53)
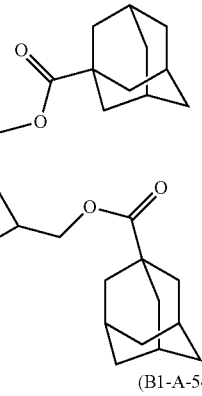

(B1-A-54)
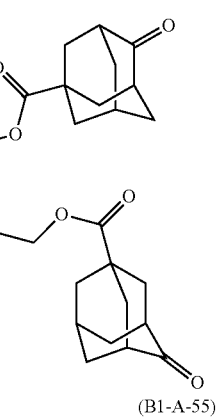

(B1-A-55)

$R^{12}$ to $R^{17}$ each independently represent, for example, an alkyl group having 1 to 4 carbon atoms, and preferably a methyl group or an ethyl group. $R^{18}$ is, for example, a chain hydrocarbon group having 1 to 12 carbon atoms, preferably an alkyl group having 1 to 4 carbon atoms, an alicyclic hydrocarbon group having 5 to 12 carbon atoms or groups formed by combining these groups, and more preferably a methyl group, an ethyl group, a cyclohexyl group or an adamantyl group. $L^{44}$ is a single bond or an alkanediyl group having 1 to 4 carbon atoms. $Q^1$ and $Q^2$ are the same as defined above.

Specific examples of the anion in the salt represented by formula (B1) include anions mentioned in JP 2010-204646 A.

Examples of the anion in the salt represented by formula (B1) preferably include anions represented by formula (B1a-1) to formula (B1a-34).

(B1a-1)
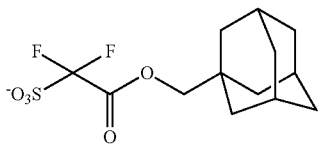

(B1a-2)
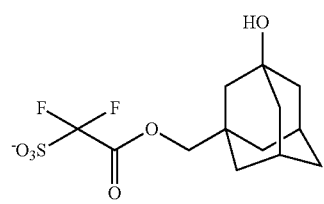
(B1a-3)
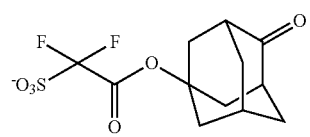
(B1a-4)
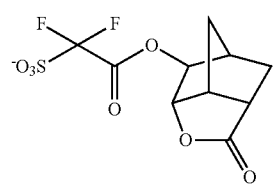
(B1a-5)
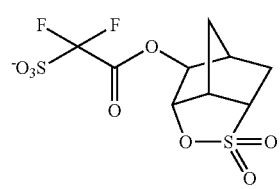
(B1a-6)
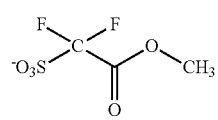
(B1a-7)
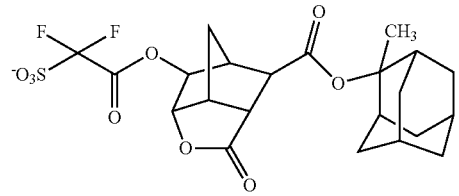
(B1a-8)
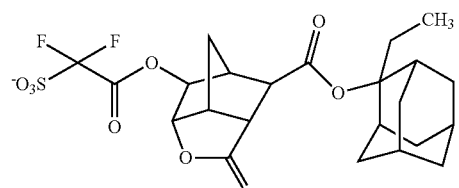
(B1a-9)
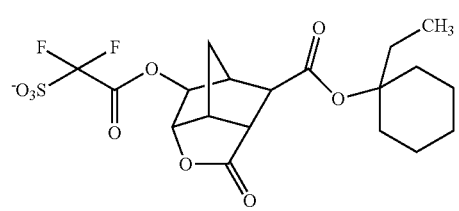
(B1a-10)
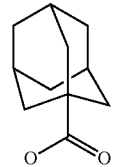
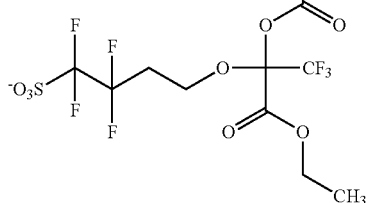
(B1a-11)
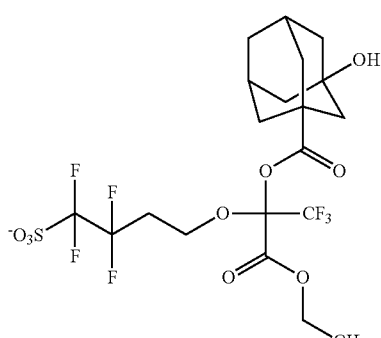
(B1a-12)
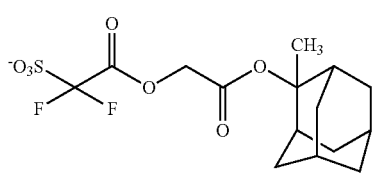
(B1a-13)
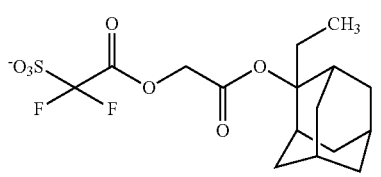
(B1a-14)
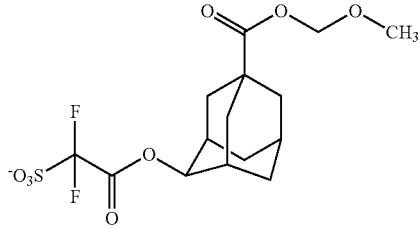
(B1a-15)
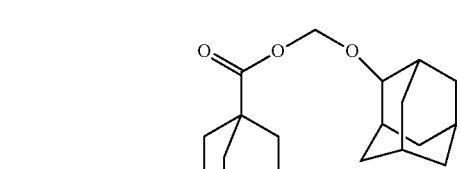
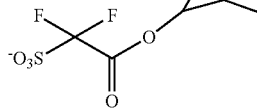

(B1a-16)
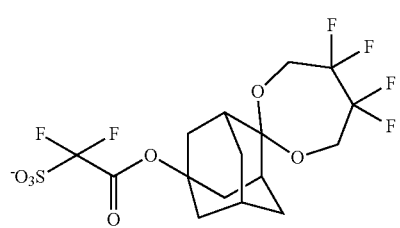
(B1a-17)
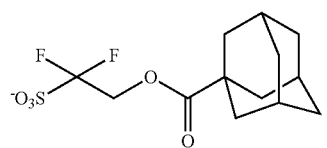
(B1a-18)
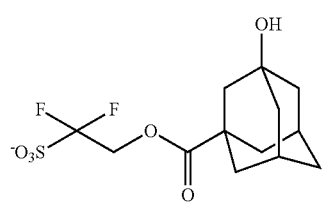
(B1a-19)
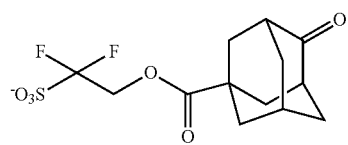
(B1a-20)
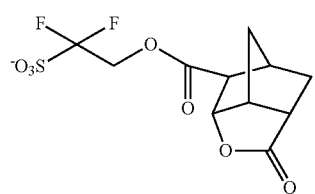
(B1a-21)
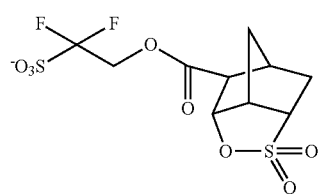
(B1a-22)
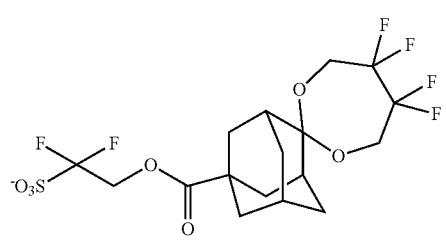
(B1a-23)
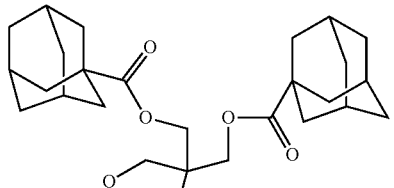
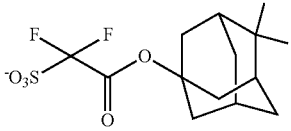
(B1a-24)
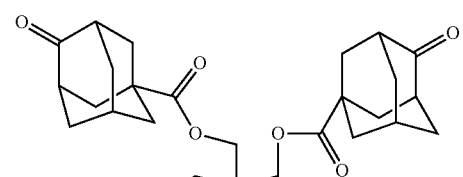
(B1a-25)
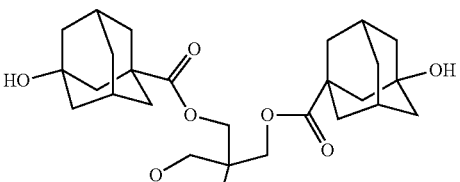
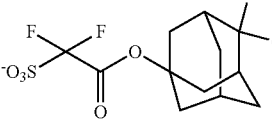
(B1a-26)
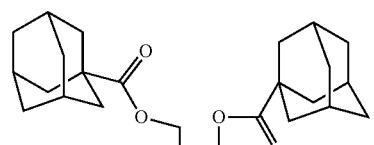
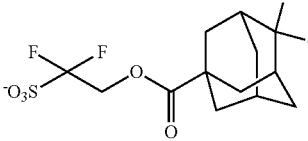

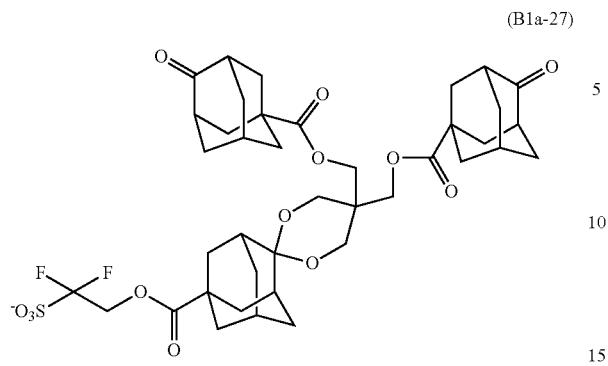

(B1a-27)

(B1a-31)

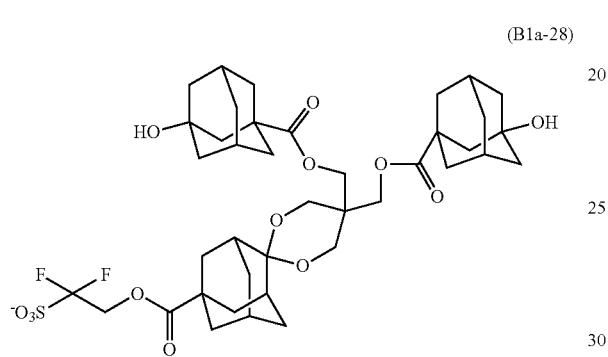

(B1a-28)

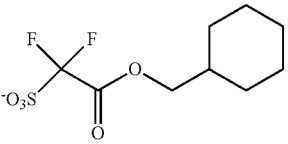

(B1a-32)

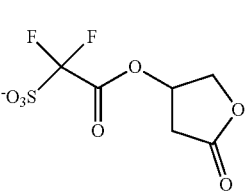

(B1a-33)

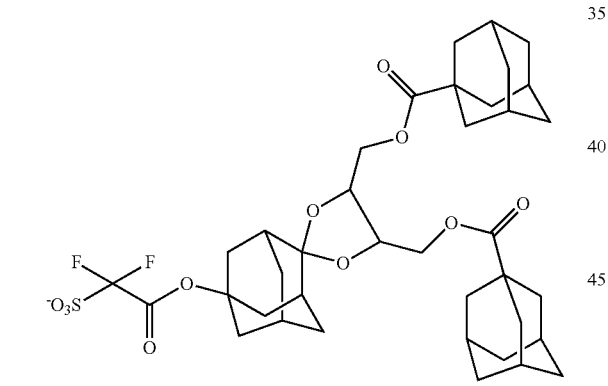

(B1a-29)

(B1a-34)

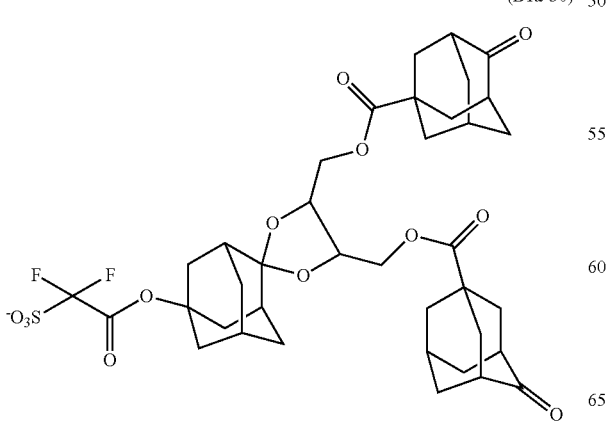

(B1a-30)

Of these anions, the anion is preferably an anion represented by any one of formula (B1a-1) to formula (B1a-3) and formula (B1a-7) to formula (B1a-16), formula (B1a-18), formula (B1a-19) and formula (B1a-22) to formula (B1a-34).

Examples of the organic cation of $Z^+$ include an organic onium cation, an organic sulfonium cation, an organic iodonium cation, an organic ammonium cation, a benzothiazolium cation and an organic phosphonium cation. Of these, an organic sulfonium cation and an organic iodonium cation are preferable, and an arylsulfonium cation is more preferable. Specific examples thereof include a cation represented by any one of formula (b2-1) to formula (b2-4) (hereinafter sometimes referred to as "cation (b2-1)" according to the number of formula).

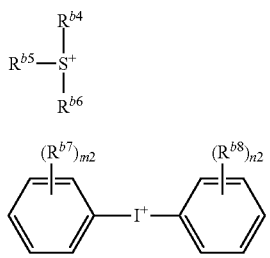 (b2-1)

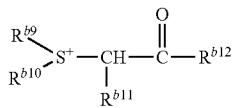 (b2-2)

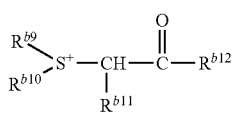 (b2-3)

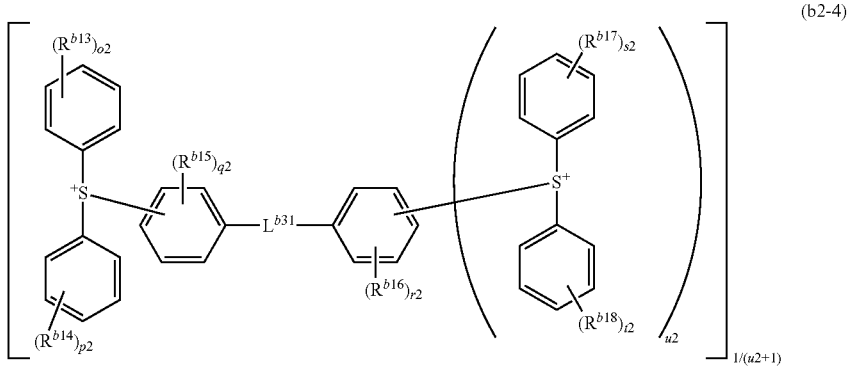 (b2-4)

In formula (b2-1) to formula (b2-4), $R^{b4}$ to $R^{b6}$ each independently represent a chain hydrocarbon group having 1 to 30 carbon atoms, an alicyclic hydrocarbon group having 3 to 36 carbon atoms or an aromatic hydrocarbon group having 6 to 36 carbon atoms, a hydrogen atom included in the chain hydrocarbon group may be substituted with a hydroxy group, an alkoxy group having 1 to 12 carbon atoms, an alicyclic hydrocarbon group having 3 to 12 carbon atoms or an aromatic hydrocarbon group having 6 to 18 carbon atoms, a hydrogen atom included in the alicyclic hydrocarbon group may be substituted with a halogen atom, an aliphatic hydrocarbon group having 1 to 18 carbon atoms, an alkylcarbonyl group having 2 to 4 carbon atoms or a glycidyloxy group, and a hydrogen atom included in the aromatic hydrocarbon group may be substituted with a halogen atom, a hydroxy group or an alkoxy group having 1 to 12 carbon atoms, $R^{b4}$ and $R^{b5}$ may form a ring together with sulfur atoms to which $R^{b7}$ and $R^{b5}$ are bonded, and —CH$_2$— included in the ring may be replaced by —O—, —SO— or —CO—, $R^{b7}$ and $R^{b8}$ each independently represent a hydroxy group, an aliphatic hydrocarbon group having 1 to 12 carbon atoms or an alkoxy group having 1 to 12 carbon atoms, m2 and n2 each independently represent an integer of 0 to 5, when m2 is 2 or more, a plurality of $R^{b7}$ may be the same or different, and when n2 is 2 or more, a plurality of $R^{b8}$ may be the same or different, $R^{b9}$ and $R^{b10}$ each independently represent a chain hydrocarbon group having 1 to 36 carbon atoms or an alicyclic hydrocarbon group having 3 to 36 carbon atoms, $R^{b9}$ and $R^{b10}$ may form a ring together with sulfur atoms to which $R^{b9}$ and $R^{b10}$ are bonded, and —CH$_2$— included in the ring may be replaced by —O—, —S— or —CO—, $R^{b12}$ represents a hydrogen atom, a chain hydrocarbon group having 1 to 36 carbon atoms, an alicyclic hydrocarbon group having 3 to 36 carbon atoms or an aromatic hydrocarbon group having 6 to 18 carbon atoms, $R^{b12}$ represents a chain hydrocarbon group having 1 to 12 carbon atoms, an alicyclic hydrocarbon group having 3 to 18 carbon atoms or an aromatic hydrocarbon group having 6 to 18 carbon atoms, a hydrogen atom included in the chain hydrocarbon group may be substituted with an aromatic hydrocarbon group having 6 to 18 carbon atoms, and a hydrogen atom included in the aromatic hydrocarbon group may be substituted with an alkoxy group having 1 to 12 carbon atoms or an alkylcarbonyloxy group having 1 to 12 carbon atoms, $R^{b11}$ and $R^{b12}$ may form a ring together with —CH—CO— to which $R^{b11}$ and $R^{b12}$ are bonded, and —CH$_2$— included in the ring may be replaced by —O—, —S— or —CO—, $R^{b13}$ to $R^{b18}$ each independently represent a hydroxy group, an aliphatic hydrocarbon group having 1 to 12 carbon atoms or an alkoxy group having 1 to 12 carbon atoms, $L^{b31}$ represents a sulfur atom or an oxygen atom, o2, p2, s2 and t2 each independently represent an integer of 0 to 5, q2 and r2 each independently represent an integer of 0 to 4, u2 represents 0 or 1, when o2 is 2 or more, a plurality of $R^{b13}$ may be the same or different, when p2 is 2 or more, a plurality of $R^{b14}$ may be the same or different, when q2 is 2 or more, a plurality of $R^{b15}$ may be the same or different, when r2 is 2 or more, a plurality of $R^{b16}$ may be the same or different, when s2 is 2 or more, a plurality of $R^{b17}$ may be the same or different, and when t2 is 2 or more, a plurality of $R^{b18}$ may be the same or different, and the aliphatic hydrocarbon group represents a chain hydrocarbon group and an alicyclic hydrocarbon group.

Examples of the chain hydrocarbon group include alkyl groups such as a methyl group, an ethyl group, a propyl group, an isopropyl group, a butyl group, a sec-butyl group, a tert-butyl group, a pentyl group, a hexyl group, an octyl group and a 2-ethylhexyl group.

Particularly, the chain hydrocarbon group for $R^{b9}$ to $R^{b12}$ preferably has 1 to 12 carbon atoms.

The alicyclic hydrocarbon group may be either monocyclic or polycyclic, and examples of the monocyclic alicyclic hydrocarbon group include cycloalkyl groups such as a cyclopropyl group, a cyclobutyl group, a cyclopentyl group, a cyclohexyl group, a cycloheptyl group, a cyclooctyl group and a cyclodecyl group. Examples of the polycyclic alicyclic hydrocarbon group include a decahydronaphthyl group, an adamantyl group, a norbornyl group, and the following groups.

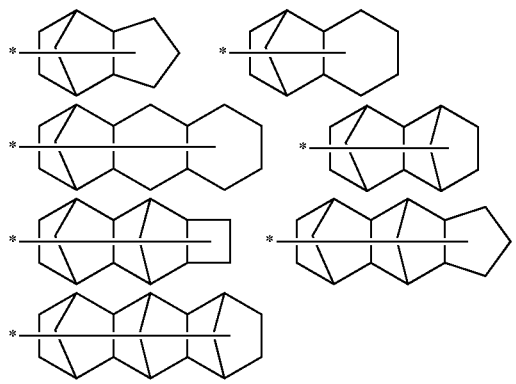

Particularly, the alicyclic hydrocarbon group for $R^{b9}$ to $R^{b12}$ preferably has 3 to 18 carbon atoms, and more preferably 4 to 12 carbon atoms.

Examples of the alicyclic hydrocarbon group in which a hydrogen atom is substituted with an aliphatic hydrocarbon group include a methylcyclohexyl group, a dimethylcyclohexyl group, a 2-methyladamantan-2-yl group, a 2-ethyladamantan-2-yl group, a 2-isopropyladamantan-2-yl group, a methylnorbornyl group, an isobornyl group and the like. In the alicyclic hydrocarbon group in which a hydrogen atom is substituted with an aliphatic hydrocarbon group, the total number of carbon atoms of the alicyclic hydrocarbon group and the aliphatic hydrocarbon group is preferably 20 or less.

Examples of the aromatic hydrocarbon group include aryl groups such as a phenyl group, a biphenyl group, a naphthyl group and a phenanthryl group. The aromatic hydrocarbon group may have a chain hydrocarbon group or an alicyclic hydrocarbon group, and examples of the aromatic hydrocarbon group having a chain hydrocarbon group include a tolyl group, a xylyl group, a cumenyl group, a mesityl group, a p-ethylphenyl group, a p-tert-butylphenyl group, a 2,6-diethylphenyl group, a 2-methyl-6-ethylphenyl group and the like, and examples of the aromatic hydrocarbon group having an alicyclic hydrocarbon group include a p-cyclohexylphenyl group, a p-adamantylphenyl group and the like. When the aromatic hydrocarbon group has the chain hydrocarbon group or the alicyclic hydrocarbon group, a chain hydrocarbon group having 1 to 18 carbon atoms and an alicyclic hydrocarbon group having 3 to 18 carbon atoms are preferable.

Examples of the aromatic hydrocarbon group in which a hydrogen atom is substituted with an alkoxy group include a p-methoxyphenyl group and the like.

Examples of the chain hydrocarbon group in which a hydrogen atom is substituted with an aromatic hydrocarbon group include aralkyl groups such as a benzyl group, a phenethyl group, a phenylpropyl group, a trityl group, a naphthylmethyl group and a naphthylethyl group.

Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the alkylcarbonyl group include an acetyl group, a propionyl group and a butyryl group.

Examples of the halogen atom include a fluorine atom, a chlorine atom, a bromine atom and an iodine atom.

Examples of the alkylcarbonyloxy group include a methylcarbonyloxy group, an ethylcarbonyloxy group, a propylcarbonyloxy group, an isopropylcarbonyloxy group, a butylcarbonyloxy group, a sec-butylcarbonyloxy group, a tert-butylcarbonyloxy group, a pentylcarbonyloxy group, a hexylcarbonyloxy group, an octylcarbonyloxy group and a 2-ethylhexylcarbonyloxy group.

The ring formed together with sulfur atoms to which $R^{b4}$ and $R^{b5}$ are bonded may be a monocyclic, polycyclic, aromatic, nonaromatic, saturated or unsaturated ring. This ring includes a ring having 3 to 18 carbon atoms and is preferably a ring having 4 to 18 carbon atoms. The ring containing a sulfur atom includes a 3-membered to 12-membered ring and is preferably a 3-membered to 7-membered ring and specifically includes the following rings. * represents a bonding site.

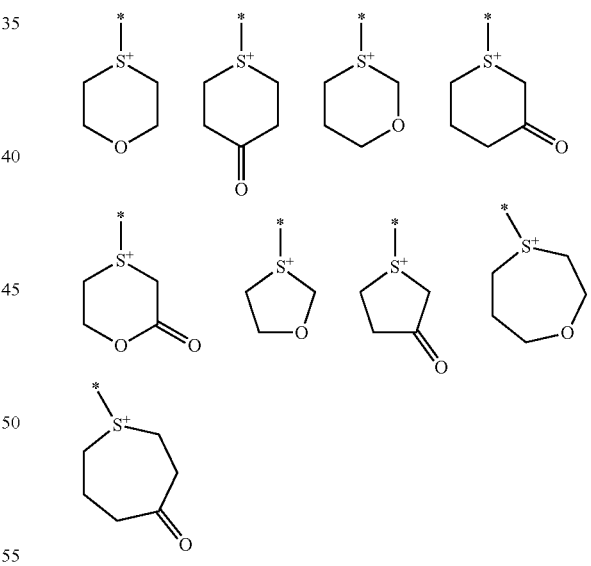

The ring formed by bonding $R^{b9}$ and $R^{b10}$ each other may be a monocyclic, polycyclic, aromatic, nonaromatic, saturated or unsaturated ring. This ring includes a 3-membered to 12-membered ring and is preferably a 3-membered to 7-membered ring. Examples of the ring include a thiolan-1-ium ring (a tetrahydrothiophenium ring), a thian-1-ium ring, a 1,4-oxathian-4-ium ring and the like.

The ring formed by bonding $R^{b11}$ and $R^{b12}$ each other may be a monocyclic, polycyclic, aromatic, nonaromatic, saturated or unsaturated ring. This ring includes a 3-membered to 12-membered ring and is preferably a 3-membered to 7-membered ring. Examples thereof include an oxocycloheptane ring, an oxocyclohexane ring, an oxonorbornane ring, an oxoadamantane ring and the like.
Of cation (b2-1) to cation (b2-4), a cation (b2-1) is preferable.
Examples of the cation (b2-1) include the following cations
(b2-c-1)
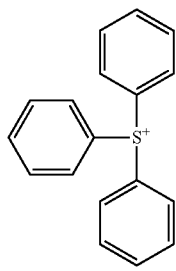
(b2-c-2)
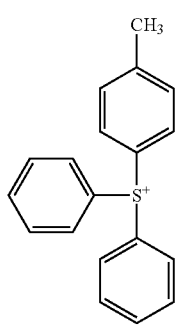
(b2-c-3)
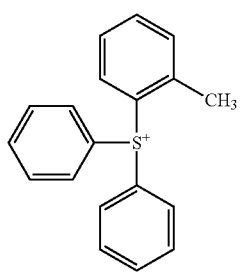
(b2-c-4)
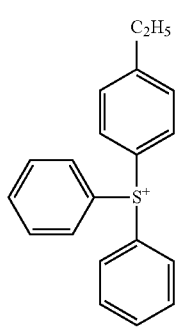
-continued
(b2-c-5)
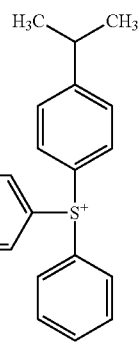
(b2-c-6)
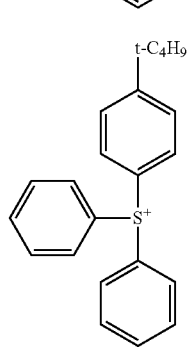
(b2-c-7)
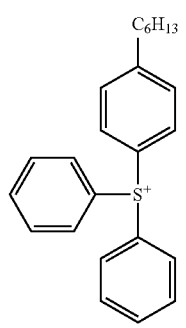
(b2-c-8)
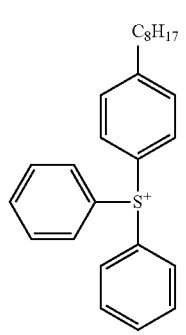
(b2-c-9)
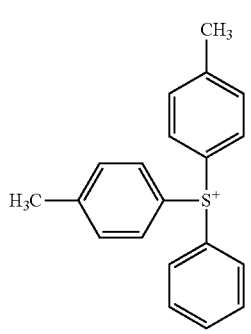

(b2-c-10) 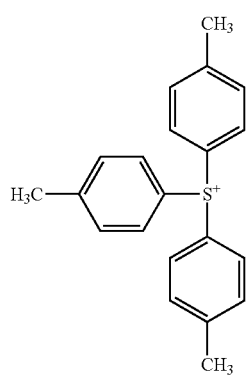
(b2-c-11) 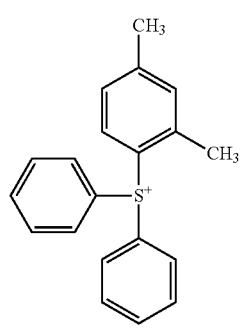
(b2-c-12) 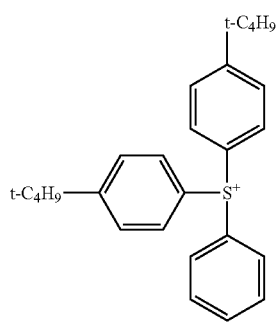
(b2-c-13) 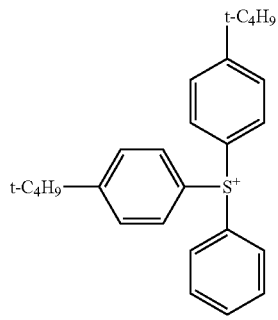
(b2-c-14) 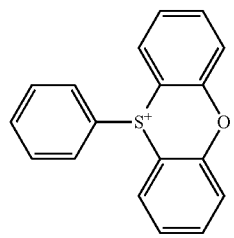
(b2-c-15) 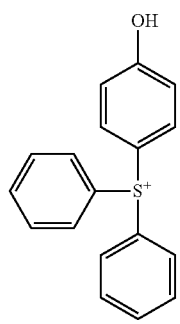
(b2-c-16) 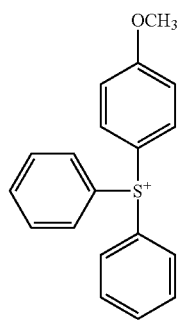
(b2-c-17) 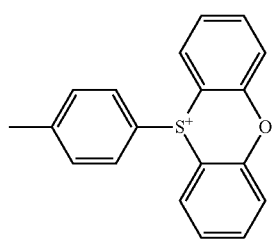
(b2-c-18) 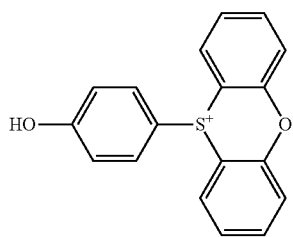
(b2-c-19) 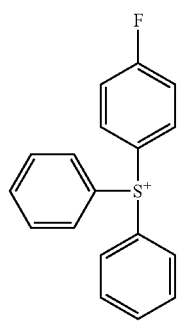

(b2-c-20)
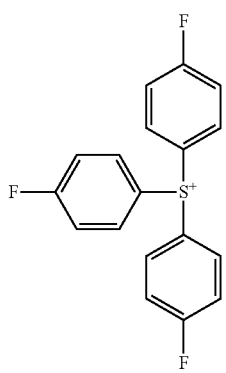
(b2-c-21)
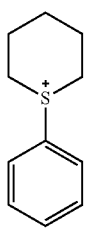
(b2-c-22)
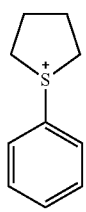
(b2-c-23)
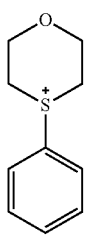
(b2-c-24)
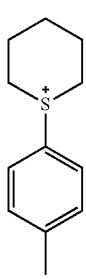
(b2-c-25)
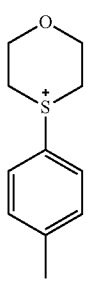
(b2-c-26)
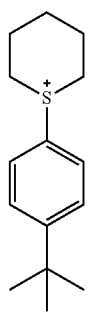
(b2-c-27)
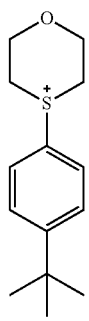
Examples of the cation (b2-2) include the following cations.
(b2-c-28)
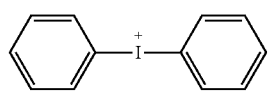
(b2-c-29)
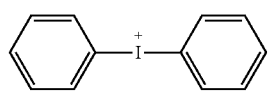
(b2-c-30)
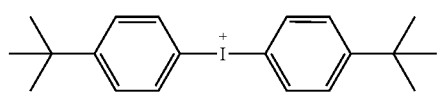
Examples of the cation (b2-3) include the following cations.
(b2-c-31)
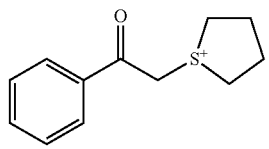
(b2-c-32)
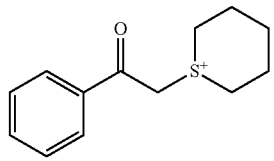

(b2-c-33)
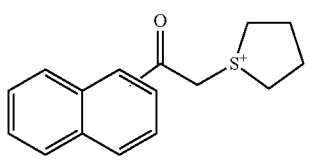
(b2-c-34)
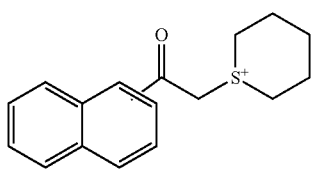
Examples of the cation (b2-4) include the following cations.
(b2-c-35)
(b2-c-36)
(b2-c-37)
(b2-c-38)
(b2-c-39)
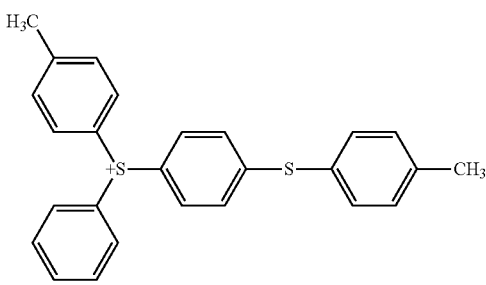
(b2-c-40)
(b2-c-41)
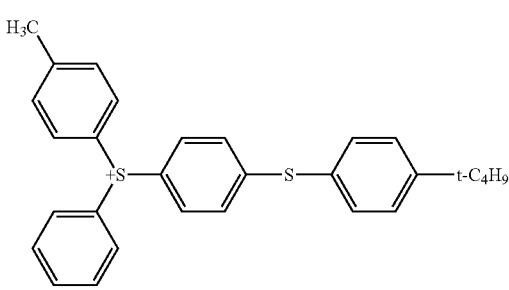
(b2-C-42)
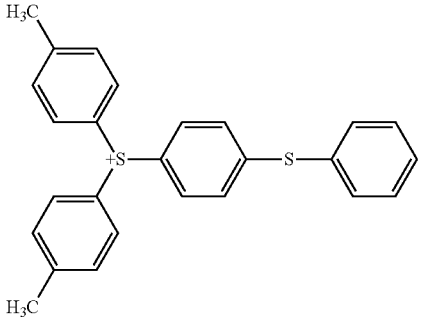
(b2-c-43)
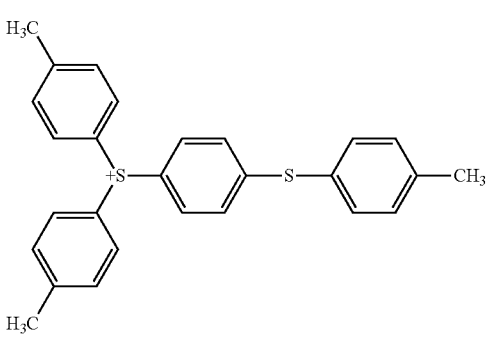
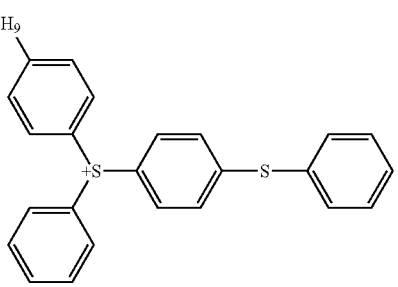

(b2-c-44)
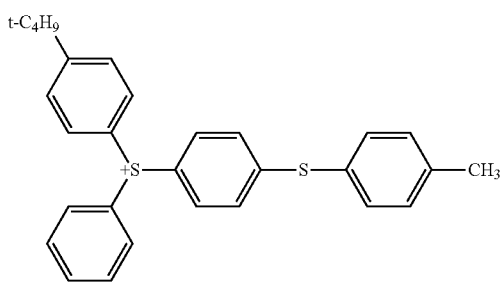

(b2-c-45)
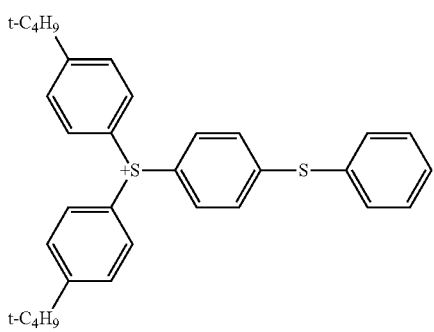

(b2-c-46)
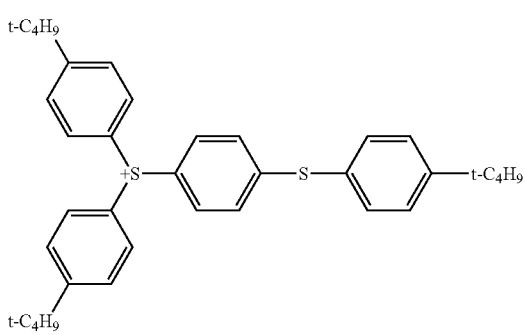

(B1-1)
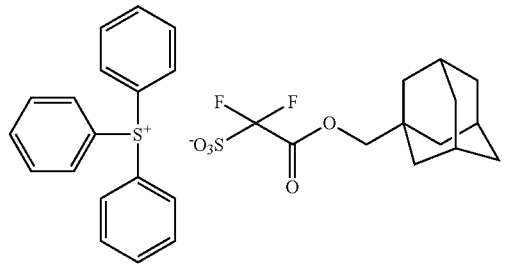

(B1-2)
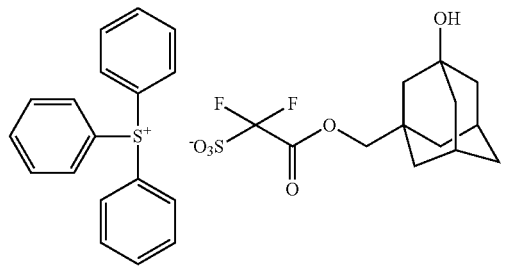

(B1-3)
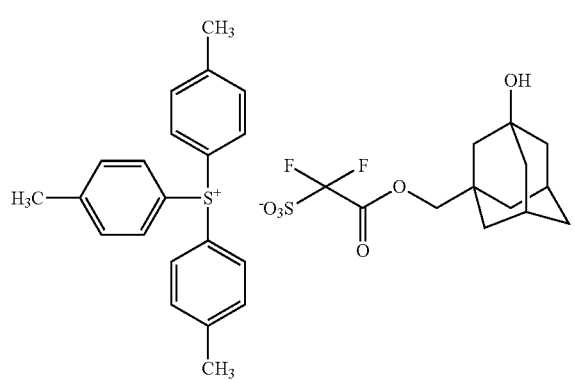

(B1-4)
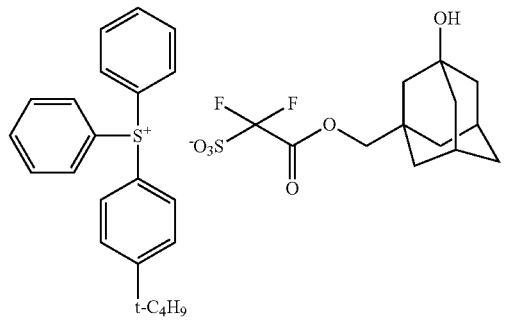

The acid generator (B) is a combination of the above-mentioned anions and the above-mentioned organic cations, and these can be optionally combined. Examples of the acid generator (B) are preferably combinations of anions represented by any one of (B1a-1) to formula (B1a-3), formula (B1a-7) to formula (B1a-16), formula (B1a-18), formula (B1a-19) and formula (B1a-22) to formula (B1a-34) with a cation (b2-1) or a cation (b2-3).

Examples of the acid generator (B) are preferably those represented by formula (B1-1) to formula (B1-48). Of these, those containing an arylsulfonium cation are preferable, and those represented by formula (B1-1) to formula (B1-3), formula (B1-5) to formula (B1-7), formula (B1-11) to formula (B1-14), formula (B1-20) to formula (B1-26), formula (B1-29) and formula (B1-31) to formula (B1-48) are particularly preferable.

-continued
(B1-5)
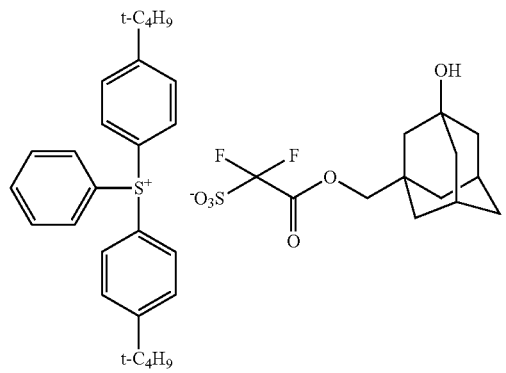
(B1-6)
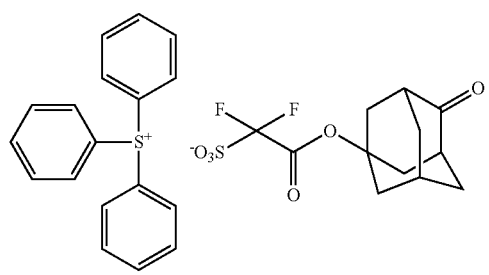
(B1-7)
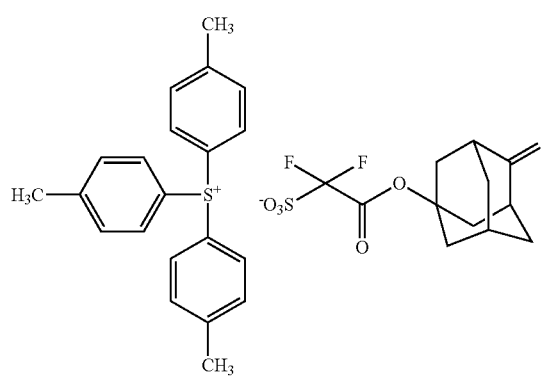
(B1-8)
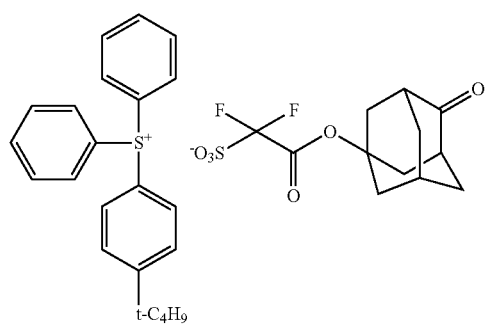
-continued
(B1-9)
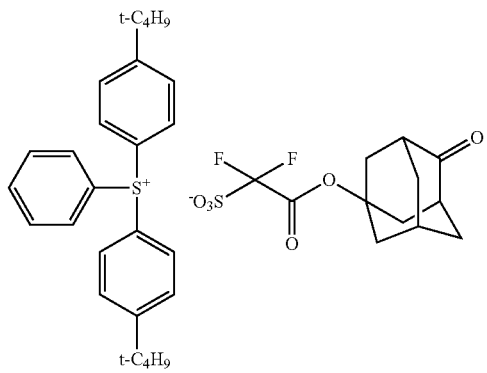
(B1-10)
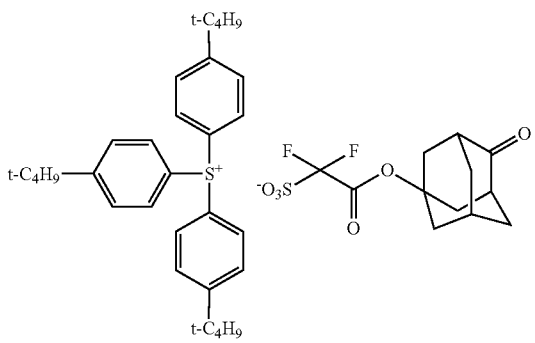
(B1-11)
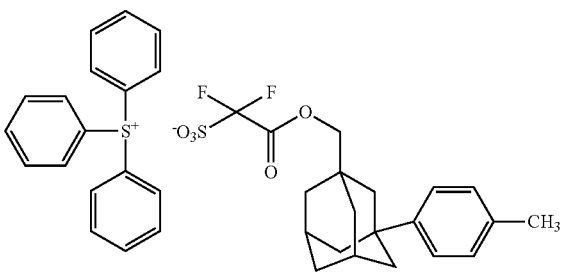
(B1-12)
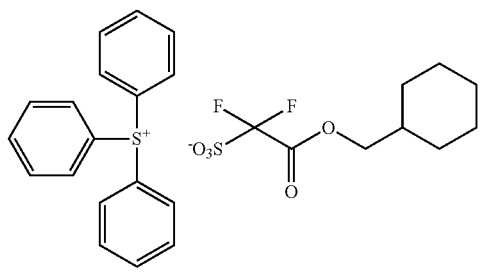
(B1-13)
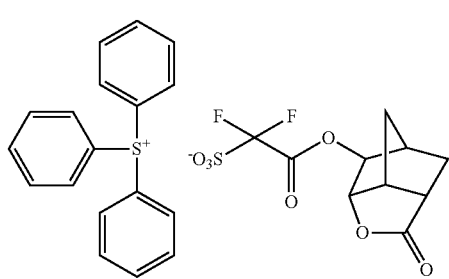

(B1-14)
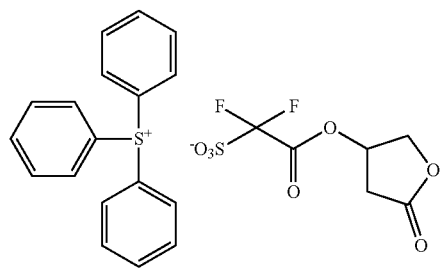
(B1-15)
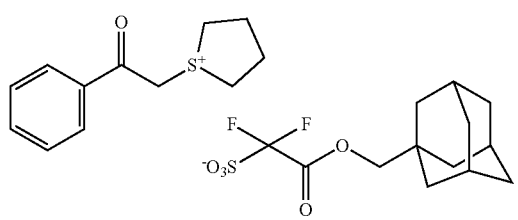
(B1-16)
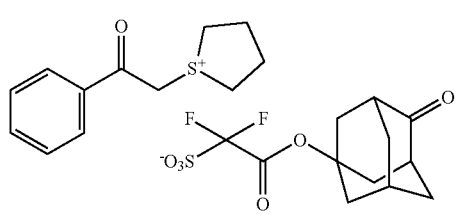
(B1-17)
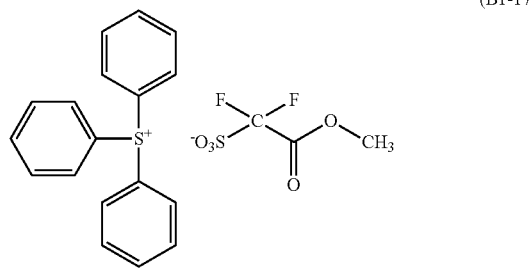
(B1-18)
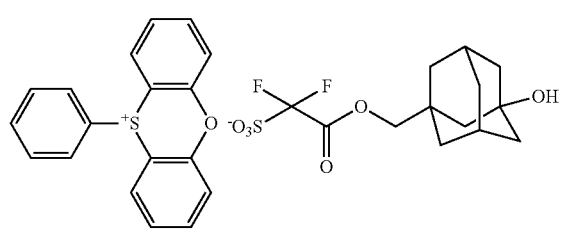
(B1-19)
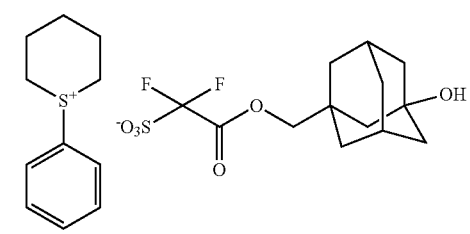
(B1-20)
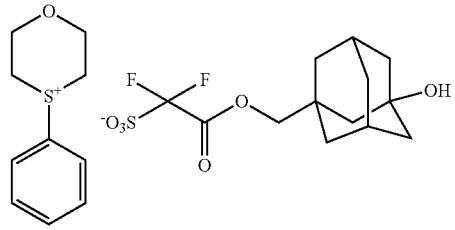
(B1-21)
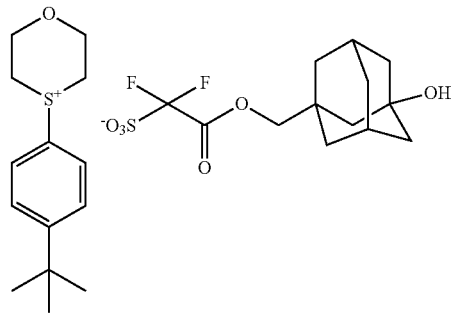
(B1-22)
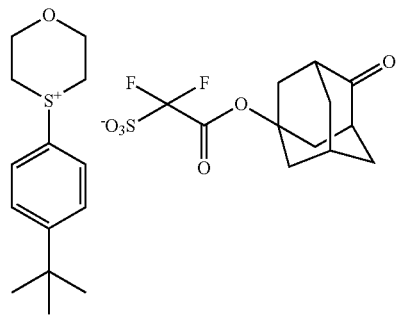
(B1-23)
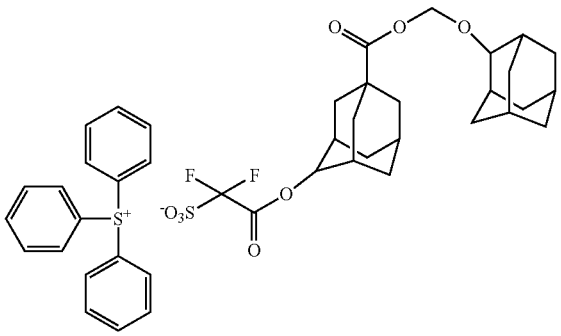
(B1-24)
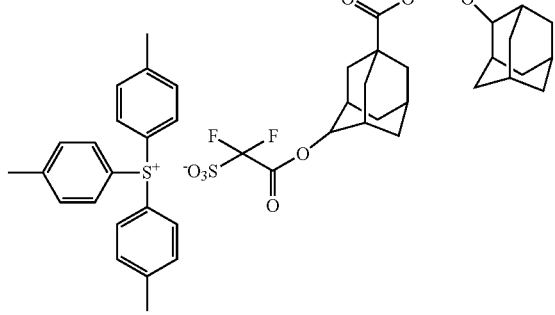

(B1-25)
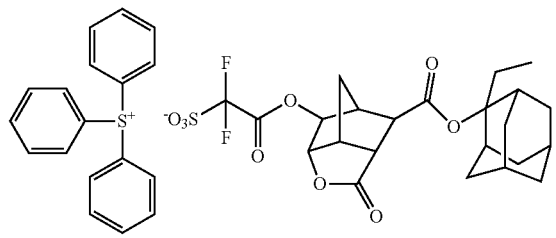
(B1-26)
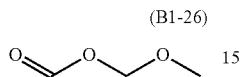
(B1-27)
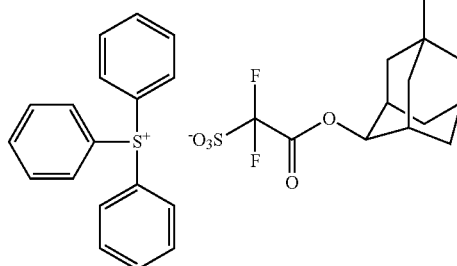
(B1-28)
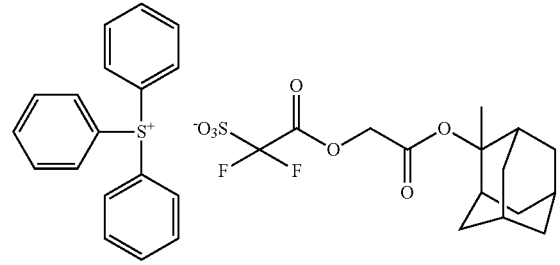
(B1-29)
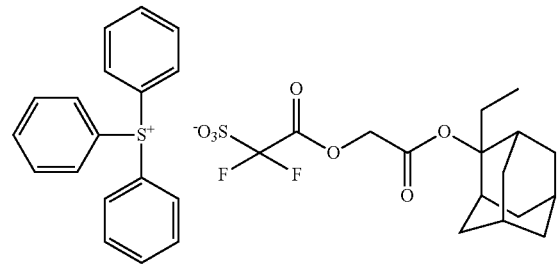
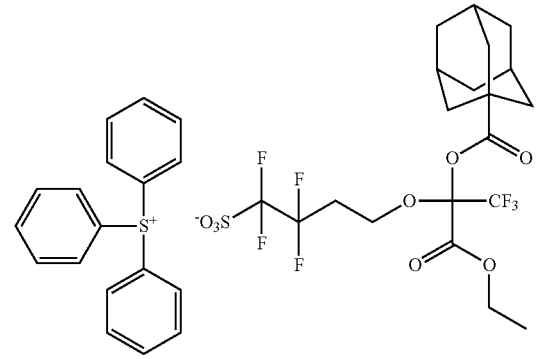
(B1-30)
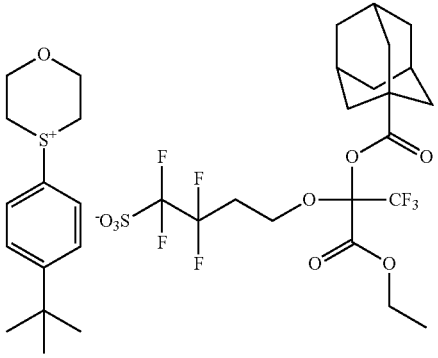
(B1-31)
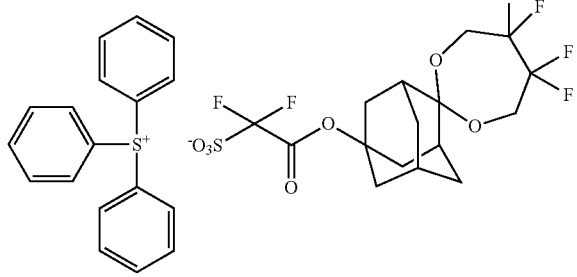
(B1-32)
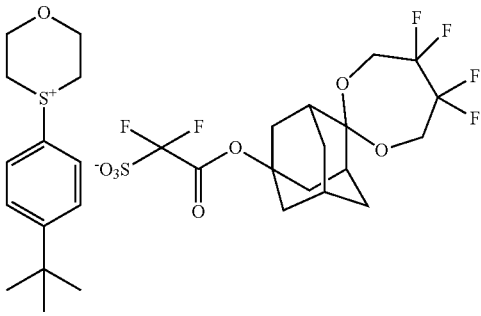
(B1-33)
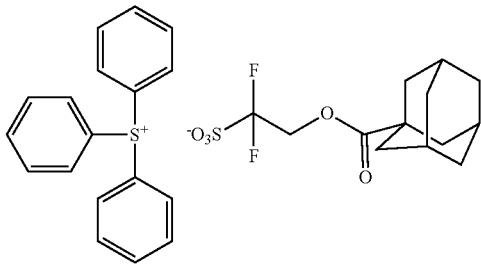
(B1-34)
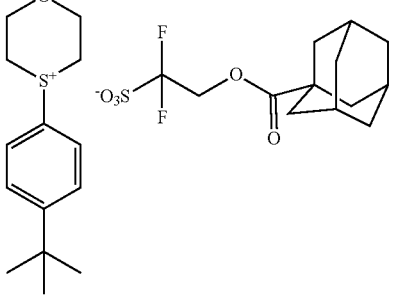

-continued
(B1-35) 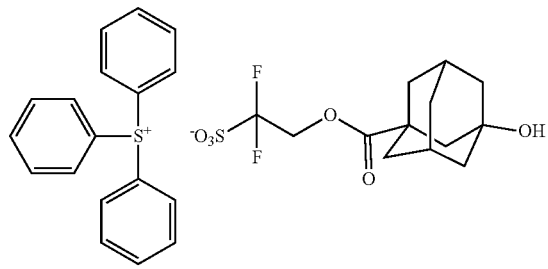
(B1-36) 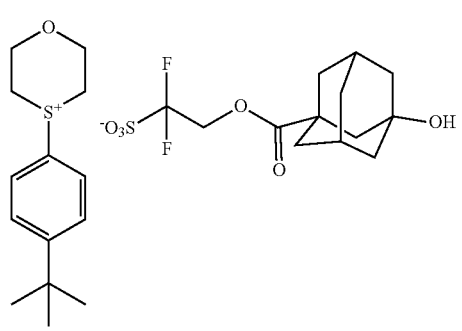
(B1-37) 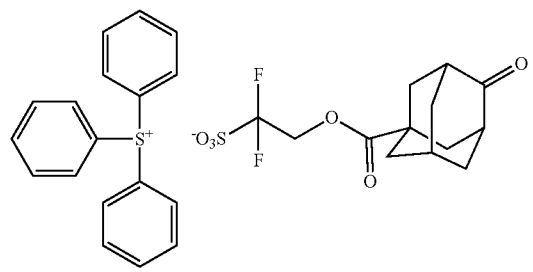
(B1-38) 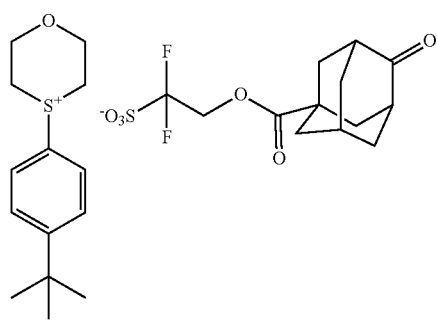
(B1-39) 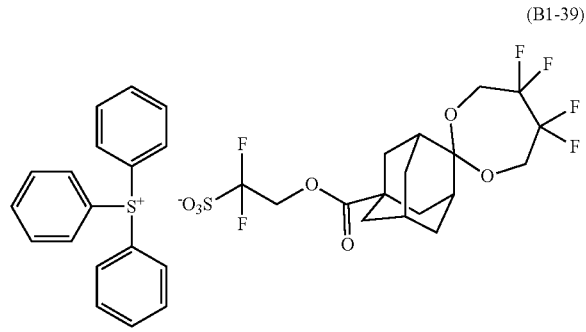
-continued
(B1-40) 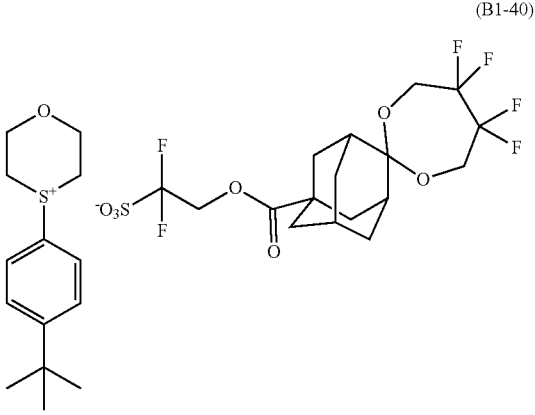
(B1-41) 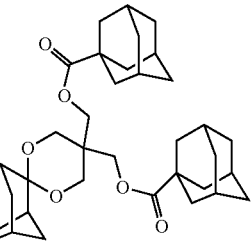
(B1-42) 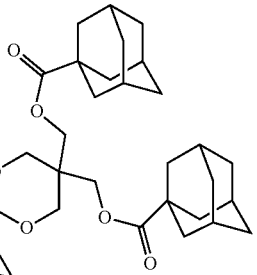
(B1-43) 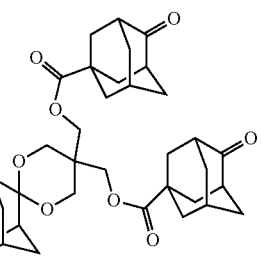

-continued (B1-44)
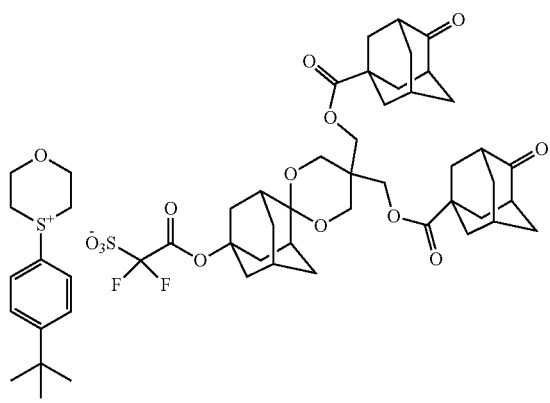

(B1-45)

(B1-46)

(B1-47)

-continued (B1-48)
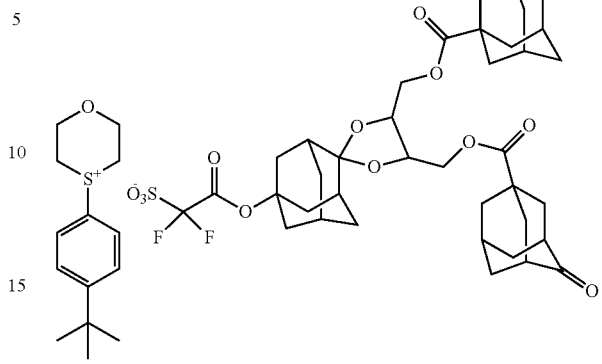

In the resist composition of the present invention, the content of the acid generator is preferably 1 part by mass or more and 45 parts by mass or less, more preferably 1 parts by mass or more and 40 parts by mass or less, and still more preferably 3 parts by mass or more and 35 parts by mass or less, based on 100 parts by mass of the resin (A).

<Solvent (E)>

The content of the solvent (E) in the resist composition is usually 90% by mass or more and 99.9% by mass or less, preferably 92% by mass or more and 99% by mass or less, and more preferably 94% by mass or more and 99% by mass or less. The content of the solvent (E) can be measured, for example, by a known analysis means such as liquid chromatography or gas chromatography.

Examples of the solvent (E) include glycol ether esters such as ethylcellosolve acetate, methylcellosolve acetate and propylene glycol monomethyl ether acetate; glycol ethers such as propylene glycol monomethyl ether; esters such as ethyl lactate, butyl acetate, amyl acetate and ethyl pyruvate; ketones such as acetone, methyl isobutyl ketone, 2-heptanone and cyclohexanone; and cyclic esters such as γ-butyrolactone. The solvent (E) may be used alone, or two or more solvents may be used.

<Quencher (C)>

Examples of the quencher (C) include a salt generating an acid having an acidity lower than that of an acid generated from an acid generator (B) and a basic nitrogen-containing organic compound. The content of the quencher (C) is preferably about 0.01 to 15% by mass, more preferably about 0.01 to 10% by mass, still more preferably about 0.01 to 5% by mass, and yet more preferably about 0.01 to 3% by mass, based on the amount of the solid component of the resist composition.

<Salt Generating Acid Having Acidity Lower than that of Acid Generated from Acid Generator>

The acidity in a salt generating an acid having an acidity lower than that of an acid generated from the acid generator (B) is indicated by the acid dissociation constant (pKa). Regarding the salt generating an acid having an acidity lower than that of an acid generated from the acid generator (B), the acid dissociation constant of an acid generated from the salt usually meets the following inequality: $-3<pKa$, preferably $-1<pKa<7$, and more preferably $0<pKa<5$.

Examples of the salt generating an acid having an acidity lower than that of an acid generated from the acid generator (B) include salts represented by the following formulas, a compound represented by formula (D) mentioned in JP 2015-147926 A (hereinafter sometimes referred to as "weak

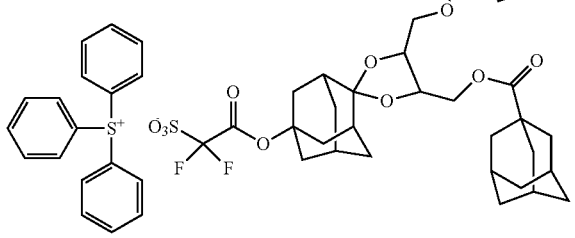

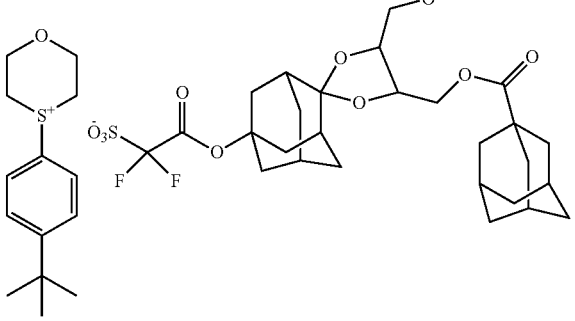

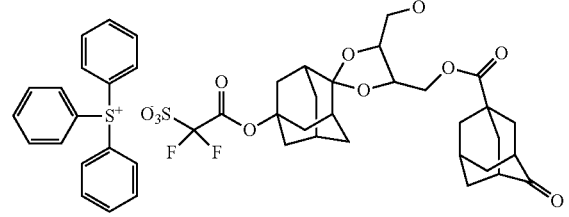

acid inner salt (D)", and salts mentioned in JP 2012-229206 A, JP 2012-6908 A, JP 2012-72109 A, JP 2011-39502 A and JP 2011-191745 A. The salt generating an acid having an acidity lower than that of an acid generated from the acid generator (B) is preferably a salt generating a carboxylic acid having an acidity lower than that of an acid generated from the acid generator (B) (a salt having a carboxylic acid anion), and more preferably a weak acid inner salt (D).

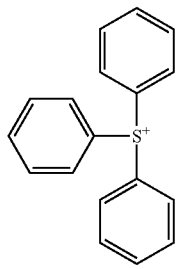

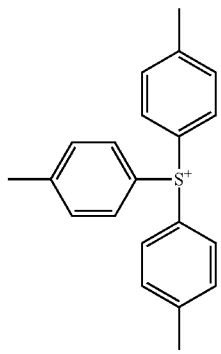

-continued

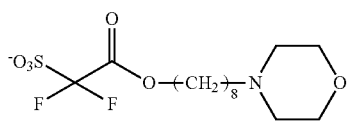

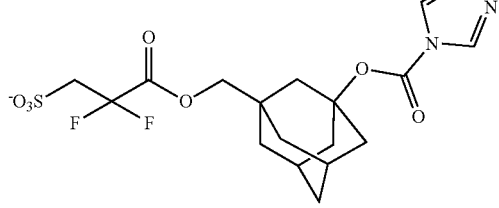

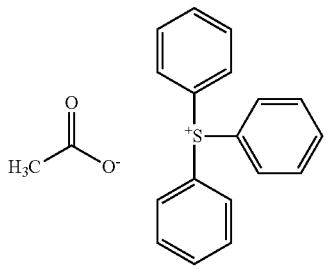

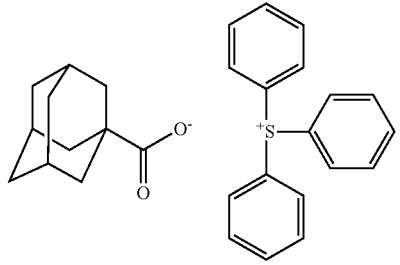

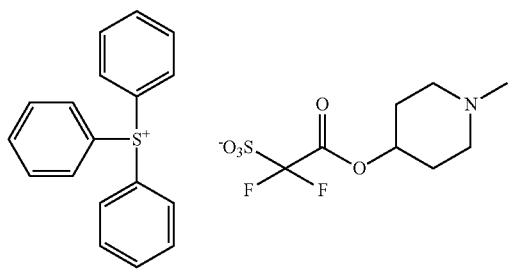

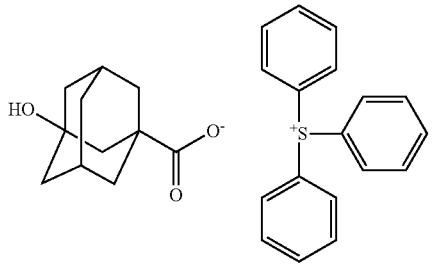

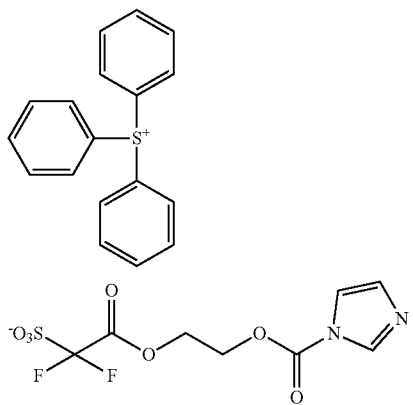

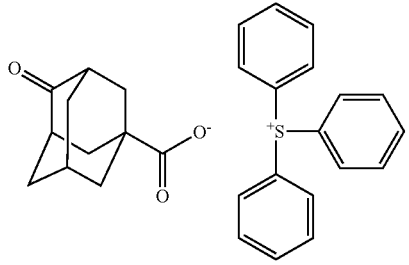

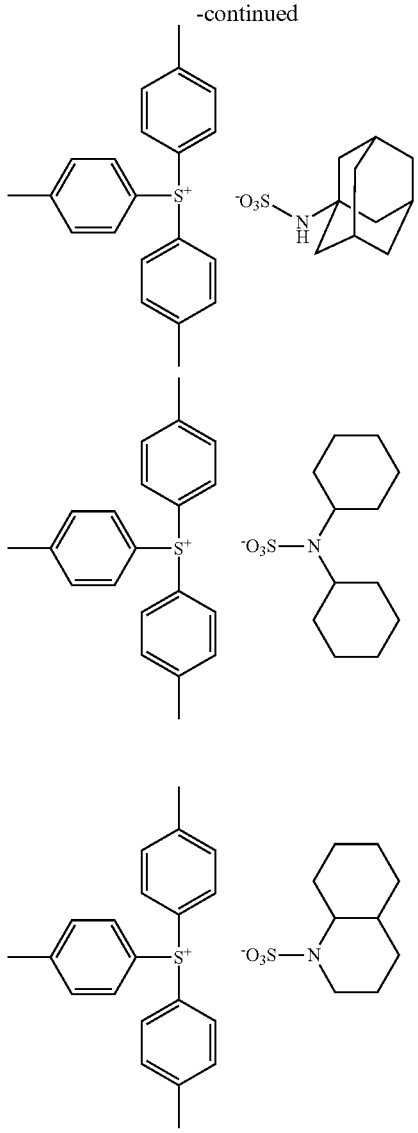
Examples of the weak acid inner salt (D) include the following salts.
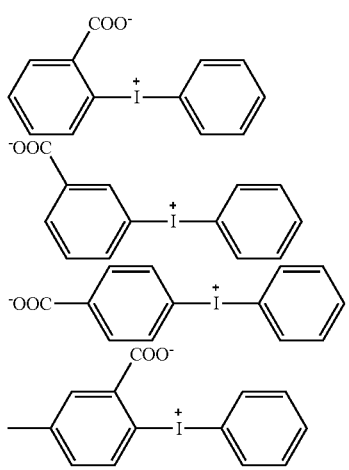
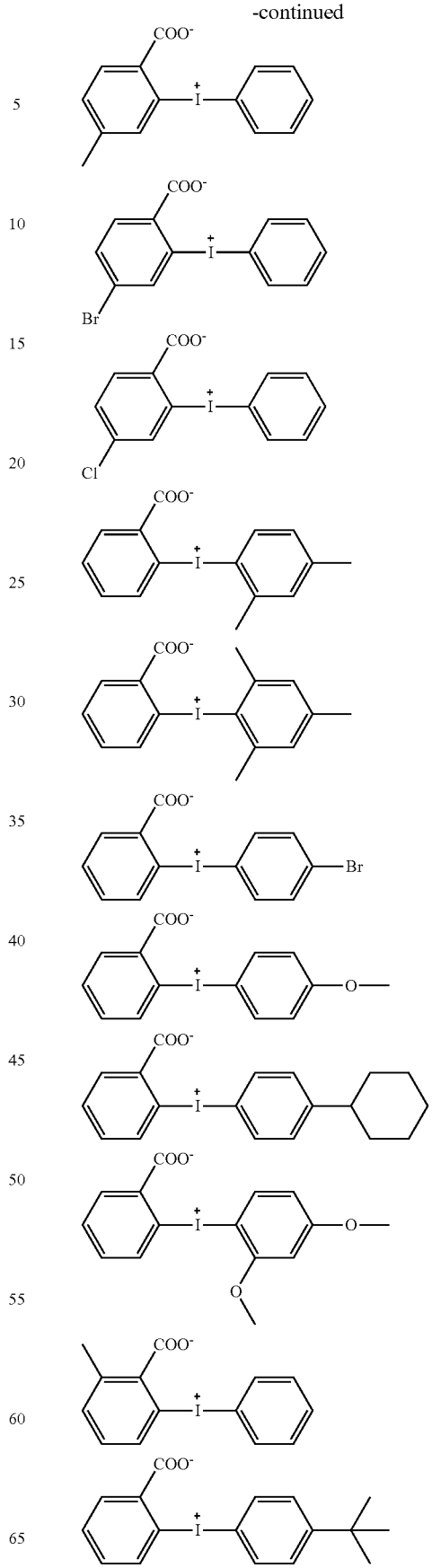

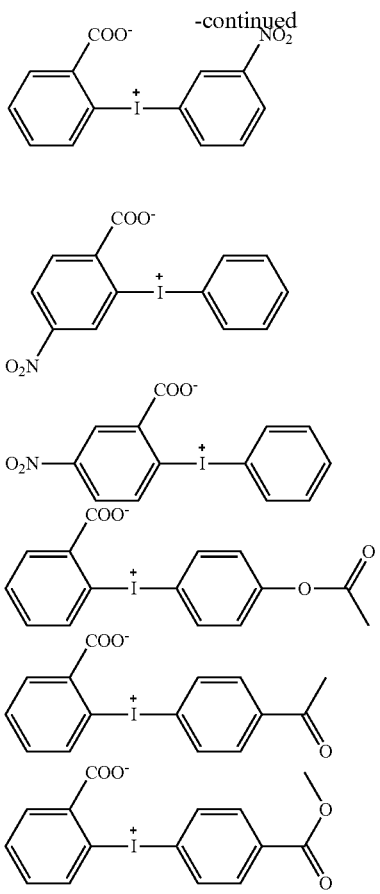

Examples of the basic nitrogen-containing organic compound include amine and an ammonium salt. Examples of the amine include an aliphatic amine and an aromatic amine. Examples of the aliphatic amine include a primary amine, a secondary amine and a tertiary amine.

Examples of the amine include 1-naphthylamine, 2-naphthylamine, aniline, diisopropylaniline, 2-, 3- or 4-methylaniline, 4-nitroaniline, N-methylaniline, N,N-dimethylaniline, diphenylamine, hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, 2,2'-methylenebisaniline, imidazole, 4-methylimidazole, pyridine, 4-methylpyridine, 1,2-di(2-pyridyl)ethane, 1,2-di(4-pyridyl)ethane, 1,2-di(2-pyridyl)ethene, 1,2-di(4-pyridyl)ethene, 1,3-di(4-pyridyl)propane, 1,2-di(4-pyridyloxy) ethane, di(2-pyridyl)ketone, 4,4'-dipyridyl sulfide, 4,4'-dipyridyl disulfide, 2,2'-dipyridylamine, 2,2'-dipicolylamine, bipyridine and the like, and aromatic amines such as diisopropylaniline are preferable and 2,6-diisopropylaniline is more preferable.

Examples of the ammonium salt include tetramethylammonium hydroxide, tetraisopropylammonium hydroxide, tetrabutylammonium hydroxide, tetrahexylammonium hydroxide, tetraoctylammonium hydroxide, phenyltrimethylammonium hydroxide, 3-(trifluoromethyl)phenyltrimethylammonium hydroxide, tetra-n-butylammonium salicylate and choline.

<Other Components>

The resist composition of the present invention may also include components other than the components mentioned above (hereinafter sometimes referred to as "other components (F)"). The other components (F) are not particularly limited and it is possible to use various additives known in the resist field, for example, sensitizers, dissolution inhibitors, surfactants, stabilizers and dyes.

<Preparation of Resist Composition>

The resist composition of the present invention can be prepared by mixing a resin (A) of the present invention and an acid generator (B) and, optionally, a salt generating an acid having an acidity lower than that of an acid generated from the acid generator, a resin (AY), a resin (X), a quencher (C), a solvent (E) and other components (F). The order of mixing these components is any order and is not particularly limited. It is possible to select, as the temperature during mixing, appropriate temperature from 10 to 40° C., according to the type of the resin, the solubility in the solvent (E) of the resin and the like. It is possible to select, as the mixing time, appropriate time from 0.5 to 24 hours according to the mixing temperature. The mixing means is not particularly limited and it is possible to use mixing with stirring.

After mixing the respective components, the mixture is preferably filtered through a filter having a pore diameter of about 0.003 to 0.2 μm.

<Method for Producing Resist Pattern>

The method for producing a resist pattern of the present invention comprises:

(1) a step of applying the resist composition of the present invention on a substrate, (2) a step of drying the applied composition to form a composition layer, (3) a step of exposing the composition layer, (4) a step of heating the exposed composition layer, and (5) a step of developing the heated composition layer.

The resist composition can be usually applied on a substrate using a conventionally used apparatus, such as a spin coater. Examples of the substrate include inorganic substrates such as a silicon wafer. Before applying the resist composition, the substrate may be washed, and an organic antireflection film may be formed on the substrate.

The solvent is removed by drying the applied composition to form a composition layer. Drying is performed by evaporating the solvent using a heating device such as a hot plate (so-called "prebake"), or a decompression device. The heating temperature is preferably 50 to 200° C. and the heating time is preferably 10 to 180 seconds. The pressure during drying under reduced pressure is preferably about 1 to $1.0 \times 10^5$ Pa.

The composition layer thus obtained is usually exposed using an aligner or a liquid immersion aligner. It is possible to use, as an exposure source, various exposure sources, for example, exposure sources capable of emitting laser beam in an ultraviolet region such as KrF excimer laser (wavelength of 248 nm), ArF excimer laser (wavelength of 193 nm) and $F_2$ excimer laser (wavelength of 157 nm), an exposure source capable of emitting harmonic laser beam in a farultraviolet or vacuum ultra violet region by wavelength-converting laser beam from a solid-state laser source (YAG or semiconductor laser), an exposure source capable of emitting electron beam or EUV and the like. In the present specification, such exposure to radiation is sometimes collectively referred to as exposure. The exposure is usually performed through a mask corresponding to a pattern to be required. When electron beam is used as the exposure source, exposure may be performed by direct writing without using the mask.

The exposed composition layer is subjected to a heat treatment (so-called "post-exposure bake") to promote the deprotection reaction in an acid-labile group. The heating temperature is usually about 50 to 200° C., and preferably about 70 to 150° C.

The heated composition layer is usually developed with a developing solution using a development apparatus. Examples of the developing method include a dipping method, a paddle method, a spraying method, a dynamic dispensing method and the like. The developing temperature is preferably, for example, 5 to 60° C. and the developing time is preferably, for example, 5 to 300 seconds. It is possible to produce a positive resist pattern or negative resist pattern by selecting the type of the developing solution as follows.

When the positive resist pattern is produced from the resist composition of the present invention, an alkaline developing solution is used as the developing solution. The alkaline developing solution may be various aqueous alkaline solutions used in this field. Examples thereof include aqueous solutions of tetramethylammonium hydroxide and (2-hydroxyethyl)trimethylammonium hydroxide (commonly known as choline). The surfactant may be contained in the alkaline developing solution.

It is preferable that the developed resist pattern is washed with ultrapure water and then water remaining on the substrate and the pattern is removed.

When the negative resist pattern is produced from the resist composition of the present invention, a developing solution containing an organic solvent (hereinafter sometimes referred to as "organic developing solution") is used as the developing solution.

Examples of the organic solvent contained in the organic developing solution include ketone solvents such as 2-hexanone and 2-heptanone; glycol ether ester solvents such as propylene glycol monomethyl ether acetate; ester solvents such as butyl acetate; glycol ether solvents such as propylene glycol monomethyl ether; amide solvents such as N,N-dimethylacetamide; and aromatic hydrocarbon solvents such as anisole.

The content of the organic solvent in the organic developing solution is preferably 90% by mass or more and 100% by mass or less, more preferably 95% by mass or more and 100% by mass or less, and still more preferably the organic developing solution is substantially composed of the organic solvent.

Particularly, the organic developing solution is preferably a developing solution containing butyl acetate and/or 2-heptanone. The total content of butyl acetate and 2-heptanone in the organic developing solution is preferably 50% by mass or more and 100% by mass or less, more preferably 90% by mass or more and 100% by mass or less, and still more preferably the organic developing solution is substantially composed of butyl acetate and/or 2-heptanone.

The surfactant may be contained in the organic developing solution. A trace amount of water may be contained in the organic developing solution.

During development, the development may be stopped by replacing by a solvent with the type different from that of the organic developing solution.

The developed resist pattern is preferably washed with a rinsing solution. The rinsing solution is not particularly limited as long as it does not dissolve the resist pattern, and it is possible to use a solution containing an ordinary organic solvent which is preferably an alcohol solvent or an ester solvent.

After washing, the rinsing solution remaining on the substrate and the pattern is preferably removed.

<Applications>

The resist composition of the present invention is suitable as a resist composition for exposure of KrF excimer laser, a resist composition for exposure of ArF excimer laser, a resist composition for exposure of electron beam (EB) or a resist composition for exposure of EUV, and more suitable as a resist composition for exposure of ArF excimer laser, a resist composition for exposure of electron beam (EB) or a resist composition for exposure of EUV, and the resist composition is useful for fine processing of semiconductors.

EXAMPLES

The present invention will be described more specifically by way of Examples. Percentages and parts expressing the contents or amounts used in the Examples are by mass unless otherwise specified.

The weight-average molecular weight is a value determined by gel permeation chromatography under the following conditions.

Equipment: HLC-8120 GPC type (manufactured by TOSOH CORPORATION)

Column: TSKgel Multipore HXL-M×3+guardcolumn (manufactured by TOSOH CORPORATION)

Eluent: tetrahydrofuran

Flow rate: 1.0 mL/min

Detector: RI detector

Column temperature: 40° C.

Injection amount: 100 μl

Molecular weight standards: polystyrene standard (manufactured by TOSOH CORPORATION)

Structures of compounds were confirmed by measuring a molecular ion peak using mass spectrometry (Liquid Chromatography: Model 1100, manufactured by Agilent Technologies, Inc., Mass Spectrometry: Model LC/MSD, manufactured by Agilent Technologies, Inc.). The value of this molecular ion peak in the following Examples is indicated by "MASS".

Example 1: Synthesis of Compound Represented by Formula (I-1)

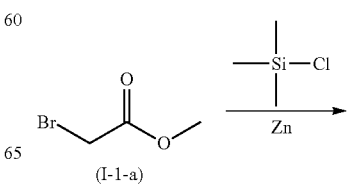

(I-1-a)

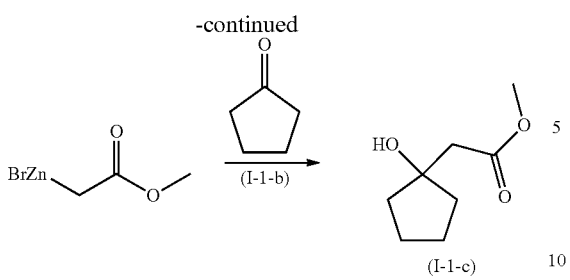

49.87 Parts of zinc and 500 parts of tert-butyl methyl ether were mixed, followed by stirring at 23° C. for 30 minutes. To the mixture thus obtained, 6.07 parts of trimethylsilyl chloride was added and, after stirring at 23° C. for 30 minutes, the temperature was raised to 35° C. To the mixture thus obtained, 88.50 parts of a compound represented by formula (I-1-a) was added, followed by stirring at 35° C. for 1 hour and further cooling to 23° C. To the mixture thus obtained, 40 parts of a compound represented by formula (I-1-b) and 60 parts of tert-butyl methyl ether were added, followed by stirring at 55° C. for 1 hour and further cooling to 23° C. To the mixture thus obtained, 75.17 parts of 37% hydrochloric acid was added, followed by stirring at 23° C. for 30 minutes and further concentration. To the concentrated residue thus obtained, 500 parts of chloroform and 350 parts of ion-exchanged water were added, followed by stirring at 23° C. for 30 minutes, standing and further isolation through separation, whereby, the organic layer was recovered. To the organic layer thus obtained, 350 parts of ion-exchanged water was added, followed by stirring at 23° C. for 30 minutes, standing and further isolation through separation, whereby, the organic layer was recovered. Such water washing operation was repeated three times. The organic layer thus recovered was concentrated to obtain 65.97 parts of a compound represented by formula (I-1-c).

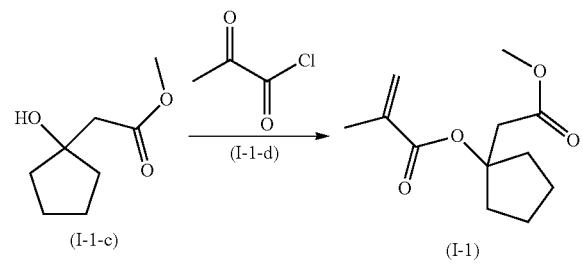

20.48 Parts of a compound represented by formula (I-1-c), 22.53 parts of pyridine, 3.16 parts of dimethylaminopyridine and 100 parts of acetonitrile were mixed, followed by stirring at 23° C. for 30 minutes and further cooling to 5° C. To the mixture thus obtained, 20.30 parts of a compound represented by formula (I-1-d) was added dropwise over 30 minutes, followed by stirring at 230° C. for 12 hours. To the mixture thus obtained, 200 parts of n-heptane and 140 parts of an aqueous 5% potassium carbonate solution were added, followed by stirring at 230° C. for 30 minutes, standing and further isolation through separation, whereby, the organic layer was recovered. To the organic layer thus obtained, 140 parts of an aqueous 5% oxalic acid solution was added, followed by stirring at 230° C. for 30 minutes, standing and further isolation through separation, whereby, the organic layer was recovered. To the organic layer thus obtained, 140 parts of ion-exchanged water was added, followed by stirring at 23° C. for 30 minutes, standing and further isolation through separation, whereby, the organic layer was recovered. Such water washing operation was repeated three times. The organic layer thus recovered was concentrated, and then the concentrated mass was isolated from a column (silica gel 60 N (spherical, neutral) 100-210 μm; manufactured by Kanto Chemical Co., Inc., developing solvent:n-heptane/ethyl acetate=20/1) to obtain 9.73 parts of a compound represented by formula (I-1).

MASS: 227.1 [M+H]$^+$

Example 2: Synthesis of Compound Represented by Formula (I-2)

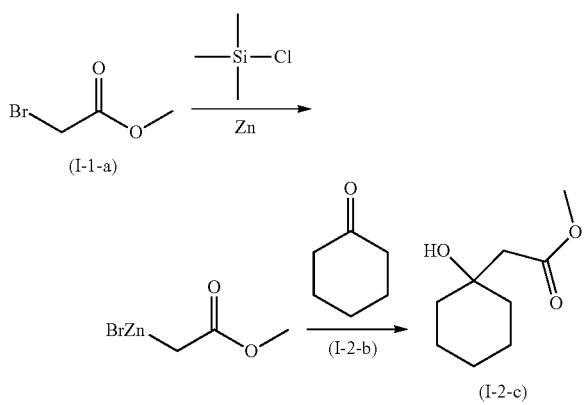

49.87 Parts of zinc and 500 parts of tert-butyl methyl ether were mixed, followed by stirring at 23° C. for 30 minutes. To the mixture thus obtained, 6.07 parts of trimethylsilyl chloride was added and, after stirring at 23° C. for 30 minutes, the temperature was raised to 35° C. To the mixture thus obtained, 88.50 parts of a compound represented by formula (I-1-a) was added, followed by stirring at 35° C. for 1 hour and further cooling to 23° C. To the mixture thus obtained, 47 parts of a compound represented by formula (I-2-b) and 70 parts of tert-butyl methyl ether were added, followed by stirring at 55° C. for 1 hour and further cooling to 23° C. To the mixture thus obtained, 75.17 parts of 37% hydrochloric acid was added, followed by stirring at 23° C. for 30 minutes and further concentration. To the concentrated residue thus obtained, 500 parts of chloroform and 350 parts of ion-exchanged water were added, followed by stirring at 23° C. for 30 minutes, standing and further isolation through separation, whereby, the organic layer was recovered. To the organic layer thus obtained, 350 parts of ion-exchanged water was added, followed by stirring at 23° C. for 30 minutes, standing and further isolation through separation, whereby, the organic layer was recovered. Such water washing operation was repeated three times. The organic layer thus recovered was concentrated to obtain 66.84 parts of a compound represented by formula (I-2-c).

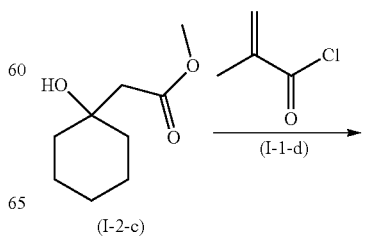

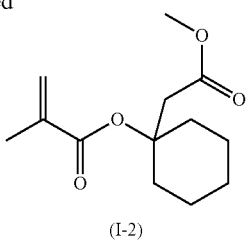

(I-2)

22.29 Parts of a compound represented by formula (I-2-c), 22.53 parts of pyridine, 3.16 parts of dimethylaminopyridine and 100 parts of acetonitrile were mixed, followed by stirring at 23° C. for 30 minutes and further cooling to 5° C. To the mixture thus obtained, 20.30 parts of a compound represented by formula (I-1-d) was added dropwise over 30 minutes, followed by stirring at 23° C. for 12 hours. To the mixture thus obtained, 200 parts of n-heptane and 140 parts of an aqueous 5% potassium carbonate solution were added, followed by stirring at 23° C. for 30 minutes, standing and further isolation through separation, whereby, the organic layer was recovered. To the organic layer thus obtained, 140 parts of an aqueous 5% oxalic acid solution was added, followed by stirring at 23° C. for 30 minutes, standing and further isolation through separation, whereby, the organic layer was recovered. To the organic layer thus obtained, 140 parts of ion-exchanged water was added, followed by stirring at 23° C. for 30 minutes, standing and further isolation through separation, whereby, the organic layer was recovered. Such water washing operation was repeated three times. The organic layer thus recovered was concentrated, and then the concentrated mass was isolated from a column (silica gel 60 N (spherical, neutral) 100-210 μm; manufactured by Kanto Chemical Co., Inc., developing solvent:n-heptane/ethyl acetate=20/1) to obtain 8.91 parts of a compound represented by formula (I-2).

MASS: 241.1 [M+H]+

Example 3: Synthesis of Compound Represented by Formula (I-5)

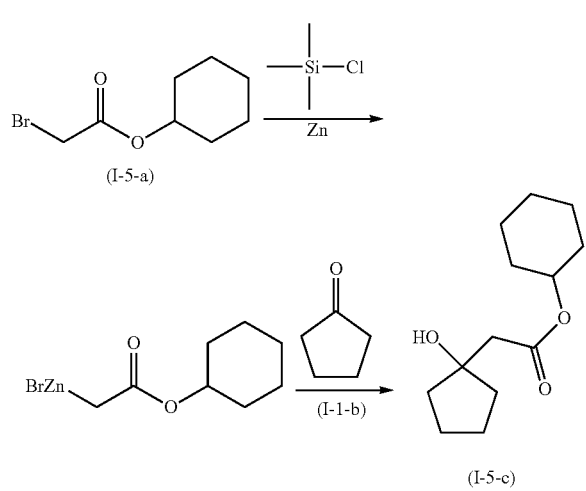

3.89 Parts of zinc and 40 parts of tert-butyl methyl ether were mixed, followed by stirring at 23° C. for 30 minutes. To the mixture thus obtained, 0.47 part of trimethylsilyl chloride was added and, after stirring at 23° C. for 30 minutes, the temperature was raised to 35° C. To the mixture thus obtained, 10 parts of a compound represented by formula (I-5-a) was added, followed by stirring at 35° C. for 1 hour and further cooling to 23° C. To the mixture thus obtained, 4 parts of a compound represented by formula (I-1-b) and 6 parts of tert-butyl methyl ether were added, followed by stirring at 55° C. for 1 hour and further cooling to 23° C. To the mixture thus obtained, 5.86 parts of 37% hydrochloric acid was added, followed by stirring at 23° C. for 30 minutes and further concentration. To the concentrated residue thus obtained, 50 parts of chloroform and 35 parts of ion-exchanged water were added, followed by stirring at 23° C. for 30 minutes, standing and further isolation through separation, whereby, the organic layer was recovered. To the organic layer thus obtained, 35 parts of ion-exchanged water was added, followed by stirring at 23° C. for 30 minutes, standing and further isolation through separation, whereby, the organic layer was recovered. Such water washing operation was repeated three times. The organic layer thus recovered was concentrated to obtain 5.57 parts of a compound represented by formula (I-5-c).

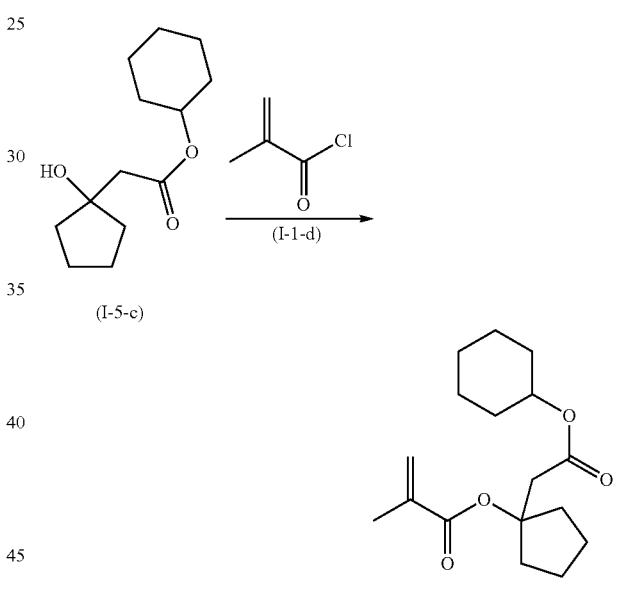

2.93 Parts of a compound represented by formula (I-5-c), 2.25 parts of pyridine, 0.32 part of dimethylaminopyridine and 20 parts of acetonitrile were mixed, followed by stirring at 23° C. for 30 minutes and further cooling to 5° C. To the mixture thus obtained, 2.03 parts of a compound represented by formula (I-1-d) was added dropwise over 30 minutes, followed by stirring at 23° C. for 12 hours. To the mixture thus obtained, 50 parts of n-heptane and 15 parts of an aqueous 5% potassium carbonate solution were added, followed by stirring at 23° C. for 30 minutes, standing and further isolation through separation, whereby, the organic layer was recovered. To the organic layer thus obtained, 15 parts of an aqueous 5% oxalic acid solution was added, followed by stirring at 23° C. for 30 minutes, standing and further isolation through separation, whereby, the organic layer was recovered. To the organic layer thus obtained, 15 parts of ion-exchanged water was added, followed by stirring at 23° C. for 30 minutes, standing and further isolation through separation, whereby, the organic layer was recovered. Such water washing operation was repeated three times. The organic layer thus recovered was concentrated, and then the concentrated mass was isolated from a column (silica gel 60 N (spherical, neutral) 100-210 µm; manufactured by Kanto Chemical Co., Inc., developing solvent:n-heptane/ethyl acetate=20/1) to obtain 2.18 parts of a compound represented by formula (I-5).

MASS: 295.2 [M+H]$^+$

Example 4: Synthesis of Compound Represented by Formula (I-7)

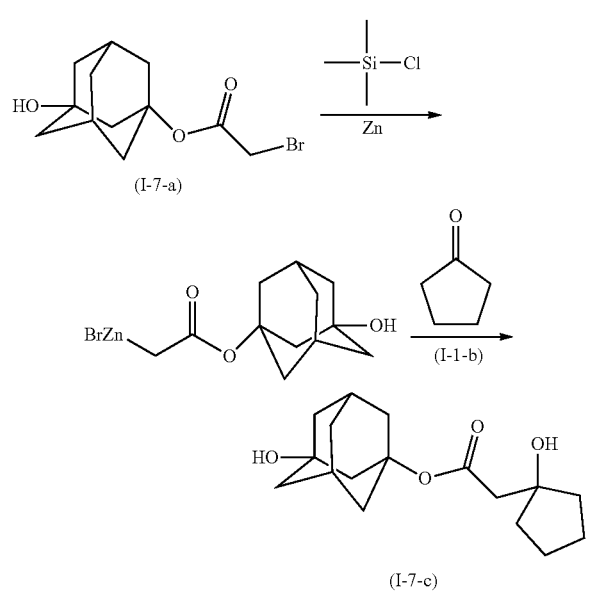

(I-7-a)

(I-1-b)

(I-7-c)

3.89 Parts of zinc and 40 parts of tert-butyl methyl ether were mixed, followed by stirring at 23° C. for 30 minutes. To the mixture thus obtained, 0.47 part of trimethylsilyl chloride was added and, after stirring at 23° C. for 30 minutes, the temperature was raised to 35° C. To the mixture thus obtained, 13 parts of a compound represented by formula (I-7-a) was added, followed by stirring at 35° C. for 1 hour and further cooling to 23° C. To the mixture thus obtained, 4 parts of a compound represented by formula (I-1-b) and 6 parts of tert-butyl methyl ether were added, followed by stirring at 55° C. for 1 hour and further cooling to 23° C. To the mixture thus obtained, 5.86 parts of 37% hydrochloric acid was added, followed by stirring at 23° C. for 30 minutes and further concentration. To the concentrated residue thus obtained, 50 parts of chloroform and 35 parts of ion-exchanged water were added, followed by stirring at 23° C. for 30 minutes, standing and further isolation through separation, whereby, the organic layer was recovered. To the organic layer thus obtained, 35 parts of ion-exchanged water was added, followed by stirring at 23° C. for 30 minutes, standing and further isolation through separation, whereby, the organic layer was recovered. Such water washing operation was repeated three times. The organic layer thus recovered was concentrated to obtain 3.89 parts of a compound represented by formula (I-7-c).

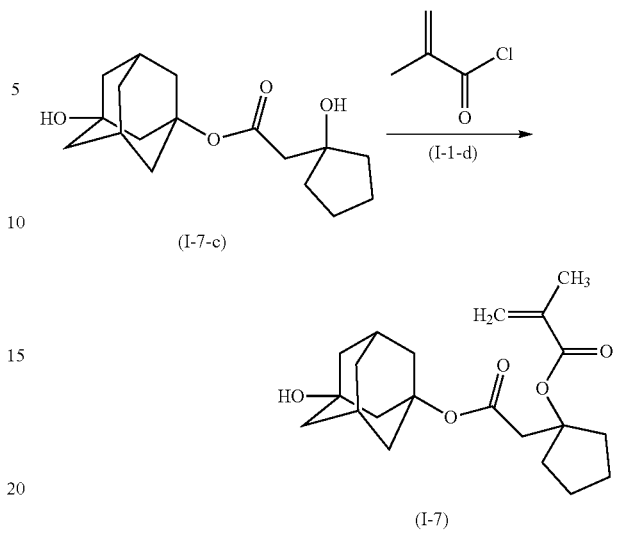

(I-7-c)

(I-1-d)

(I-7)

3.81 Parts of a compound represented by formula (I-7-c), 2.25 parts of pyridine, 0.32 part of dimethylaminopyridine and 20 parts of acetonitrile were mixed, followed by stirring at 23° C. for 30 minutes and further cooling to 5° C. To the mixture thus obtained, 2.03 parts of a compound represented by formula (I-1-d) was added dropwise over 30 minutes, followed by stirring at 23° C. for 12 hours. To the mixture thus obtained, 50 parts of n-heptane and 15 parts of an aqueous 5% potassium carbonate solution were added, followed by stirring at 23° C. for 30 minutes, standing and further isolation through separation, whereby, the organic layer was recovered. To the organic layer thus obtained, 15 parts of an aqueous 5% oxalic acid solution was added, followed by stirring at 23° C. for 30 minutes, standing and further isolation through separation, whereby, the organic layer was recovered. To the organic layer thus obtained, 15 parts of ion-exchanged water was added, followed by stirring at 23° C. for 30 minutes, standing and further isolation through separation, whereby, the organic layer was recovered. Such water washing operation was repeated three times. The organic layer thus recovered was concentrated, and then the concentrated mass was isolated from a column (silica gel 60 N (spherical, neutral) 100-210 µm; manufactured by Kanto Chemical Co., Inc., developing solvent:n-heptane/ethyl acetate=10/1) to obtain 0.99 part of a compound represented by formula (I-7).

MASS: 363.2 [M+H]$^+$

Example 5: Synthesis of Compound Represented by Formula (I-13)

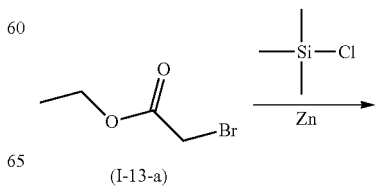

(I-13-a)

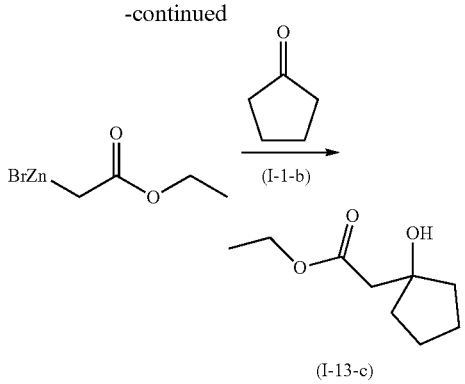

3.89 Parts of zinc and 40 parts of tert-butyl methyl ether were mixed, followed by stirring at 23° C. for 30 minutes. To the mixture thus obtained, 0.47 part of trimethylsilyl chloride was added and, after stirring at 23° C. for 30 minutes, the temperature was raised to 35° C. To the mixture thus obtained, 7.51 parts of a compound represented by formula (I-13-a) was added, followed by stirring at 35° C. for 1 hour and further cooling to 23° C. To the mixture thus obtained, 4 parts of a compound represented by formula (I-1-b) and 6 parts of tert-butyl methyl ether were added, followed by stirring at 55° C. for 1 hour and further cooling to 23° C. To the mixture thus obtained, 5.86 parts of 37% hydrochloric acid was added, followed by stirring at 23° C. for 30 minutes and further concentration. To the concentrated residue thus obtained, 50 parts of chloroform and 35 parts of ion-exchanged water were added, followed by stirring at 23° C. for 30 minutes, standing and further isolation through separation, whereby, the organic layer was recovered. To the organic layer thus obtained, 35 parts of ion-exchanged water was added, followed by stirring at 23° C. for 30 minutes, standing and further isolation through separation, whereby, the organic layer was recovered. Such water washing operation was repeated three times. The organic layer thus recovered was concentrated to obtain 2.89 parts of a compound represented by formula (I-13-c).

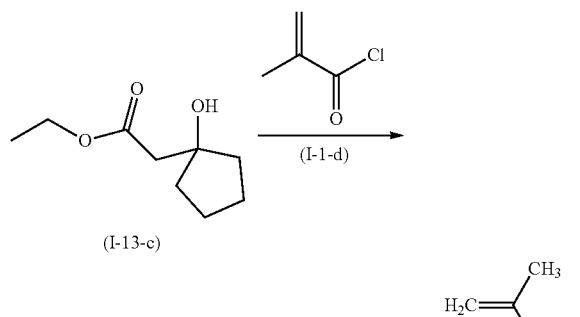

2.23 Parts of a compound represented by formula (I-13-c), 2.25 parts of pyridine, 0.32 part of dimethylaminopyridine and 20 parts of acetonitrile were mixed, followed by stirring at 23° C. for 30 minutes and further cooling to 5° C. To the mixture thus obtained, 2.03 parts of a compound represented by formula (I-1-d) was added dropwise over 30 minutes, followed by stirring at 23° C. for 12 hours. To the mixture thus obtained, 50 parts of n-heptane and 15 parts of an aqueous 5% potassium carbonate solution were added, followed by stirring at 23° C. for 30 minutes, standing and further isolation through separation, whereby, the organic layer was recovered. To the organic layer thus obtained, 15 parts of an aqueous 5% oxalic acid solution was added, followed by stirring at 23° C. for 30 minutes, standing and further isolation through separation, whereby, the organic layer was recovered. To the organic layer thus obtained, 15 parts of ion-exchanged water was added, followed by stirring at 23° C. for 30 minutes, standing and further isolation through separation, whereby, the organic layer was recovered. Such water washing operation was repeated three times. The organic layer thus recovered was concentrated, and then the concentrated mass was isolated from a column (silica gel 60 N (spherical, neutral) 100-210 μm; manufactured by Kanto Chemical Co., Inc., developing solvent:n-heptane/ethyl acetate=10/1) to obtain 1.88 parts of a compound represented by formula (I-13).

MASS: 241.1 [M+H]$^+$

Example 6: Synthesis of Compound Represented by Formula (I-4)

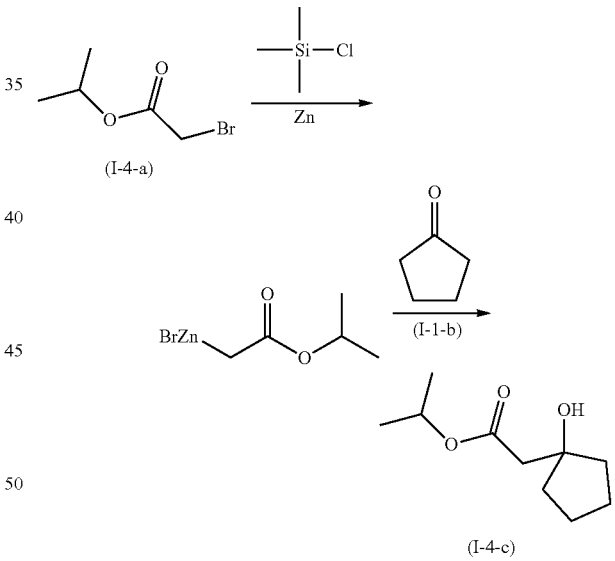

3.89 Parts of zinc and 40 parts of tert-butyl methyl ether were mixed, followed by stirring at 23° C. for 30 minutes. To the mixture thus obtained, 0.47 part of trimethylsilyl chloride was added and, after stirring at 23° C. for 30 minutes, the temperature was raised to 35° C. To the mixture thus obtained, 8.14 parts of a compound represented by formula (I-4-a) was added, followed by stirring at 35° C. for 1 hour and further cooling to 23° C. To the mixture thus obtained, 4 parts of a compound represented by formula (I-1-b) and 6 parts of tert-butyl methyl ether were added, followed by stirring at 55° C. for 1 hour and further cooling to 23° C. To the mixture thus obtained, 5.86 parts of 37% hydrochloric acid was added, followed by stirring at 23° C.

for 30 minutes and further concentration. To the concentrated residue thus obtained, 50 parts of chloroform and 35 parts of ion-exchanged water were added, followed by stirring at 23° C. for 30 minutes, standing and further isolation through separation, whereby, the organic layer was recovered. To the organic layer thus obtained, 35 parts of ion-exchanged water was added, followed by stirring at 23° C. for 30 minutes, standing and further isolation through separation, whereby, the organic layer was recovered. Such water washing operation was repeated three times. The organic layer thus recovered was concentrated to obtain 2.77 parts of a compound represented by formula (I-4-c).

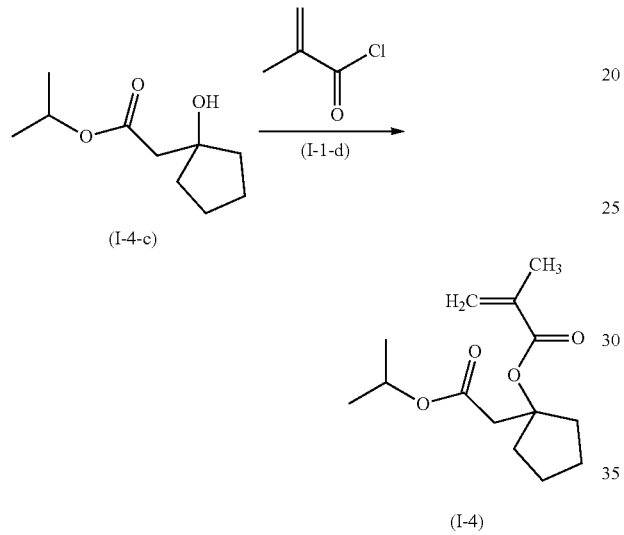

2.41 Parts of a compound represented by formula (I-4-c), 2.25 parts of pyridine, 0.32 part of dimethylaminopyridine and 20 parts of acetonitrile were mixed, followed by stirring at 23° C. for 30 minutes and further cooling to 5° C. To the mixture thus obtained, 2.03 parts of a compound represented by formula (I-1-d) was added dropwise over 30 minutes, followed by stirring at 23° C. for 12 hours. To the mixture thus obtained, 50 parts of n-heptane and 15 parts of an aqueous 5% potassium carbonate solution were added, followed by stirring at 23° C. for 30 minutes, standing and further isolation through separation, whereby, the organic layer was recovered. To the organic layer thus obtained, 15 parts of an aqueous 5% oxalic acid solution was added, followed by stirring at 23° C. for 30 minutes, standing and further isolation through separation, whereby, the organic layer was recovered. To the organic layer thus obtained, 15 parts of ion-exchanged water was added, followed by stirring at 23° C. for 30 minutes, standing and further isolation through separation, whereby, the organic layer was recovered. Such water washing operation was repeated three times. The organic layer thus recovered was concentrated, and then the concentrated mass was isolated from a column (silica gel 60 N (spherical, neutral) 100-210 μm; manufactured by Kanto Chemical Co., Inc., developing solvent:n-heptane/ethyl acetate=10/1) to obtain 1.69 parts of a compound represented by formula (I-4).

MASS: 255.2 [M+H]$^+$

Example 7: Synthesis of Compound Represented by Formula (I-3)

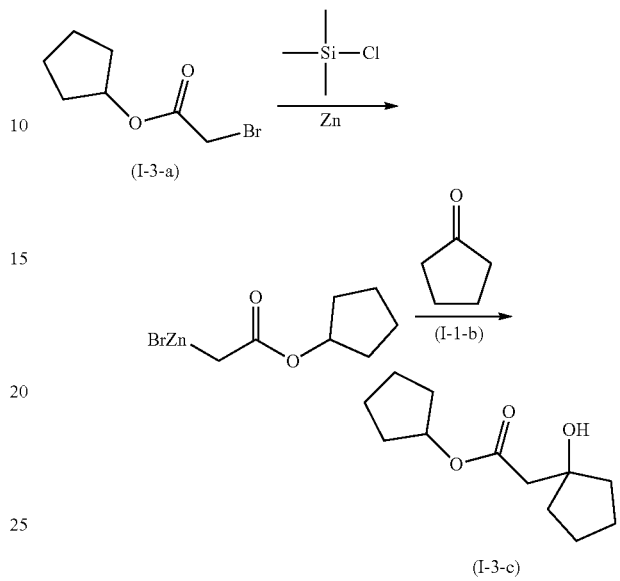

3.89 Parts of zinc and 40 parts of tert-butyl methyl ether were mixed, followed by stirring at 23° C. for 30 minutes. To the mixture thus obtained, 0.47 part of trimethylsilyl chloride was added and, after stirring at 23° C. for 30 minutes, the temperature was raised to 35° C. To the mixture thus obtained, 9.31 parts of a compound represented by formula (I-3-a) was added, followed by stirring at 35° C. for 1 hour and further cooling to 23° C. To the mixture thus obtained, 4 parts of a compound represented by formula (I-1-b) and 6 parts of tert-butyl methyl ether were added, followed by stirring at 55° C. for 1 hour and further cooling to 23° C. To the mixture thus obtained, 5.86 parts of 37% hydrochloric acid was added, followed by stirring at 23° C. for 30 minutes and further concentration. To the concentrated residue thus obtained, 50 parts of chloroform and 35 parts of ion-exchanged water were added, followed by stirring at 23° C. for 30 minutes, standing and further isolation through separation, whereby, the organic layer was recovered. To the organic layer thus obtained, 35 parts of ion-exchanged water was added, followed by stirring at 23° C. for 30 minutes, standing and further isolation through separation, whereby, the organic layer was recovered. Such water washing operation was repeated three times. The organic layer thus recovered was concentrated to obtain 4.58 parts of a compound represented by formula (I-3-c).

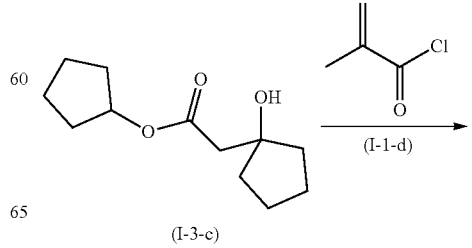

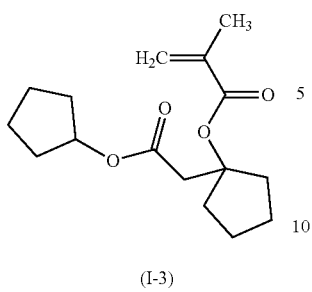

(I-3)

2.75 Parts of a compound represented by formula (I-3-c), 2.25 parts of pyridine, 0.32 part of dimethylaminopyridine and 20 parts of acetonitrile were mixed, followed by stirring at 23° C. for 30 minutes and further cooling to 5° C. To the mixture thus obtained, 2.03 parts of a compound represented by formula (I-1-d) was added dropwise over 30 minutes, followed by stirring at 23° C. for 12 hours. To the mixture thus obtained, 50 parts of n-heptane and 15 parts of an aqueous 5% potassium carbonate solution were added, followed by stirring at 23° C. for 30 minutes, standing and further isolation through separation, whereby, the organic layer was recovered. To the organic layer thus obtained, 15 parts of an aqueous 5% oxalic acid solution was added, followed by stirring at 23° C. for 30 minutes, standing and further isolation through separation, whereby, the organic layer was recovered. To the organic layer thus obtained, 15 parts of ion-exchanged water was added, followed by stirring at 23° C. for 30 minutes, standing and further isolation through separation, whereby, the organic layer was recovered. Such water washing operation was repeated three times. The organic layer thus recovered was concentrated, and then the concentrated mass was isolated from a column (silica gel 60 N (spherical, neutral) 100-210 μm; manufactured by Kanto Chemical Co., Inc., developing solvent:n-heptane/ethyl acetate=10/1) to obtain 1.91 parts of a compound represented by formula (I-3).

MASS: 281.2 $[M+H]^+$

Example 8: Synthesis of Compound Represented by Formula (I-8)

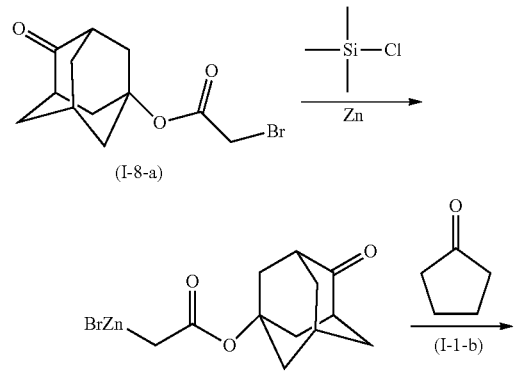

(I-8-c)

3.89 Parts of zinc and 40 parts of tert-butyl methyl ether were mixed, followed by stirring at 23° C. for 30 minutes. To the mixture thus obtained, 0.47 part of trimethylsilyl chloride was added and, after stirring at 23° C. for 30 minutes, the temperature was raised to 35° C. To the mixture thus obtained, 12.91 parts of a compound represented by formula (I-8-a) was added, followed by stirring at 35° C. for 1 hour and further cooling to 23° C. To the mixture thus obtained, 4 parts of a compound represented by formula (I-1-b) and 6 parts of tert-butyl methyl ether were added, followed by stirring at 55° C. for 1 hour and further cooling to 23° C. To the mixture thus obtained, 5.86 parts of 37% hydrochloric acid was added, followed by stirring at 23° C. for 30 minutes and further concentration. To the concentrated residue thus obtained, 50 parts of chloroform and 35 parts of ion-exchanged water were added, followed by stirring at 23° C. for 30 minutes, standing and further isolation through separation, whereby, the organic layer was recovered. To the organic layer thus obtained, 35 parts of ion-exchanged water was added, followed by stirring at 23° C. for 30 minutes, standing and further isolation through separation, whereby, the organic layer was recovered. Such water washing operation was repeated three times. The organic layer thus recovered was concentrated to obtain 3.81 parts of a compound represented by formula (I-8-c).

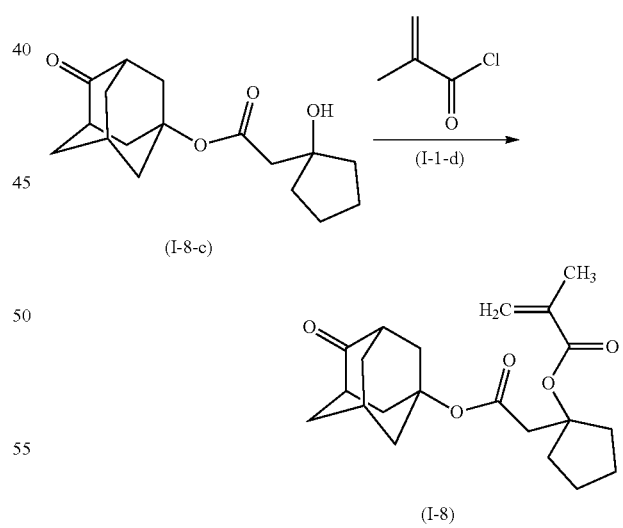

3.78 Parts of a compound represented by formula (I-8-c), 2.25 parts of pyridine, 0.32 part of dimethylaminopyridine and 20 parts of acetonitrile were mixed, followed by stirring at 23° C. for 30 minutes and further cooling to 5° C. To the mixture thus obtained, 2.03 parts of a compound represented by formula (I-1-d) was added dropwise over 30 minutes, followed by stirring at 23° C. for 12 hours. To the mixture thus obtained, 50 parts of n-heptane, 15 parts of an aqueous 5% potassium carbonate solution were added, followed by stirring at 23° C. for 30 minutes, standing and further isolation through separation, whereby, the organic layer was recovered. To the organic layer thus obtained, 15 parts of an aqueous 5% oxalic acid solution was added, followed by stirring at 23° C. for 30 minutes, standing and further isolation through separation, whereby, the organic layer was recovered. To the organic layer thus obtained, 15 parts of ion-exchanged water was added, followed by stirring at 23° C. for 30 minutes, standing and further isolation through separation, whereby, the organic layer was recovered. Such water washing operation was repeated three times. The organic layer thus recovered was concentrated, and then the concentrated mass was isolated from a column (silica gel 60 N (spherical, neutral) 100-210 μm; manufactured by Kanto Chemical Co., Inc., developing solvent:n-heptane/ethyl acetate=10/1) to obtain 1.42 parts of a compound represented by formula (I-8).

MASS: 361.2 [M+H]$^+$

Example 9: Synthesis of Compound Represented by Formula (I-9)

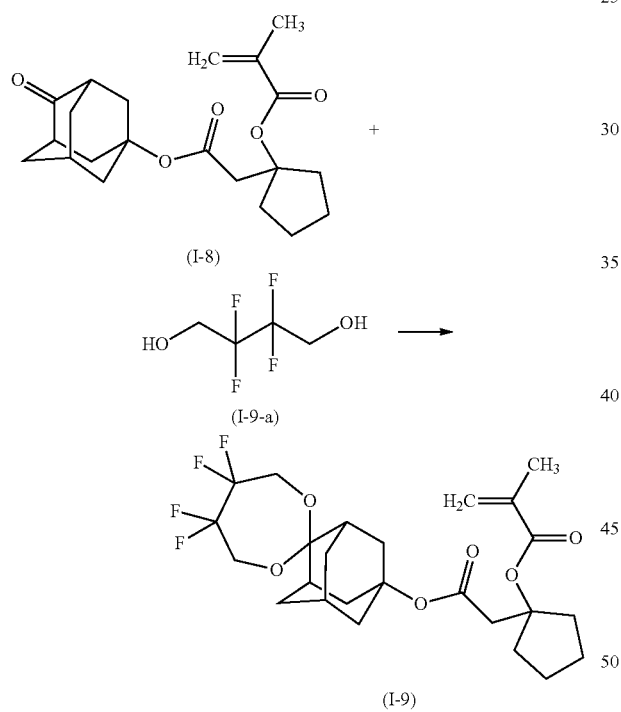

2.26 Parts of a compound represented by formula (I-8), 1.52 parts of a compound represented by formula (I-9-a) and 30 parts of chloroform were mixed and, after stirring at 23° C. for 30 minutes, 0.06 part of sulfuric acid was added, followed by stirring at 40° C. for 2 hours and further cooling to 23° C. To the reaction product thus obtained, 10 parts of an aqueous 10% potassium carbonate solution was added, followed by stirring at 23° C. for 30 minutes, standing and further isolation through separation. To the organic layer thus obtained, 10 parts of ion-exchanged water was added, followed by stirring at 23° C. for 30 minutes and further isolation through separation, whereby the organic layer was recovered. This water washing solution was performed four times. The organic layer thus obtained was concentrated, and then the concentrated mass was isolated from a column (silica gel 60 N (spherical, neutral) 100-210 μm; manufactured by Kanto Chemical Co., Inc., developing solvent:n-heptane/ethyl acetate=10/1) to obtain 0.65 part of a compound represented by formula (I-9).

MASS: 505.2 [M+H]$^+$

Synthesis of Resin

Compounds (monomers) used by adding to acetoxystyrene in the synthesis of the resin are shown below.

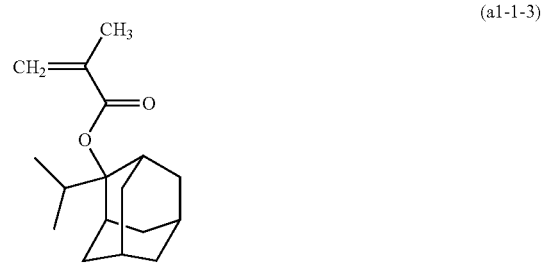
(a1-1-3)

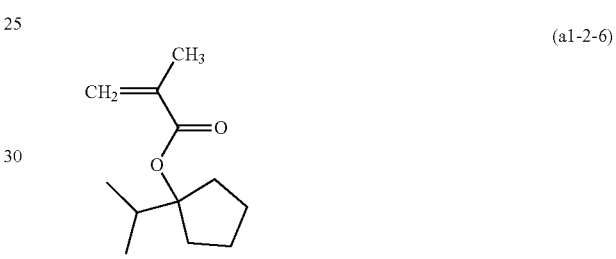
(a1-2-6)

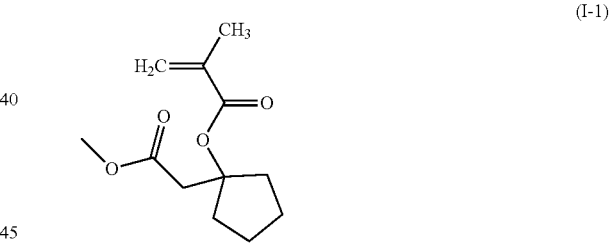
(I-1)

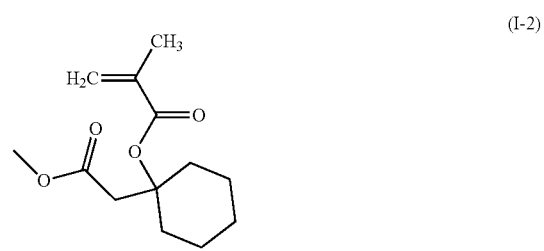
(I-2)

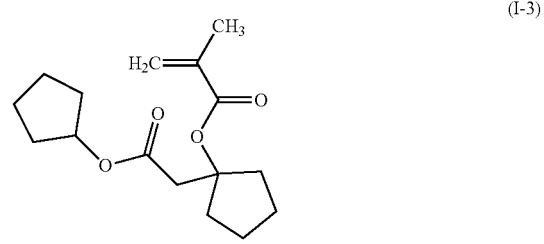
(I-3)

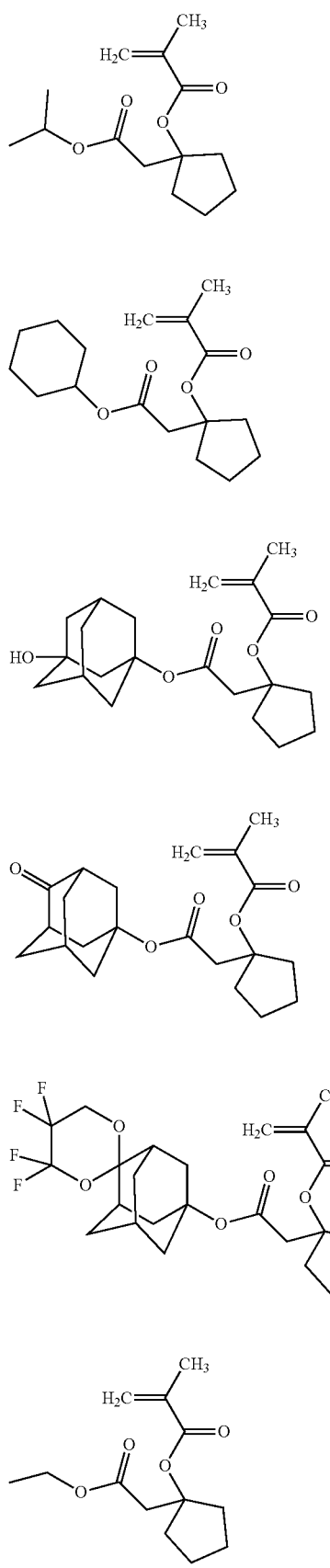
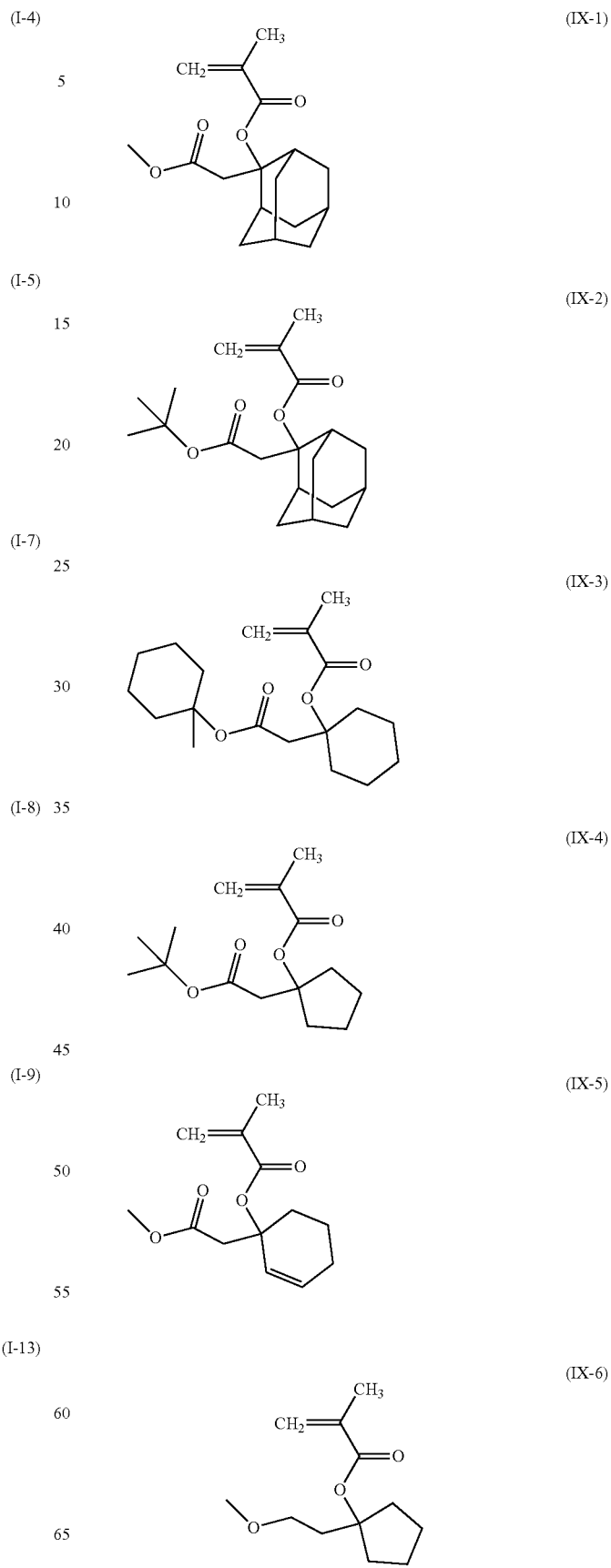

-continued

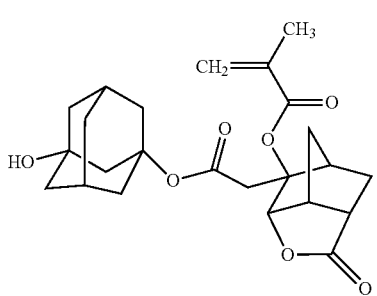

(IX-7)

Hereinafter, these monomers are referred to as "monomer (a1-1-3)" according to the formula number.

Example 10 [Synthesis of Resin A1]

Using acetoxystyrene, a monomer (a1-1-3) and a monomer (I-1) as monomers, these monomers were mixed in a molar ratio of 38:24:38 [acetoxystyrene:monomer (a1-1-3):monomer (I-1)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 2.1 mol % and 6.3 mol % based on the total molar number of all monomers, and then the mixture was polymerized by heating at 73° C. for about 5 hours. To the polymerization reaction solution thus obtained, an aqueous 25% tetramethylammonium hydroxide solution was added, followed by stirring for 12 hours and further isolation through separation. The organic layer thus obtained was poured into a large amount of n-heptane to precipitate a resin, followed by filtration and recovery to obtain a resin A1 (copolymer) having a weight-average molecular weight of about $5.4 \times 10^3$ in a yield of 72%. This resin A1 has the following structural units.

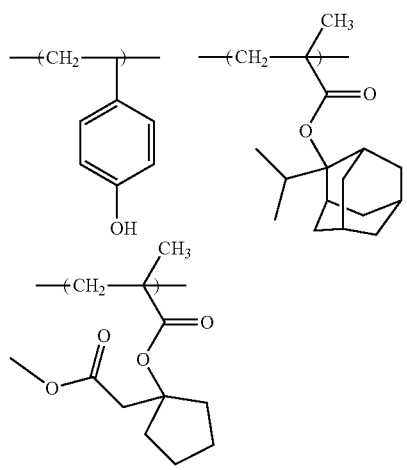

A1

Example 11 [Synthesis of Resin A2]

Using acetoxystyrene, a monomer (a1-1-3) and a monomer (1-2) as monomers, these monomers were mixed in a molar ratio of 38:24:38 [acetoxystyrene:monomer (a1-1-3):monomer (1-2)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 2.1 mol % and 6.3 mol % based on the total molar number of all monomers, and then the mixture was polymerized by heating at 73° C. for about 5 hours. To the polymerization reaction solution thus obtained, an aqueous 25% tetramethylammonium hydroxide solution was added, followed by stirring for 12 hours and further isolation through separation. The organic layer thus obtained was poured into a large amount of n-heptane to precipitate a resin, followed by filtration and recovery to obtain a resin A2 (copolymer) having a weight-average molecular weight of about $5.4 \times 10^3$ in a yield of 70%. This resin A2 has the following structural units.

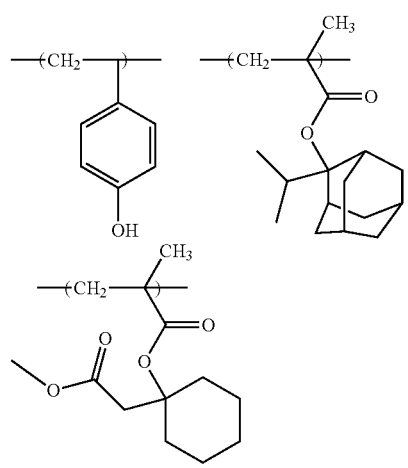

A2

Example 12 [Synthesis of Resin A3]

Using acetoxystyrene, a monomer (a1-1-3) and a monomer (I-5) as monomers, these monomers were mixed in a molar ratio of 38:24:38 [acetoxystyrene:monomer (a1-1-3):monomer (1-5)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 2.1 mol % and 6.3 mol % based on the total molar number of all monomers, and then the mixture was polymerized by heating at 73° C. for about 5 hours. To the polymerization reaction solution thus obtained, an aqueous 25% tetramethylammonium hydroxide solution was added, followed by stirring for 12 hours and further isolation through separation. The organic layer thus obtained was poured into a large amount of n-heptane to precipitate a resin, followed by filtration and recovery to obtain a resin A3 (copolymer) having a weight-average molecular weight of about $5.4 \times 10^3$ in a yield of 76%. This resin A3 has the following structural units.

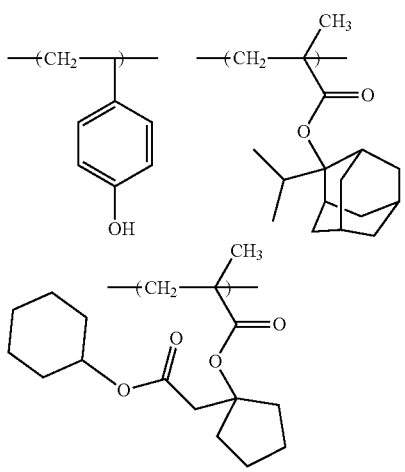

A3

Example 13 [Synthesis of Resin A4]

Using acetoxystyrene, a monomer (a1-1-3) and a monomer (1-7) as monomers, these monomers were mixed in a molar ratio of 38:24:38 [acetoxystyrene:monomer (a1-1-3): monomer (1-7)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 2.1 mol % and 6.3 mol % based on the total molar number of all monomers, and then the mixture was polymerized by heating at 73° C. for about 5 hours. To the polymerization reaction solution thus obtained, an aqueous 25% tetramethylammonium hydroxide solution was added, followed by stirring for 12 hours and further isolation through separation. The organic layer thus obtained was poured into a large amount of n-heptane to precipitate a resin, followed by filtration and recovery to obtain a resin A4 (copolymer) having a weight-average molecular weight of about $5.5 \times 10^3$ in a yield of 64%. This resin A4 has the following structural units.

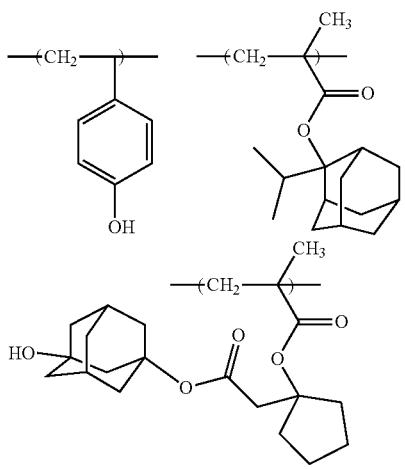

A4

Example 14 [Synthesis of Resin A5]

Using acetoxystyrene, a monomer (a1-2-6) and a monomer (I-1) as monomers, these monomers were mixed in a molar ratio of 38:38:24 [acetoxystyrene:monomer (a1-2-6): monomer (I-1)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 2.1 mol % and 6.3 mol % based on the total molar number of all monomers, and then the mixture was polymerized by heating at 73° C. for about 5 hours. To the polymerization reaction solution thus obtained, an aqueous 25% tetramethylammonium hydroxide solution was added, followed by stirring for 12 hours and further isolation through separation. The organic layer thus obtained was poured into a large amount of n-heptane to precipitate a resin, followed by filtration and recovery to obtain a resin A5 (copolymer) having a weight-average molecular weight of about $5.2 \times 10^3$ in a yield of 89%. This resin A5 has the following structural units.

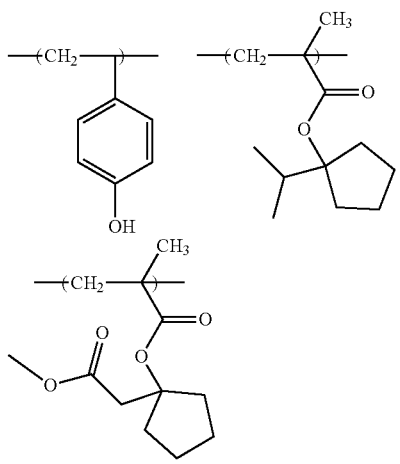

A5

Example 15 [Synthesis of Resin A6]

Using acetoxystyrene and a monomer (I-1) as monomers, these monomers were mixed in a molar ratio of 38:62 [acetoxystyrene:monomer (I-1)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 2.1 mol % and 6.3 mol % based on the total molar number of all monomers, and then the mixture was polymerized by heating at 73° C. for about 5 hours. To the polymerization reaction solution thus obtained, an aqueous 25% tetramethylammonium hydroxide solution was added, followed by stirring for 12 hours and further isolation through separation. The organic layer thus obtained was poured into a large amount of n-heptane to precipitate a resin, followed by filtration and recovery to obtain a resin A6 (copolymer) having a weight-average molecular weight of about $5.3 \times 10^3$ in a yield of 67%. This resin A6 has the following structural units.

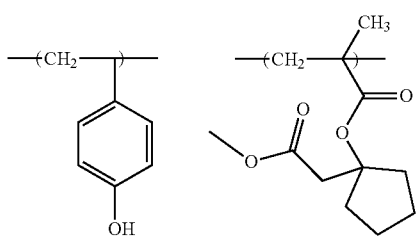

A6

Example 16 [Synthesis of Resin A7]

Using acetoxystyrene, a monomer (a1-2-6) and a monomer (I-13) as monomers, these monomers were mixed in a molar ratio of 38:38:24 [acetoxystyrene:monomer (a1-2-6):monomer (I-13)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 2.1 mol % and 6.3 mol % based on the total molar number of all monomers, and then the mixture was polymerized by heating at 73° C. for about 5 hours. To the polymerization reaction solution thus obtained, an aqueous 25% tetramethylammonium hydroxide solution was added, followed by stirring for 12 hours and further isolation through separation. The organic layer thus obtained was poured into a large amount of n-heptane to precipitate a resin, followed by filtration and recovery to obtain a resin A7 (copolymer) having a weight-average molecular weight of about $5.3 \times 10^3$ in a yield of 88%. This resin A7 has the following structural units.

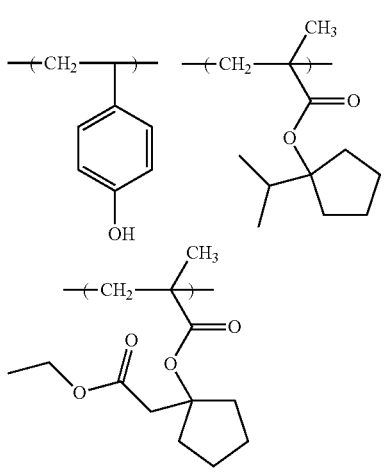

A7

Example 17 [Synthesis of Resin A8]

Using acetoxystyrene, a monomer (a1-2-6) and a monomer (1-4) as monomers, these monomers were mixed in a molar ratio of 38:38:24 [acetoxystyrene:monomer (a1-2-6):monomer (1-4)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 2.1 mol % and 6.3 mol % based on the total molar number of all monomers, and then the mixture was polymerized by heating at 73° C. for about 5 hours. To the polymerization reaction solution thus obtained, an aqueous 25% tetramethylammonium hydroxide solution was added, followed by stirring for 12 hours and further isolation through separation. The organic layer thus obtained was poured into a large amount of n-heptane to precipitate a resin, followed by filtration and recovery to obtain a resin A8 (copolymer) having a weight-average molecular weight of about $5.4 \times 10^3$ in a yield of 86%. This resin A8 has the following structural units.

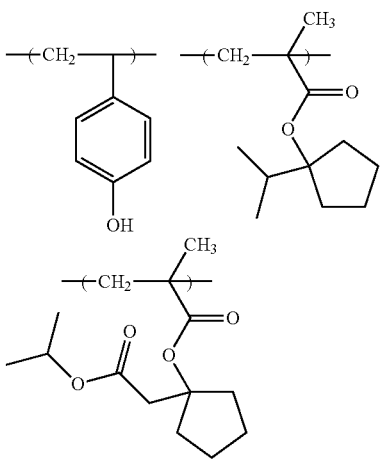

A8

Example 18 [Synthesis of Resin A9]

Using acetoxystyrene, a monomer (a1-2-6) and a monomer (1-3) as monomers, these monomers were mixed in a molar ratio of 38:38:24 [acetoxystyrene:monomer (a1-2-6):monomer (1-3)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 2.1 mol % and 6.3 mol % based on the total molar number of all monomers, and then the mixture was polymerized by heating at 73° C. for about 5 hours. To the polymerization reaction solution thus obtained, an aqueous 25% tetramethylammonium hydroxide solution was added, followed by stirring for 12 hours and further isolation through separation. The organic layer thus obtained was poured into a large amount of n-heptane to precipitate a resin, followed by filtration and recovery to obtain a resin A9 (copolymer) having a weight-average molecular weight of about $5.6 \times 10^3$ in a yield of 80%. This resin A9 has the following structural units.

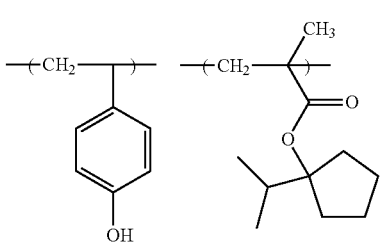

A9

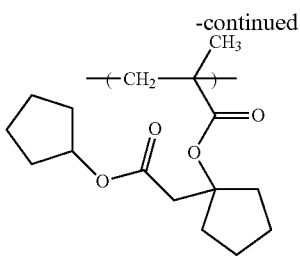

Example 19 [Synthesis of Resin A10]

Using acetoxystyrene, monomer (a1-2-6) and monomer (I-7) as monomers, these monomers were mixed in a molar ratio of 38:38:24 [acetoxystyrene:monomer (a1-2-6):monomer (1-7)], and methyl isobutyl ketone was added in the amount of 1.5 mass times the total mass of all monomers. To the mixture thus obtained, azobisisobutyronitrile and azobis (2,4-dimethylvarelonitrile) as initiators were added in the amounts of 2.1 mol % and 6.3 mol % based on the total molar number of all monomers, and then the mixture was polymerized by heating at 73° C. for about 5 hours. To the polymerization reaction solution thus obtained, an aqueous 25% tetramethylammonium hydroxide solution was added, followed by stirring for 12 hours and further isolation through separation. The organic layer thus obtained was poured into a large amount of n-heptane to precipitate a resin, followed by filtration and recovery to obtain a resin A10 (copolymer) having a weight-average molecular weight of about $5.4 \times 10^3$ in a yield of 77%. This resin A10 has the following structural units.

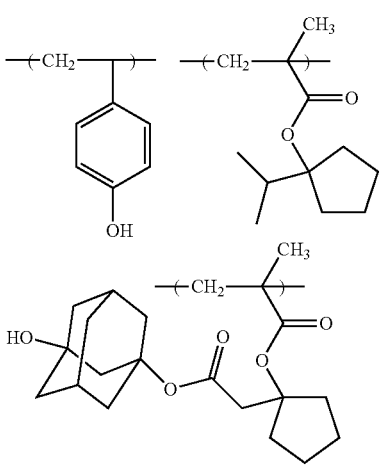

A10

Example 20 [Synthesis of Resin A11]

Using acetoxystyrene, a monomer (a1-2-6) and a monomer (I-8) as monomers, these monomers were mixed in a molar ratio of 38:38:24 [acetoxystyrene:monomer (a1-2-6):monomer (I-8)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 2.1 mol % and 6.3 mol % based on the total molar number of all monomers, and then the mixture was polymerized by heating at 73° C. for about 5 hours. To the polymerization reaction solution thus obtained, an aqueous 25% tetramethylammonium hydroxide solution was added, followed by stirring for 12 hours and further isolation through separation. The organic layer thus obtained was poured into a large amount of n-heptane to precipitate a resin, followed by filtration and recovery to obtain a resin A11 (copolymer) having a weight-average molecular weight of about $5.5 \times 10^3$ in a yield of 79%. This resin A11 has the following structural units.

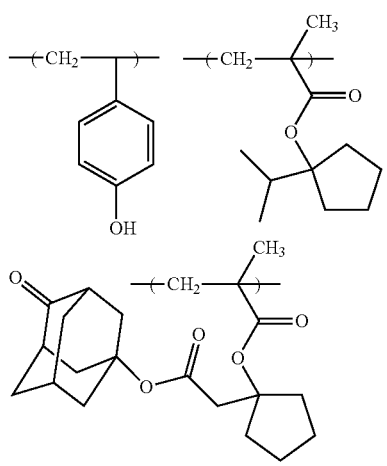

A11

Example 21 [Synthesis of Resin A12]

Using acetoxystyrene, a monomer (a1-2-6) and a monomer (I-9) as monomers, these monomers were mixed in a molar ratio of 38:38:24 [acetoxystyrene:monomer (a1-2-6):monomer (I-9)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 2.1 mol % and 6.3 mol % based on the total molar number of all monomers, and then the mixture was polymerized by heating at 73° C. for about 5 hours. To the polymerization reaction solution thus obtained, an aqueous 25% tetramethylammonium hydroxide solution was added, followed by stirring for 12 hours and further isolation through separation. The organic layer thus obtained was poured into a large amount of n-heptane to precipitate a resin, followed by filtration and recovery to obtain a resin A12 (copolymer) having a weight-average molecular weight of about $5.2 \times 10^3$ in a yield of 71%. This resin A12 has the following structural units.

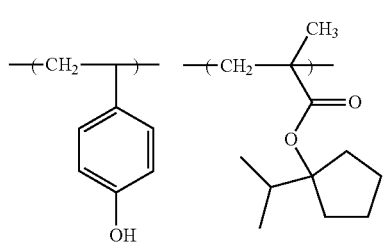

A12

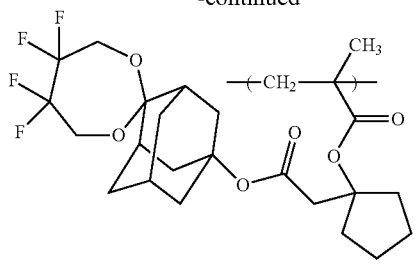

Synthesis Example 1 [Synthesis of Resin AX1]

Using acetoxystyrene and a monomer (IX-1) as monomers, these monomers were mixed in a molar ratio of 38:62 [acetoxystyrene:monomer (IX-1)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 2.1 mol % and 6.3 mol % based on the total molar number of all monomers, and then the mixture was polymerized by heating at 73° C. for about 5 hours. To the polymerization reaction solution thus obtained, an aqueous 25% tetramethylammonium hydroxide solution was added, followed by stirring for 12 hours and further isolation through separation. The organic layer thus obtained was poured into a large amount of n-heptane to precipitate a resin, followed by filtration and recovery to obtain a resin AX1 (copolymer) having a weight-average molecular weight of about $5.4 \times 10^3$ in a yield of 66%. This resin AX1 has the following structural units.

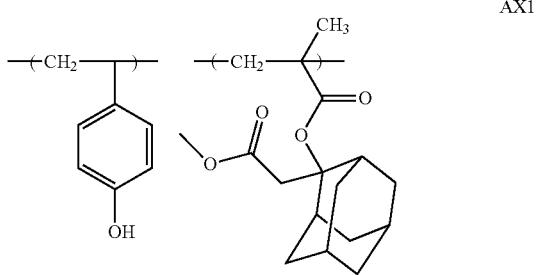

Synthesis Example 2 [Synthesis of Resin AX2]

Using acetoxystyrene and a monomer (IX-2) as monomers, these monomers were mixed in a molar ratio of 38:62 [acetoxystyrene:monomer (IX-2)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 2.1 mol % and 6.3 mol % based on the total molar number of all monomers, and then the mixture was polymerized by heating at 73° C. for about 5 hours. To the polymerization reaction solution thus obtained, an aqueous 25% tetramethylammonium hydroxide solution was added, followed by stirring for 12 hours and further isolation through separation. The organic layer thus obtained was poured into a large amount of n-heptane to precipitate a resin, followed by filtration and recovery to obtain a resin AX2 (copolymer) having a weight-average molecular weight of about $5.3 \times 10^3$ in a yield of 60%. This resin AX2 has the following structural units.

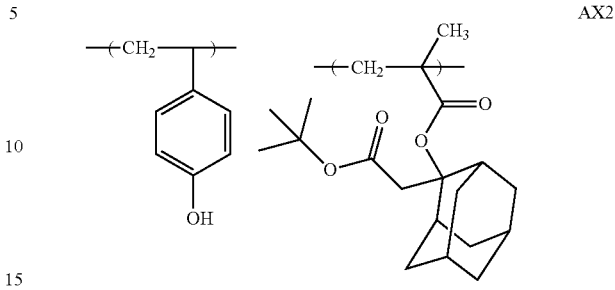

Synthesis Example 3 [Synthesis of Resin AX3]

Using acetoxystyrene and a monomer (IX-3) as monomers, these monomers were mixed in a molar ratio of 38:62 [acetoxystyrene:monomer (IX-3)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 2.1 mol % and 6.3 mol % based on the total molar number of all monomers, and then the mixture was polymerized by heating at 73° C. for about 5 hours. To the polymerization reaction solution thus obtained, an aqueous 25% tetramethylammonium hydroxide solution was added, followed by stirring for 12 hours and further isolation through separation. The organic layer thus obtained was poured into a large amount of n-heptane to precipitate a resin, followed by filtration and recovery to obtain a resin AX3 (copolymer) having a weight-average molecular weight of about $5.5 \times 10^3$ in a yield of 72%. This resin AX3 has the following structural units.

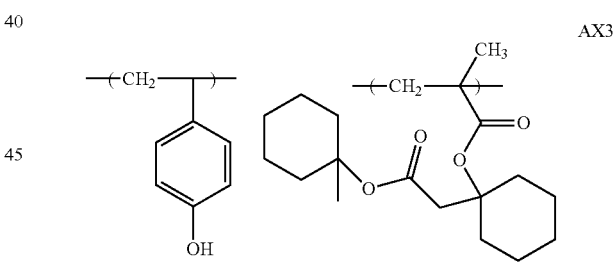

Synthesis Example 4 [Synthesis of Resin AX4]

Using acetoxystyrene and a monomer (IX-4) as monomers, these monomers were mixed in a molar ratio of 38:62 [acetoxystyrene:monomer (IX-4)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 2.1 mol % and 6.3 mol % based on the total molar number of all monomers, and then the mixture was polymerized by heating at 73° C. for about 5 hours. To the polymerization reaction solution thus obtained, an aqueous 25% tetramethylammonium hydroxide solution was added, followed by stirring for 12 hours and further isolation through separation. The organic layer thus obtained was poured into a large amount of n-heptane to precipitate a resin, followed by filtration and recovery to obtain a resin AX4 (copolymer) having a weight-average molecular weight of about $5.6\times10^3$ in a yield of 78%. This resin AX4 has the following structural units.

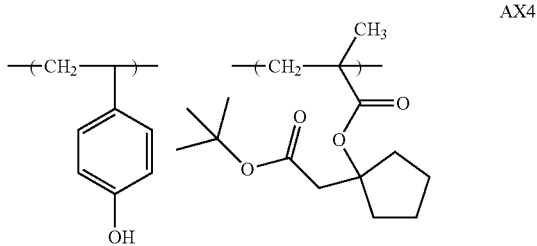

AX4

Synthesis Example 5 [Synthesis of Resin AX5]

Using acetoxystyrene and a monomer (IX-5) as monomers, these monomers were mixed in a molar ratio of 38:62 [acetoxystyrene:monomer (IX-5)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 2.1 mol % and 6.3 mol % based on the total molar number of all monomers, and then the mixture was polymerized by heating at 73° C. for about 5 hours. To the polymerization reaction solution thus obtained, an aqueous 25% tetramethylammonium hydroxide solution was added, followed by stirring for 12 hours and further isolation through separation. The organic layer thus obtained was poured into a large amount of n-heptane to precipitate a resin, followed by filtration and recovery to obtain a resin AX5 (copolymer) having a weight-average molecular weight of about $5.3\times10^3$ in a yield of 66%. This resin AX5 has the following structural units.

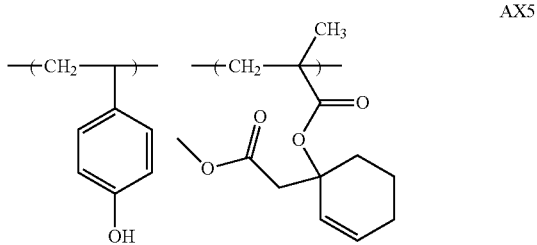

AX5

Synthesis Example 6 [Synthesis of Resin AX6]

Using acetoxystyrene and a monomer (IX-6) as monomers, these monomers were mixed in a molar ratio of 38:62 [acetoxystyrene:monomer (IX-6)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 2.1 mol % and 6.3 mol % based on the total molar number of all monomers, and then the mixture was polymerized by heating at 73° C. for about 5 hours. To the polymerization reaction solution thus obtained, an aqueous 25% tetramethylammonium hydroxide solution was added, followed by stirring for 12 hours and further isolation through separation. The organic layer thus obtained was poured into a large amount of n-heptane to precipitate a resin, followed by filtration and recovery to obtain a resin AX6 (copolymer) having a weight-average molecular weight of about $5.7\times10^3$ in a yield of 82%. This resin AX6 has the following structural units.

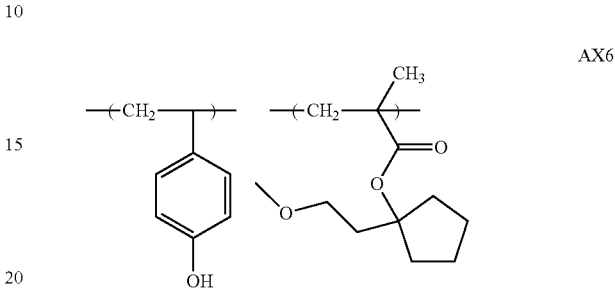

AX6

Synthesis Example 7 [Synthesis of Resin AX7]

Using acetoxystyrene and a monomer (IX-7) as monomers, these monomers were mixed in a molar ratio of 38:62 [acetoxystyrene:monomer (IX-7)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 2.1 mol % and 6.3 mol % based on the total molar number of all monomers, and then the mixture was polymerized by heating at 73° C. for about 5 hours. To the polymerization reaction solution thus obtained, an aqueous 25% tetramethylammonium hydroxide solution was added, followed by stirring for 12 hours and further isolation through separation. The organic layer thus obtained was poured into a large amount of n-heptane to precipitate a resin, followed by filtration and recovery to obtain a resin AX7 (copolymer) having a weight-average molecular weight of about $5.1\times10^3$ in a yield of 59%. This resin AX7 has the following structural units.

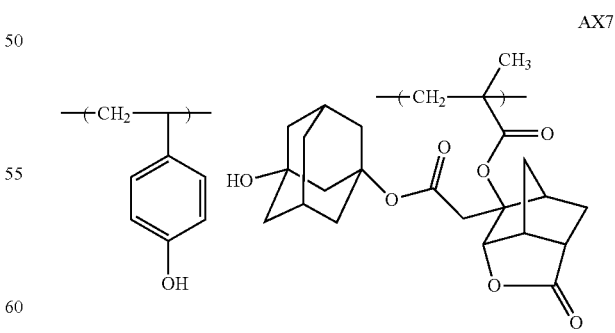

AX7

<Preparation of Resist Composition>

The mixture obtained by mixing the respective components shown in Table 1, followed by dissolving was filtered through a fluororesin filter having a pore diameter of 0.2 μm to prepare resist compositions.

TABLE 1

| Resist composition | Resin | Acid generator | Quencher | PB/PEB |
|---|---|---|---|---|
| Composition 1 | A1 = 10 parts | B1-25 = 3.4 parts | DI = 0.7 parts | 130° C./120° C. |
| Composition 2 | A2 = 10 parts | B1-25 = 3.4 parts | DI = 0.7 parts | 130° C./120° C. |
| Composition 3 | A3 = 10 parts | B1-25 = 3.4 parts | DI = 0.7 parts | 130° C./120° C. |
| Composition 4 | A4 = 10 parts | B1-25 = 3.4 parts | DI = 0.7 parts | 130° C./120° C. |
| Composition 5 | A5 = 10 parts | B1-25 = 3.4 parts | DI = 0.7 parts | 130° C./120° C. |
| Composition 6 | A6 = 10 parts | B1-25 = 3.4 parts | DI = 0.7 parts | 130° C./120° C. |
| Composition 7 | A7 = 10 parts | B1-25 = 3.4 parts | DI = 0.7 parts | 130° C./120° C. |
| Composition 8 | A8 = 10 parts | B1-25 = 3.4 parts | DI = 0.7 parts | 130° C./120° C. |
| Composition 9 | A9 = 10 parts | B1-25 = 3.4 parts | DI = 0.7 parts | 130° C./120° C. |
| Composition 10 | A10 = 10 parts | B1-25 = 3.4 parts | DI = 0.7 parts | 130° C./120° C. |
| Composition 11 | A11 = 10 parts | B1-25 = 3.4 parts | DI = 0.7 parts | 130° C./120° C. |
| Composition 12 | A12 = 10 parts | B1-25 = 3.4 parts | DI = 0.7 parts | 130° C./120° C. |
| Comparative Composition 1 | AX1 = 10 parts | B1-25 = 3.4 parts | DI = 0.7 parts | 130° C./120° C. |
| Comparative Composition 2 | AX2 = 10 parts | B1-25 = 3.4 parts | DI = 0.7 parts | 130° C./120° C. |
| Comparative Composition 3 | AX3 = 10 parts | B1-25 = 3.4 parts | DI = 0.7 parts | 130° C./120° C. |
| Comparative Composition 4 | AX4 = 10 parts | B1-25 = 3.4 parts | DI = 0.7 parts | 130° C./120° C. |
| Comparative Composition 5 | AX5 = 10 parts | B1-25 = 3.4 parts | DI = 0.7 parts | 130° C./120° C. |
| Comparative Composition 6 | AX6 = 10 parts | B1-25 = 3.4 parts | DI = 0.7 parts | 130° C./120° C. |
| Comparative Composition 7 | AX7 = 10 parts | B1-25 = 3.4 parts | DI = 0.7 parts | 130° C./120° C. |

A1 to A12, AX1 to AX7: Resin A1 to Resin A12, Resin AX1 to Resin AX7

<Acid Generator (B)>

B1-25: Salt represented by formula (B1-25); synthesized by the method mentioned in JP 2011-126869 A

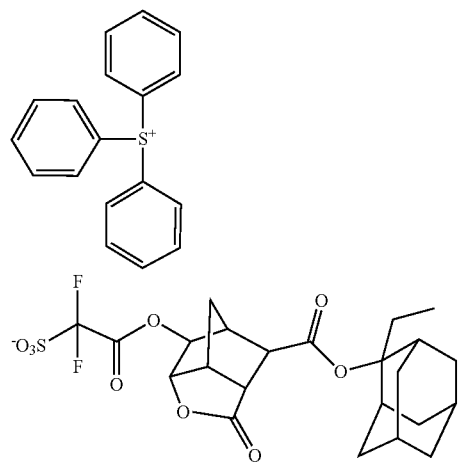

<Quencher (C)>
(Salt Generating an Acid Having an Acidity Lower than that of an Acid Generated from an Acid Generator)

D1: synthesized by the method mentioned in JP 2011-39502 A

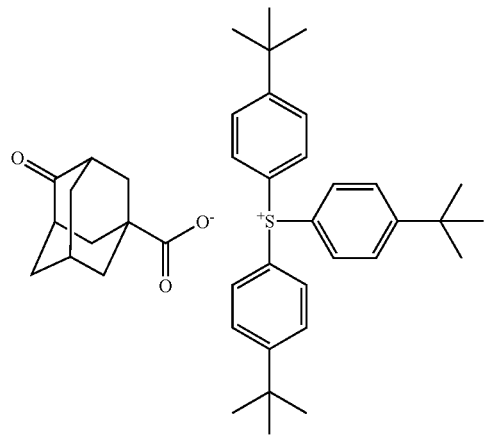 [SMILES: O=C1C2CC3CC1CC(C(=O)[O-])(C3)C2 ; CC(C)(C)c1ccc([S+](c2ccc(C(C)(C)C)cc2)c2ccc(C(C)(C)C)cc2)cc1]

<Solvent>

| | |
|---|---|
| Propylene glycol monomethyl ether acetate | 400 parts |
| Propylene glycol monomethyl ether | 150 parts |
| γ-Butyrolactone | 5 parts |

(Evaluation of Exposure of Resist Composition with Electron Beam)

Each 6 inch-diameter silicon wafer was treated with hexamethyldisilazane and then baked on a direct hot plate at 90° C. for 60 seconds. A resist composition was spin-coated on the silicon wafer so that the thickness of the composition layer became 0.04 μm. The coated silicon wafer was pre-baked on the direct hot plate at the temperature shown in the column "PB" of Table 1 for 60 seconds. Using an electron-beam direct-write system ("ELS-F125 125 keV", manufactured by ELIONIX INC.), contact hole patterns (hole pitch: 40 nm/hole diameter: 17 nm) were directly written on the composition layer formed on the wafer while changing the exposure dose stepwise.

After the exposure, post-exposure baking was performed on the hot plate at the temperature shown in the column "PEB" of Table 1 for 60 seconds, followed by paddle development with an aqueous 2.38% by mass tetramethyl-ammonium hydroxide solution for 60 seconds to obtain a resist pattern.

In the resist pattern obtained after development, the exposure dose at which the hole diameter became 17 nm was regarded as effective sensitivity.

<Evaluation of CD Uniformity (CDU)>

In the effective sensitivity, the hole diameter of the pattern formed with a hole diameter of 17 nm was determined by measuring 24 times per one hole and the average of the measured values was regarded as the average hole diameter. The standard deviation was determined under the conditions that the average diameter of 400 holes about the patterns formed with a hole diameter of 17 nm in the same wafer was regarded to as population.

The results are shown in Table 2. The numerical value in the table represents the standard deviation (nm).

TABLE 2

| | Resist composition | CDU |
|---|---|---|
| Example 22 | Composition 1 | 3.05 |
| Example 23 | Composition 2 | 3.14 |

TABLE 2-continued

| | Resist composition | CDU |
|---|---|---|
| Example 24 | Composition 3 | 3.13 |
| Example 25 | Composition 4 | 3.06 |
| Example 26 | Composition 5 | 3.01 |
| Example 27 | Composition 6 | 3.09 |
| Example 28 | Composition 7 | 3.02 |
| Example 29 | Composition 8 | 3.04 |
| Example 30 | Composition 9 | 3.07 |
| Example 31 | Composition 10 | 3.01 |
| Example 32 | Composition 11 | 3.03 |
| Example 33 | Composition. 12 | 2.97 |
| Comparative Example 1 | Comparative Composition 1 | 3.38 |
| Comparative Example 2 | Comparative Composition 2 | 3.49 |
| Comparative Example 3 | Comparative Composition 3 | 3.41 |
| Comparative Example 4 | Comparative Composition 4 | 3.32 |
| Comparative Example 5 | Comparative Composition 5 | 3.24 |
| Comparative Example 6 | Comparative Composition 6 | 3.23 |
| Comparative Example 7 | Comparative Composition 7 | 3.25 |

As compared with Comparative Compositions 1 to 7, Compositions 1 to 12 exhibited small standard deviation and satisfactory evaluation of CD uniformity (CDU).

INDUSTRIAL APPLICABILITY

A resist composition comprising a resin including a structural unit derived from a compound of the present invention is capable of producing a resist pattern with satisfactory CD uniformity (CDU), and is therefore suited for fine processing of semiconductor and is industrially very useful.

The invention claimed is:

1. A compound represented by formula (I):

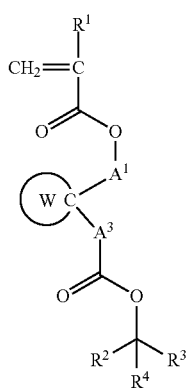

(I)

wherein, in formula (I),
$R^1$ represents an alkyl group having 1 to 6 carbon atoms which may have a halogen atom, a hydrogen atom or a halogen atom,
$A^1$ represents a single bond or * -$A^2$-CO—O—, and * represents a bonding site to an oxygen atom,
$A^2$ represents an alkanediyl group having 1 to 6 carbon atoms,
W represents a divalent monocyclic saturated alicyclic hydrocarbon group having 3 to 12 carbon atoms,
$A^3$ represents an alkanediyl group having 1 to 6 carbon atoms, and
(i) $R^2$ represents a hydrocarbon group having 1 to 18 carbon atoms which may have a fluorine atom and —$CH_2$— included in the hydrocarbon group may be replaced by —O—, —S—, —CO— or —$SO_2$—,
$R^3$ represents a hydrogen atom or a hydrocarbon group having 1 to 18 carbon atoms which may have a flourine atom and —$CH_2$— included in the hydrocarbon group may be replaced by —O—, —S—, —CO— or —$SO_2$—, and
$R^4$ represents a hydrogen atom, or
(ii) $R^2$ and $R^3$ are bonded each other to form a monocyclic saturated hydrocarbon ring having 3 to 36 carbon atoms which may have a fluorine atom or an alkyl group having 1 to 12 carbon atoms and —$CH_2$— included in the alkyl group may be replaced by —O— or —CO—, and —$CH_2$— included in the monocyclic saturated hydrocarbon ring may be replaced by —O—, —S—, —CO— or —$SO_2$—, and
$R^4$ represents a hydrogen atom, or
(iii) $R^2$, $R^3$ and $R^4$ are bonded each other to form a polycyclic saturated hydrocarbon ring having 3 to 36 carbon atoms which may have a fluorine atom or an alkyl group having 1 to 12 carbon atoms and —$CH_2$— included in the alkyl group may be replaced by —O— or —CO—, and —$CH_2$— included in the polycyclic saturated hydrocarbon ring may be replaced by —O—, —S—, —CO— or —$SO_2$—.

2. The compound according to claim 1, wherein W is a cyclopentanediyl group or a cyclohexanediyl group.

3. The compound according to claim 1, wherein $A^1$ is a single bond.

4. The compound according to claim 1, wherein $A^3$ is a methylene group.

5. The compound according to claim 1, wherein
$R^2$ represents a hydrocarbon group having 1 to 18 carbon atoms which may have a fluorine atom and —$CH_2$— included in the hydrocarbon group may be replaced by —O—, —S—, —CO— or —$SO_2$—,
$R^3$ represents a hydrogen atom or a hydrocarbon group having 1 to 18 carbon atoms which may have a fluorine atom and —$CH_2$— included in the hydrocarbon group may be replaced by —O—, —S—, —CO— or —$SO_2$—, and
$R^4$ represents a hydrogen atom.

6. The compound according to claim 1, wherein
$R^2$ and $R^3$ are bonded each other to form the monocyclic saturated hydrocarbon ring having 3 to 36 carbon atoms which may have a fluorine atom or an alkyl group having 1 to 12 carbon atoms and —$CH_2$— included in the alkyl group may be replaced by —O— or —CO—, and —$CH_2$— included in the ring may be replaced by —O—, —S—, —CO— or —$SO_2$—, and
$R^4$ represents a hydrogen atom.

7. The compound according to claim 1, wherein
$R^2$, $R^3$ and $R^4$ are bonded each other to form a polycyclic saturated hydrocarbon ring having 3 to 36 carbon atoms which may have a fluorine atom or an alkyl group having 1 to 12 carbon atoms and —$CH_2$— included in the alkyl group may be replaced by —O— or —CO—, and —$CH_2$— included in the polycyclic saturated hydrocarbon ring may be replaced by —O—, —S—, —CO— or —$SO_2$—.

8. The compound according to claim 1, wherein
$R^2$, $R^3$ and $R^4$ form one selected from monocyclic and polycyclic saturated hydrocarbon rings represented below:

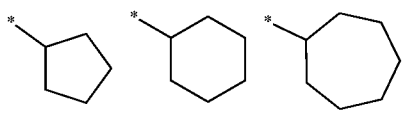

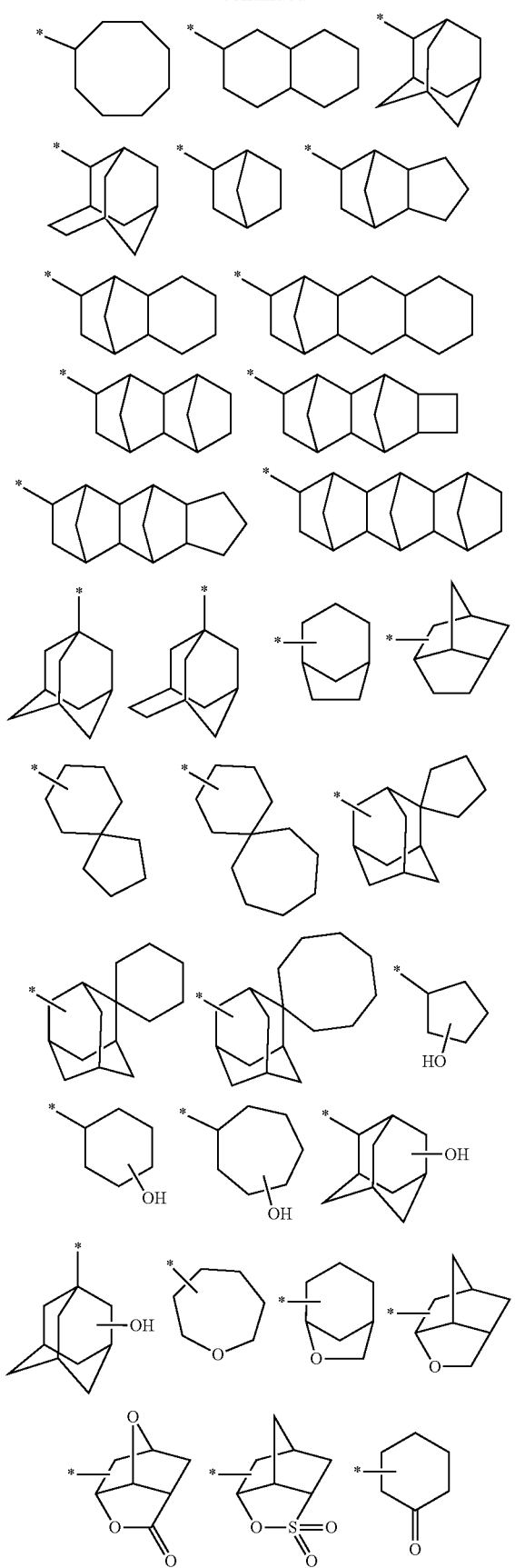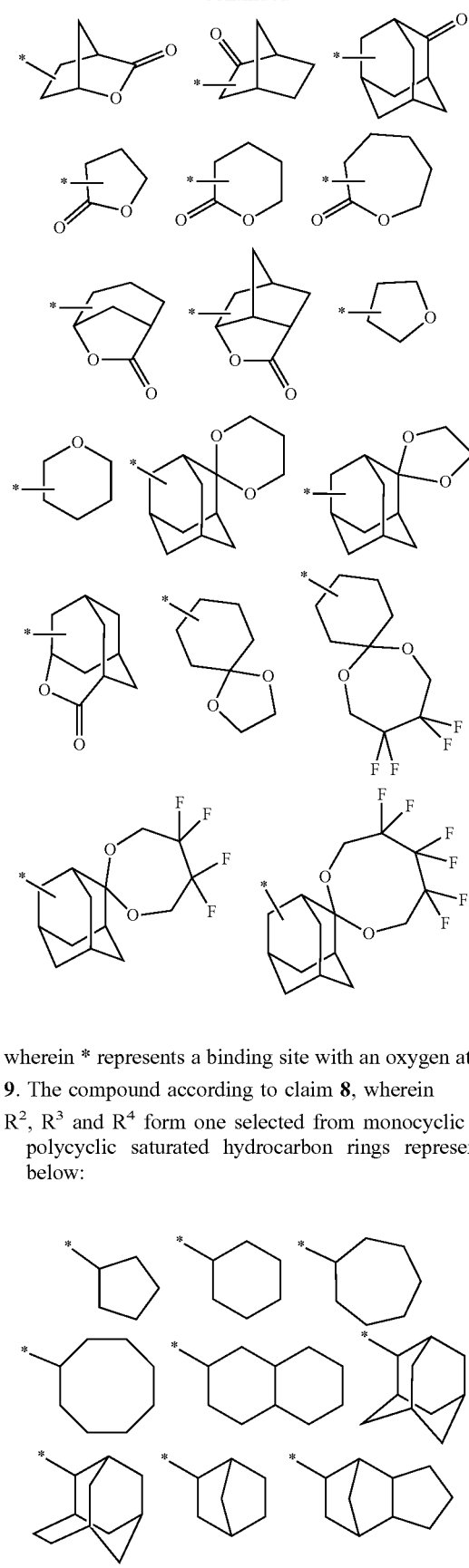
wherein * represents a binding site with an oxygen atom.
9. The compound according to claim 8, wherein
$R^2$, $R^3$ and $R^4$ form one selected from monocyclic and polycyclic saturated hydrocarbon rings represented below:
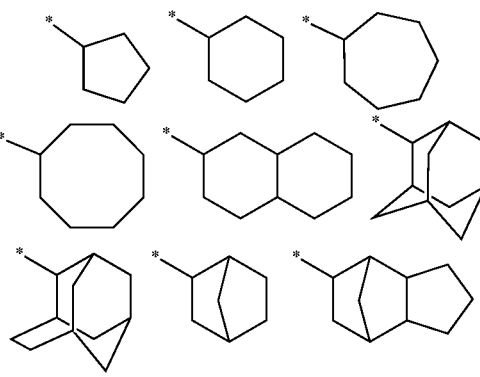

215

-continued

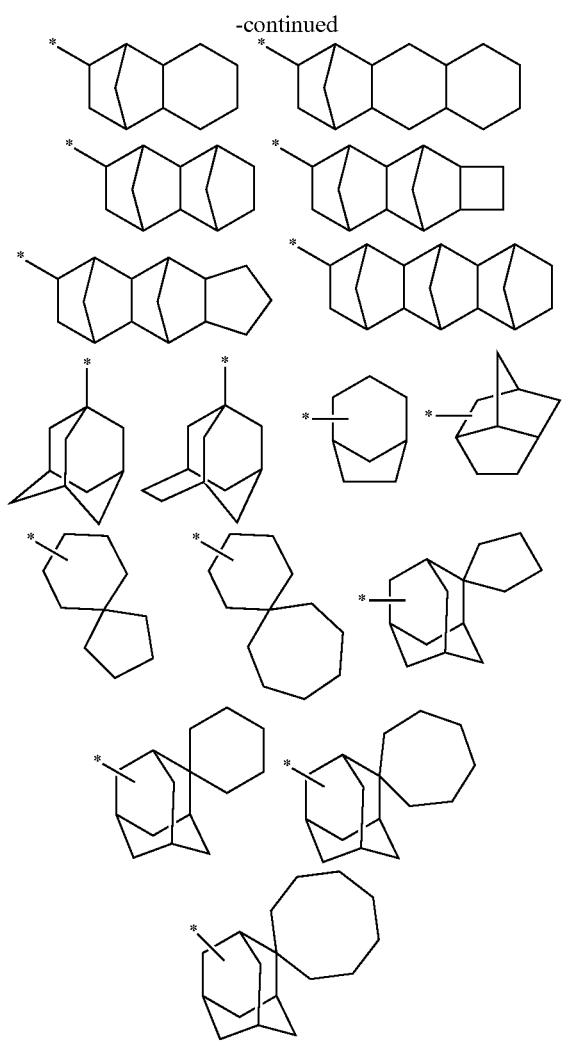

wherein * represents a binding site with an oxygen atom.

10. The compound according to claim 8, wherein R², R³ and R⁴ form one selected from monocyclic and polycyclic saturated hydrocarbon rings represented below:

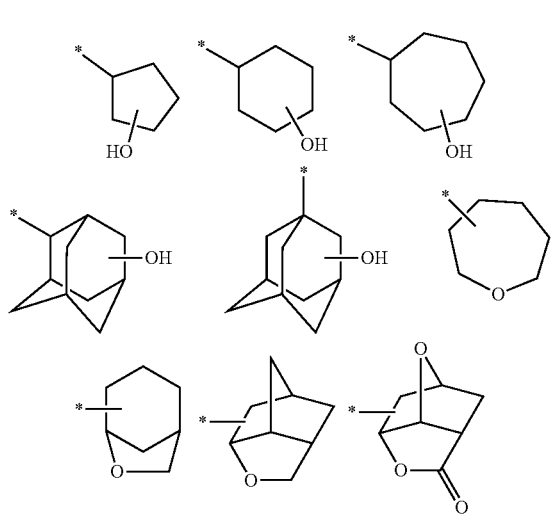

216

-continued

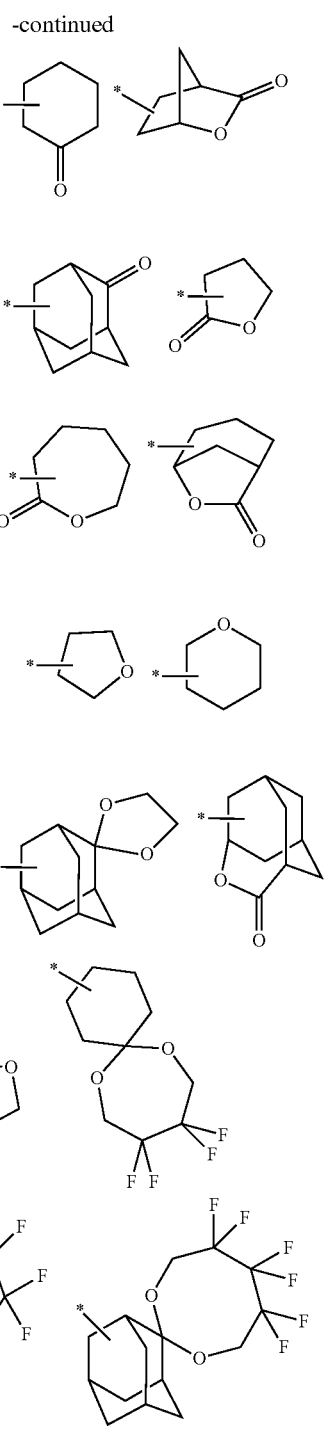

wherein * represents a binding site with an oxygen atom.

11. The compound according to claim 1, wherein W represents a cyclopropanediyl group, a cyclobutanediyl group, a cyclopentanediyl group, a cyclohexanediyl group, a cycloheptanediyl group, or a cyclooctanediyl group.

12. A resin comprising a structural unit derived from the compound according to claim 1.

13. The resin according to claim 12, further comprising a structural unit represented by formula (a2-A):

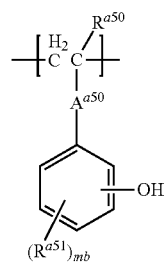

(a2-A)

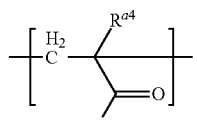

(a1-1)

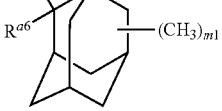

(a1-2)

wherein, in formula (a2-A),
- $R^{a50}$ represents a hydrogen atom, a halogen atom, or an alkyl group having 1 to 6 carbon atoms which may have a halogen atom,
- $R^{a51}$ represents a halogen atom, a hydroxy group, an alkyl group having 1 to 6 carbon atoms, an alkoxy group having 1 to 6 carbon atoms, an alkylcarbonyl group having 2 to 4 carbon atoms, an alkylcarbonyloxy group having 2 to 4 carbon atoms, an acryloyloxy group or a methacryloyloxy group,
- $A^{a50}$ represents a single bond or *—$X^{a51}$-($A^{a52}$-$X^{a52}$)$_{nb}$—, and * represents a bonding site to carbon atoms to which —$R^{a50}$ is bonded,
- $A^{a52}$ represents an alkanediyl group having 1 to 6 carbon atoms,
- $X^{a51}$ and $X^{a52}$ each independently represent —O—, —CO—O— or —O—CO—,
- nb represents 0 or 1, and
- mb represents an integer of 0 to 4, and when mb is an integer of 2 or more, a plurality of $R^{a51}$ may be the same or different from each other.

14. The resin according to claim 12, further comprising a structural unit having an acid-labile group which is different from the structural unit derived from compound represented by formula (I).

15. The resin according to claim 14, wherein the resin including a structural unit having an acid-labile group which is different from the structural unit derived from compound represented by formula (I) is a resin including at least one selected from the group consisting of a structural unit represented by formula (a1-1) and a structural unit represented by formula (a1-2):

wherein, in formula (a1-1) and formula (a1-2),
- $L^{a1}$ and $L^{a2}$ each independently represent —O— or *—O—(CH$_2$)$_{k1}$—CO—O—, k1 represents an integer of 1 to 7, and * represents a bonding site to —CO—,
- $R^{a4}$ and $R^{a5}$ each independently represent a hydrogen atom or a methyl group,
- $R^{a6}$ and $R^{a7}$ each independently represent an alkyl group having 1 to 8 carbon atoms, an alicyclic hydrocarbon group having 3 to 18 carbon atoms, or a group obtained by combining these groups,
- m1 represents an integer of 0 to 14,
- n1 represents an integer of 0 to 10, and
- n1' represents an integer of 0 to 3.

16. A resist composition comprising the resin according to claim 12, and an acid generator.

17. The resist composition according to claim 16, further comprising a salt generating an acid having an acidity lower than that of an acid generated from the acid generator.

18. A method for producing a resist pattern, which comprises:
  (1) a step of applying the resist composition according to claim 16 on a substrate,
  (2) a step of drying the applied composition to form a composition layer,
  (3) a step of exposing the composition layer,
  (4) a step of heating the exposed composition layer, and
  (5) a step of developing the heated composition layer.

* * * * *